(12) United States Patent
Viola et al.

(10) Patent No.: US 8,337,515 B2
(45) Date of Patent: Dec. 25, 2012

(54) FLEXIBLE ENDOSCOPIC STITCHING DEVICES

(75) Inventors: Frank Viola, Sandy Hook, CT (US);
Eric J. Taylor, East Hampton, CT (US);
Peter Hathaway, Lebanon, CT (US);
Kenneth W. Horton, South Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 657 days.

(21) Appl. No.: 12/442,872

(22) PCT Filed: Oct. 5, 2007

(86) PCT No.: PCT/US2007/021449
§ 371 (c)(1),
(2), (4) Date: Mar. 25, 2009

(87) PCT Pub. No.: WO2008/045355
PCT Pub. Date: Apr. 17, 2008

(65) Prior Publication Data
US 2010/0030238 A1    Feb. 4, 2010

Related U.S. Application Data

(60) Provisional application No. 60/849,561, filed on Oct. 5, 2006, provisional application No. 60/849,562, filed on Oct. 5, 2006, provisional application No. 60/849,508, filed on Oct. 5, 2006, provisional application No. 60/923,804, filed on Apr. 16, 2007, provisional application No. 60/923,980, filed on Apr. 17, 2007, provisional application No. 60/958,474, filed on Jul. 6, 2007.

(51) Int. Cl.
*A61B 17/04* (2006.01)

(52) U.S. Cl. .................................................... 606/144
(58) Field of Classification Search ............... 606/144, 606/148, 205, 207, 208, 213; 604/411
See application file for complete search history.

(56) References Cited

U.S. PATENT DOCUMENTS

| | | | |
|---|---|---|---|
| 1,822,330 A | 9/1931 | Ainslie | |
| 2,327,353 A | 8/1943 | Karle | |
| 3,073,311 A | 1/1963 | Tibbs et al. | |
| 4,236,470 A | 12/1980 | Stenson | |
| 5,037,433 A | 8/1991 | Wilk et al. | |
| 5,042,707 A | 8/1991 | Taheri | |
| 5,100,430 A | 3/1992 | Avellanet et al. | |

(Continued)

OTHER PUBLICATIONS

International Search Report for PCT/US07/021449 date of completion is Jan. 28, 2008 (2 pages).

*Primary Examiner* — Corrine M McDermott
*Assistant Examiner* — Christina Lauer

(57) ABSTRACT

An endoscopic stitching device is provided including a handle assembly and an end effector operatively connected to the handle assembly. The handle assembly includes a housing; a trigger operatively supported on the housing; and an actuation cable operatively connected to the trigger and extending from the housing in such a manner that an actuation of the trigger imparts axial translation and rotation to the actuation cable. The end effector includes a tool assembly configured and adapted to perform at least a pair of operations. The actuation cable is operatively connected to the tool assembly in such a manner that the actuation cable is capable of effecting a first operation of the pair of operations of the end effector upon the axial translation thereof and/or effecting a second operation of the pair of operations of the end effector upon the rotation thereof.

28 Claims, 101 Drawing Sheets

U.S. PATENT DOCUMENTS

| | | |
|---|---|---|
| 5,209,747 A | 5/1993 | Knoepfler |
| 5,271,543 A * | 12/1993 | Grant et al. ................. 227/179.1 |
| 5,300,082 A | 4/1994 | Sharpe et al. |
| 5,308,353 A | 5/1994 | Beurrier |
| 5,314,445 A | 5/1994 | Heidmueller née Degwitz et al. |
| 5,330,502 A | 7/1994 | Hassler et al. |
| 5,350,391 A | 9/1994 | Iacovelli |
| 5,374,277 A | 12/1994 | Hassler |
| 5,389,103 A | 2/1995 | Melzer et al. |
| 5,403,342 A | 4/1995 | Tovey et al. |
| 5,439,478 A | 8/1995 | Palmer |
| 5,454,823 A | 10/1995 | Richardson et al. |
| 5,454,827 A | 10/1995 | Aust et al. |
| 5,480,406 A | 1/1996 | Nolan et al. |
| 5,540,706 A | 7/1996 | Aust et al. |
| 5,564,615 A | 10/1996 | Bishop et al. |
| 5,575,799 A | 11/1996 | Bolanos et al. |
| 5,582,617 A | 12/1996 | Klieman et al. |
| 5,591,181 A | 1/1997 | Stone et al. |
| 5,601,224 A | 2/1997 | Bishop et al. |
| 5,620,415 A | 4/1997 | Lucey et al. |
| 5,643,294 A * | 7/1997 | Tovey et al. ................... 606/148 |
| 5,674,229 A | 10/1997 | Tovey et al. |
| 5,690,652 A | 11/1997 | Wurster et al. |
| 5,690,653 A | 11/1997 | Richardson et al. |
| 5,752,973 A | 5/1998 | Kieturakis |
| 5,759,188 A | 6/1998 | Yoon |
| 5,766,196 A | 6/1998 | Griffiths |
| 5,779,646 A | 7/1998 | Koblish et al. |
| 5,792,165 A | 8/1998 | Klieman et al. |
| 5,797,537 A | 8/1998 | Oberlin et al. |
| 5,797,927 A | 8/1998 | Yoon |
| 5,814,054 A | 9/1998 | Kortenbach et al. |
| 5,817,119 A | 10/1998 | Klieman et al. |
| 5,827,323 A | 10/1998 | Klieman et al. |
| 5,876,412 A | 3/1999 | Piraka |
| 5,897,563 A | 4/1999 | Yoon et al. |
| 5,906,630 A | 5/1999 | Anderhub et al. |
| 5,928,136 A | 7/1999 | Barry |
| 5,954,731 A | 9/1999 | Yoon |
| 5,954,733 A | 9/1999 | Yoon |
| 5,957,937 A | 9/1999 | Yoon |
| 5,984,932 A | 11/1999 | Yoon |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,017,358 A | 1/2000 | Yoon et al. |
| 6,027,522 A | 2/2000 | Palmer |
| 6,077,287 A | 6/2000 | Taylor et al. |
| 6,080,180 A | 6/2000 | Yoon |
| 6,086,601 A | 7/2000 | Yoon |
| 6,126,665 A | 10/2000 | Yoon |
| 6,139,563 A | 10/2000 | Cosgrove, III et al. |
| 6,143,005 A | 11/2000 | Yoon et al. |
| 6,171,316 B1 | 1/2001 | Kovac et al. |
| 6,206,893 B1 | 3/2001 | Klein et al. |
| 6,214,028 B1 | 4/2001 | Yoon et al. |
| 6,223,100 B1 | 4/2001 | Green |
| 6,224,614 B1 | 5/2001 | Yoon |
| 6,261,307 B1 | 7/2001 | Yoon et al. |
| 6,319,262 B1 | 11/2001 | Bates et al. |
| 6,358,259 B1 | 3/2002 | Swain et al. |
| 6,494,888 B1 | 12/2002 | Laufer et al. |
| 6,506,196 B1 | 1/2003 | Laufer |
| 6,517,539 B1 | 2/2003 | Smith et al. |
| 6,569,105 B1 | 5/2003 | Kortenbach et al. |
| 6,582,450 B2 | 6/2003 | Ouchi |
| 6,638,287 B2 | 10/2003 | Danitz et al. |
| 6,663,639 B1 | 12/2003 | Laufer et al. |
| 6,663,641 B1 | 12/2003 | Kovac et al. |
| 6,666,854 B1 | 12/2003 | Lange |
| 6,676,676 B2 | 1/2004 | Danitz et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,773,441 B1 | 8/2004 | Laufer et al. |
| 6,821,285 B2 | 11/2004 | Laufer et al. |
| 6,835,200 B2 | 12/2004 | Laufer et al. |
| 6,889,116 B2 | 5/2005 | Jinno |
| 6,936,061 B2 | 8/2005 | Sasaki |
| 6,972,017 B2 | 12/2005 | Smith et al. |
| 6,981,628 B2 | 1/2006 | Wales |
| 6,997,931 B2 | 2/2006 | Sauer et al. |
| 7,052,489 B2 | 5/2006 | Griego et al. |
| 7,063,715 B2 | 6/2006 | Onuki et al. |
| 7,107,124 B2 | 9/2006 | Green |
| 7,153,314 B2 | 12/2006 | Laufer et al. |
| 7,248,944 B2 | 7/2007 | Green |
| 2004/0087976 A1 * | 5/2004 | DeVries et al. ................ 606/142 |
| 2005/0256533 A1 * | 11/2005 | Roth et al. .................... 606/167 |
| 2006/0025817 A1 * | 2/2006 | Ortiz et al. .................... 606/219 |
| 2006/0036232 A1 * | 2/2006 | Primavera et al. ........... 604/411 |
| 2006/0111209 A1 * | 5/2006 | Hinman et al. ............... 474/206 |
| 2006/0253126 A1 | 11/2006 | Bjerken et al. |
| 2006/0282093 A1 | 12/2006 | Shelton, IV et al. |

* cited by examiner

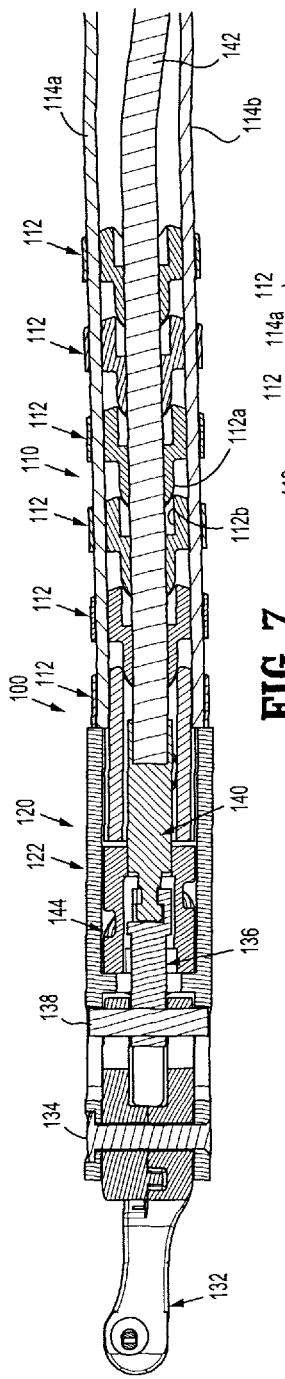
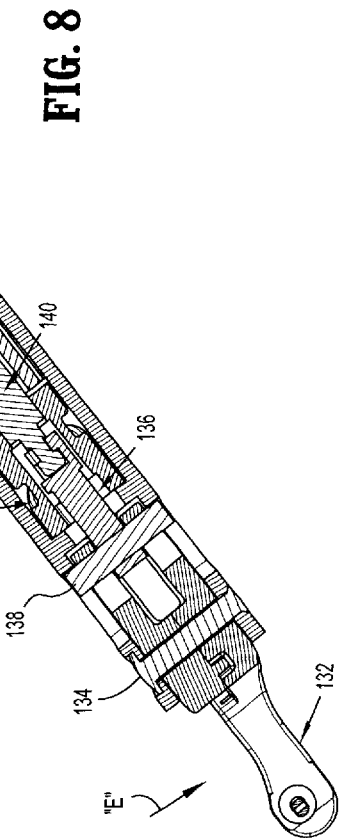
FIG. 7
FIG. 8

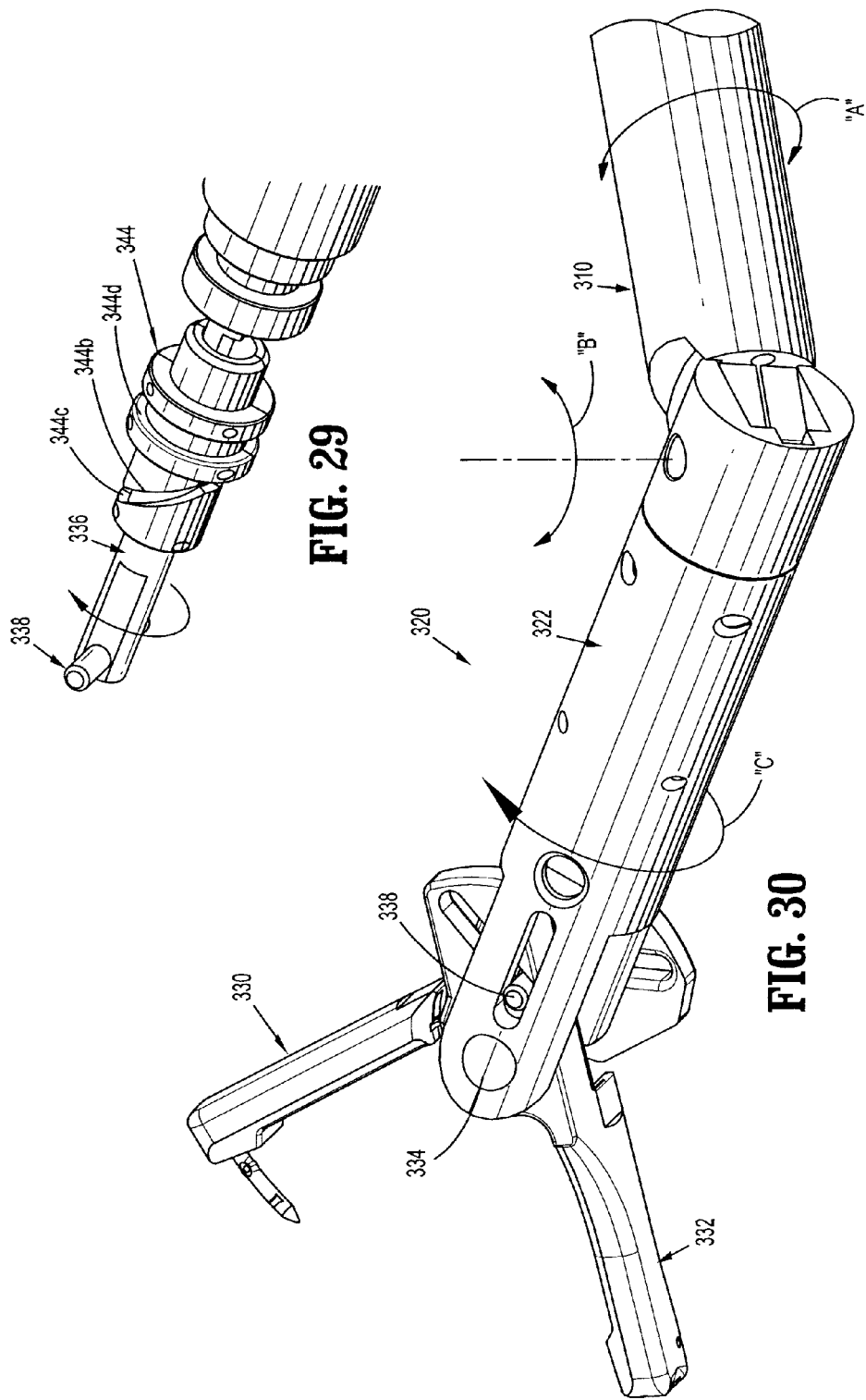

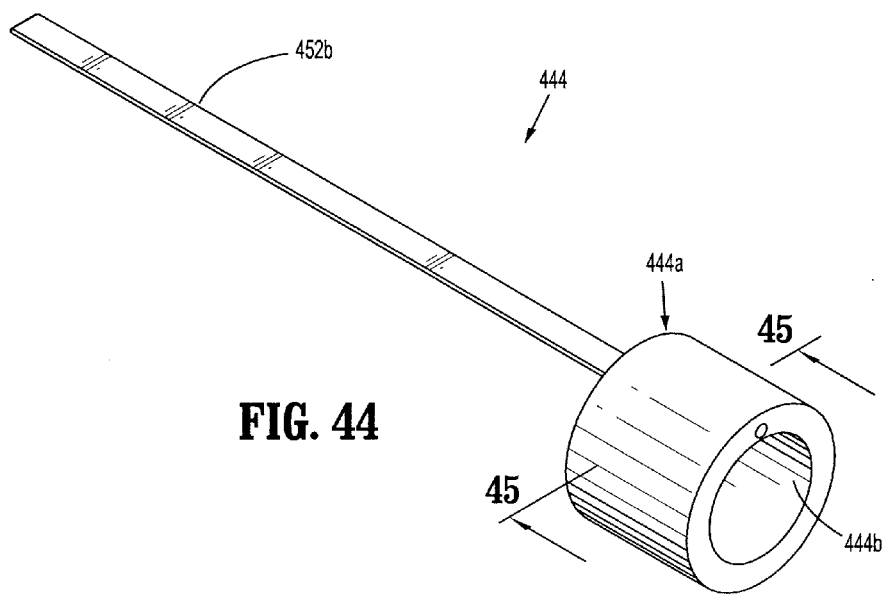
FIG. 44
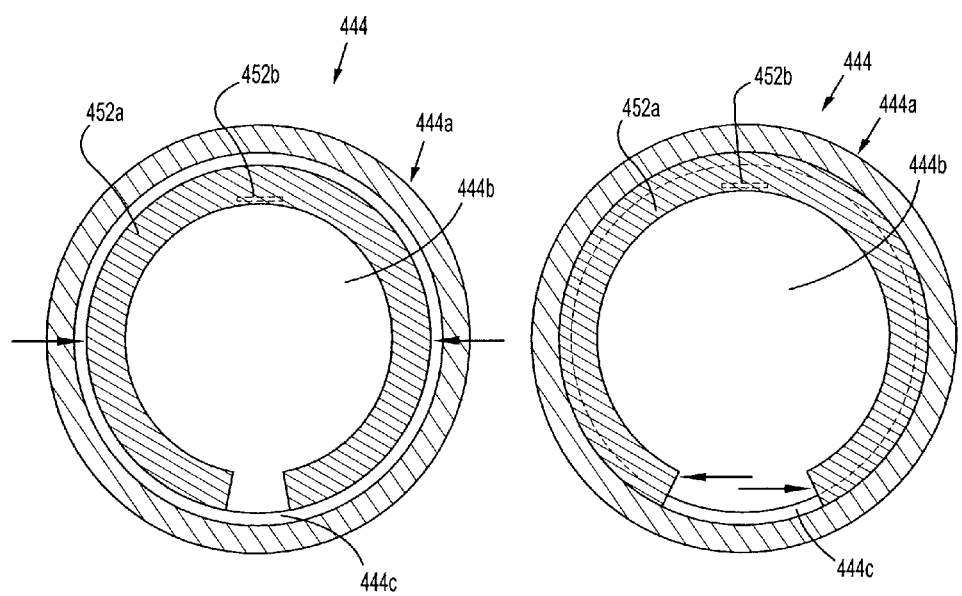
FIG. 45   FIG. 46

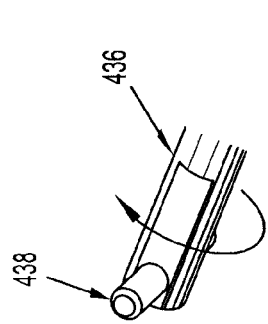
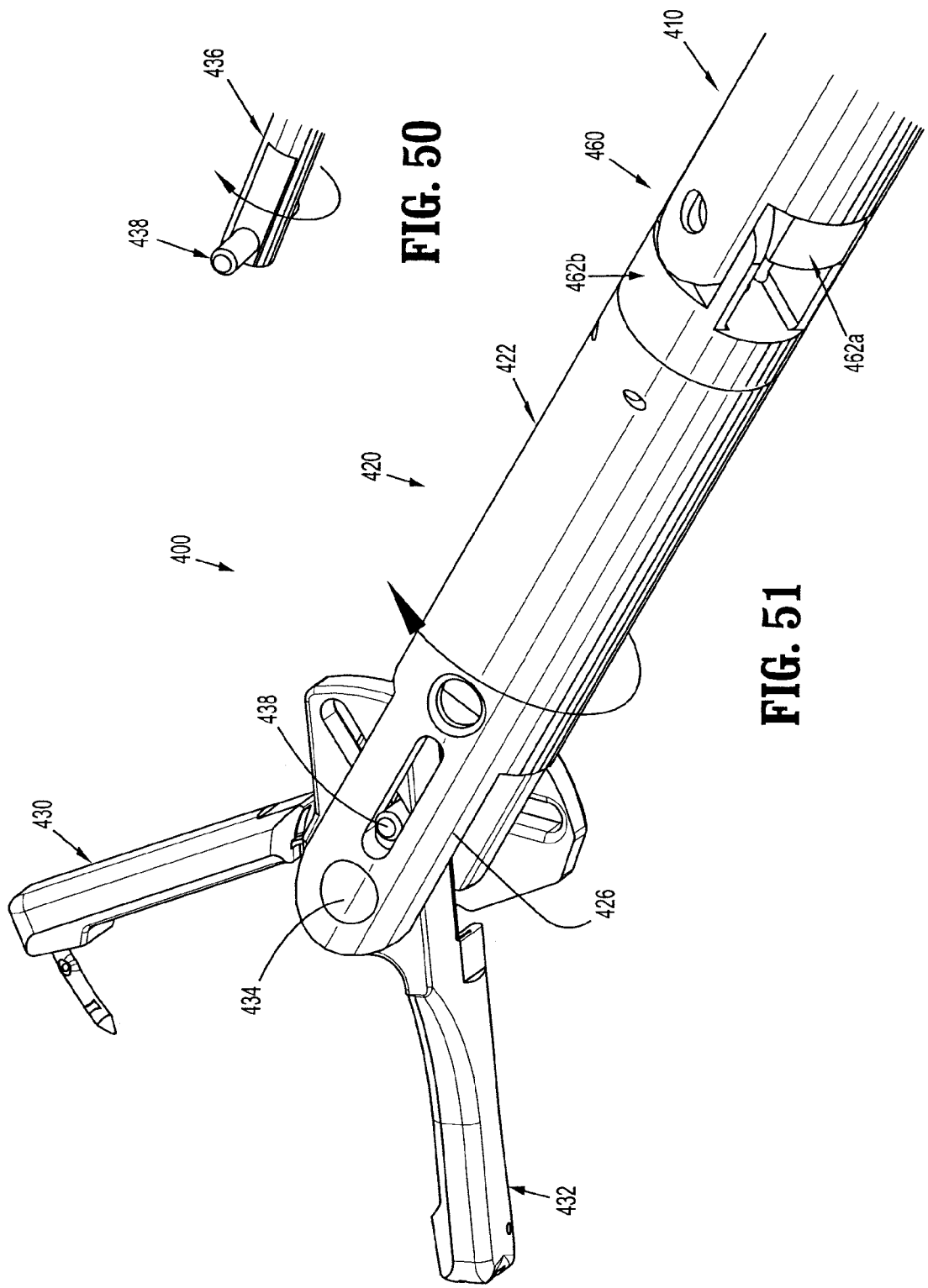

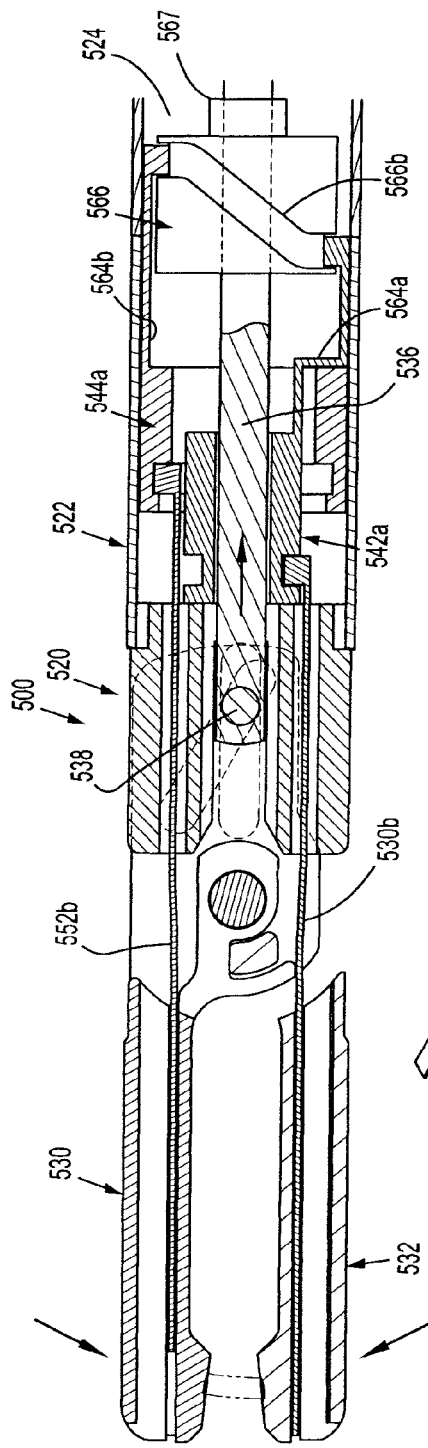
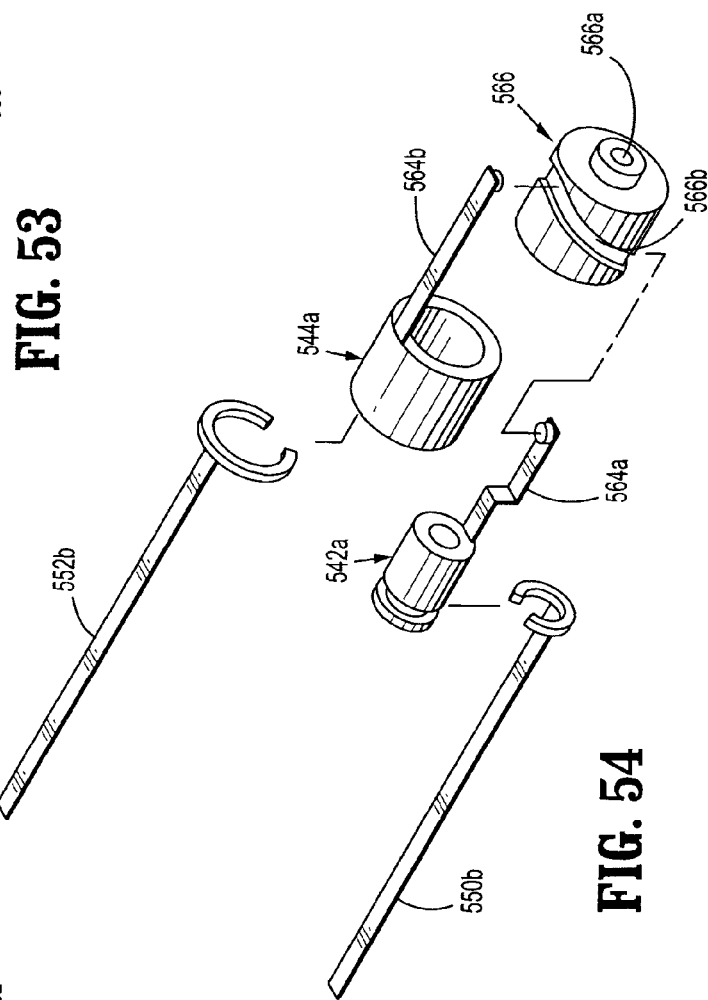
FIG. 53
FIG. 54

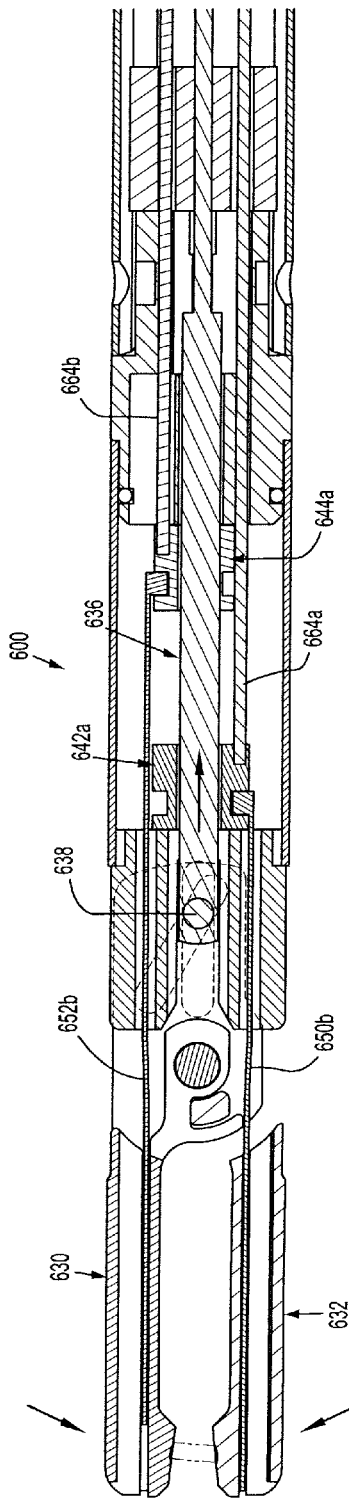
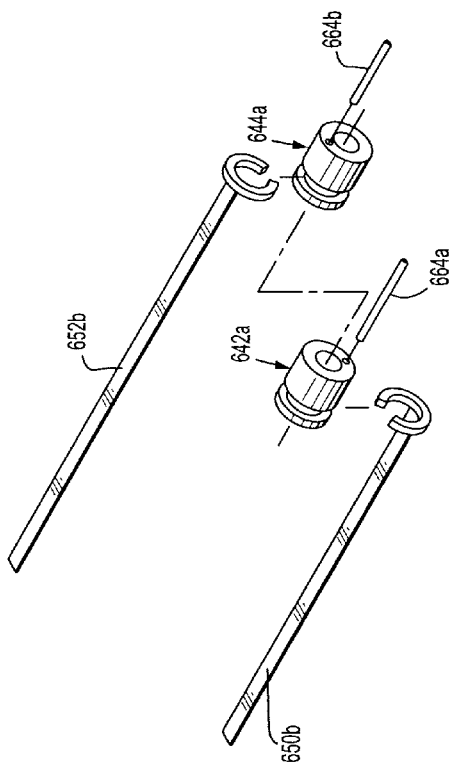
FIG. 57
FIG. 58

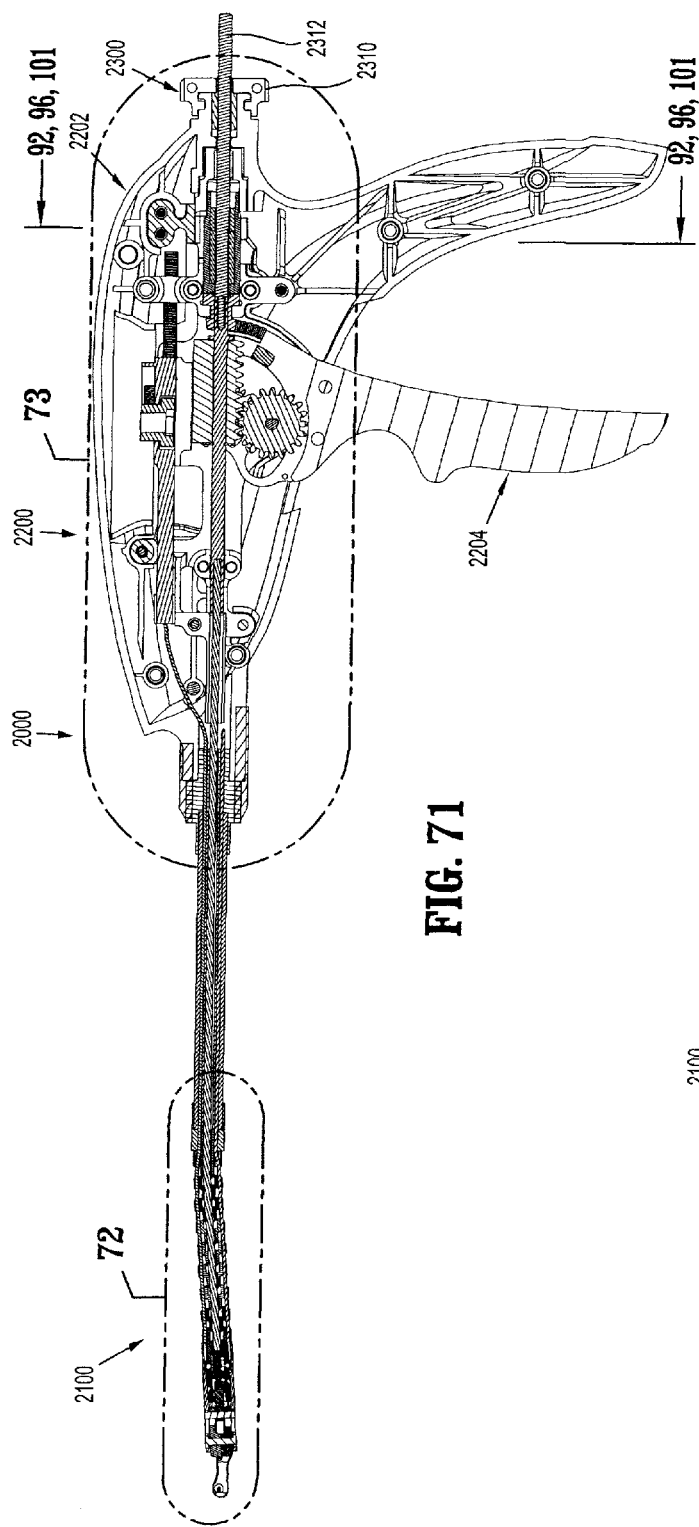
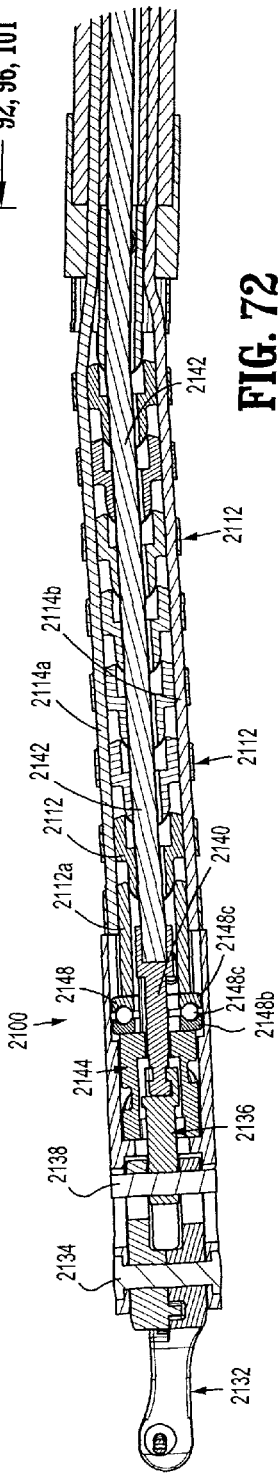

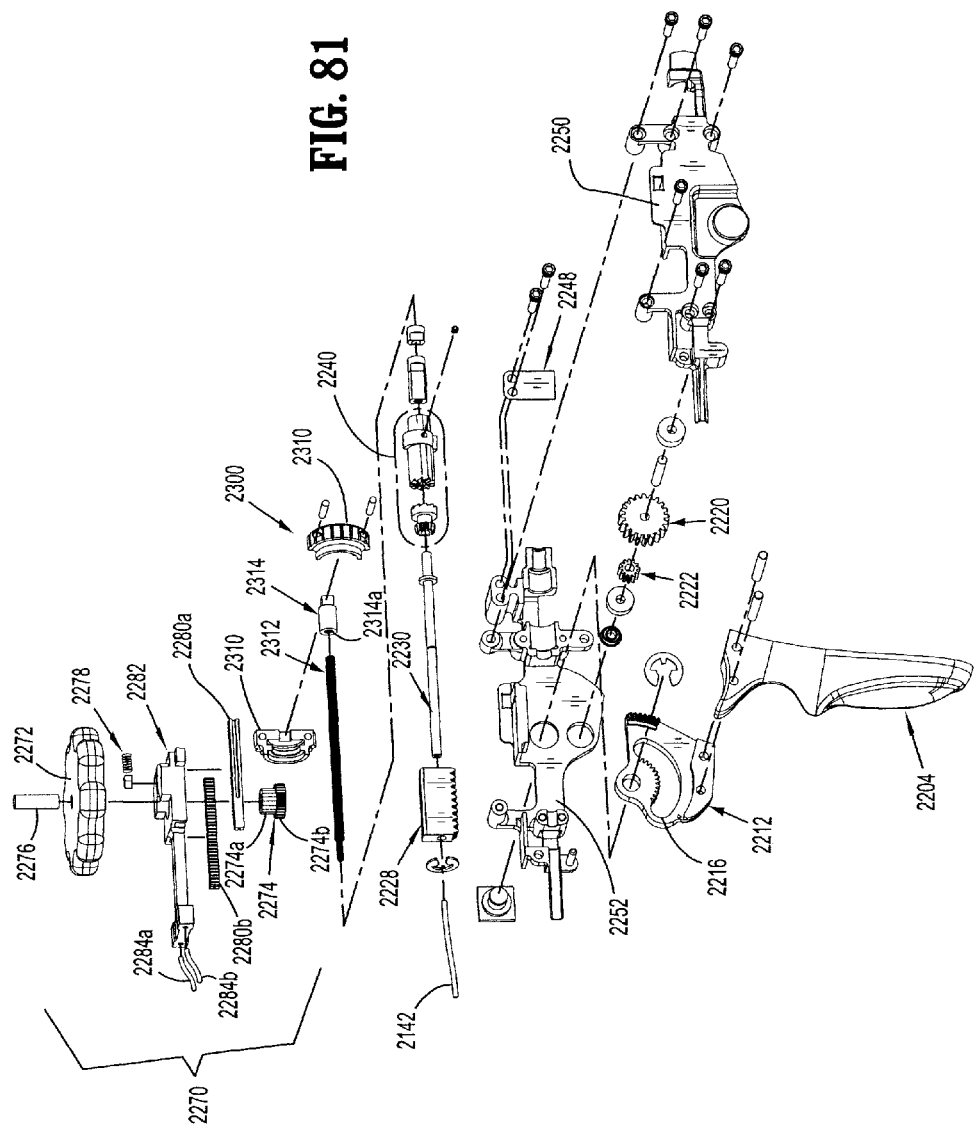

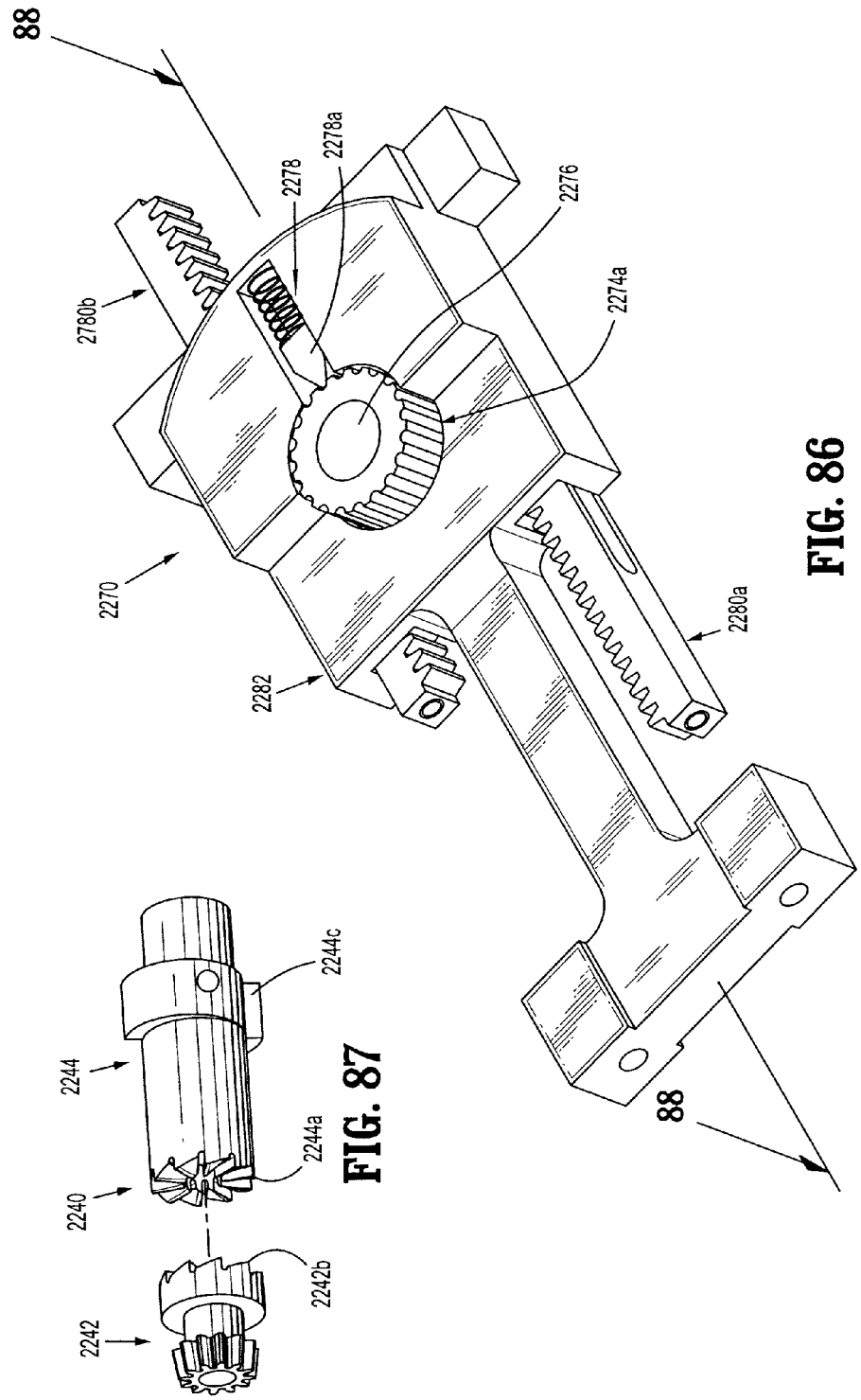

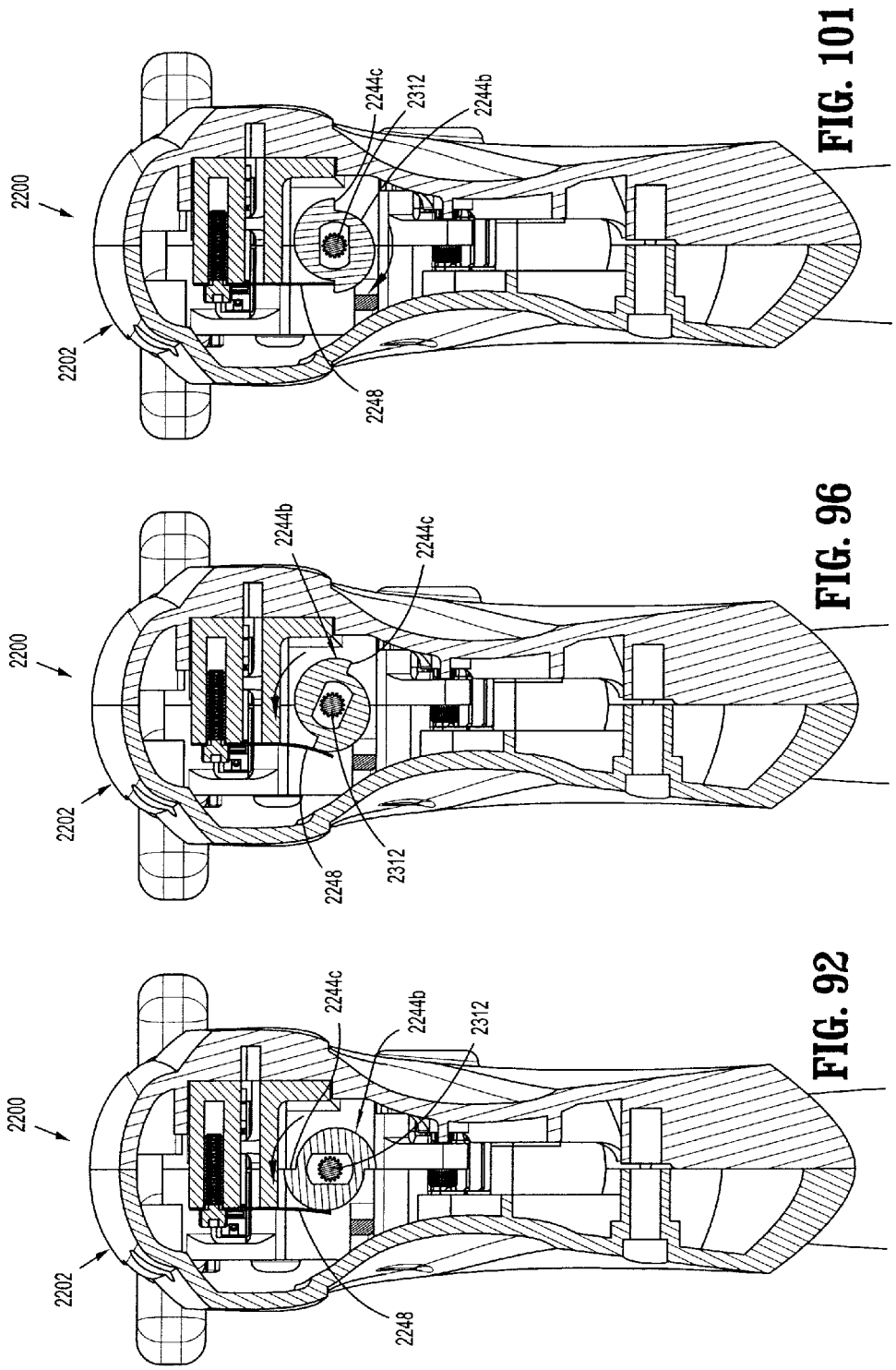

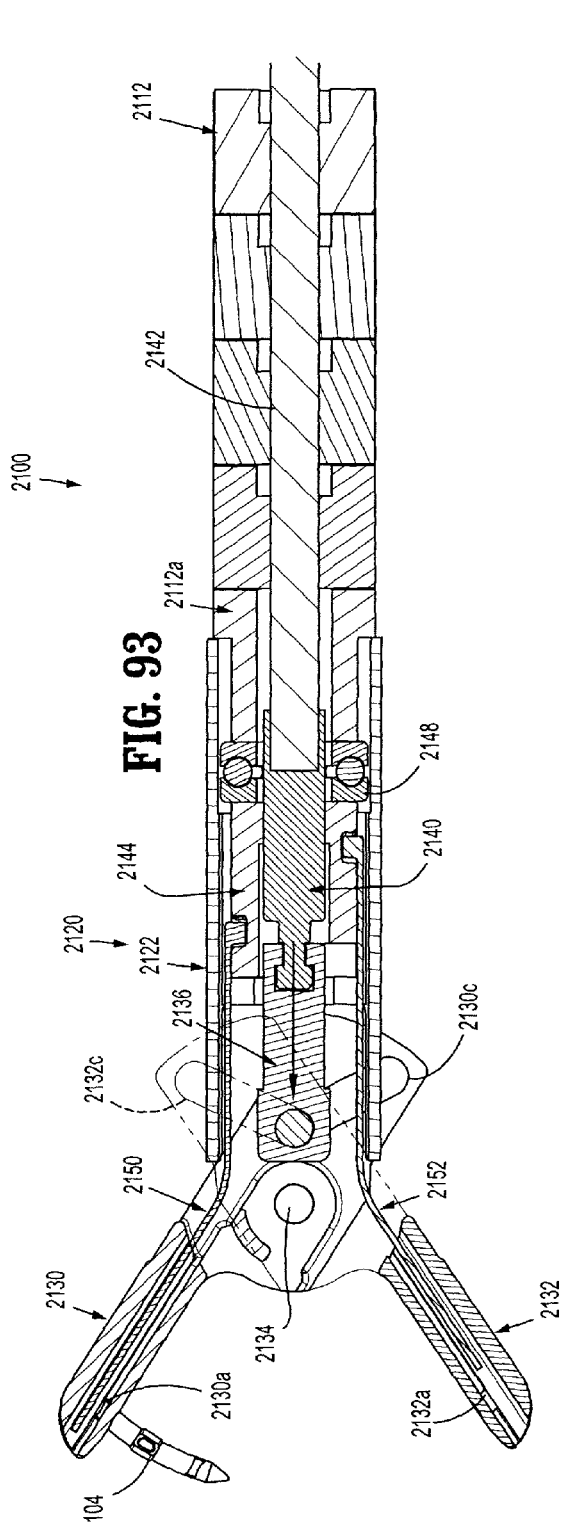
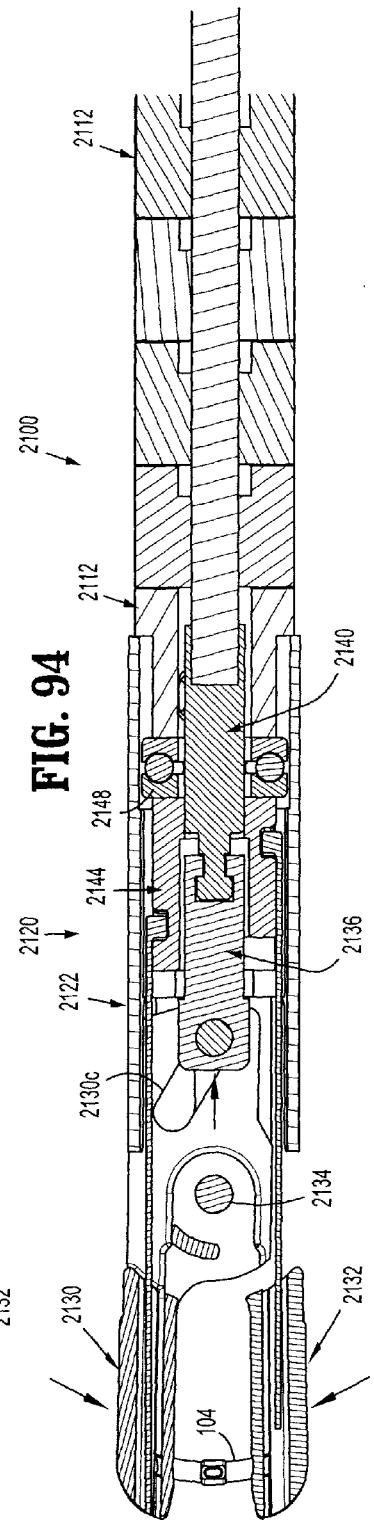

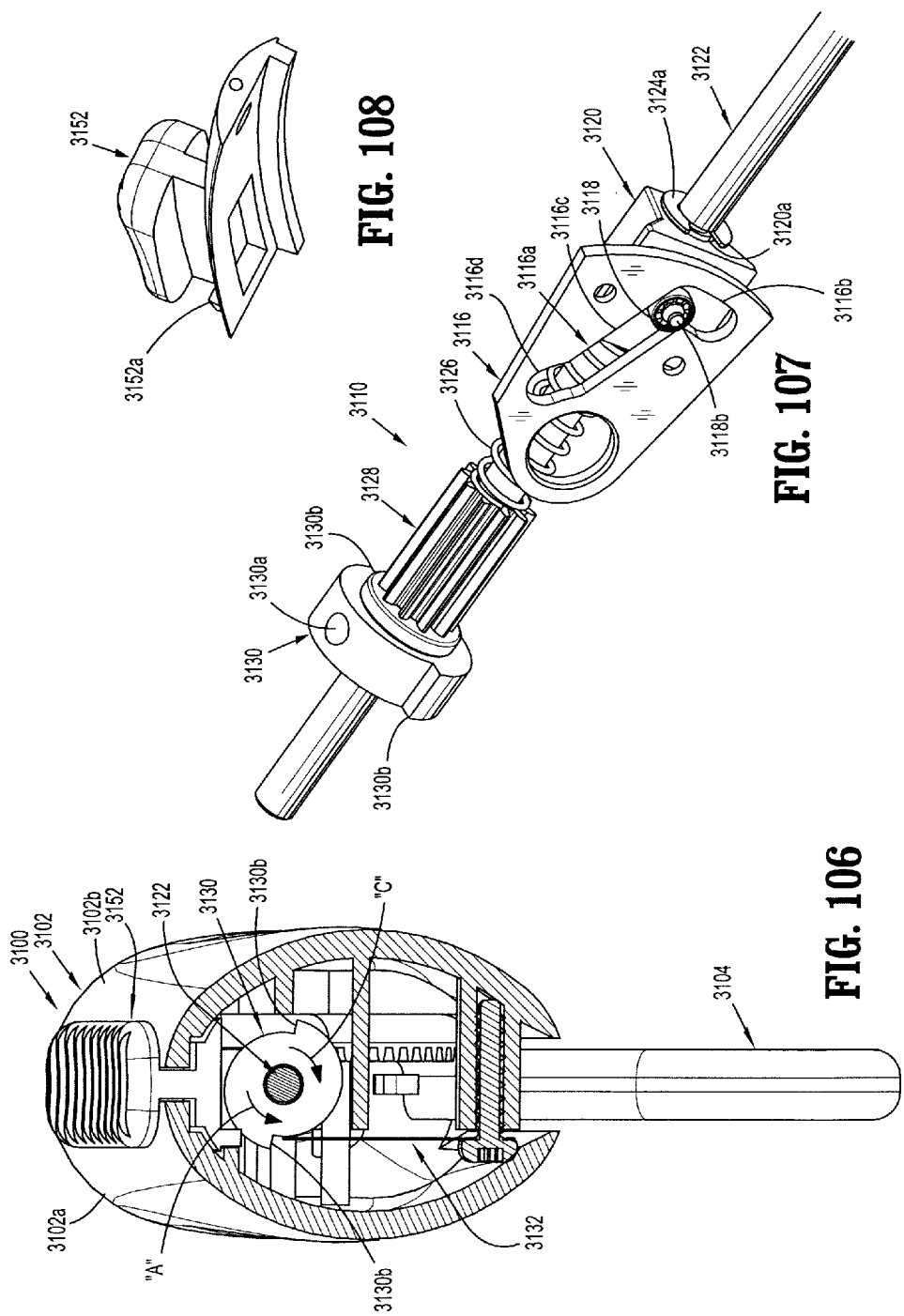

FLEXIBLE ENDOSCOPIC STITCHING DEVICES

CROSS-REFERENCE TO RELATED APPLICATIONS

This application is a National Stage Application of PCT/US2007/021449 filed Oct. 5, 2007 under 35 USC §371 (a), which claims benefit of and priority to U.S. Provisional Patent Application Ser. No. 60/849,561 filed Oct. 5, 2006; U.S. Provisional Patent Application Ser. No. 60/849,562 filed Oct. 5, 2006; U.S. Provisional Patent Application Ser. No. 60/849,508 filed Oct. 5, 2006; U.S. Provisional Patent Application Ser. No. 60/923,804 filed Apr. 16, 2007; U.S. Provisional Patent Application Ser. No. 60/923,980 filed Apr. 17, 2007 and U.S. Provisional Patent Application Ser. No. 60/958,474 filed Jul. 6, 2007 the disclosures of each of the above-identified applications are hereby incorporated by reference in their entirety.

BACKGROUND

1. Technical Field

The present disclosure relates to devices, systems and methods for endoscopic suturing or stitching and, more particularly, to end effectors, systems and methods for endoscopic suturing and/or stitching through an access tube or the like.

2. Background

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

One of the truly great advances in recent years to reduce the invasiveness of surgical procedures is endoscopic surgery. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions.

In many surgical procedures, including those involved in endoscopic surgery, it is often necessary to suture bodily organs or tissue. The latter is especially challenging during endoscopic surgery because of the small openings through which the suturing of bodily organs or tissues must be accomplished.

In the past, suturing of bodily organs or tissue through endoscopic surgery was achieved through the use of a sharp metal suture needle which had attached at one of its ends a length of suture material. The surgeon would cause the suture needle to penetrate and pass through bodily tissue, pulling the suture material through the bodily tissue. Once the suture material was pulled through the bodily tissue, the surgeon proceeded to tie a knot in the suture material. The knotting of the suture material allowed the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed.

However, during endoscopic surgery, knotting of the suture material is time consuming and burdensome due to the difficult maneuvers and manipulation which are required through the small endoscopic openings.

Many attempts have been made to provide devices to overcome the disadvantages of conventional suturing. Such prior art devices have essentially been staples, clips, clamps or other fasteners. However, none of these above listed devices overcome the disadvantages associated with suturing bodily tissue during endoscopic surgery.

Accordingly, there is a need for improvements in suturing devices which overcome the shortcomings and drawbacks of prior art apparatus.

SUMMARY

The present disclosure relates to end effectors, systems and methods for endoscopic suturing and/or stitching through an access tube or the like.

According to an aspect of the present disclosure, an endoscopic stitching device is provided, including an articulatable neck assembly configured and adapted for articulation in at least one direction transverse to a longitudinal axis thereof; a tool assembly operatively supported on a distal end of the neck assembly; and a suture needle operatively associated with the tool assembly. The tool assembly includes a pair of juxtaposed jaws pivotally associated with one another. Each jaw defines a needle receiving recess formed in a tissue contacting surface thereof.

The tool assembly of the endoscopic stitching device may further include an axially translatable needle engaging blade slidably supported in each jaw. Each blade includes an advanced position wherein a distal end of the blade engages the suture needle when the suture needle is in the respective jaw to thereby secure the suture needle therewith. Each blade includes a retracted position wherein a distal end of the blade is out of engagement with the suture needle. The pair of blades may be operatively joined to one another so as to translate in opposite directions relative to one another.

The endoscopic stitching device includes an actuation cable translatably extending through the neck assembly and operatively connected to the pair of jaws. The actuation cable includes a first position wherein the jaws are spaced apart from one another and a second position wherein the pair of jaws are in close spaced relation to one another. The actuation cable may be disposed along a central axis of the neck assembly.

The endoscopic stitching device may further include at least one articulation cable slidably extending through the neck assembly and having a distal end fixedly connected to the tool assembly. The articulation cable may be disposed along an axis spaced a distance from the central axis of the neck assembly. The endoscopic stitching device may include a pair of articulation cables slidably extending through the neck assembly along opposed sides of the actuation cable.

The endoscopic stitching device further includes a camming hub keyed to a distal end of the actuation cable so as to enable axial movement of the actuation cable relative to the camming hub. The camming hub rotates upon a rotation of the actuation cable. The camming hub is operatively connected to a proximal end of each blade in such a manner that rotation of the camming hub results in axial translation of each of the pair of blades.

The suture needle may include a length of barbed suture extending therefrom.

According to another aspect of the present disclosure, an endoscopic stitching device is provided including an end effector configured and adapted to perform at least a pair of functions; and a single actuation cable operatively connected to the end effector. The actuation cable is capable of effecting operation of at least the pair of functions. The actuation cable is capable of effecting a first operation of the pair of functions upon an axial translation thereof; and a second operation of the pair of functions upon a rotation thereof.

The end effector may include a tool assembly operatively supported on a distal end of an articulatable neck assembly. The neck assembly may be configured and adapted for articulation in at least one direction transverse to a longitudinal axis thereof.

The endoscopic stitching device may further include a suture needle operatively associated with the tool assembly. The tool assembly may include a pair of juxtaposed jaws pivotally associated with one another. Each jaw may define a needle receiving recess formed in a tissue contacting surface thereof.

The endoscopic stitching device may further include an axially translatable needle engaging blade slidably supported in each jaw. Each blade may include an advanced position wherein a distal end of the blade engages the suture needle when the suture needle is in the respective jaw to thereby secure the suture needle therewith, and wherein each blade may include a retracted position wherein a distal end of the blade is out of engagement with the suture needle. The pair of blades may be operatively joined to one another so as to translate in opposite directions relative to one another upon a rotation of the actuation cable. In use, axial, reciprocal translation of the actuation cable may result in opening and closing of the pair of jaws.

The actuation cable may translatably extend through the neck assembly. The actuation cable may include a first position wherein the jaws are spaced apart from one another and a second position wherein the pair of jaws are in close spaced relation to one another.

The endoscopic stitching device may further include at least one articulation cable slidably extending through the neck assembly and having a distal end fixedly connected to the tool assembly. The articulation cable may be disposed along an axis spaced a distance from a central axis of the neck assembly.

The endoscopic stitching device may further include a camming hub keyed to the actuation cable so as to enable an axial translation of the actuation cable relative to the camming hub. In use, the camming hub may rotate upon a rotation of the actuation cable. The camming hub may be operatively connected to a proximal end of each blade in such a manner that rotation of the camming hub results in axial translation of each of the pair of blades.

The suture needle may include a length of barbed suture extending therefrom.

According to a further aspect of the present disclosure, an endoscopic stitching device is provided which includes an articulatable neck assembly configured and adapted for articulation in at least one direction transverse to a longitudinal axis thereof; and a tool assembly operatively supported on a distal end of the neck assembly. The tool assembly also includes a pair of juxtaposed jaws pivotally associated with one another, each jaw defining a needle receiving recess formed in a tissue contacting surface thereof; a rotatably supported camming hub, the camming hub defining a central lumen therethrough and a helical groove formed in an outer surface thereof; a pair of axially translatable needle engaging blades slidably supported, one each, in a respective jaw, each blade having an advanced position wherein a distal end of the blade engages a suture needle when the suture needle is in the respective jaw to thereby secure the suture needle to the jaw, and a retracted position wherein the distal end of the blade is out of engagement with the suture needle to thereby permit the suture needle to be removed from the jaw, wherein a proximal end of each blade is configured for slidable engagement in the helical groove of the camming hub. The endoscopic stitching device further includes a suture needle operatively associated with the tool assembly.

In use, rotation of the camming hub may result in reciprocal axial translation of the pair of blades in opposite directions to one another.

The camming hub may define a first clutch formed in a proximal surface thereof. The endoscopic stitching device may further include a second clutch selectively engageable with the first clutch of the camming hub. In use, rotation of the second clutch, when engaged with the first clutch, may result in rotation of the camming hub.

The second clutch may be axially translatable relative to the camming hub between an engaged position and a disengaged position. In use, it is contemplated that rotation of the second clutch when in the disengaged position will impart no rotation to the camming hub. The second clutch may be rotatably supported on a distal end of shaft. The shaft supporting the second clutch may be hollow.

The endoscopic stitching device may further include an actuation cable translatably and rotatably extending through the hollow shaft. A distal end of the actuation cable may be operatively connected to the pair of jaws. The actuation cable may include a first position wherein the jaws are spaced apart from one another and a second position wherein the pair of jaws are in close spaced relation to one another.

The endoscopic stitching device may further include a pair of articulation cables slidably extending through the neck assembly and having a distal end fixedly connected to the tool assembly.

The suture needle may include a barbed suture.

The endoscopic stitching device may further include a jaw support member defining a lumen therethrough and a clevis at a distal end thereof. The pair of jaws may be pivotably supported in the clevis and the camming hub may be rotatably supported in the lumen of the jaw support member. The jaw support member may define a pair of opposed axially extending grooves formed in a surface thereof, wherein the grooves may be configured to slidably receive a respective blade therein.

According to yet another aspect of the present disclosure, an endoscopic stitching device is provided and includes a tool assembly having a pair of juxtaposed jaws pivotally associated with one another, each jaw defining a needle receiving recess formed in a tissue contacting surface thereof; a selectively rotatably camming hub defining a central lumen therethrough and a helical groove formed in an outer surface thereof; a pair of axially translatable needle engaging blades slidably supported, one each, in a respective jaw, each blade having an advanced position wherein a distal end of the blade engages a suture needle when the suture needle is in the respective jaw to thereby secure the suture needle to the jaw, and a retracted position wherein the distal end of the blade is out of engagement with the suture needle to thereby permit the suture needle to be removed from the jaw, wherein a proximal end of each blade is configured for slidable engagement in the helical groove of the camming hub; and a suture needle operatively associated with the tool assembly.

The endoscopic stitching device may further include a neck assembly configured to support the tool assembly on a distal end thereof. The neck assembly may be articulatable in at least one direction transverse to a longitudinal axis thereof.

The camming hub may define a first clutch formed in a proximal surface thereof. The endoscopic stitching device may further include a second clutch selectively engageable with the first clutch of the camming hub, wherein rotation of the second clutch, when engaged with the first clutch, results in rotation of the camming hub. In use, rotation of the camming hub may result in reciprocal axial translation of the pair of blades in opposite directions to one another.

The second clutch may be axially translatable relative to the camming hub between an engaged position and a disengaged position. In use, rotation of the second clutch when in the disengaged position will impart no rotation to the camming hub. The second clutch may be rotatably supported on a distal end of shaft. The shaft supporting the second clutch may be hollow.

The endoscopic stitching device may further include an actuation cable translatably and rotatably extending through the hollow shaft, wherein a distal end of the actuation cable is operatively connected to the pair of jaws. The actuation cable may include a first position wherein the jaws are spaced apart from one another and a second position wherein the pair of jaws are in close spaced relation to one another.

The endoscopic stitching device may further include a pair of articulation cables fixedly connected to the too assembly, wherein retraction of one of the pair of articulation cables may result in articulation of the tool assembly in a first direction, and retraction of the other of the pair of articulation cables may result in articulation of the tool assembly in a second direction.

The suture needle may include a barbed suture.

The endoscopic stitching device may further include a jaw support member defining a lumen therethrough and a clevis at a distal end thereof, wherein the pair of jaws are pivotally supported in the clevis and the camming hub is rotatable supported in the lumen of the jaw support member. The jaw support member may define a pair of opposed axially extending grooves formed in a surface thereof, wherein the grooves are configured to slidably receive a respective blade therein.

According to yet another embodiment of the present disclosure, an endoscopic stitching device is provided which includes an articulatable neck assembly configured and adapted for articulation in at least one direction transverse to a longitudinal axis thereof; and a tool assembly operatively supported on a distal end of the neck assembly. The tool assembly includes a pair of juxtaposed jaws pivotally associated with one another, each jaw defining a needle receiving recess formed in a tissue contacting surface thereof; a rotatably supported camming hub, the camming hub defining a central lumen therethrough and a groove formed in an inner surface thereof; and a center rod slidably and rotatably disposed within the lumen of the camming hub. The center rod is operatively engaged with the groove formed in the inner surface of the camming hub and being operatively engaged with the pair of jaws. The endoscopic stitching device further includes a suture needle operatively associated with the tool assembly. The inner groove of the camming hub is configured such that, in at least one position, axial translation of the center rod relative to the camming hub results in rotation of the camming hub and at least one of opening and closing of the pair of jaws; and the inner groove of the camming hub is configured such that, in at least one other position, rotation of the canter rod results in rotation of the tool assembly.

The groove formed in the inner surface of the camming hub may include a pair of diametrically opposed axially oriented grooves, and a pair of helical grooves interconnecting the axially oriented grooves.

The tool assembly may further include a pair of axially translatable needle engaging blades slidably supported, one each, in a respective jaw. Each blade may have an advanced position wherein a distal end of the blade engages a suture needle when the suture needle is in the respective jaw to thereby secure the suture needle to the jaw, and a retracted position wherein the distal end of the blade is out of engagement with the suture needle to thereby permit the suture needle to be removed from the jaw.

The camming hub may define a helical groove formed in an outer surface thereof, and a proximal end of each blade may be configured for slidable engagement in the helical groove of the camming hub. In use, rotation of the camming hub may result in reciprocal axial translation of the pair of blades in opposite directions to one another.

The tool assembly may include a support member defining a lumen therein. The camming hub may be rotatably supported in the lumen of the support member, and the camming hub may be fixed against movement within the lumen of the support member. The camming hub may define an annular groove formed in the outer surface thereof, wherein the outer annular groove of the camming hub may slidably receive a projection of the support member therein.

The endoscopic stitching device further includes an actuation cable translatably and rotatably extending through the neck assembly, wherein a distal end of the actuation cable is operatively connected to the center rod. The actuation cable may be translatable to axially translate the center rod between a first position wherein the jaws are spaced apart from one another and a second position wherein the pair of jaws are in a close spaced relation to one another.

The endoscopic stitching device may further include a pair of articulation cables slidably extending through the neck assembly and having a distal end fixedly connected to the tool assembly.

The suture needle may include a barbed suture.

The tool assembly may further include a keyed block disposed distally of the camming hub. The keyed block may define a lumen therethrough and a pair of diametrically opposed, axially extending grooved formed in an inner surface of the lumen. The axial grooves may be configured to slidably receive a respective blade therein.

According to still another aspect of the present disclosure, an endoscopic stitching device is provided and includes a tool assembly. The tool assembly includes a pair of juxtaposed jaws pivotally associated with one another; a rotatably supported camming hub, the camming hub defining a central lumen therethrough and a groove formed in an inner surface thereof; and a center rod slidably and rotatably disposed within the lumen of the camming hub, the center rod being operatively engaged with the groove formed in the inner surface of the camming hub and being operatively engaged with the pair of jaws. The inner groove of the camming hub is configured such that, in at least one position, axial translation of the center rod relative to the camming hub results in rotation of the camming hub and at least one of opening and closing of the pair of jaws. The inner groove of the camming hub is configured such that, in at least one other position, rotation of the canter rod results in rotation of the tool assembly.

The endoscopic stitching device may further include an articulatable neck assembly configured and adapted for articulation in at least one direction transverse to a longitudinal axis thereof. The tool assembly may be supported on a distal end of the neck assembly.

Each jaw may define a needle receiving recess formed in a tissue contacting surface thereof.

The groove formed in the inner surface of the camming hub may include a pair of diametrically opposed axially oriented grooves, and a pair of helical grooves interconnecting the axially oriented grooves.

The tool assembly may further include a pair of axially translatable needle engaging blades slidably supported, one each, in a respective jaw. Each blade may have an advanced position wherein a distal end of the blade engages a suture needle when the suture needle is in the respective jaw to thereby secure the suture needle to the jaw, and a retracted position wherein the distal end of the blade is out of engagement with the suture needle to thereby permit the suture needle to be removed from the jaw.

The camming hub may define a helical groove formed in an outer surface thereof, and wherein a proximal end of each blade may be configured for slidable engagement in the helical groove of the camming hub. In use, rotation of the camming hub may result in reciprocal axial translation of the pair of blades in opposite directions to one another.

The tool assembly may include a support member defining a lumen therein, wherein the camming hub is rotatably supported in the lumen of the support member, and wherein the camming hub is fixed against movement within the lumen of the support member. The camming hub may define an annular groove formed in the outer surface thereof The outer annular groove of the camming hub may slidably receive a projection of the support member therein.

The endoscopic stitching device may further include an actuation cable translatably and rotatably extending through the neck assembly, wherein a distal end of the actuation cable may be operatively connected to the center rod. The actuation cable may be translatable to axially translate the center rod between a first position wherein the jaws are spaced apart from one another and a second position wherein the pair of jaws are in a close spaced relation to one another.

The endoscopic stitching device may further include a pair of articulation cables slidably extending through the neck assembly and having a distal end fixedly connected to the tool assembly.

The tool assembly may further include a keyed block disposed distally of the camming hub. The keyed block defines a lumen therethrough and a pair of diametrically opposed, axially extending grooves formed in an inner surface of the lumen. The axial grooves may be configured to slidably receive a respective blade therein.

The endoscopic stitching device may further include a suture needle operatively associated with the tool assembly. The suture needle may include a barbed suture.

According to still another aspect of the present disclosure an endoscopic stitching device is provided including an articulatable neck assembly configured and adapted for articulation in at least one direction transverse to a longitudinal axis thereof; and a tool assembly operatively supported on a distal end of the neck assembly. The tool assembly includes a pair of juxtaposed jaws pivotally associated with one another, each jaw defining a needle receiving recess formed in a tissue contacting surface thereof, a drive assembly including a pair of concentric, individually rotatably and translatably supported barrels, each barrel defining a central lumen therethrough; and a pair of axially translatable needle engaging blades slidably supported, one each, in a respective jaw, each blade having an advanced position wherein a distal end of the blade engages a suture needle when the suture needle is in the respective jaw to thereby secure the suture needle to the jaw, and a retracted position wherein the distal end of the blade is out of engagement with the suture needle to thereby permit the suture needle to be removed from the jaw, wherein a proximal end of each blade is rotatably connected to a respective barrel. The endoscopic stitching device further includes a center rod slidably and rotatably disposed through the lumen of the barrels, a distal end of the center rod being operatively engaged with the pair of jaws; and a suture needle operatively associated with the tool assembly.

An outer barrel of the pair of concentric barrels may define an annular groove formed in a surface of the lumen thereof, and an inner barrel of the pair of concentric barrels may define an annular groove formed in an outer surface thereof. Each blade may include a ring supported at a proximal end thereof, wherein the ring of each blade is rotatably disposed in a respective one of the grooves formed in the outer and inner barrels.

The endoscopic stitching device may further include a pair of pusher rods operatively connected, one each, to a respective inner and outer barrel, wherein axial translation of the pusher rods results in corresponding axial translation of a respective inner and outer barrel and a respective one of the pair of blades. The pusher rods may be flexible.

The tool assembly may include a support member defining a lumen therein. The barrels of the drive assembly may be supported in the lumen of the support member in such a manner so as to permit rotation and axial translation thereof. The endoscopic stitching device may further include an actuation cable translatably and rotatably extending through the lumen defined by the barrels of the drive assembly, wherein a distal end of the actuation cable is operatively connected to the center rod such that rotation of the actuation cable results in rotation of the pair of jaws. The actuation cable may be translatable to axially translate the center rod between a first position wherein the jaws are spaced apart from one another and a second position wherein the pair of jaws are in a close spaced relation to one another.

The endoscopic stitching device may further include a camming hub rotatably supported proximally of the pair of barrels. The camming hub may define a central lumen through which the center rod passes and a helical groove formed in an outer surface thereof.

Each of the pair of barrels may include an arm extending proximally therefrom. Each arm may be operatively engaged in the helical groove of the camming hub. The arms extending from the pair of barrels are diametrically opposed to one another, wherein rotation of the camming hub results in reciprocal axial translation of the pair of barrels relative to one another.

The endoscopic stitching device may further include an actuation cable translatably and rotatably extending through the lumen defined by the barrels of the drive assembly. A distal end of the actuation cable may be operatively connected to the center rod such that rotation of the actuation cable results in rotation of the pair of jaws. The actuation cable may be translatable to axially translate the center rod between a first position wherein the jaws are spaced apart from one another and a second position wherein the pair of jaws are in a close spaced relation to one another.

The endoscopic stitching device may further include a hollow shaft extending proximally from the camming hub. The actuation cable may extend through a lumen of the hollow shaft.

The drive assembly may include a pair of axially spaced apart barrels. Each barrel may be axially translatable. A distal barrel of the pair of barrels may define an annular groove formed in an outer surface thereof, and a proximal barrel of the pair of barrels may define an annular groove formed in an outer surface thereof. Each blade may include a ring supported at a proximal end thereof. The ring of each blade may be rotatably disposed in a respective one of the grooves formed in the distal and proximal barrels.

The endoscopic stitching device may further include a pair of pusher rods operatively connected, one each, to a respective distal and proximal barrel. In use, axial translation of the pusher rods may result in corresponding axial translation of a respective distal and proximal barrel and a respective one of the pair of blades.

According to another aspect of the present disclosure, an endoscopic stitching device is provided which includes a tool assembly. The tool assembly includes a pair of juxtaposed jaws pivotally associated with one another, each jaw defining a needle receiving recess formed in a tissue contacting surface thereof; a drive assembly including a pair of concentric, individually rotatably and translatably supported barrels, each barrel defining a central lumen therethrough; and a pair of axially translatable needle engaging blades slidably supported, one each, in a respective jaw. Each blade has an advanced position wherein a distal end of the blade engages a suture needle when the suture needle is in the respective jaw to thereby secure the suture needle to the jaw, and a retracted position wherein the distal end of the blade is out of engagement with the suture needle to thereby permit the suture needle to be removed from the jaw, wherein a proximal end of each blade is rotatably connected to a respective barrel. The tool assembly further includes a center rod slidably and rotatably disposed through the lumen of the barrels, wherein a distal end of the center rod is operatively engaged with the pair of jaws.

The endoscopic stitching device may further include an articulatable neck assembly to operatively support the tool assembly at a distal end thereof. The neck assembly may be configured and adapted for articulation in at least one direction transverse to a longitudinal axis thereof.

An outer barrel of the pair of concentric barrels may define an annular groove formed in a surface of the lumen thereof, and an inner barrel of the pair of concentric barrels may define an annular groove formed in an outer surface thereof. Each blade may include a ring supported at a proximal end thereof. The ring of each blade may be rotatably disposed in a respective one of the grooves formed in the outer and inner barrels.

The endoscopic stitching device may further include a pair of pusher rods operatively connected, one each, to a respective inner and outer barrel. In use, axial translation of the pusher rods may result in corresponding axial translation of a respective inner and outer barrel and a respective one of the pair of blades. The pusher rods may be flexible.

The tool assembly may include a support member defining a lumen therein, wherein the barrels of the drive assembly are supported in the lumen of the support member in such a manner so as to permit rotation and axial translation thereof.

The endoscopic stitching device may further include an actuation cable translatably and rotatably extending through the lumen defined by the barrels of the drive assembly. A distal end of the actuation cable may be operatively connected to the center rod such that rotation of the actuation cable may result in rotation of the pair of jaws. The actuation cable may be translatable to axially translate the center rod between a first position wherein the jaws are spaced apart from one another and a second position wherein the pair of jaws are in a close spaced relation to one another.

The endoscopic stitching device may further include a camming hub rotatably supported proximally of the pair of barrels. The camming hub may define a central lumen through which the center rod passes and a helical groove formed in an outer surface thereof.

Each of the pair of barrels may include an arm extending proximally therefrom. Each arm may be operatively engaged in the helical groove of the camming hub. The arms extending from the pair of barrels may be diametrically opposed to one another. In use, rotation of the camming hub may result in reciprocal axial translation of the pair of barrels relative to one another.

The endoscopic stitching device may further include an actuation cable translatably and rotatably extending through the lumen defined by the barrels of the drive assembly. A distal end of the actuation cable may be operatively connected to the center rod such that rotation of the actuation cable results in rotation of the pair of jaws.

The actuation cable may be translatable to axially translate the center rod between a first position wherein the jaws are spaced apart from one another and a second position wherein the pair of jaws are in a close spaced relation to one another.

The endoscopic stitching device may further include a hollow shaft extending proximally from the camming hub. The actuation cable may extend through a lumen of the hollow shaft.

The drive assembly may include a pair of axially spaced apart barrels, wherein each barrel may be axially translatable. A distal barrel of the pair of barrels may define an annular groove formed in an outer surface thereof, and a proximal barrel of the pair of barrels may define an annular groove formed in an outer surface thereof.

Each blade may include a ring supported at a proximal end thereof. The ring of each blade may be rotatably disposed in a respective one of the grooves formed in the distal and proximal barrels.

The endoscopic stitching device may further include a pair of pusher rods operatively connected, one each, to a respective distal and proximal barrel. In use, axial translation of the pusher rods may result in corresponding axial translation of a respective distal and proximal barrel and a respective one of the pair of blades.

The endoscopic stitching device may further include a suture needle operatively associated with the pair of jaws. The suture needle may include a barbed suture.

According to still another embodiment of the present disclosure, a handle assembly for operating a surgical instrument is provided. The handle assembly includes a housing; a trigger operatively supported on the housing; and at least one actuation cable operatively connected to the trigger and extending from the housing in such a manner that an actuation of the trigger imparts axial translation and rotation to the actuation cable.

The handle assembly may further include at least one articulation cable operable from the housing. Each articulation cable may include a distal end operatively connectable with an end effector and a proximal end operatively connected to a control element supported on the housing.

The control element may be selected from the group consisting of a slider, a dial, and a lever. In use, movement of the control element may result in movement of the at least one articulation cable. Additionally, in use, movement of the at least one articulation cable in a first direction may cause an articulation of the end effector in a first direction and movement of the at least one articulation cable in a second direction may result in an articulation of the end effector in a second direction.

The control element may include a trigger plate defining a gear segment operatively engaging at least one gear which is operatively connected to an actuation shaft, and wherein movement of the control element may result in at least rotation of the actuation shaft. The control element may be operatively connected to the actuation shaft in such a manner that movement of the control element may result in axial translation of the actuation cable.

According to another aspect of the present disclosure, an endoscopic stitching device is provided including a handle assembly and an end effector operatively connected to the handle assembly. The handle assembly includes a housing; a trigger operatively supported on the housing; and an actuation cable operatively connected to the trigger and extending from the housing in such a manner that an actuation of the trigger imparts axial translation and rotation to the actuation cable. The end effector includes a tool assembly configured and adapted to perform at least a pair of operations. The actuation cable is operatively connected to the tool assembly in such a manner that the actuation cable is capable of effecting a first operation of the pair of operations of the end effector upon the axial translation thereof. Also, the actuation cable is operatively connected to the tool assembly in such a manner that the actuation cable is capable of effecting a second operation of the pair of operations of the end effector upon the rotation thereof.

The endoscopic stitching device may further include an articulatable neck assembly interconnecting the handle assembly and the end effector. The neck assembly may be configured and adapted for articulation in at least one direction transverse to a longitudinal axis thereof.

The endoscopic stitching device may further include a suture needle operatively associated with the tool assembly. The tool assembly may include a pair of juxtaposed jaws pivotally associated with one another. Each jaw may define a needle receiving recess formed in a tissue contacting surface thereof.

The endoscopic stitching device may further include an axially translatable needle engaging blade slidably supported in each jaw. Each blade may include an advanced position wherein a distal end of the blade engages the suture needle when the suture needle is in the respective jaw to thereby secure the suture needle therewith, and wherein each blade includes a retracted position wherein a distal end of the blade is out of engagement with the suture needle.

The pair of blades may be operatively joined to one another so as to translate in opposite directions relative to one another upon a rotation of the actuation cable. In use, axial, reciprocal translation of the actuation cable may result in opening and closing of the pair of jaws.

The actuation cable may translatably extend between the handle assembly and the end effector. In use, when the actuation cable is in a first position the pair of jaws may be spaced apart from one another, and when the actuation cable is in a second position the pair of jaws may be in a close spaced relation to one another.

The endoscopic stitching device may further include at least one articulation cable slidably extending through the neck assembly and having a distal end fixedly connected to the tool assembly.

The articulation cable may be disposed along an axis spaced a distance from a central axis of the neck assembly.

The endoscopic stitching device may further include a camming hub keyed to the actuation cable so as to enable an axial translation of the actuation cable relative to the camming hub, wherein the camming hub rotates upon a rotation of the actuation cable. The camming hub may be operatively connected to a proximal end of each blade in such a manner that rotation of the camming hub results in axial translation of each of the pair of blades.

A proximal end of each articulation cable may be operatively connected to a control element supported on the housing.

The control element of the handle assembly may be selected from the group consisting of a slider, a dial, and a lever. In use, movement of the control element of the handle assembly may result in movement of the at least one articulation cable. Movement of the at least one articulation cable in a first direction may cause an articulation of the end effector in a first direction and movement of the at least one articulation cable in a second direction may result in articulation of the end effector in a second direction.

The control element of the handle assembly may include a trigger plate defining a gear segment operatively engaging at least one gear which is operatively connected to an actuation shaft, wherein movement of the control element may result in at least rotation of the actuation shaft, and wherein the actuation cable may be connected to the actuation shaft.

The control element of the handle assembly may be operatively connected to the actuation shaft in such a manner that movement of the control element may result in axial translation of the actuation cable.

According to a further aspect of the present disclosure, a handle assembly for operating a surgical instrument is provided and includes a housing; a trigger operatively supported on the housing; and at least one actuation cable operatively associated with the trigger and extending from the housing in such a manner that an actuation of the trigger imparts both an axial translation of the actuation cable and a rotation to the actuation cable. Each of the axial translation and rotation of the actuation cable performs a separate function.

The handle assembly may further include a pair of articulation cables operable from the housing. Each articulation cable may include a proximal end operatively connected to a control element supported on the housing. In use, a first movement of the control element may result in axial translation of the pair of articulation cables in opposed directions to one another, and wherein a second movement of the control element may result in a reversed axial translation of the pair of articulation cables.

The control element may be rotatably supported on the housing. Accordingly, the first movement of the control element may be a rotation of the control element in a first direction; and the second movement of the control element may be a rotation of the control element in a second direction.

The trigger may include a trigger plate defining a first gear segment operatively engagable with a spur gear which is operatively supported on an actuation shaft. In use, actuation of the trigger may result in at least a rotation of the spur gear and the actuation shaft. The actuation shaft may be coupled to the actuation cable.

The trigger may be operatively connected to the actuation shaft in such a manner that actuation of the trigger results in axial translation of the actuation shaft and actuation cable.

The trigger plate may define a second gear segment operatively engagable with a gear rack operatively supported on the actuation shaft, wherein actuation of the trigger may result in an axial translation of the gear rack and the actuation shaft.

The handle assembly may further include a follower block rotatably supported on the actuation shaft and coupled to the gear rack via a biasing element. Accordingly, in use, actuation of the trigger may result in axial translation of the gear rack, biasing of the biasing member and subsequent axial translation of the follower block and actuation shaft.

The spur gear may form a part of a slip clutch which is slidably supported on the actuation rod. A proximal portion of the slip clutch may be operatively engaged with the spur gear in such a manner so as to enable unidirectional rotation of the proximal portion upon a rotation of spur gear.

The handle assembly may further include a biasing member configured to maintain the proximal portion of the slip clutch in engagement with the spur gear. The handle assembly may further include a pawl and wherein the proximal portion of the slip clutch is configured for engagement with the pawl in such a manner that the pawl limits the direction of rotation of the proximal portion of the slip clutch.

According to another aspect of the present disclosure, an endoscopic stitching device is provided including a handle assembly and an end effector operatively connected to the handle assembly. The handle assembly includes a housing; a trigger operatively supported on the housing; and at least one actuation cable operatively associated with the trigger and extending from the housing in such a manner that an actuation of the trigger imparts both an axial translation of the actuation cable and a rotation to the actuation cable. Each of the axial translation and rotation of the actuation cable performs a separate function. The end effector includes a tool assembly configured and adapted to perform at least a pair of operations. The actuation cable is operatively connected to the tool assembly in such a manner that the actuation cable is capable of effecting a first operation of the pair of operations of the end effector upon the axial translation thereof; and capable of effecting a second operation of the pair of operations of the end effector upon the rotation thereof.

The endoscopic stitching device may further include an articulatable neck assembly interconnecting the handle assembly and the end effector. The neck assembly may be configured and adapted for articulation in at least one direction transverse to a longitudinal axis thereof.

The endoscopic stitching device may further include a suture needle operatively associated with the tool assembly. The tool assembly may include a pair of juxtaposed jaws pivotally associated with one another, and wherein each jaw may define a needle receiving recess formed in a tissue contacting surface thereof.

The endoscopic stitching device may further comprise an axially translatable needle engaging blade slidably supported in each jaw. Each blade may include an advanced position wherein a distal end of the blade engages the suture needle when the suture needle is in the respective jaw to thereby secure the suture needle therewith, and wherein each blade may include a retracted position wherein a distal end of the blade is out of engagement with the suture needle.

The pair of blades may be operatively joined to one another so as to translate in opposite directions relative to one another upon a rotation of the actuation cable. In use, axial, reciprocal translation of the actuation cable may result in opening and closing of the pair of jaws.

The actuation cable may translatably extend between the handle assembly and the end effector. In use, when the actuation cable is in a first position the pair of jaws may be spaced apart from one another, and when the actuation cable is in a second position the pair of jaws may be in a close spaced relation to one another.

The endoscopic stitching device may further include at least one articulation cable slidably extending through the neck assembly and having a distal end fixedly connected to the tool assembly. The articulation cable may be disposed along an axis spaced a distance from a central axis of the neck assembly.

The endoscopic stitching device may further include a camming hub keyed to the actuation cable so as to enable an axial translation of the actuation cable relative to the camming hub. The camming hub may rotate upon a rotation of the actuation cable. The camming hub may be operatively connected to a proximal end of each blade in such a manner that rotation of the camming hub results in axial translation of each of the pair of blades.

The endoscopic stitching device may further include a pair of articulation cables operable from the housing. Each articulation cable may include a proximal end operatively connected to a control element supported on the housing. Accordingly, in use, a first movement of the control element may result in axial translation of the pair of articulation cables in opposed directions to one another, and a second movement of the control element may result in a reversed axial translation of the pair of articulation cables.

The control element may be rotatably supported on the housing. Accordingly, in use, the first movement of the control element may be a rotation of the control element in a first direction; and the second movement of the control element may be a rotation of the control element in a second direction.

The trigger may include a trigger plate defining a first gear segment operatively engagable with a spur gear which is operatively supported on an actuation shaft. Accordingly, in use, actuation of the trigger may result in at least a rotation of the spur gear and the actuation shaft, wherein the actuation shaft is coupled to the actuation cable.

The trigger may be operatively connected to the actuation shaft in such a manner that actuation of the trigger results in axial translation of the actuation shaft and actuation cable.

The trigger plate may define a second gear segment operatively engagable with a gear rack operatively supported on the actuation shaft. Accordingly, in use, actuation of the trigger may result in an axial translation of the gear rack and the actuation shaft.

The handle assembly may further include a follower block rotatably supported on the actuation shaft and coupled to the gear rack via a biasing element. Accordingly, in use, actuation of the trigger may result in axial translation of the gear rack, biasing of the biasing member and subsequent axial translation of the follower block and actuation shaft.

The spur gear may form a part of a slip clutch which is slidably supported on the actuation rod. A proximal portion of the slip clutch may be operatively engaged with the spur gear in such a manner so as to enable uni-directional rotation of the proximal portion upon a rotation of spur gear.

The handle assembly may further include a biasing member configured to maintain the proximal portion of the slip clutch in engagement with the spur gear. The handle assembly may further include a pawl. The proximal portion of the slip clutch may be configured for engagement with the pawl in such a manner that the pawl limits the direction of rotation of the proximal portion of the slip clutch.

The handle assembly may further include a spline shaft, co-axially aligned with the actuation shaft, and extending from a proximal end of the housing, and a knob supported on a proximal end of the spline shaft extending from the proximal end of the housing in such a manner so as to transmit rotation to the spline shaft and to the actuation shaft and actuation cable.

The end effector may further include a thrust bearing disposed proximally of the camming hub in operatively engaged therewith.

According to yet another aspect of the present disclosure, a handle assembly for operating a surgical instrument is provided. The handle assembly includes a housing; a trigger operatively supported on the housing; and an articulation assembly supported on the housing for effectuating an articulation of an end effector operatively connected to the housing. The articulation assembly is operable to effect articulation of the end effector in a first pair of opposed directions and a second pair of opposed direction which is substantially transverse to the first pair of opposed directions.

According to a further aspect of the present disclosure, an endoscopic stitching device is provided and includes a handle assembly and an end effector operatively connected to the handle assembly. The handle assembly includes a housing; a trigger operatively supported on the housing; and an articulation assembly supported on the housing for effectuating an articulation of an end effector operatively connected to the housing. The end effector includes a tool assembly configured and adapted to perform at least a pair of operations. The articulation assembly is connected to the end effector in such a manner that operation of the articulation assembly imparts an articulation to the end effector in a first pair of opposed directions and a second pair of opposed direction which is substantially transverse to the first pair of opposed directions.

The handle assembly may further include at least one actuation cable operatively associated with the trigger and extending from the housing in such a manner that an actuation of the trigger imparts both an axial translation of the actuation cable and a rotation to the actuation cable. Each of the axial translation and rotation of the actuation cable may perform a separate function.

The articulation assembly may include a pair of control elements supported on the housing, wherein each control element may be operatively connected to a proximal end of pair of articulation cables.

In use, a first movement of a first of the control elements may result in axial translation of the respective pair of articulation cables in opposed directions to one another. A second movement of the first of the control elements may result in a reversed axial translation of the respective pair of articulation cables. The first of the control elements may be rotatably supported on the housing. The first movement of the first of the control elements may be a rotation of the first of the control elements in a first direction. The second movement of the first of the control elements may be a rotation of the first of the control elements in a second direction.

In use, a first movement of a second of the control elements may result in axial translation of the respective pair of articulation cables in opposed directions to one another. A second movement of the second of the control elements may result in a reversed axial translation of the respective pair of articulation cables. The second of the control elements may be rotatably supported on the housing. The first movement of the second of the control elements may be a rotation of the second of the control elements in a first direction. The second movement of the second of the control elements may be a rotation of the second of the control elements in a second direction.

The first and second control elements may be co-axially supported on the housing.

The articulation assembly may further include a gear connected to and controlled by each control element, and a pair of gear racks engaged with the gear of each control element such that rotation of the control element results in opposed axial translation of the respective pair of gear racks. Each pair of articulation cables may be operatively connected, one each, to a respective pair of gear racks.

The handle assembly may further include at least one actuation cable operatively associated with the trigger and extending from the housing in such a manner that an actuation of the trigger imparts both an axial translation of the actuation cable and a rotation to the actuation cable, wherein each of the axial translation and rotation of the actuation cable performs a separate function.

The actuation cable may be operatively connected to the tool assembly in such a manner that the actuation cable is capable of effecting a first operation of the pair of operations of the end effector upon the axial translation thereof; and wherein the actuation cable is operatively connected to the tool assembly in such a manner that the actuation cable is capable of effecting a second operation of the pair of operations of the end effector upon the rotation thereof.

According to still another aspect of the present disclosure, an endoscopic stitching device is provided including a handle assembly including a needle loading assembly; an end effector supported on the handle assembly and configured and adapted to perform at least a pair of functions; and a single actuation cable operatively connected between the handle assembly and the end effector. The actuation cable is capable of effecting operation of at least the pair of functions, wherein the actuation cable is capable of effecting a first operation of the pair of functions upon an axial translation thereof; and a second operation of the pair of functions upon a rotation thereof, and wherein the actuation cable is rotatable upon a manual actuation of the needle loading assembly.

The end effector may include a tool assembly operatively supported on a distal end of an articulatable neck assembly. The neck assembly may be configured and adapted for articulation in at least one direction transverse to a longitudinal axis thereof.

The endoscopic stitching device may further include a suture needle operatively associated with the tool assembly. The tool assembly may include a pair of juxtaposed jaws pivotally associated with one another, and wherein each jaw defines a needle receiving recess formed in a tissue contacting surface thereof.

According to a further aspect of the present disclosure, an endoscopic stitching device is provided and includes a handle assembly supporting a manually operated suture needle loading assembly; a tool assembly operatively supported on and connected to the handle assembly; a suture needle operatively associated with the tool assembly, wherein the tool assembly includes a pair of juxtaposed jaws pivotally associated with one another, and wherein each jaw defines a needle receiving recess formed in a tissue contacting surface thereof; and an actuation cable extending between the handle assembly and the tool assembly, wherein axial displacement of the actuation shaft results in opening and closing of the jaws and rotation of the actuation cable results in selective retention of the suture needle in the jaws. A proximal end of the actuation cable is connected to the suture needle loading assembly such that actuation of the suture needle loading assembly imparts rotation to the actuation cable to selectively engage the suture needle in one of the jaws.

The endoscopic stitching device may further include an articulatable neck assembly interconnecting the handle assembly and the tool assembly. The neck assembly may be configured and adapted for articulation in at least one direction transverse to a longitudinal axis thereof.

The endoscopic stitching device may further include an axially translatable needle engaging blade slidably supported in each jaw and operatively associated with the actuation cable. Each blade may include an advanced position wherein a distal end of the blade engages the suture needle when the suture needle is in the respective jaw to thereby secure the suture needle therewith. Each blade may include a retracted position wherein a distal end of the blade is out of engagement with the suture needle.

The pair of blades may be operatively joined to one another so as to translate in opposite directions relative to one another upon a rotation of the actuation cable.

The actuation cable may translatably extend through the neck assembly and may be operatively connected to the pair of jaws. The actuation cable may include a first position wherein the jaws are spaced apart from one another and a second position wherein the pair of jaws are in close spaced relation to one another.

The suture needle loading assembly may include a knob keyed to the actuation shaft such that rotation of the knob results in rotation of the actuation cable and such that the actuation shaft is free to axially translate with respect to the knob. The suture needle loading assembly may be configured for unidirectional rotation of the knob.

The endoscopic stitching device may further include at least one articulation cable slidably extending through the neck assembly and having a distal end fixedly connected to the tool assembly. The articulation cable may be disposed along an axis spaced a distance from a central axis of the neck assembly.

The endoscopic stitching device may further include a camming hub interconnecting the pair of blades and keyed to a distal end of the actuation shaft so as to enable axial movement of the actuation cable relative to the camming hub, wherein the camming hub rotates upon a rotation of the actuation cable.

The camming hub may be operatively connected to a proximal end of each blade in such a manner that rotation of the camming hub results in axial translation of each of the pair of blades.

According to yet another embodiment of the present disclosure, an endoscopic stitching device is provided and includes a handle assembly defining a passage therethrough, wherein the passage is configured to selectively accommodate a surgical instrument therein; an end effector configured and adapted to perform at least a pair of functions, the end effector being operatively connected to the handle assembly; and a single actuation cable operatively connected to the end effector, wherein the actuation cable is capable of effecting operation of at least the pair of functions, wherein the actuation cable is capable of effecting a first operation of the pair of functions upon an axial translation thereof; and a second operation of the pair of functions upon a rotation thereof.

The endoscopic stitching device may further include a channel extending substantially between the passage of the handle assembly and the end effector. The channel may be secured to a neck assembly extending between and interconnecting the handle assembly and the end effector.

DETAILED DESCRIPTION OF THE DRAWINGS

The foregoing objects, features and advantages of the disclosure will become more apparent from a reading of the following description in connection with the accompanying drawings, in which:

FIG. 7 is a longitudinal, cross-sectional view of the end effector of the stitching device of FIGS. 1 and 2, illustrating the distal end in an un-articulated condition;

FIG. 8 is a longitudinal, cross-sectional view of the end effector of the stitching device of FIG. 7, illustrating the distal end in an articulated condition;

FIG. 29 is a perspective view of the end effector of FIGS. 17-28, with the jaws and the jaw supporting member removed therefrom, illustrating a rotation of a center rod thereof;

FIG. 30 is a perspective view of the end effector of FIGS. 17-28, illustrating a rotation thereof;

FIG. 44 is a perspective view of an outer drive assembly of the end effector of FIGS. 39 and 40;

FIG. 45 is a cross-sectional view, as taken though 45-45 of FIG. 44, illustrating a connection of a blade member to an outer barrel of the outer drive assembly of FIG. 44;

FIG. 46 is a cross-sectional view, as taken though 45-45 of FIG. 44, illustrating the blade member and the outer barrel of the outer drive assembly of FIG. 44 connected to one another;

FIG. 50 is a perspective view of a center rod of the end effector of FIGS. 39 and 40, illustrating an axial rotation thereof;

FIG. 51 is a perspective view of the end effector of FIGS. 39 and 40, illustrating an axial rotation thereof based on the axial rotation of the center rod;

FIG. 53 is a longitudinal, cross-sectional view of the end effector of FIG. 52, shown in a second condition;

FIG. 54 is a perspective view, with parts separated, of a drive assembly of the end effector of FIGS. 52 and 53;

FIG. 57 is a longitudinal, cross-sectional view of the end effector of FIG. 56, shown in a second condition;

FIG. 58 is a perspective view, with parts separated, of a drive assembly of the end effector of FIGS. 56 and 57;

FIG. 71 is a longitudinal cross-sectional view of the endoscopic stitching device of FIG. 69;

FIG. 72 is an enlarged view of the indicated area of detail of FIG. 71;

FIG. 81 is an exploded perspective view of the internal components of the handle assembly of the endoscopic stitching device of FIG. 69;

FIG. 86 is a perspective view of an articulation control mechanism of the handle assembly of FIGS. 73-81;

FIG. 87 is a perspective view of a slip-clutch of the handle assembly of FIGS. 73-81;

FIG. 92 is a cross-sectional view of the handle assembly of FIGS. 73-81, as taken through 92-92 of FIG. 71, illustrating a first position of a uni-directional pawl assembly;

FIG. 93 is a longitudinal, cross-sectional view of the end effector of the endoscopic stitching device of FIG. 69, illustrating the jaws thereof in a first, open condition;

FIG. 94 is a longitudinal, cross-sectional view of the end effector of the endoscopic stitching device of FIG. 69, illustrating the jaws thereof in a second, closed condition;

FIG. 96 is a cross-sectional view of the handle assembly of FIGS. 73-81, as taken through 95-95 of FIG. 71, illustrating a second position of the uni-directional pawl assembly;

FIG. 101 is a cross-sectional view of the handle assembly of FIGS. 73-81, as taken through 101-101 of FIG. 71, illustrating a third position of the unidirectional pawl assembly;

FIG. 106 is a cross-sectional view of the handle assembly of FIGS. 102-105, as taken through 106-106 of FIG. 104;

FIG. 107 is a perspective view of drive assembly of the handle assembly of FIGS. 102-106;

FIG. 108 is a perspective view of a slide actuator of the handle assembly of FIGS. 102-106;

FIG. 122 is a cross-sectional view of the handle assembly of FIGS. 111-114, as taken through 122-122 of FIG. 112, illustrating a second position of the uni-directional pawl assembly;

FIG. 125 is a cross-sectional view of the handle assembly of FIGS. 111-114, as taken through 125-125 of FIG. 112, illustrating a third position of the uni-directional pawl assembly;

DETAILED DESCRIPTION OF EMBODIMENTS

Figure 1:
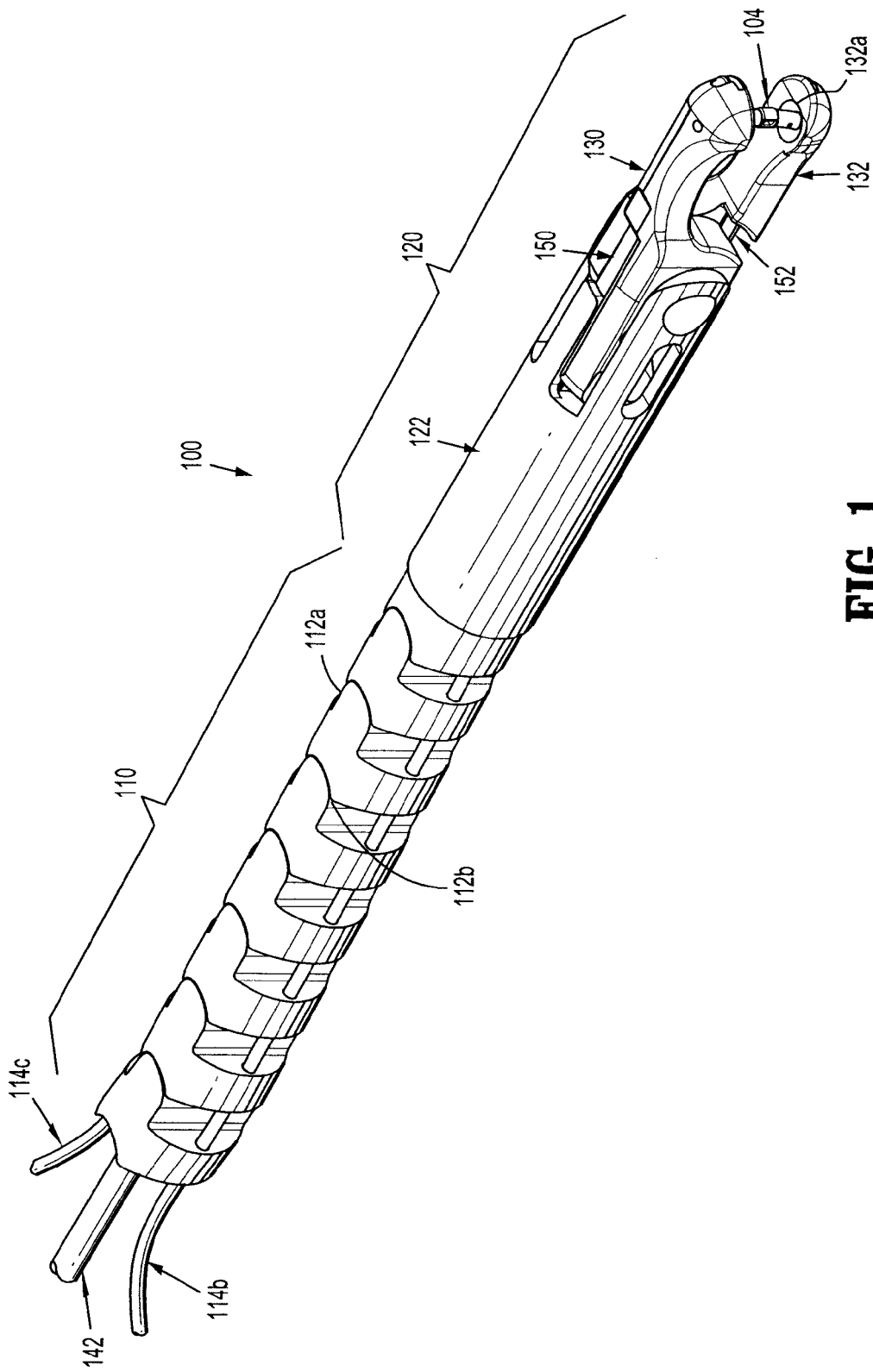
FIG. 1 is a perspective view of an end effector of a stitching device according to an embodiment of the present disclosure.

The present disclosure relates to devices, systems and methods for endoscopic, laparoscopic, endoluminal, and/or transluminal suturing. In one embodiment, for example, such a device comprises a handle, handle assembly or other suitable actuating mechanism (e.g., robot, etc.) connected to a proximal end of a flexible, elongated body portion. A neck assembly operatively supported on a distal end of the flexible, elongated body portion allows an end effector, operatively supported at a distal end of the neck assembly, to articulate in response to actuation of articulation cables. The end effector includes a suture needle and a pair of jaws. In operation, the suture needle is passed back and forth through tissue from one jaw to the other. The device is adapted to be placed in a lumen of a flexible endoscope and then inserted into a natural orifice of a patient and transited endoluminally through the anatomy of the natural lumen to a treatment site within or outside the natural lumen.

In the drawings and in the description which follow, the term "proximal", as is traditional, will refer to the end of the device which is closest to the operator, while the term "distal" will refer to the end of the device which is furthest from the operator.

Figure 2:
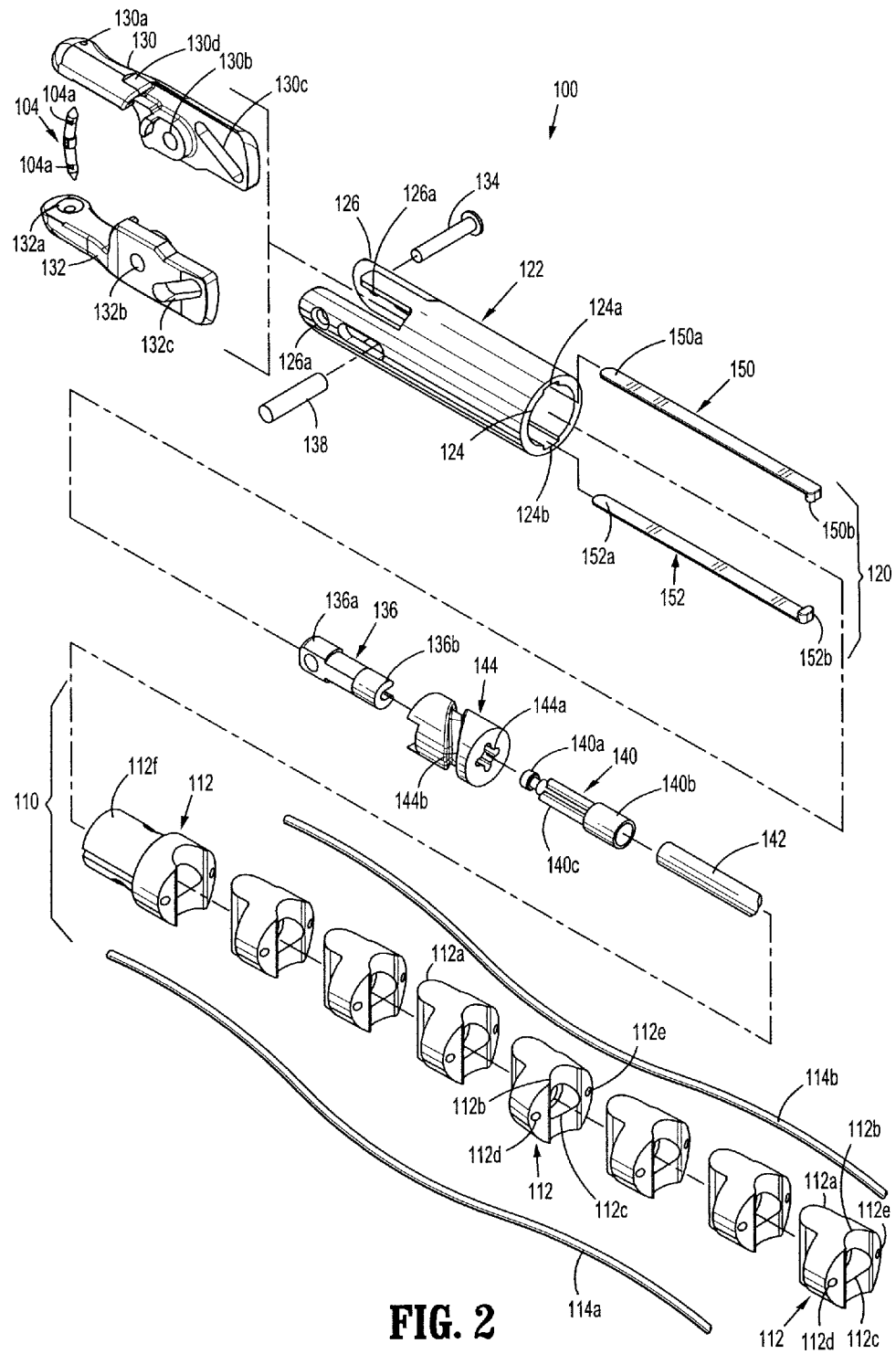
FIG. 2 is an exploded perspective view of the end effector of the stitching device of FIG. 1.
Figure 3:
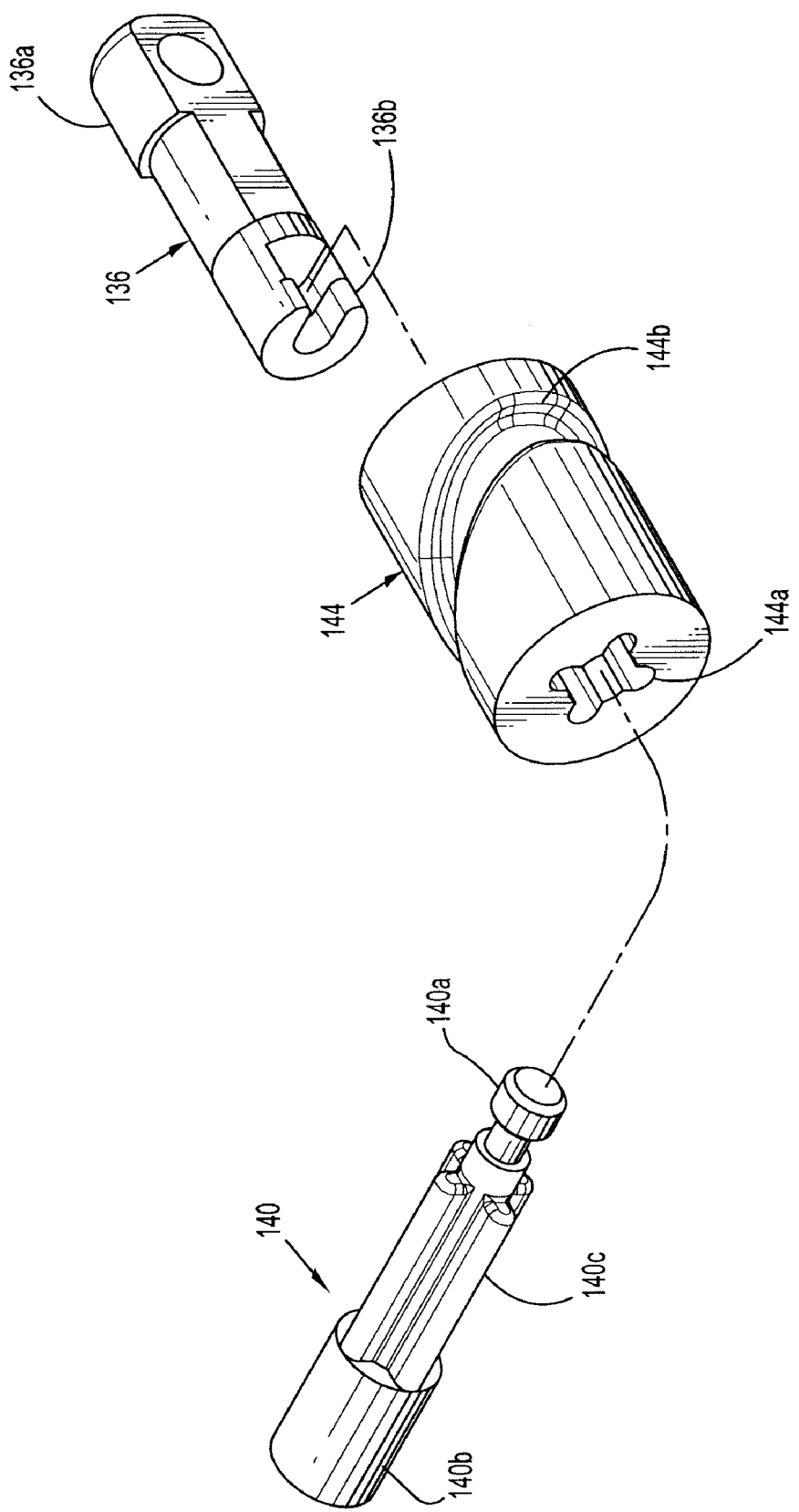
FIG. 3 is an exploded perspective view of a cam mechanism of the end effector of the stitching device of FIGS. 1 and 2.

Referring now in specific detail to the drawings, in which like reference numbers identify similar or identical elements, FIGS. 1-3 illustrate one embodiment of an end effector of a stitching device, shown generally at 100. End effector 100 of the stitching device is adapted to be particularly useful in endoscopic or laparoscopic procedures wherein an endoscopic portion of the stitching device, i.e., end effector 100, is insertable into an operative site, via a cannula assembly or the like (not shown).

As seen in FIGS. 1-3, end effector 100 of the stitching device is supportable on or extends from a handle assembly (not shown) and/or a distal end of an elongate tubular body portion (not shown) extending distally from the handle assembly and defining a longitudinal axis and a lumen therethrough. End effector 100 may be operatively associated with or supported on a distal end of elongate body portion and may be remotely operable by the handle assembly.

End effector 100 includes a neck assembly 110 supported on a distal end of a shaft extending from a handle assembly, and a tool assembly 120 supported on a distal end of neck assembly 110. Neck assembly 110 includes a plurality of joints 112 each including a distal knuckle 112a and a proximal clevis 112b formed therewith. Each knuckle 112a operatively engages a clevis 112b of an adjacent joint 112. Each joint 112 defines a central lumen 112c formed therein and a pair of opposed lumen 112d, 112e formed on either side of central lumen 112c. A pair of articulation cables 114a, 114b slidably extend through respective lumens 112d, 112e of joints 112. Operation of neck assembly 110 to articulate end effector 100 thereabout, will be discussed in greater detail below.

As seen in FIGS. 1-3, tool assembly 120 of end effector 100 includes a jaw support member 122, and a pair of jaws 130, 132 mounted for pivotable movement on jaw support member 122. Jaw support member 122 defines a lumen 124 in a proximal end thereof and a pair of spaced apart arms 126 in a distal end thereof. Lumen 124 is configured and dimensioned to receive a stem 112f extending from a distal-most joint 112 of neck portion 110. Lumen 124 defines a pair of opposed channels 124a, 124b in a surface thereof.

Each jaw 130, 132 includes a needle receiving recess 130a, 132a, respectively, configured to surround and hold at least a portion of a surgical needle 104 disposed therein substantially perpendicular to tissue engaging surfaces thereof. As seen in FIG. 2, needle 104 includes a groove 104a formed near each end thereof. A suture (not shown) may be secured to surgical needle 104 at a location between grooves 104a.

Suture of surgical needle 104 may comprise a one-way or barbed suture, wherein the suture includes an elongated body having a plurality of barbs extending therefrom. The barbs are oriented in such a way that the barbs cause the suture to resist movement in an opposite direction relative to the direction in which the barb faces.

Suitable sutures for use with surgical needle 104 include, and are not limited to, those sutures described and disclosed in U.S. Pat. No. 3,123,077; U.S. Pat. No. 5,931,855; and U.S. Patent Publication No. 2004/0060409, filed on Sep. 30, 2002, the entire content of each of which being incorporated herein by reference.

Jaws 130, 132 are pivotably mounted on support member 122 by means of a jaw pivot pin 134 which extend through holes 126a formed in arms 126 of support member 122 and respective pivot holes 130b, 132b formed in jaws 130, 132. To move jaws 130, 132 between an open position and a closed position there is provided an axially or longitudinally movable center rod 136 having a camming pin 138 mounted at a distal end 136a thereof. Camming pin 138 rides in and engages angled camming slots 130c, 132c formed in respective jaws 130, 132 such that axial or longitudinal movement of center rod 136 causes jaws 130, 132 to be cammed between open and closed positions.

Tool assembly 120 includes a keyed rod 140 having a distal end 140a rotatably connected to a proximal end 136b of center rod 136. Keyed rod 140 includes a proximal end 140b fixedly connected to a distal end of an actuation cable 142, and a body portion 140c, disposed between distal end 140a and proximal end 140b, having a non-circular cross-sectional profile.

Tool assembly 120 further includes a camming hub 144 defining a lumen 144a therethrough configured and adapted to slidably receive body portion 140c of keyed rod 140 therein. Camming hub 144 defines a helical or spiral groove 144b in an outer surface thereof. Camming hub 144 is configured for rotatable disposition within lumen 124 of support member 122.

In operation, rotation of actuation cable 142 imparts rotation to keyed rod 140 which, in turn, imparts rotation to camming hub 144. However, since keyed rod 140 is rotatably connected to center rod 136, no rotation is imparted thereto. Also, axial displacement of actuation cable 142 imparts axial displacement to keyed rod 140 which, in turn, imparts axial displacement to center rod 136. However, since camming hub 144 is axially slidably supported on keyed rod 140, no axial displacement is imparted thereto.

Tool assembly 120 further includes a pair of needle engaging members or blades 150, 152 which are slidably supported within respective channels 124a, 124b of support member 122. Each blade 150, 152 includes a distal end 150a, 152a slidably extending into blade receiving channels 130d, 132d (see FIGS. 4-5) of respective jaws 130, 132. Channels 130d, 132d are dimensioned and configured so as to at least partially intersect needle recesses 130a, 132a. Thus, by advancing blade 150 or 152 within respective channel 130d, 132d, a distal end 150a, 152a of the advancing blade 150 or 152 engages or "locks in" a groove 104a formed in needle 104 disposed within the respective recess 130a, 132a. Each blade 150, 152 includes a proximal end 150b, 152b slidably disposed within groove 144b of camming hub 144. In operation, as camming hub 144 is rotated, proximal ends 150b, 152b of blades 150, 152 ride within groove 144b of camming hub 144 and are moved in an axial direction relative thereto. In particular, upon rotation of camming hub 144, as blade 150 is moved distally, blade 152 is moved proximally and vise-versa.

Figures 4, 5:
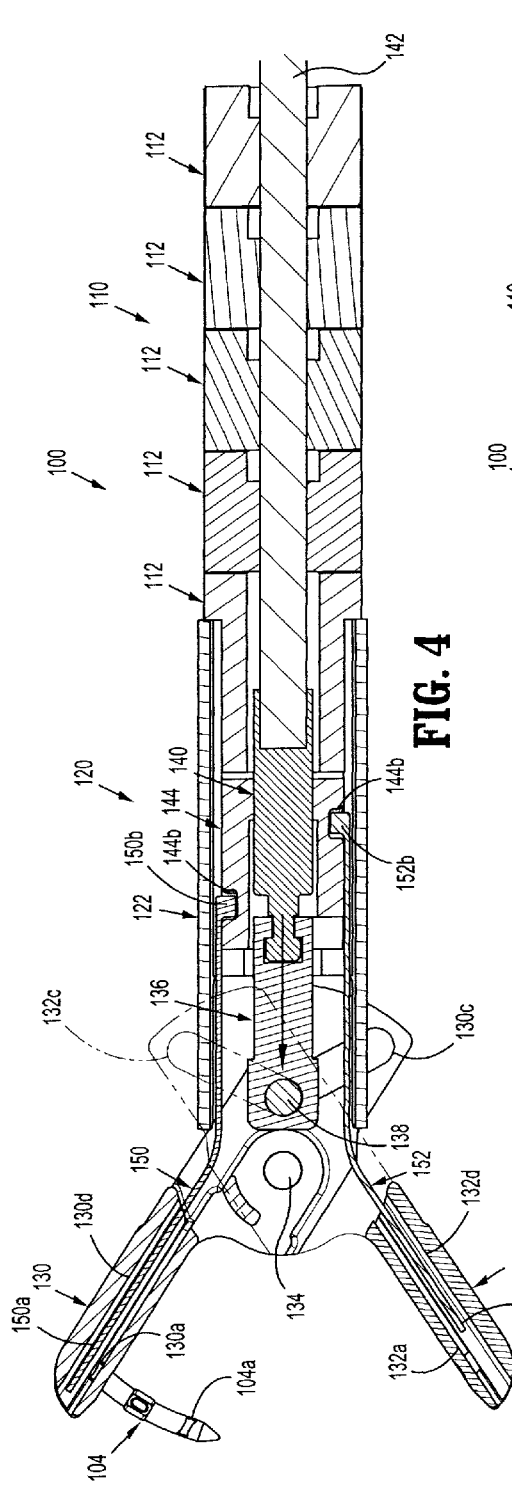
FIG. 4 is a longitudinal, cross-sectional view of the end effector of the stitching device of FIGS. 1 and 2, illustrating the jaws thereof in a first, open condition.
FIG. 5 is a longitudinal, cross-sectional view of the end effector of the stitching device of FIGS. 1 and 2, illustrating the jaws thereof in a second, closed condition.
Figure 6:
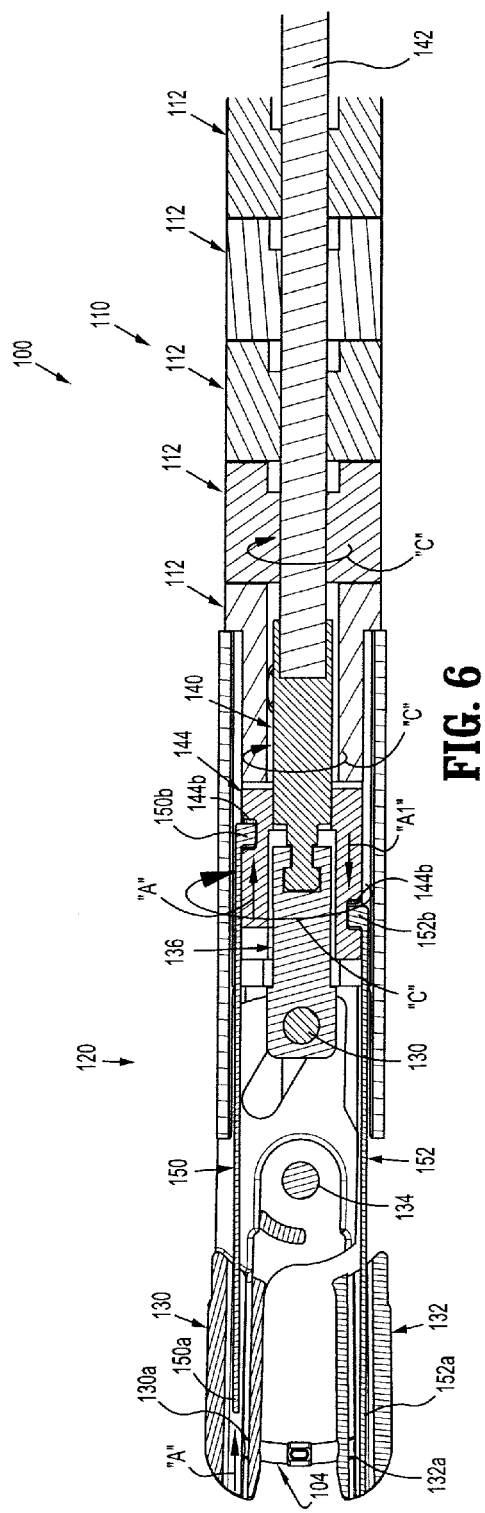
FIG. 6 is a longitudinal, cross-sectional view of the end effector of the stitching device of FIGS. 1 and 2, illustrating the jaws thereof in a third, re-opened condition.
Figure 9:
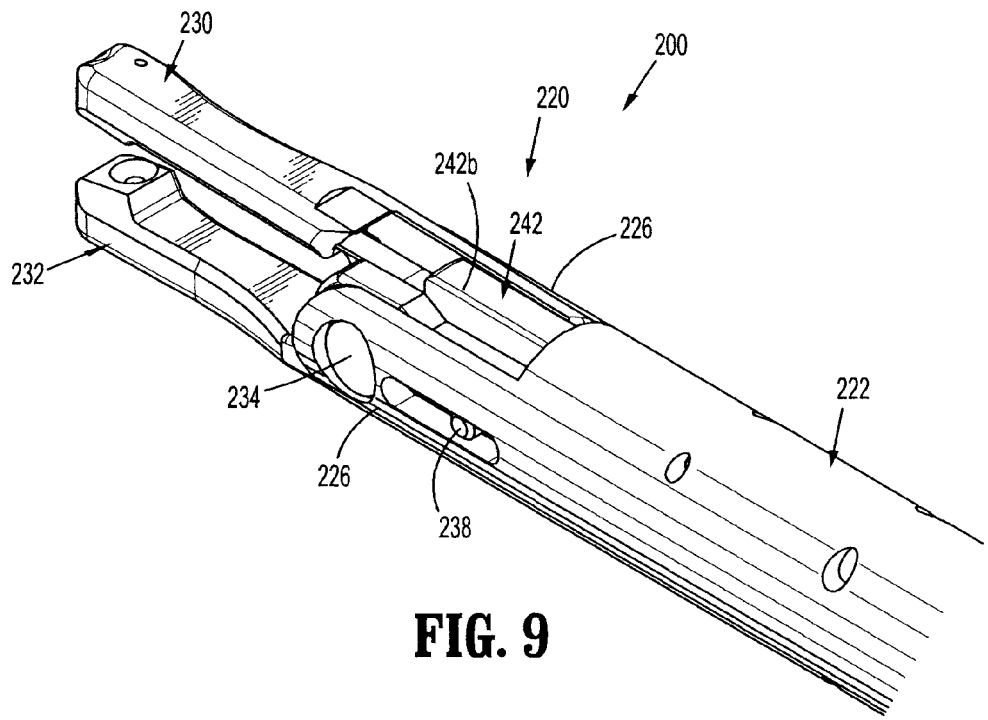
FIG. 9 is a perspective view of an end effector of a stitching device according to another embodiment of the present disclosure.

Turning now to FIGS. 4-6, a method of operating end effector 100 is shown and described. As seen in FIG. 4, needle 104 is held within recess 130a by distal end 150a of blade 150 engaging a groove 104a of needle 104. Additionally, as seen in FIG. 4, jaws 130, 132 are maintained in an open position by having center rod 136 at a distal-most position which, in turn, positions camming pin 138 at a distal-most end of camming slots 130c, 132c.

Turning now to FIG. 5, in order to approximate jaws 130, 132, actuation cable 142 is moved in a proximal direction, as indicated by arrow "A", thereby moving keyed rod 140 and, in turn, center rod 136 in a proximal direction. In so doing, camming pin 138 rides proximally through camming slots 130c, 132b of jaws 130, 132 thus causing jaws to pivot about pivot pin 134 and, in turn, cause distal ends of jaws 130, 132 to approximate towards one another, as indicated by arrows "B". In so doing, a free end of needle 104 is moved into recess 132a of jaw 132. If tissue were present between the distal ends of jaws 130, 132, the free end of needle 104 would penetrate through the tissue prior to the entrance into recess 132a of jaw 132.

Turning now to FIG. 6, in order to release needle 104 from jaw 130 and secure or lock needle 104 in jaw 132, actuation cable 142 is rotated in the direction of arrow "C", thereby imparting rotation to keyed rod 140 which, in turn, imparts rotation to camming hub 144. As camming hub 144 is rotated in the direction of arrow "C", proximal ends 150b, 152b of blades 150, 152 ride along or through groove 144b. In particular, as seen in FIG. 6, as camming hub 144 is rotated in the direction of arrow "C", blade 150 is moved in a proximal direction (as indicated by arrow "A") while blade 152 is moved in a distal direction (as indicated by arrow "A1"). In so doing, distal end 150a of blade 150 disengages groove 104a of needle 104 disposed within recess 130a of jaw 130, and distal end 152b of blade 152 engages groove 104a of needle 104 disposed within recess 132a of jaw 132. As such, needle 104 is secured or locked within recess 132a of jaw 132.

Turning now to FIGS. 7 and 8, a method of articulating end effector 100 is shown and described. As seen in FIG. 7, with end effector 100 in an axially aligned condition, in order to articulate end effector 100 about neck assembly 110, a first articulation 114b (i.e., the lower articulation cable as depicted in FIGS. 7 and 8) is withdrawn in a proximal direction, as indicated by arrow "D" of FIG. 8. As articulation cable 114b is drawn in a proximal direction, a distal end of articulation cable 114b, anchored to a distal-most joint 112, at a location spaced a distance from a central axis thereof, joints 112 to rotate about the interface between knuckles 112a and clevis' 112b thereby causing gaps defined therebetween, along a side surface thereof, to constrict. In so doing, end effector 100 is articulated along neck assembly 110 to displace tool assembly 120 in a downward direction, in the direction of arrow "E" (as depicted in FIG. 8), i.e., in a direction transverse to a longitudinal axis thereof.

In order to return end effector 100 to an un-articulated condition or to articulate end effector in an opposite direction, articulation cable 114a (i.e., the upper articulation cable as depicted in FIGS. 7 and 8) is withdrawn in a proximal direction.

Turning now to FIGS. 9-16, an end effector, according to another embodiment of the present disclosure, is generally designated as end effector 200. End effector 200 is substantially similar to end effector 100 and thus will only be described herein to the extent necessary to identify differences in construction and operation thereof. Throughout the following disclosure, like reference numeral will be used to identify like elements.

Figure 11:
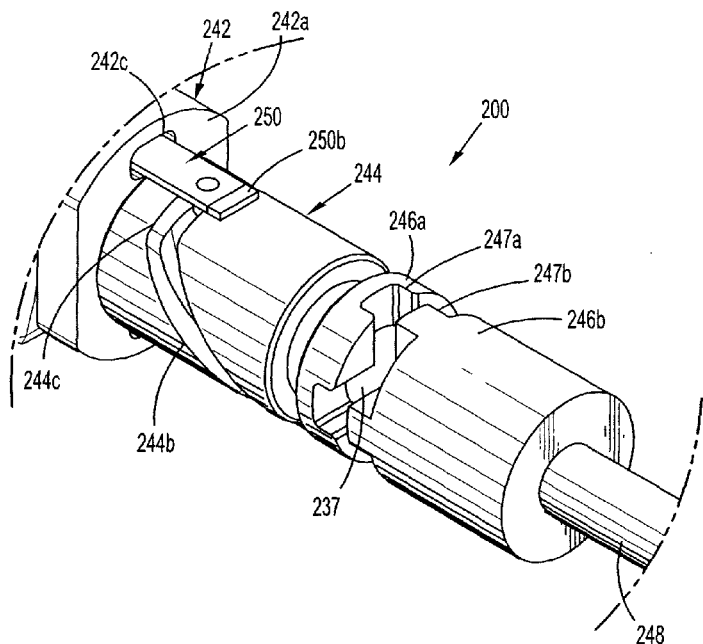
FIG. 11 is an enlarged view if the indicated area of detail of FIG. 10.
Figure 12:
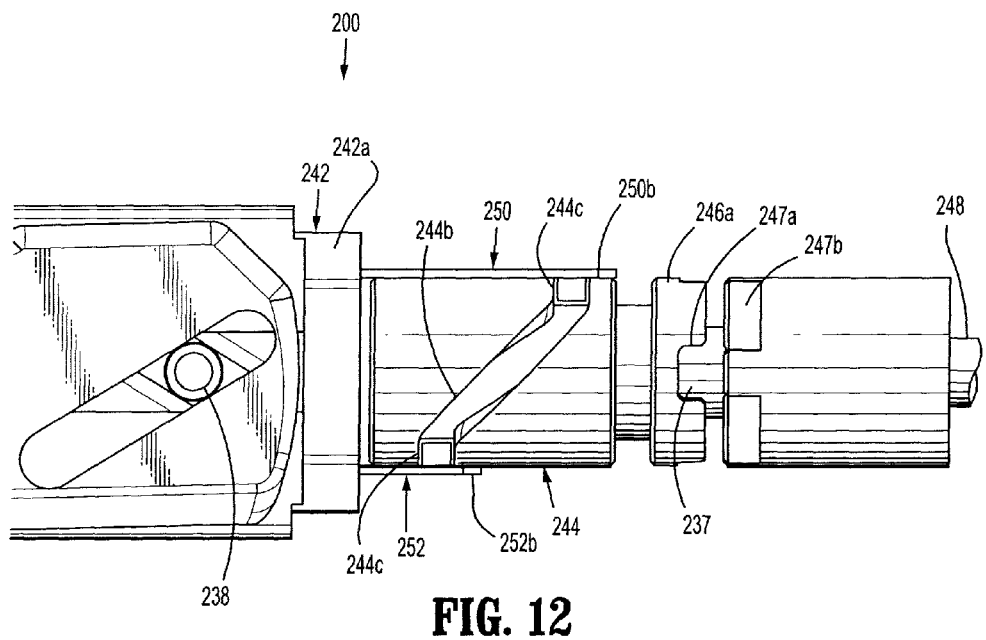
FIG. 12 is a side, elevational view of a positive clutch of the end effector of FIGS. 9-11, shown in a first or disconnected condition.
Figure 13:
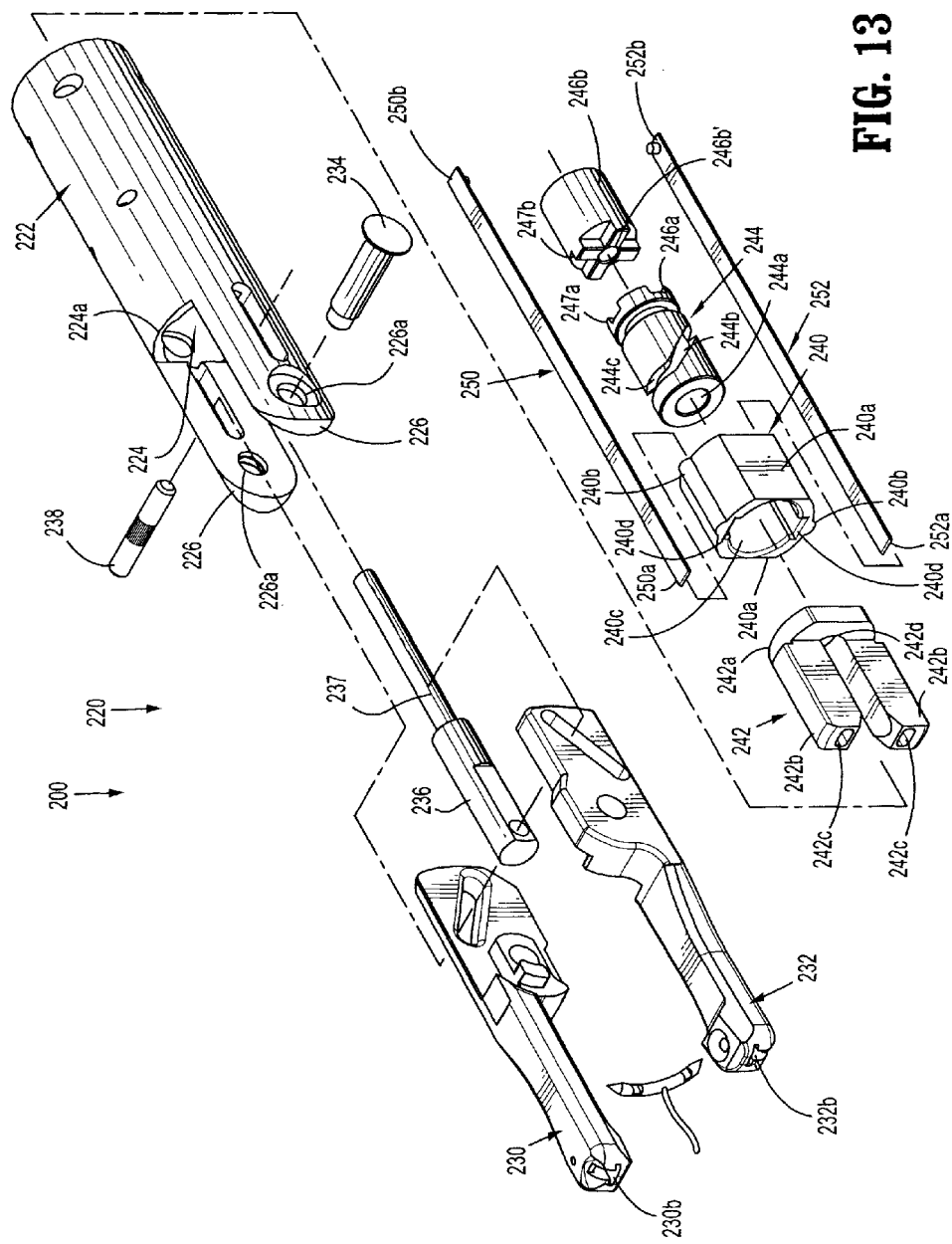
FIG. 13 is an exploded perspective view of the end effector of FIGS. 9-12.

As seen in FIGS. 9-14, end effector 200 includes a tool assembly 220 supported on an end of a neck assembly (not shown). Tool assembly 220 includes a jaw support member 222, and a pair of jaws 230, 232 mounted for pivotable movement on jaw support member 222. As seen in FIG. 13, jaw support member 222 defines a lumen 224 in a proximal end thereof and a pair of spaced apart arms 226 in a distal end thereof. Lumen 224 defines a pair of opposed channels 224a formed in a surface thereof (only one being shown).

Each jaw 230, 232 is substantially similar to jaws 130, 132 described above in regard to end effector 100 and thus the construction of jaws 230, 232 will not be discussed in further detail herein below.

Jaws 230, 232 are pivotably mounted on support member 222 by means of a jaw pivot pin 234 which extend through holes 226a formed in arms 226 of support member 222 and respective pivot holes formed in jaws. To move jaws 230, 232 between an open position and a closed position there is provided an axially or longitudinally movable center rod 236 having a camming pin 238 mounted at a distal end thereof. Camming pin 238 rides in and engages angled camming slots formed in respective jaws 230, 232 such that axial or longitudinal movement of center rod 236 causes jaws 230, 232 to be cammed between open and closed positions.

Tool assembly 220 includes a keyed block 240 slidably disposed within lumen 224 of support member 222. Keyed block 240 includes a pair of opposed flattened outer surfaces 240a, and a pair of opposed axial ribs 240b projecting from an outer surface thereof. Keyed block 240 further includes a lumen 240c extending therethrough and a pair of opposed axially extending grooves 240d formed in a wall of lumen 240c. Grooves 240d may be aligned with or in registration with ribs 240b. Ribs 240b are configured for slidable receipt in channels 224a formed in lumen 224 of support member 222.

Tool assembly 220 further includes a clevis 242 disposed distally of keyed block 240. Clevis 242 includes a pair of spaced apart arms 242b extending from a base 242a. Each arm 242b defines a lumen 242c therethrough. Clevis 242 defines a central aperture 242d formed in base 242a. Arms 242b are spaced apart an amount sufficient and central aperture 242d of base 242b is dimensioned so as to slidably and rotatably receive center rod 236 therein.

Tool assembly 220 further includes a camming hub 244 defining a lumen 244a therethrough configured and adapted to slidably receive a portion of center rod 236 therein. Camming hub 244 defines a substantially helical or spiral groove 244b in an outer surface thereof. A distal and a proximal end 244c of helical groove 244b may be flattened or may be configured to extend or run parallel to a plane oriented orthogonal to a longitudinal axis thereof.

Camming hub 244 is configured for rotatable disposition within lumen 224 of support member 222. In particular, camming hub 244 may include an outer circumferential groove 244d formed therein for slidable engagement with a nub, boss or the like (not shown) projecting inwardly from support member 222. In this manner, the axial location of camming hub 244 is fixed with respect to support member 222.

Camming hub 244 includes a first clutch portion 246a provided or formed at a proximal end thereof, wherein lumen 244a of camming hub 244 extends through first clutch portion 246a. Tool assembly 220 further includes a second clutch portion 246b supported on a distal end of a hollow shaft 248. Second clutch portion 246b defines a central lumen 246b' therethrough. Each of first and second clutch portions 246a, 246b includes or defines complementary inter-engaging structure, elements or formations 247a, 247b provided on opposed surfaces thereof.

In operation, as will be discussed in greater detail below, second clutch portion 246b is translatable relative to first clutch portion 246a, via hollow shaft 248, in order to selectively engage and disengage inter-engaging elements 247a, 247b with one another. When inter-engaging elements 247a, 247b are engaged with one another, rotation of hollow shaft 248 will rotate second clutch portion 246b, which will in turn rotate camming hub 244 via second clutch portion 246b. When inter-engaging elements 247a, 247b are disengaged from one another, rotation of hollow shaft 248 will rotate second clutch portion 246b, however, no rotation will be imparted to camming hub 244. Also, when inter-engaging elements 247a, 247b are disengaged from one another, rotation of central shaft 237, extending from center rod 236 and through clevis 242, keyed block 240, camming hub 244, second clutch portion 246b and hollow shaft 248, will result in rotation of jaws 230, 232 without an axial movement of blades 250, 252.

Tool assembly 220 further includes a pair of needle engaging members or blades 250, 252 which are slidably supported within a respective lumen 242c of arms 242b of clevis 342 and through respective grooves 240d of keyed block 240.

Each blade 250, 252 includes a distal end 250a, 252a slidably extending into blade receiving channels 230d, 232d (see FIG. 13) of respective jaws 230, 232. Each blade 250, 252 includes a proximal end 250b, 252b slidably disposed within groove 244b of camming hub 244. In operation, as camming hub 244 is rotated, proximal ends 250b, 252b of blades 250, 252 ride within groove 244b of camming hub 244 and are translated, in an axial direction, relative thereto. In particular, upon rotation of camming hub 244, as blade 250 is moved distally, blade 252 is moved proximally and vise-versa.

Figure 10:
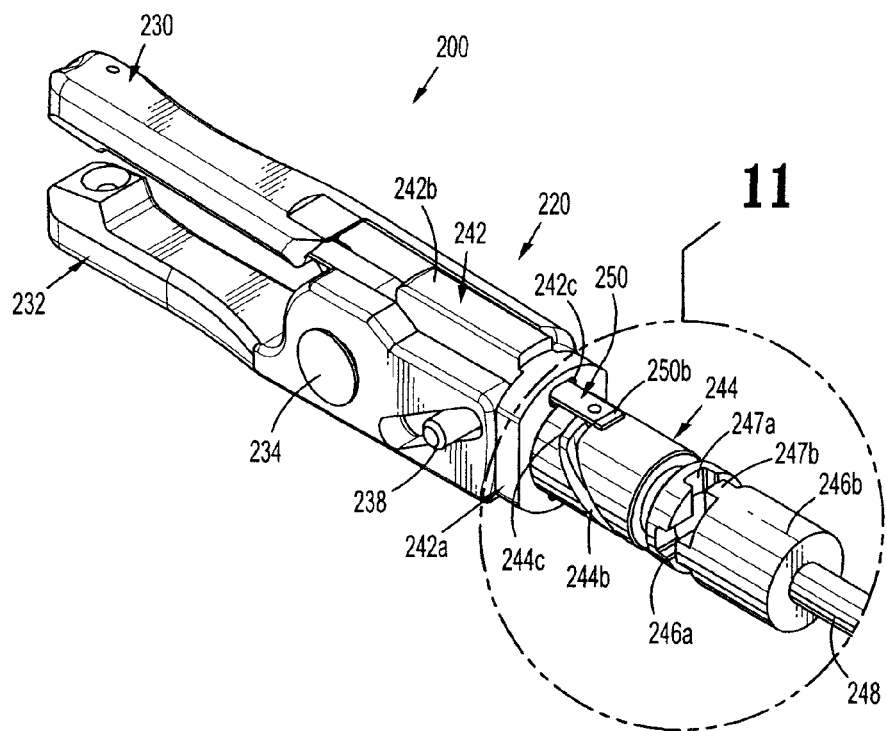
FIG. 10 is a perspective view of the end effector of FIG. 9, with a jaw supporting member removed therefrom.

Turning now to FIGS. 10-12 and 14-16, a method of operating end effector 200 is shown and described. As seen in FIGS. 10-12, when first and second clutch portions 246a, 246b are axially spaced from one another or are disengaged from one another, jaws 230, 232 are free to rotate about a longitudinal axis thereof without effectuating axial translation of blades 250, 252. In particular, when first and second clutch portions 246a, 246b are axially spaced from one another or are disengaged from one another, rotation of second clutch portion 246b, via hollow shaft 248, does not transmit any rotation to first clutch portion 246a and, in turn, to jaws 230, 232, i.e., jaws 230, 232 remain stationary. Moreover, as central shaft 237 is rotated about a longitudinal axis thereof, center rod 236 to rotate which in turn causes jaws 230, 232 to rotate about the longitudinal axis.

Figure 14:
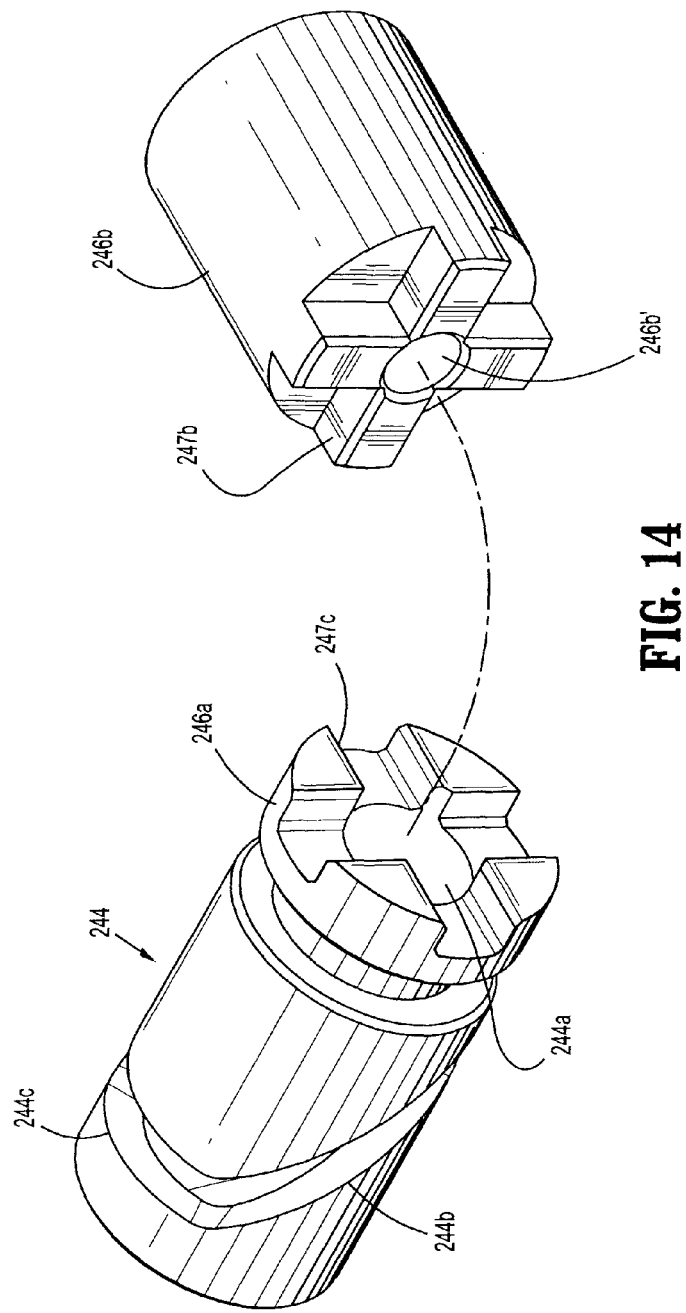
FIG. 14 is an exploded perspective view of the positive clutch of the end effector of FIGS. 9-13.
Figure 15:
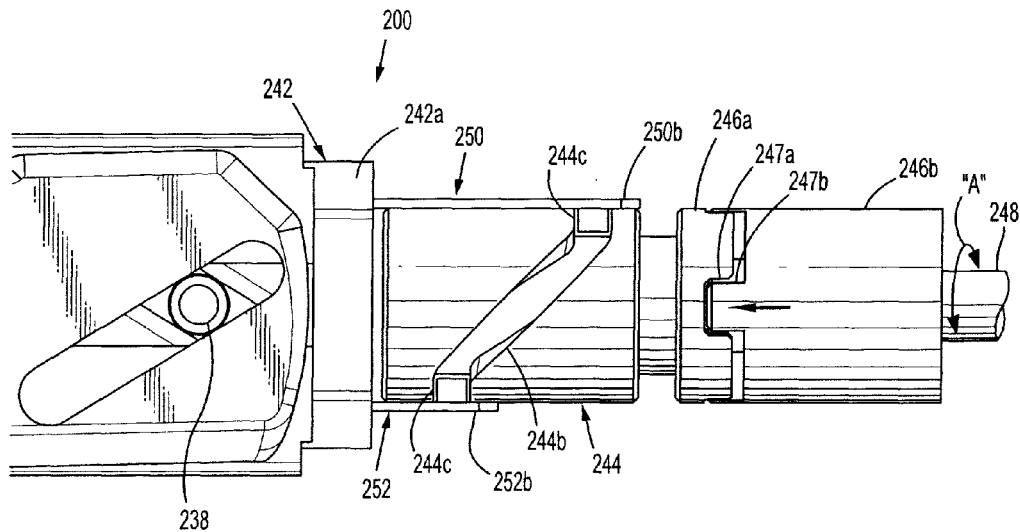
FIG. 15 is a side, elevational view of the positive clutch of the end effector of FIGS. 9-14, shown in a second or connected condition.
Figure 16:
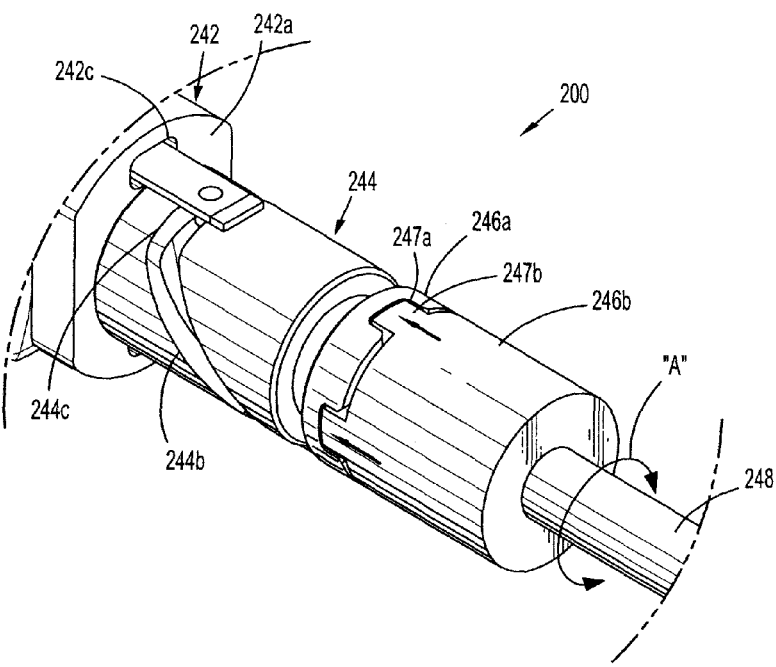
FIG. 16 is a perspective view of the positive clutch of the end effector of FIGS. 9-15, shown in the second or connected condition.

As seen in FIGS. 14-16, when first and second clutch portions 246a, 246b engaged with one another, jaws 230, 232 may not be rotated about the longitudinal axis thereof without effectuating axial translation of blades 250, 252. In particular, when first and second clutch portions 246a, 246b are engaged with one another, rotation of second clutch portion 246b in the direction of arrow "A", via hollow shaft 248, transmits a rotation to first clutch portion 246a and, in turn, to camming hub 244.

As camming hub 244 is rotated, proximal ends 250b, 252b of blades 250, 252 ride within groove 244b of camming hub 244 and are translated, in an axial direction, relative thereto. In particular, upon rotation of camming hub 244, as blade 250 is moved distally, blade 252 is moved proximally and vise-versa.

Similar to end effector 100, in order to open or close jaws 230, 232, of end effector 200, central shaft or cable 248 is translated in an axial direction, thereby moving center rod 236 to move camming pin 238. Camming pin 238 rides through the camming slots of jaws 230, 232 thus causing jaws to pivot about pivot pin 234 and cause distal ends of jaws 230, 232 to open or close.

Turning now to FIGS. 17-30, an end effector, according to yet another embodiment of the present disclosure, is generally designated end effector 300. End effector 300 is substantially similar to end effector 200 and thus will only be described herein to the extent necessary to identify differences in construction and operation thereof. Throughout the following disclosure, like reference numeral will be used to identify like elements.

Figure 20:
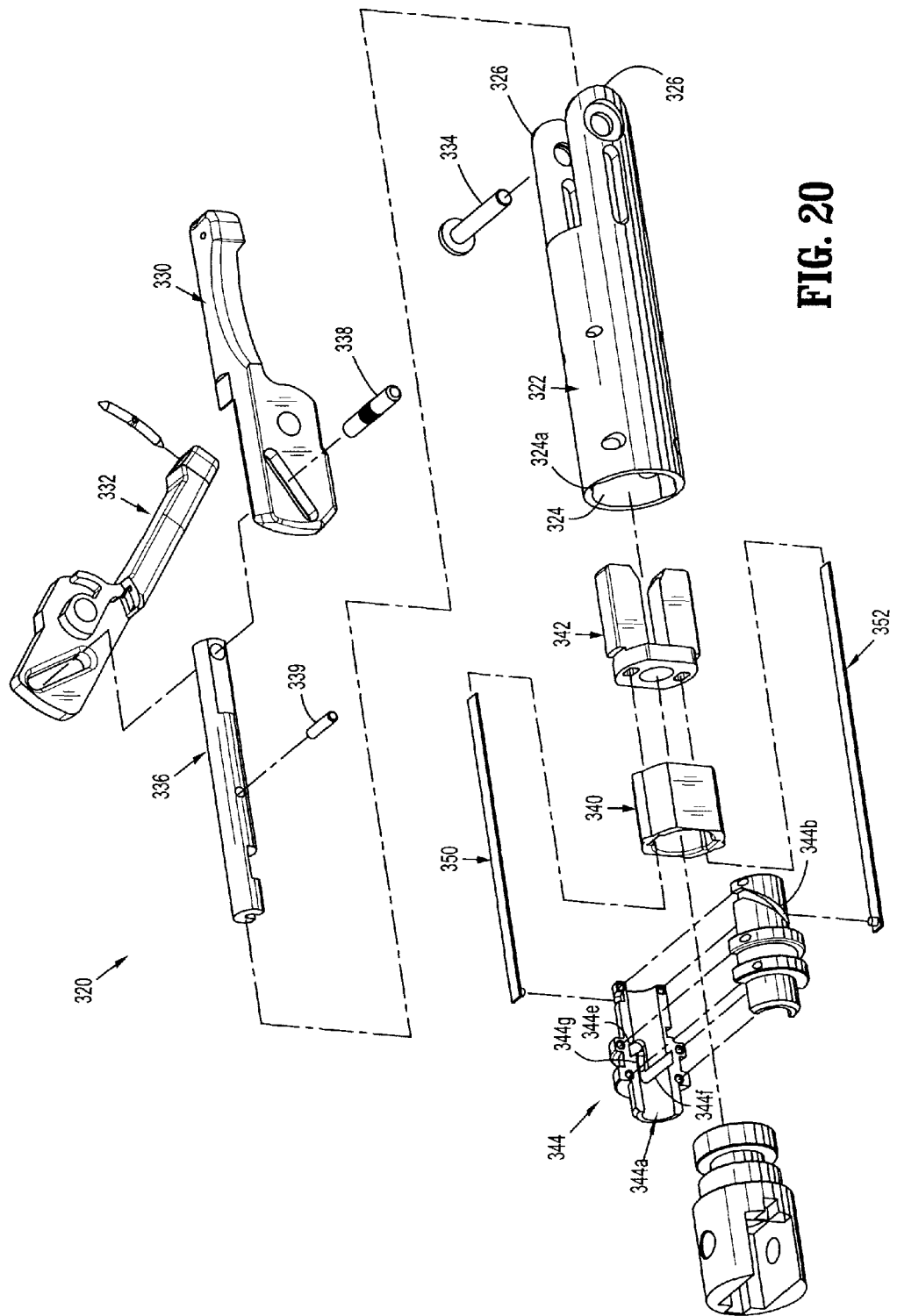
FIG. 20 is an exploded perspective view of the end effector of FIGS. 17-19.
Figure 21:
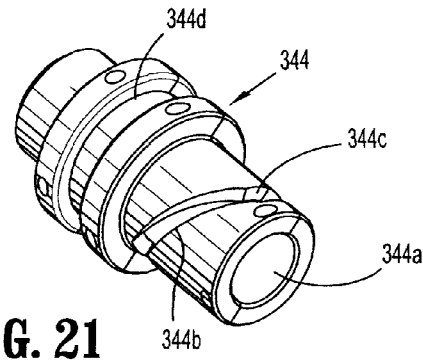
FIG. 21 is a perspective view of a camming hub of the end effector of FIGS. 17-20.
Figure 22:
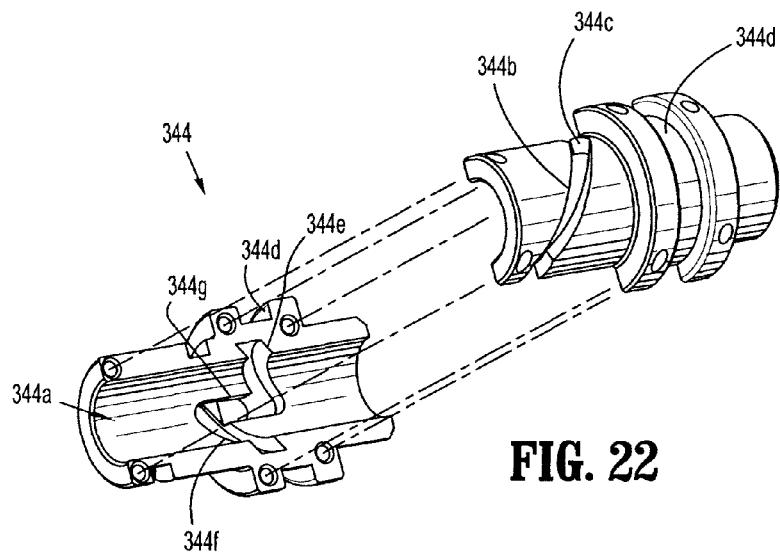
FIG. 22 is an exploded perspective view of the camming hub of FIG. 21.
Figure 23:
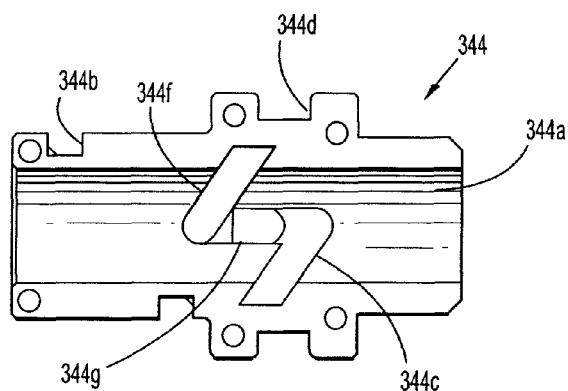
FIG. 23 is a plan view of a half of the camming hub of FIGS. 21 and 22.

As seen in FIGS. 17-30, end effector 300 includes a tool assembly 320 supported on an end of a neck assembly (not shown). Tool assembly 320 includes a jaw support member 322, and a pair of jaws 330, 332 mounted for pivotable movement on jaw support member 322. As seen in FIG. 20, jaw support member 322 defines a lumen 324 in a proximal end thereof and a pair of spaced apart arms 326 in a distal end thereof. Lumen 324 defines a pair of opposed channels 324a formed in a surface thereof (only one being shown).

Each jaw 330, 332 is substantially similar to jaws 230, 232 described above in regard to end effector 200 and thus the construction of jaws 330, 332 will not be discussed in further detail herein below.

Jaws 330, 332 are pivotably mounted on support member 322 by means of a jaw pivot pin 334 which extend through holes 326a formed in arms 326 of support member 322 and respective pivot holes formed in jaws. To move jaws 330, 332 between an open position and a closed position there is provided an axially or longitudinally movable center rod 336 having a camming pin 338 mounted at a distal end thereof. Camming pin 338 rides in and engages angled camming slots formed in respective jaws 330, 332 such that axial or longitudinal movement of center rod 336 causes jaws 330, 332 to be cammed between open and closed positions.

Tool assembly 320 includes a keyed block 340 and a clevis 342. Keyed block 340 and a clevis 342 are substantially similar to keyed block 240 and a clevis 242 and thus the construction of keyed block 340 and a clevis 342 will not be discussed in further detail herein below.

Tool assembly 320 further includes a camming hub 344 defining a lumen 344a therethrough configured and adapted to slidably receive a portion of center rod 336 therein. Camming hub 344 defines a substantially helical or spiral groove 344b in an outer surface thereof. A distal and a proximal end 344c of helical groove 344b may be flattened or may be configured to extend or run parallel to a plane oriented orthogonal to a longitudinal axis thereof.

Camming hub 344 is configured for rotatable disposition within lumen 324 of support member 322. In particular, camming hub 344 may include an outer circumferential groove 344d formed therein for slidable engagement with a nub, boss or the like 345 (see FIG. 24) projecting inwardly from support member 322. In this manner, the axial location of camming hub 344 is fixed with respect to support member 322.

As seen in FIGS. 20-25 and 27-28, camming hub 344 includes a pair of spaced apart helical grooves 344e, 344f formed in a surface of lumen 344a, and a pair of opposed axially oriented grooves 344g formed in a surface of lumen 344a and interconnecting helical grooves thereof 344e, 344f.

With continued reference to FIGS. 20-25 and 27-28, a cam pin 339 is provided with extending transversely through camming rod 336 and which is dimensioned for slidable interengagement in internal helical grooves 344e, 344f and internal axial grooves 344g of camming hub 344.

Tool assembly 320 further includes a pair of needle engaging members or blades 350, 352 which are operatively associated with clevis 342 and keyed block 340 in a manner substantially similar to blades 250, 252 with clevis 242 and keyed block 240. Blades 350, 352 are substantially similar to blades 250, 252 and thus the construction of blades 350, 352 will not be discussed in further detail herein below.

Figures 24, 25:
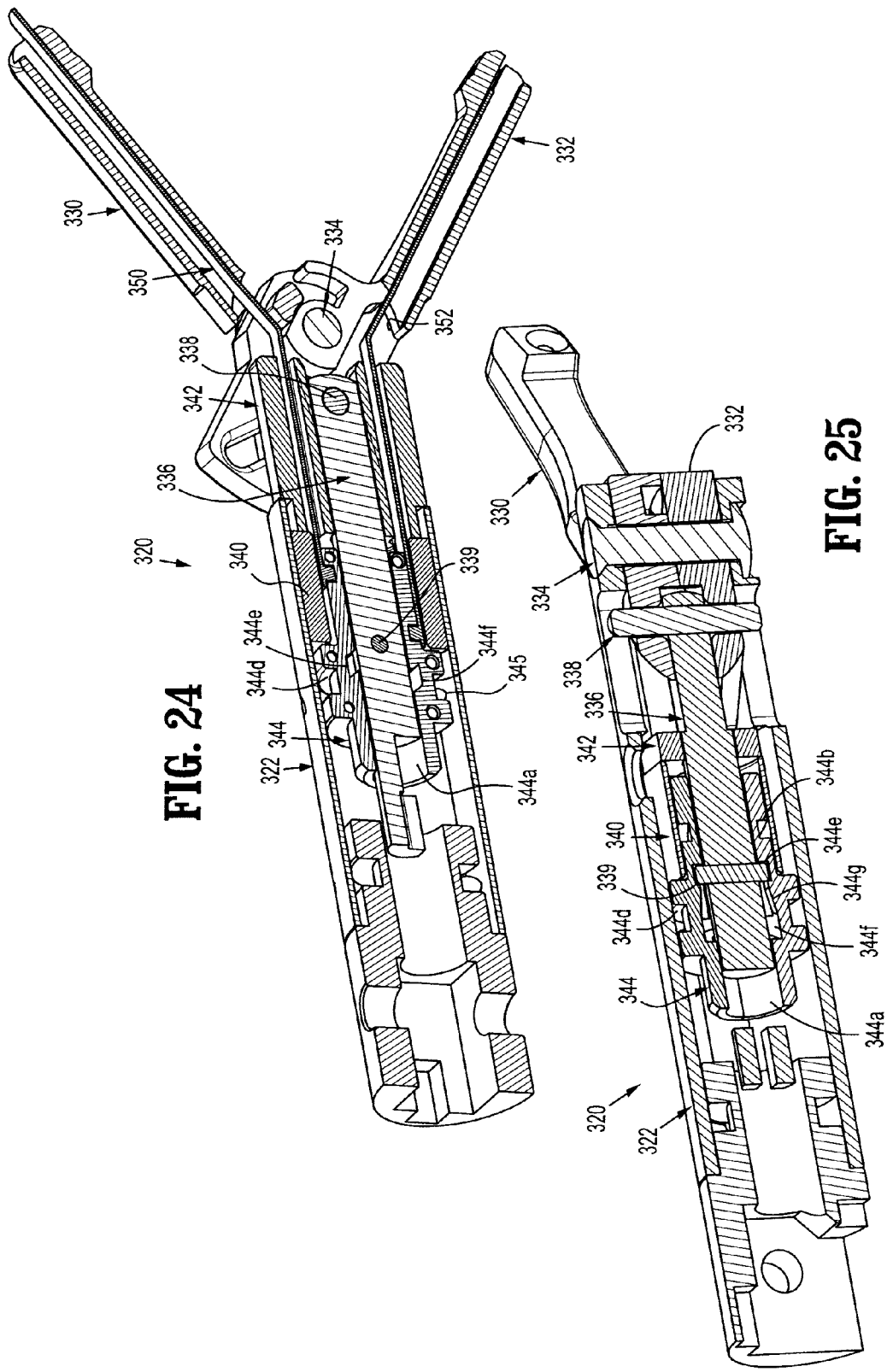
FIG. 24 is a longitudinal, cross-sectional view of the end effector of FIGS. 17-23, as taken through a plane that extends longitudinally through the jaws of the end effector, illustrating the jaws in an open configuration.
FIG. 25 is a longitudinal, cross-sectional view of the end effector of FIGS. 17-23, as taken through a plane that extends longitudinally between the jaws of the end effector, illustrating the jaws in an open configuration.

Turning now to FIGS. 24-25 and 27-30, a method of operating end effector 300 is shown and described. As seen in FIGS. 24-25, when camming pin 339 is at a distal-most position in internal axial grooves 344g of camming hub 344, center rod 336 is at a distal-most portion and jaws 330, 332 are spaced apart from one another. As seen in FIGS. 29 and 30, while camming pin 339 is in the distal-most position of internal axial groove 344g of camming hub 344, rotation of center rod 336 transmits a rotational force to camming pin 338 which, in turn causes tool assembly 320 to rotate about the longitudinal axis while jaws 330, 332 are opened. Concomitantly therewith, as center rod 336 is rotated, a rotational force is transmitted to camming pin 339, however, since camming hub 334 is journaled in support member 332, camming hub 344 is prevented from translational movement and thus merely rotates with the rotation of jaws 330, 332.

In one configuration, as center rod 336 and camming pin 339 are moved proximally, camming pin 339 operatively engages against inner helical grooves 344e, 344f to create a rotation of camming hub 344. As camming hub 344 is rotated, the proximal ends of blades 350, 352 ride within outer helical groove 344b of camming hub 344 and are translated, in an axial direction, relative thereto. In particular, upon rotation of camming hub 344, as blade 350 is moved distally, blade 352 is moved proximally and vise-versa.

In another configuration, as center rod 336 and camming pin 339 are moved proximally, camming pin 339 merely translates through inner axial groove 344g of camming hub 344. In so doing, no rotation or translation is transmitted to camming hub 344.

While camming rod 336 is moved proximally, camming pin 338 urges jaws 330, 332 to an approximated position.

Figure 26:
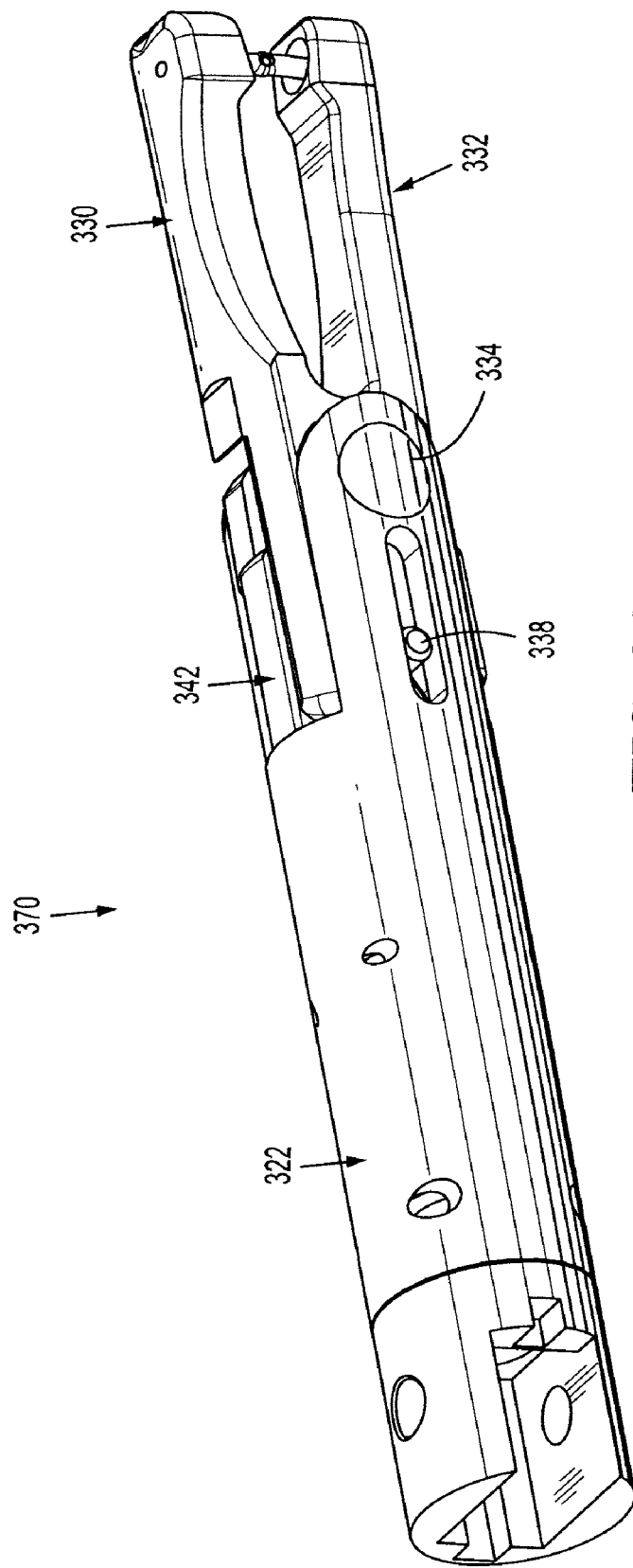
FIG. 26 is a perspective view of the end effector of FIGS. 17-25, illustrating the jaws in a closed configuration.
Figure 27:
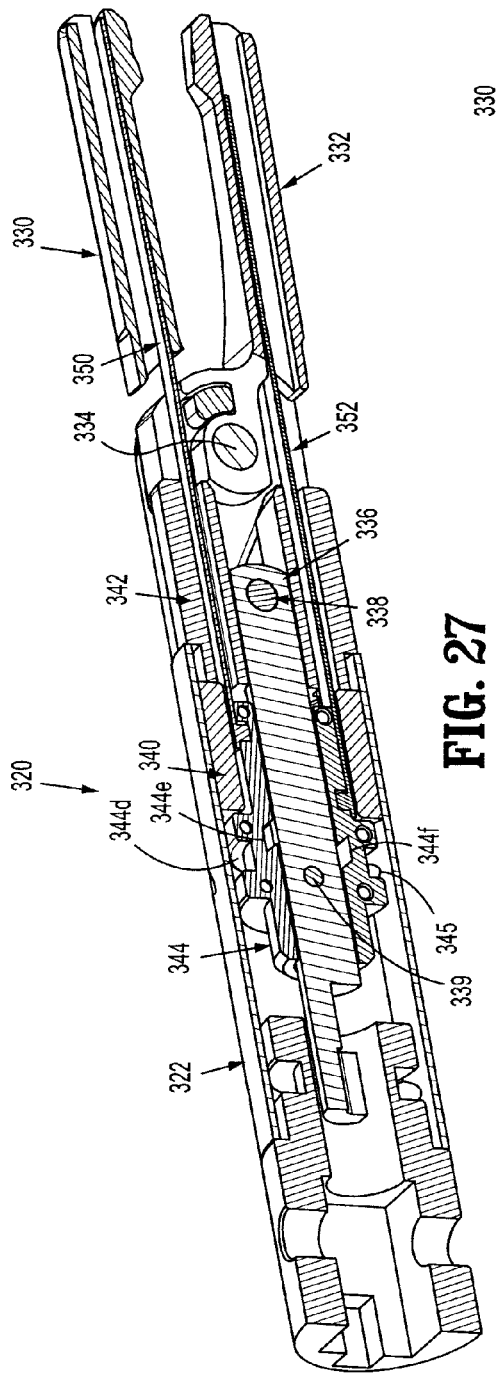
FIG. 27 is a longitudinal, cross-sectional view of the end effector of FIGS. 17-26, as taken through a plane that extends longitudinally through the jaws of the end effector, illustrating the jaws in the closed configuration.
Figure 28:
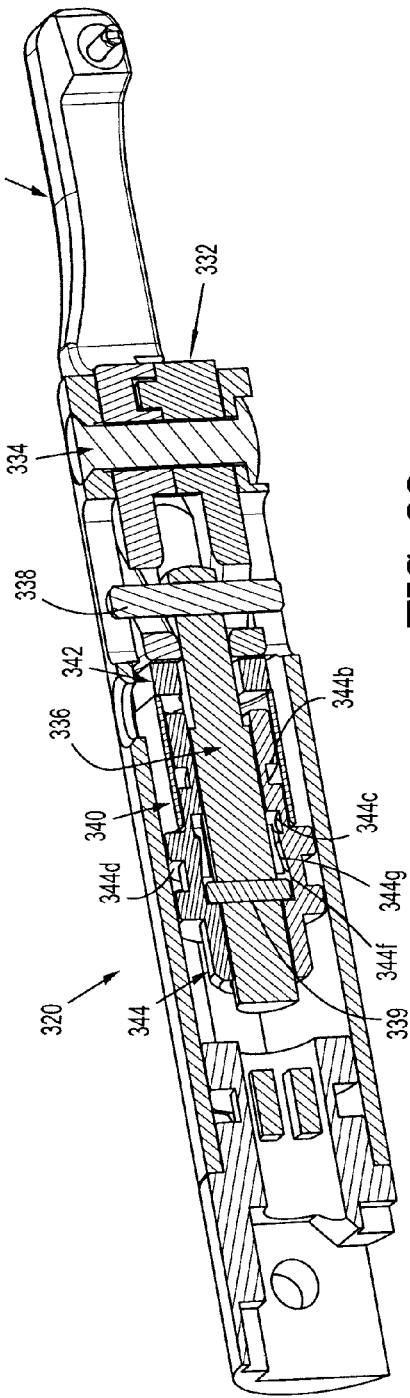
FIG. 28 is a longitudinal, cross-sectional view of the end effector of FIGS. 17-27, as taken through a plane that extends longitudinally between the jaws of the end effector, illustrating the jaws in the closed configuration.
Figure 31:
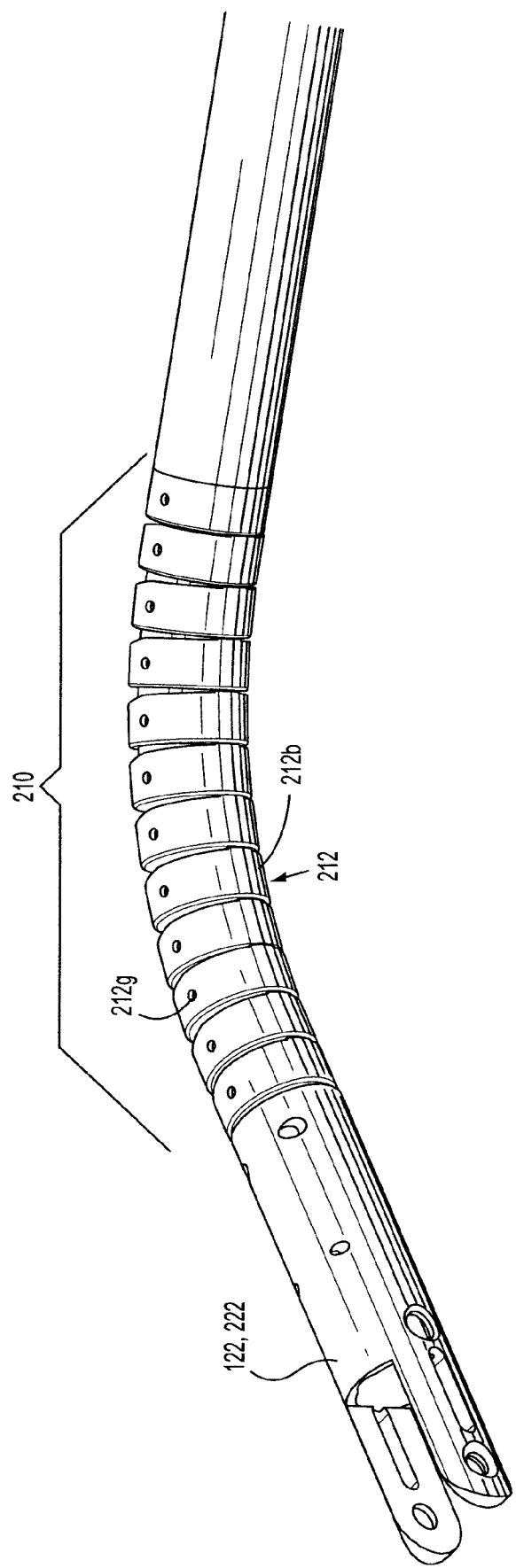
FIG. 31 is a perspective view of a neck assembly of an end effector according to another embodiment of the present disclosure.

Additionally, as seen in FIGS. 26-28, when camming pin 339 is at a proximal-most position in internal axial grooves 344g of camming hub 344, center rod 336 is at a proximal-most portion and jaws 330, 332 are approximated towards one another.

While camming pin 339 is in the proximal-most position of internal axial groove 344g of camming hub 344, rotation of center rod 336 transmits a rotational force to camming pin 338 which, in turn causes tool assembly 320 to rotate about the longitudinal axis while jaws 330, 332 are in the approximated position. Concomitantly therewith, as center rod 336 is rotated, a rotational force is transmitted to camming pin 339, however, since camming hub 334 is journaled in support member 332, camming hub 344 is prevented from translational movement and thus merely rotates with the rotation of tool assembly 320.

In one configuration, as center rod 336 and camming pin 339 are moved distally, camming pin 339 operatively engages against inner helical grooves 344e, 344f to create a rotation of camming hub 344. As camming hub 344 is rotated, the proximal ends of blades 350, 352 ride within outer helical groove 344b of camming hub 344 and are translated, in an axial direction, relative thereto. In particular, upon rotation of camming hub 344, as blade 350 is moved distally, blade 352 is moved proximally and vise-versa.

In another configuration, as center rod 336 and camming pin 339 are moved distally, camming pin 339 merely translates through inner axial groove 344g of camming hub 344. In so doing, no rotation or translation is transmitted to camming hub 344.

In an embodiment, inner axial groove 344g may include structure which prevents camming pin 339 from moving in both a distal and a proximal direction. In particular, inner axial groove 344g may include a ramp-like structure or the like formed therein which allows for camming pin 339 to move only in a first direction, i.e., either distally or proximally, and not a second direction, opposite to the first direction.

Figure 17:
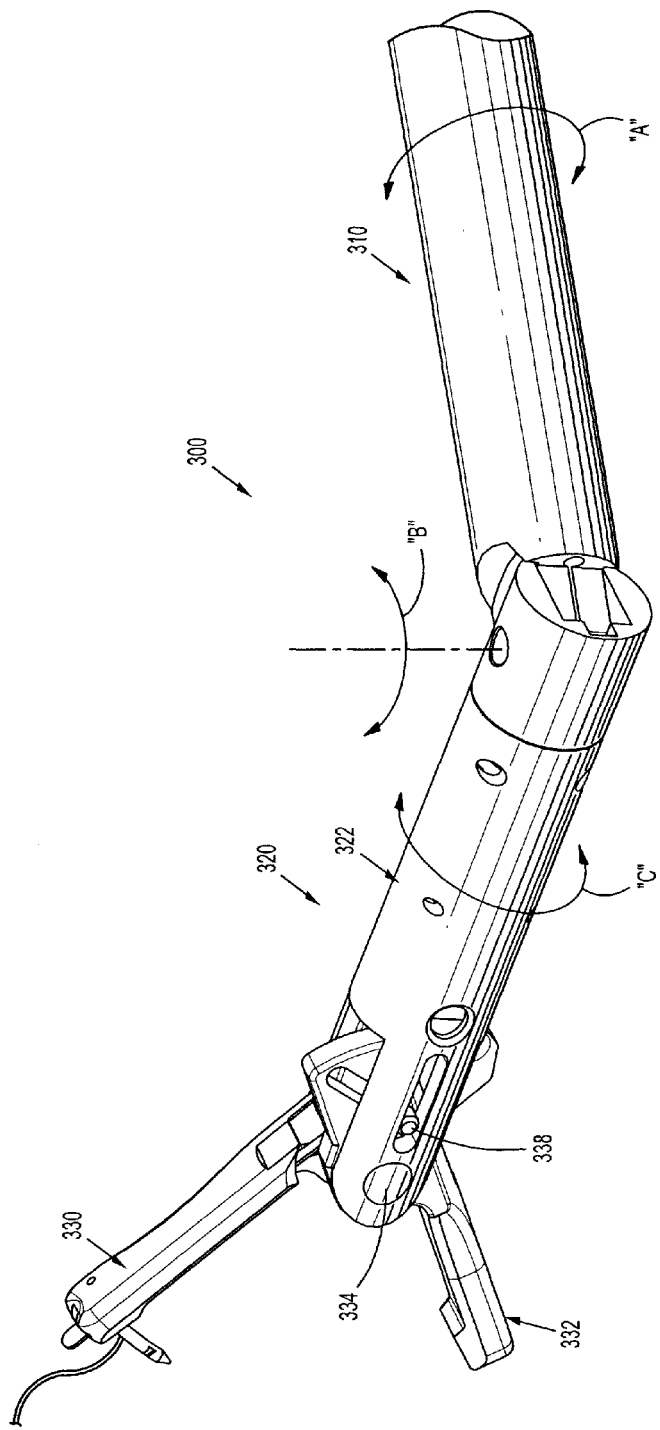
FIG. 17 is a perspective view of an end effector of a stitching device according to yet another embodiment of the present disclosure.
Figure 18:
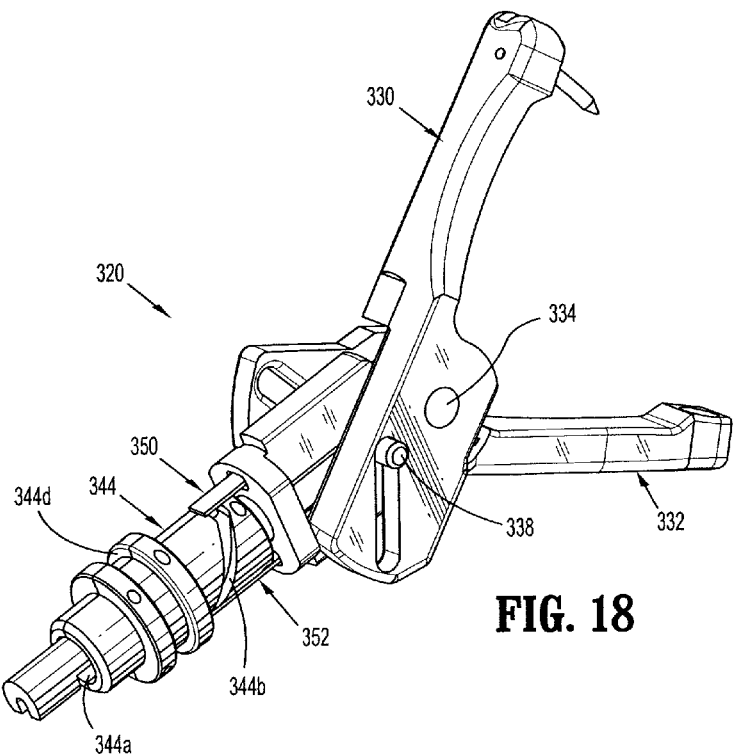
FIG. 18 is a perspective view of the end effector of FIG. 17, with a jaw supporting member removed therefrom.
Figure 19:
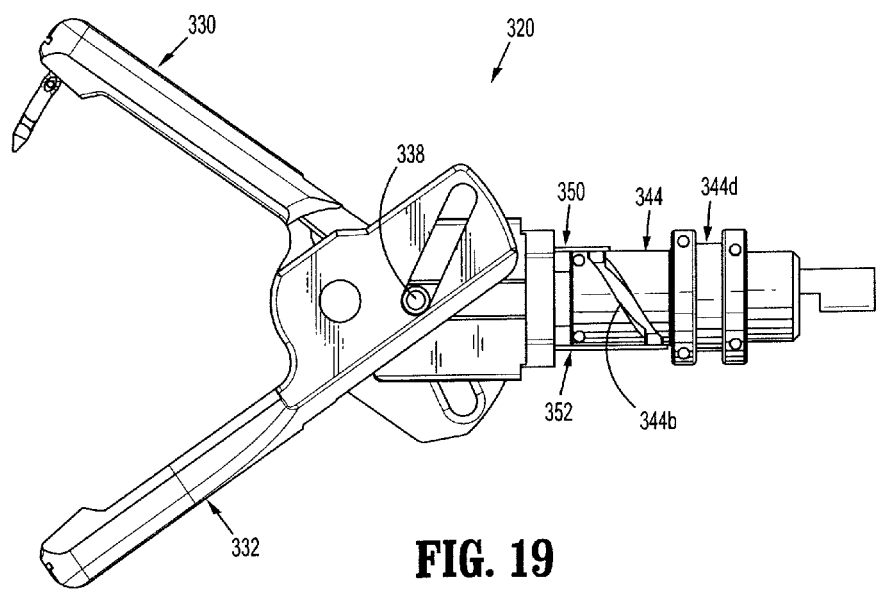
FIG. 19 is a side, elevational view of the end effector of FIGS. 17 and 18, with a jaw supporting member removed therefrom.

As seen in FIGS. 17 and 30, end effector 300 is configured for rotation about a longitudinal axis of a neck assembly 310, as indicated by double-headed arrow "A"; for pivotal movement of tool assembly 320 relative to neck assembly 310, as indicated by double-headed arrow "B"; and tool assembly 320 is configured for rotation about a longitudinal axis thereof, as indicated by double-headed arrow "C".

Turning now to FIGS. 31-37, a neck assembly, according to another embodiment of the present disclosure, is generally designated neck assembly 210. Neck assembly 210 is substantially similar to neck assembly 110 and thus will only be described herein to the extent necessary to identify differences in construction and operation thereof. Throughout the following disclosure, like reference numeral will be used to identify like elements.

As seen in FIGS. 31-37, neck assembly 210 is configured for support on a distal end of a shaft extending from a handle assembly (not shown) and for supporting a jaws support member 122, 222 of a tool assembly at a distal end thereof.

Neck assembly 210 includes a plurality of joints 212 each including a distal knuckle 212a extending from a proximal housing 212b. Each knuckle 212a operatively engages a proximal housing 212b of an adjacent joint 212. Each joint 212 defines a central lumen 212c formed therein and a pair of opposed lumens 212d, 212e formed on either side of central lumen 212c. A pair of articulation cables (not shown) slidably extend through respective lumens 212d, 212e of joints 212.

Each joint 212 further includes a pair of opposed nubs 212f extending from opposed side surfaces of distal knuckle 212a. Nubs 212f define a pivot axis "B" extending therethrough. Each nub 212f is configured for selective receipt in a respective complementarily configured aperture 212g formed in proximal housing 212b.

In use, adjacent joints 212 may be pivotally connected to one another in tip-to-tail fashion such that distal knuckles 212a are received within proximal housing 212b and, more particularly, nubs 212f of distal knuckles 212a are operatively received within apertures 212g of proximal housing 212b. As seen in FIGS. 33-36, when adjacent joints 212 are joined to one another, during interconnection thereof, distal knuckle 212a is flexed or biased such that nubs 212f thereof are approximated toward one another see FIG. 35) as distal knuckle 212a is advanced into proximal housing 212b until nubs 212f are in registration with or are received in apertures 212g. When nubs 212f are so positioned, distal knuckle 212a is un-biased so as to fit nubs 212f into apertures 212g (see FIG. 36).

Figure 37:
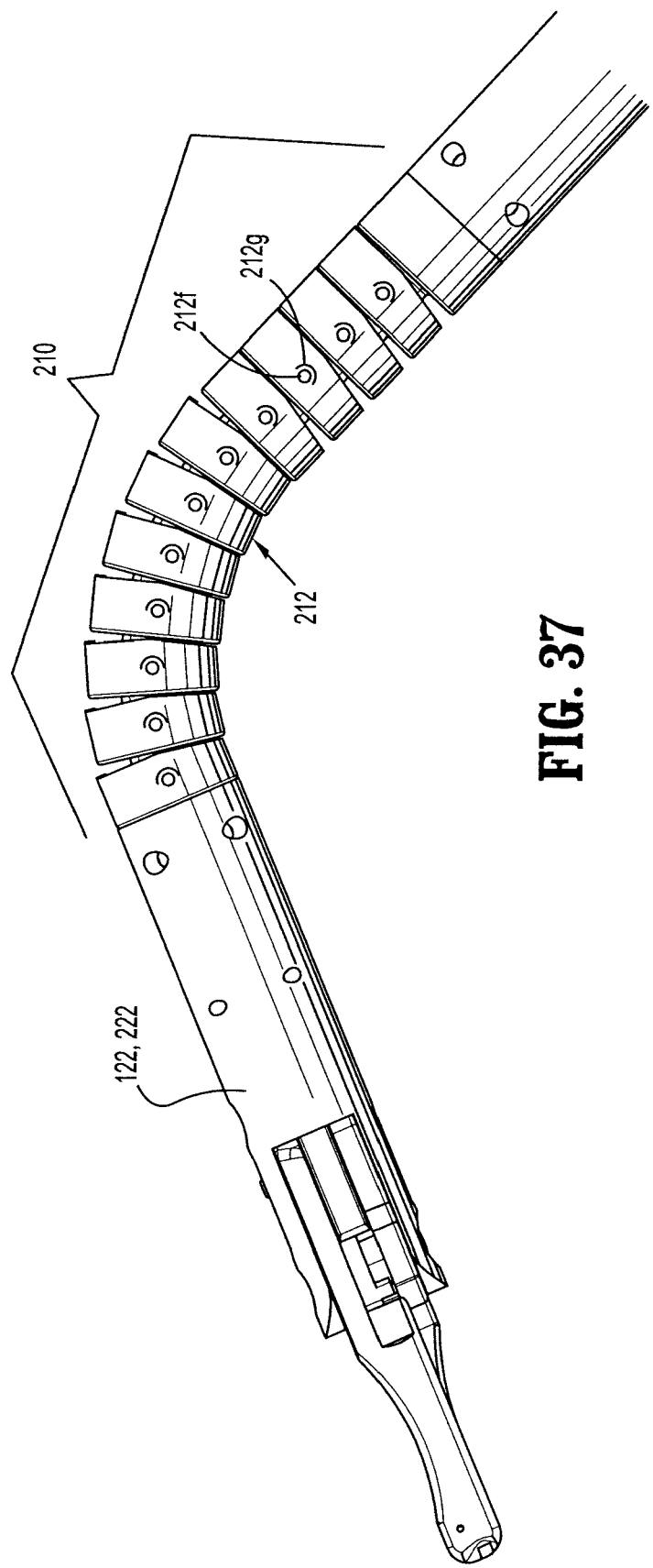
FIG. 37 is a plan view of the neck assembly of FIGS. 31 and 32, shown in an articulated condition.

As seen in FIG. 37, with a plurality of joints 212 connected to one another, neck assembly 210 may be shaped in an arcuate configuration as needed. While joints 212 are shown as being connected to one another such that the pivot axes "B" thereof are all substantially parallel to one another, it is envisioned and contemplated that the pivot axes "B" thereof may be at any angle or inclination relative to one another, thereby allowing for neck assembly 210 to deflect in any direction relative to a longitudinal axis thereof.

Figure 32:
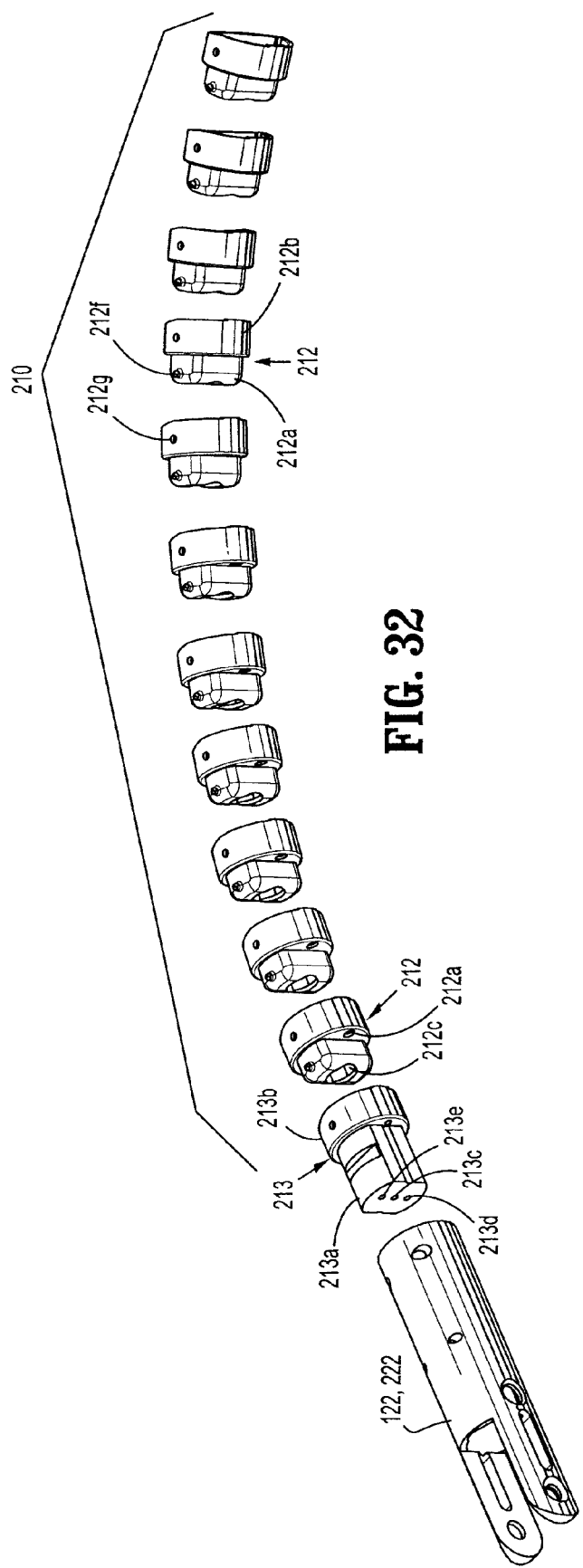
FIG. 32 is an exploded perspective view of the neck assembly of FIG. 31.
Figure 33:
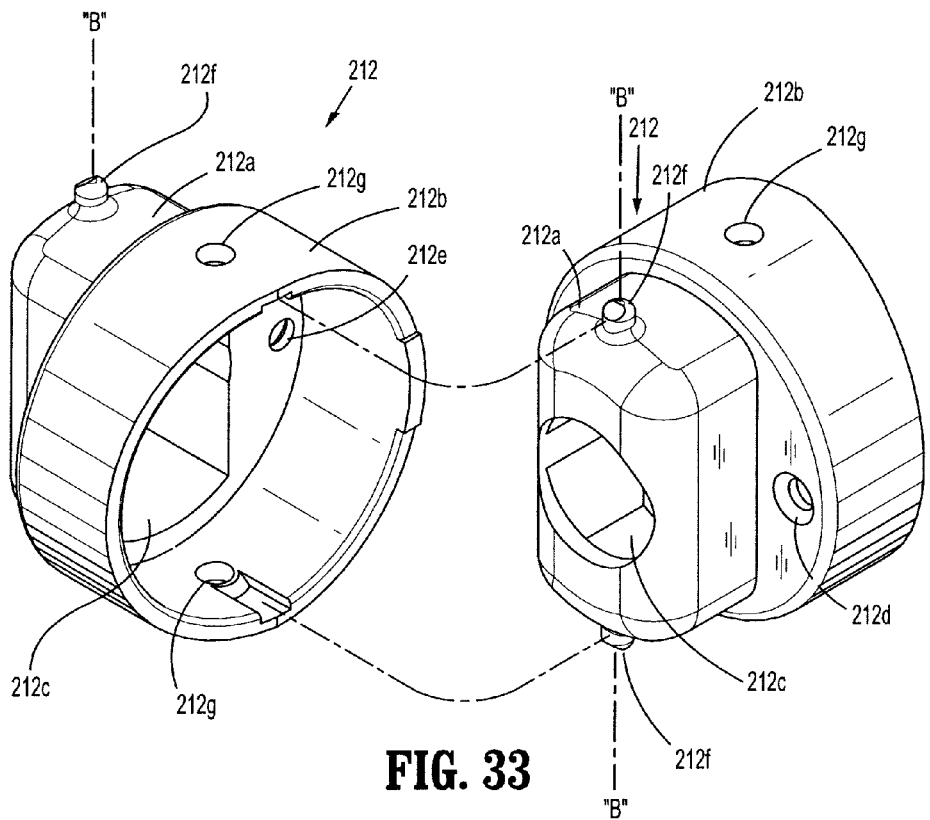
FIG. 33 is a perspective view of a pair of joints of the neck assembly of FIGS. 31 and 32, shown separated from one another.
Figure 34:
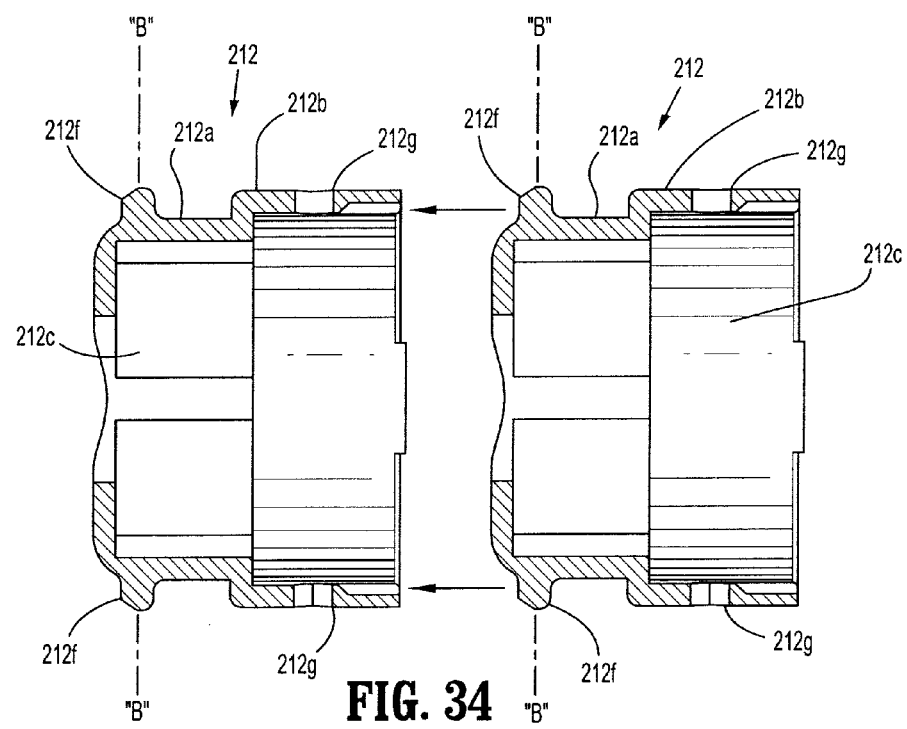
FIGS. 34-36 are longitudinal, cross-sectional view, taken through a plane defines by a pair of nubs of the joints, illustrating the connecting of adjacent joints to one another.
Figure 35:
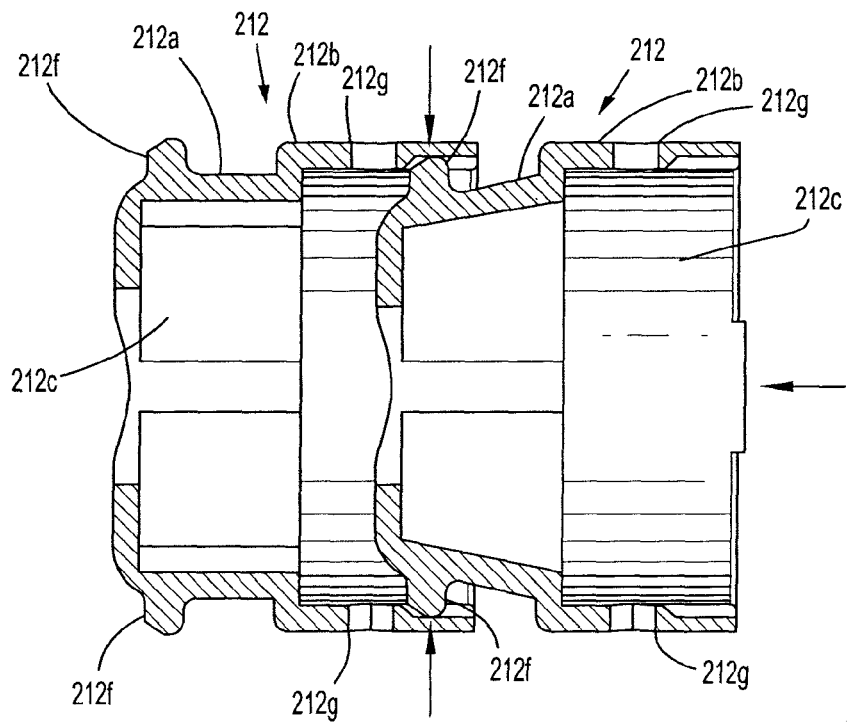
Figure 36:
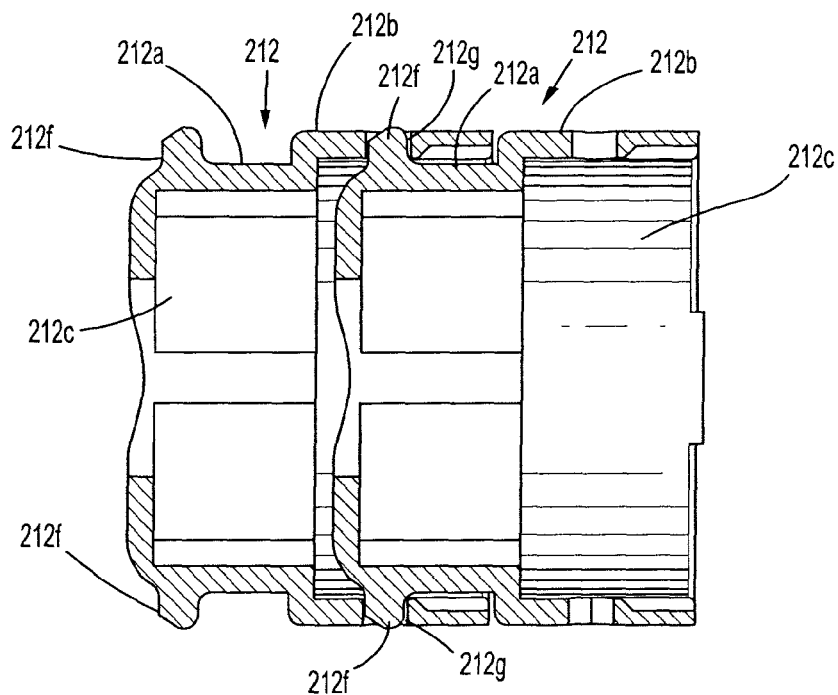

As seen in FIG. 32, a distal-most joint 213 of neck assembly 210 may be configured to connection to jaw support member 122, 222. In particular, distal-most joint 213 includes a distal housing 213a extending from a proximal housing 213b. Proximal housing 213b of distal-most joint 213 is configured for pivotal connection with distal knuckle 212a of joint 212.

Distal-most joint 213 defines a central lumen 213c formed therein and a pair of opposed lumens 213d, 213e formed on either side of central lumen 213c. Central lumen 213c and opposed lumens 213d, 213e of distal-most joint 213 are disposed in a plane which is substantially orthogonal to a plane defined by central lumen 212c and opposed lumens 212d, 212e of joint 212.

In order to articulate any of the end effectors about neck assembly 210 a first articulation (not shown), extending through lumens 212d of joints 212 may be withdrawn in a proximal direction. As the first articulation cable is drawn in a proximal direction, a distal end of the first articulation cable, anchored to support member 122, 222, at a location spaced a distance from a central axis thereof, causes joints 212 to pivot about pivot axes "B" thereof, thereby causing gaps defined between adjacent joints 212 to constrict. In so doing, the end effector is articulated along neck assembly 210 to displace support member 122, 222 in a first direction. In order to return the end effector to an un-articulated condition or to articulate the end effector in an opposite direction, a second articulation cable (not shown), extending through lumens 212e of joints 212 may be withdrawn in a proximal direction.

Figure 38:
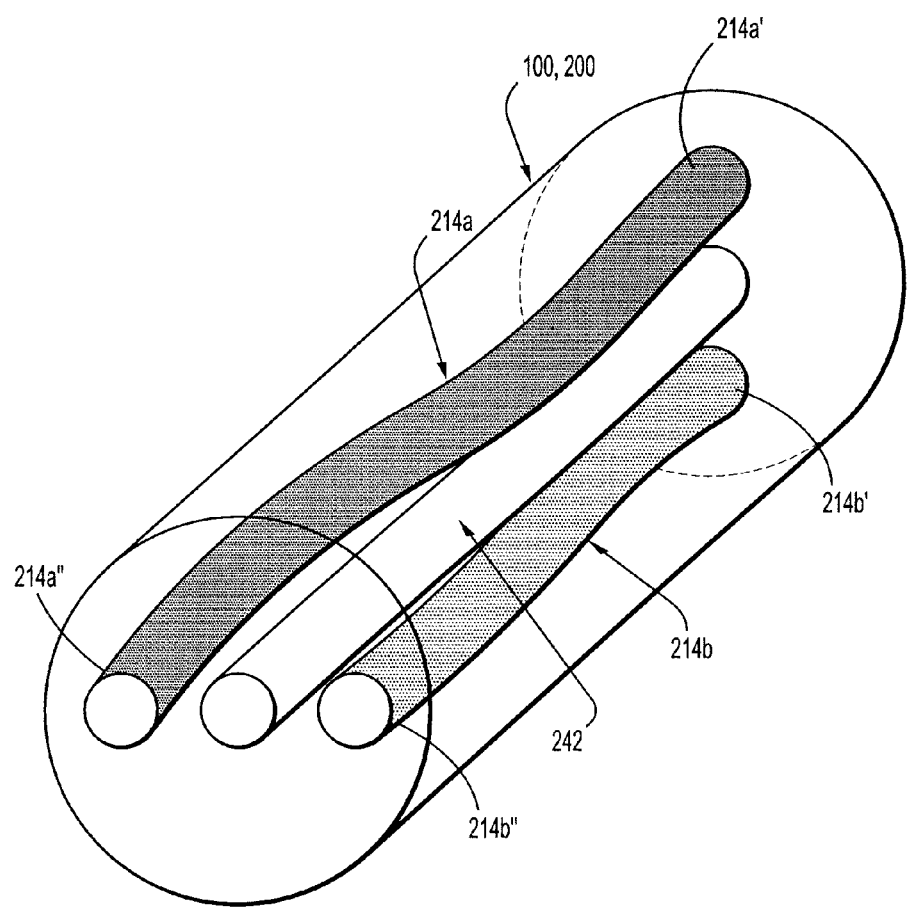
FIG. 38 is a schematic, perspective illustration of twisted wire arrangement for use in any of the end effectors disclosed herein.
Figure 39:
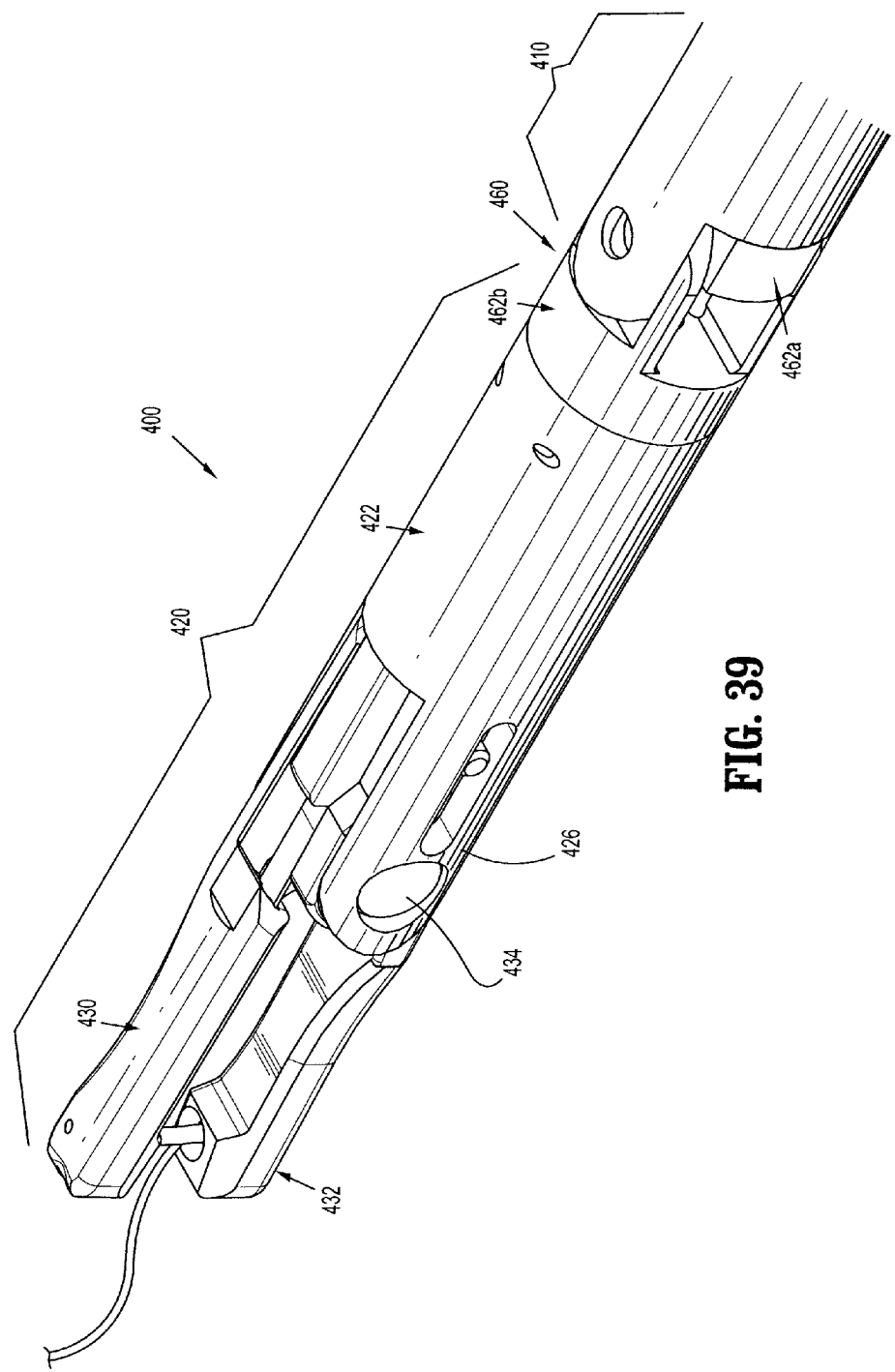
FIG. 39 is a perspective view of an end effector of a stitching device according to still another embodiment of the present disclosure.

Turning now to FIG. 38, a twisted wire arrangement for incorporation into any of the end effectors disclosed herein, is shown. As seen in FIG. 38, a central actuation cable 242 extends substantially longitudinally along a central axis of end effector 100, 200. A pair of opposed actuation cables 214a, 214b extend along opposed sides of central actuation cable 242. Proximal ends 214a', 214b' of each opposed actuation cable 214a, 214b define a first plane, while distal ends 214a", 214b" of each opposed actuation cable 214a, 214b define a second plane that is oriented at an angle with respect to the first plane, preferably oriented orthogonally with respect to the first plane. In other words, opposed actuation cables 214a, 214b wrap around central actuation cable 242 approximately 90° from a proximal end thereof to a distal end thereof.

In use, for example, proximal ends 214a', 214b' of opposed actuation cables 214a, 214b may extend through respective lumens 212d, 212e of joints 212 (see FIG. 32) and twist around central actuation cable 242 while passing through distal-most joint 213 such that distal ends 214a", 214b" enter opposed lumens 213d, 213e, respectively (see FIG. 32).

Alternatively, the end effector may be provided with a segment wherein each actuation cable 214a, 214b, 242 is un-guided (i.e., does not pass through a lumen or the like). In this manner, opposed actuation cables 214a, 214b may be wrapped around central actuation cable 242 by at least about 0°-180° in a clockwise and counter-clockwise direction, preferably about 90° in a clockwise and counter-clockwise direction.

It is contemplated that each actuation cable 214a, 214b, 242 is constructed from a flexible material capable of transmitting torsional forces and which is substantially incompressible and inextendable. Each actuation cable 214a, 214b, 242 may be constructed from stainless steel or any other material suitable for the intended purpose of transmitting torsional forces along a length thereof.

Turning now to FIGS. 39-51, an end effector, according to another embodiment of the present disclosure, is generally designated as end effector 400. End effector 400 is substantially similar to end effector 200 and thus will only be described herein to the extent necessary to identify differences in construction and operation thereof. Throughout the following disclosure, like reference numeral will be used to identify like elements.

Figure 40:
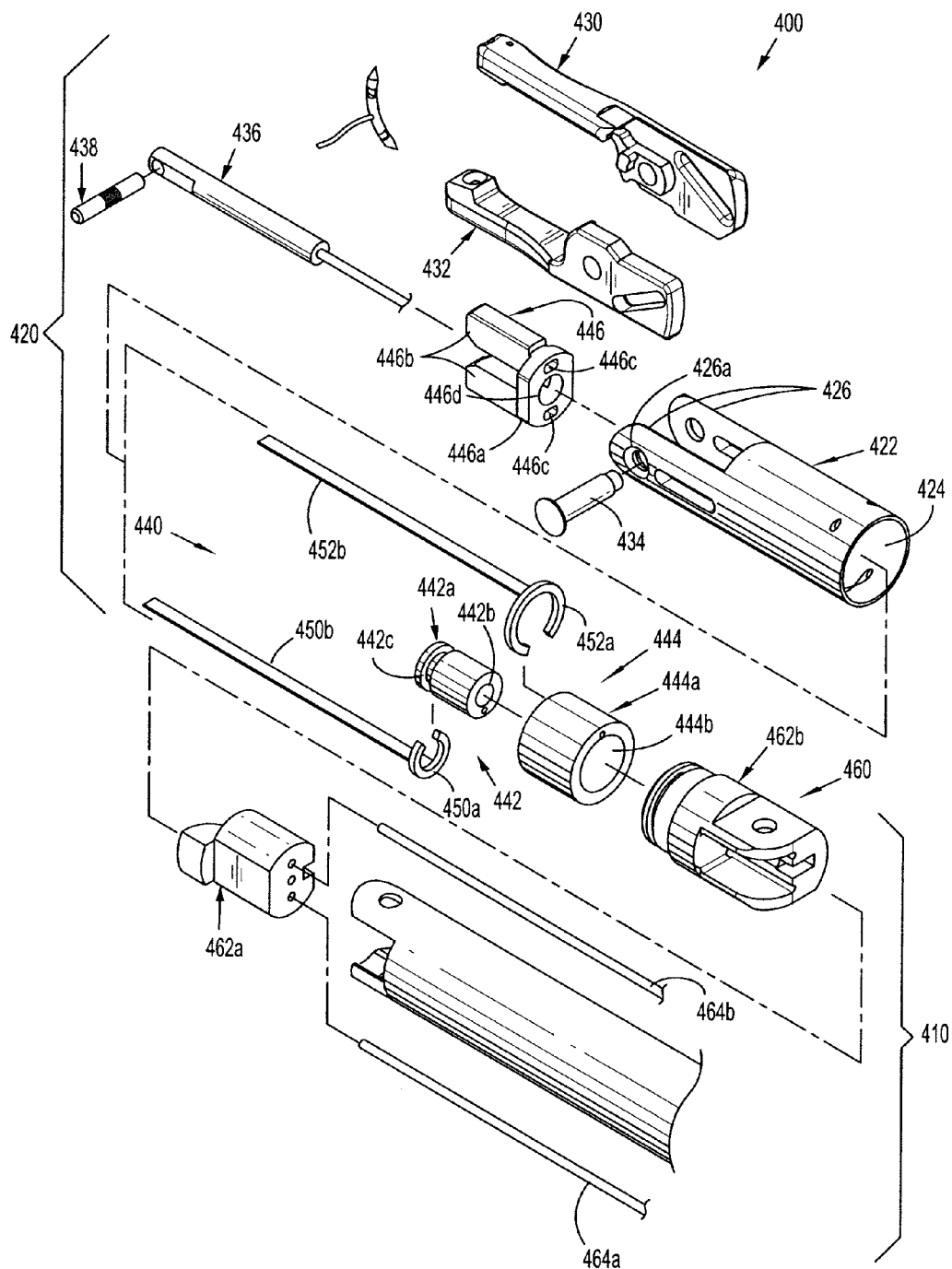
FIG. 40 is an exploded perspective view of the end effector of the stitching device of FIG. 39.
Figure 41:
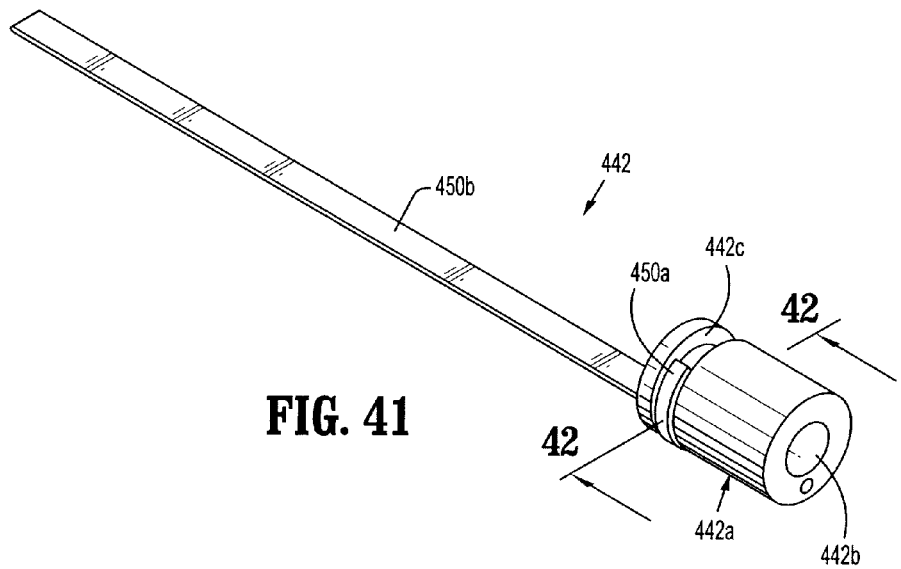
FIG. 41 is a perspective view of an inner drive assembly of the end effector of FIGS. 39 and 40.
Figure 42:
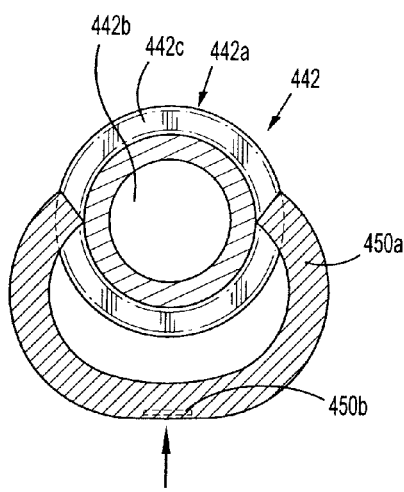
FIG. 42 is a cross-sectional view, as taken though 42-42 of FIG. 41, illustrating a connection of a blade member to an inner barrel of the inner drive assembly of FIG. 41.
Figure 43:
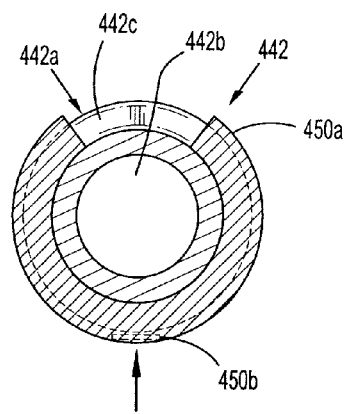
FIG. 43 is a cross-sectional view, as taken though 42-42 of FIG. 41, illustrating the blade member and the inner barrel of the inner drive assembly of FIG. 41 connected to one another.

As seen in FIGS. 39-51, end effector 400 includes a tool assembly 420 supported on an end of a neck assembly 410. Tool assembly 420 includes a jaw support member 422, and a pair of jaws 430, 432 mounted for pivotable movement on jaw support member 422. As seen in FIG. 40, jaw support member 422 defines a lumen 424 in a proximal end thereof and a pair of spaced apart arms 426 in a distal end thereof.

Each jaw 430, 432 is substantially similar to jaws 130, 132 described above in regard to end effector 100 and thus the construction of jaws 430, 432 will not be discussed in further detail herein below.

Jaws 430, 432 are pivotably mounted on support member 422 by means of a jaw pivot pin 434 which extend through holes 426a formed in arms 426 of support member 422 and respective pivot holes formed in jaws 430, 432. To move jaws 430, 432 between an open position and a closed position there is provided an axially or longitudinally movable center rod 436 having a camming pin 438 mounted at a distal end thereof. Camming pin 438 rides in and engages angled camming slots formed in respective jaws 430, 432 such that axial or longitudinal movement of center rod 436 causes jaws 430, 432 to be cammed between open and closed positions.

Tool assembly 420 includes a drive assembly 440 slidably and rotatably disposed within lumen 424 of support member 422. Drive assembly 440 includes an inner drive assembly 442 and an outer drive assembly 444. As seen in FIGS. 40-43, inner drive assembly 442 includes an inner barrel or collar 442a defining a lumen 442b there through and an annular groove 442c therearound. Lumen 442b is configured to slidably and rotatably receive center rod 436 therein. Inner drive assembly 442 further includes a ring 450a slidably supported in annular groove 442c, and a first blade 450b extending from ring 442d. Blade 450b extends from ring 450a in a direction substantially parallel to a central longitudinal axis of lumen 442b of inner barrel 442a.

As seen in FIGS. 40 and 44-46, outer drive assembly 444 includes an outer barrel or collar 444a defining a lumen 444b there through and an annular groove 444c formed in a surface of lumen 444b. Lumen 444b is configured to slidably and rotatably receive inner barrel 442a therein, such that inner barrel 442a is nested within lumen 444b of outer barrel 444a. Outer drive assembly 444 further includes a ring 452a slidably supported in annular groove 444c, and a second blade 452b extending from ring 444d. Blade 452b extends from ring 452a in a direction substantially parallel to a central longitudinal axis of lumen 444b of outer barrel 444a.

Tool assembly 420 further includes a clevis 446 disposed between arms 426 of support member 422. Clevis 446 includes a pair of spaced apart arms 446b extending from a base 446a. Each arm 446b defines a lumen 446c therethrough. Clevis 446 defines a central aperture 446d formed in base 446a. Arms 446b are spaced apart an amount sufficient and central aperture 446d of base 446b is dimensioned so as to slidably and rotatably receive center rod 436 therein.

Tool assembly 420, as discussed above, further includes a pair of needle engaging members or blades 450b, 452b which are slidably supported within a respective lumen 446c of arms 446b of clevis 446. Each blade 450b, 452b includes a distal end slidably extending into blade receiving channels 430d, 432d (see FIGS. 47-49) of respective jaws 430, 432.

In operation, as inner drive assembly 442 and outer drive assembly 444 are translated, in an axial direction, relative to one another, blades 450b, 452b are also translated with respect to one another.

End effector 400 includes a joint assembly 460 interconnecting neck assembly 410 and tool assembly 420. Joint assembly 460 may be in the form of a knuckle joint, wherein a first member 462a of joint assembly 460 is supported in or at a distal end of a shaft or tubular housing 412 of neck assembly 410, and a second member 462b of joint assembly 460 is supported at or in a proximal end of support member 422 of tool assembly 420. Joint assembly 460 enables tool assembly 420 to articulate or pivot, about at least one axis, relative to neck assembly 410.

End effector 400 further includes a pair of pusher-rods 464a, 464b each extending through respective lumens formed in first member 462a and second member 464b of joint assembly 460, and secured to inner barrel 442a of inner drive assembly 442 and outer barrel 444a of outer drive assembly 444, respectively. In use, as pusher-rods 464a, 464b are translated relative to one another respective inner barrel 442a and outer barrel 444a are translated relative to one another.

Figure 47:
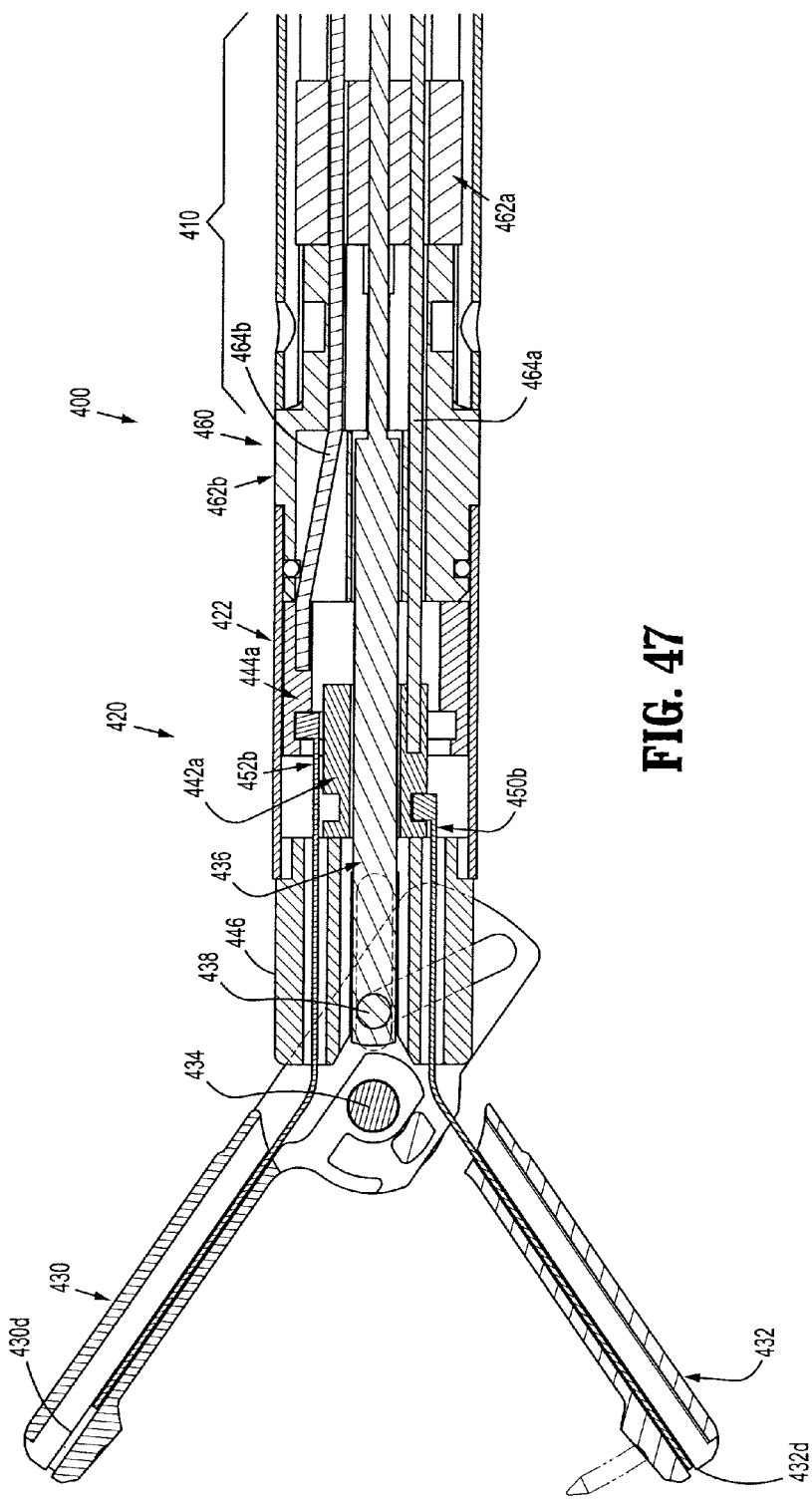
FIG. 47 is a longitudinal, cross-sectional view of the end effector of FIGS. 39 and 40, illustrating the end effector is a first condition.

Turning now to FIGS. 47-51, a method of operating end effector 400 is shown and described. As seen in FIG. 47, when pusher-rod 464a is at a distal-most position, inner barrel 442a and blade 450b are at a distal-most position, meanwhile pusher-rod 464b may be desirably maintained at a proximal-most position so as to maintain outer barrel 444a and blade 452b at a proximal-most position. It is contemplated that pusher-rods 464a, 464b may be maintained at any axial location relative to one another so as to maintain respective inner barrel 442a and blade 450b, and outer barrel 444a and blade 452b at any axial location relative to one another.

Figure 48:
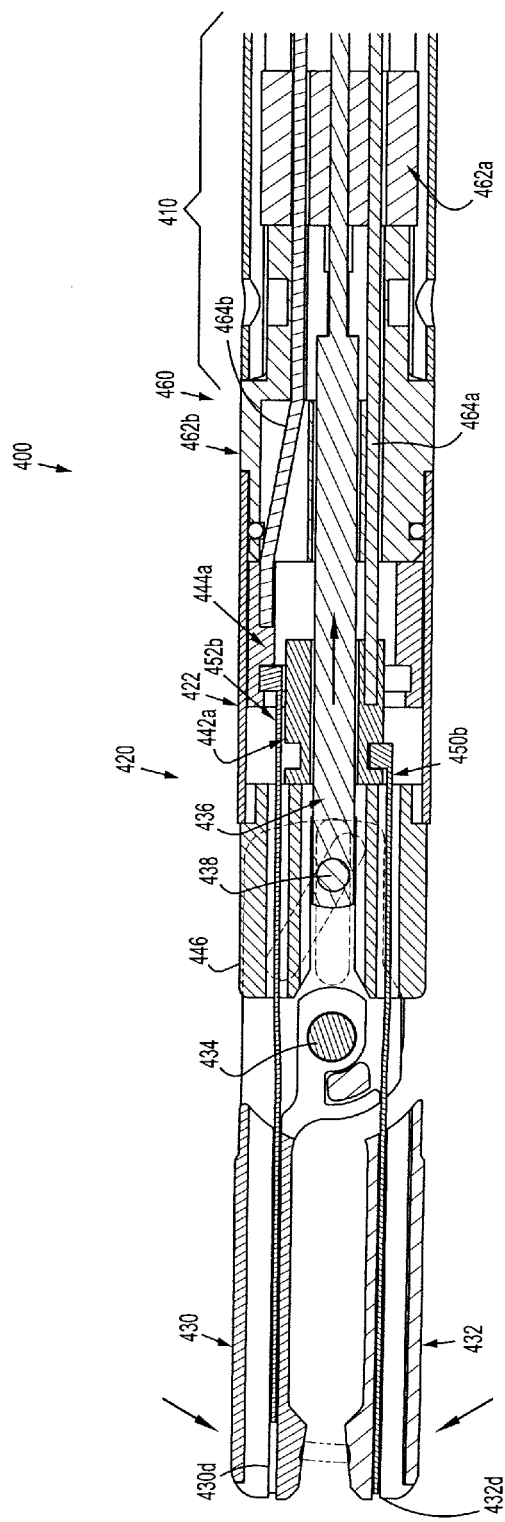
FIG. 48 is a longitudinal, cross-sectional view of the end effector of FIGS. 39 and 40, illustrating the end effector is a second condition.

As seen in FIGS. 47 and 48, when center rod 436 is at a distal-most position, jaws 430, 432 are in an open condition, and when center rod 436 is retracted, relative to end effector 400, jaws 430, 432 are in a closed condition. Similar to end effector 200, in order to open or close jaws 430, 432, of end effector 400, central rod 436 is translated in an axial direction to move camming pin 438. Camming pin 438 rides through the camming slots of jaws 430, 432 thus causing jaws 430, 432 to pivot about pivot pin 434 and cause distal ends of jaws 430, 432 to open or close.

Figure 49:
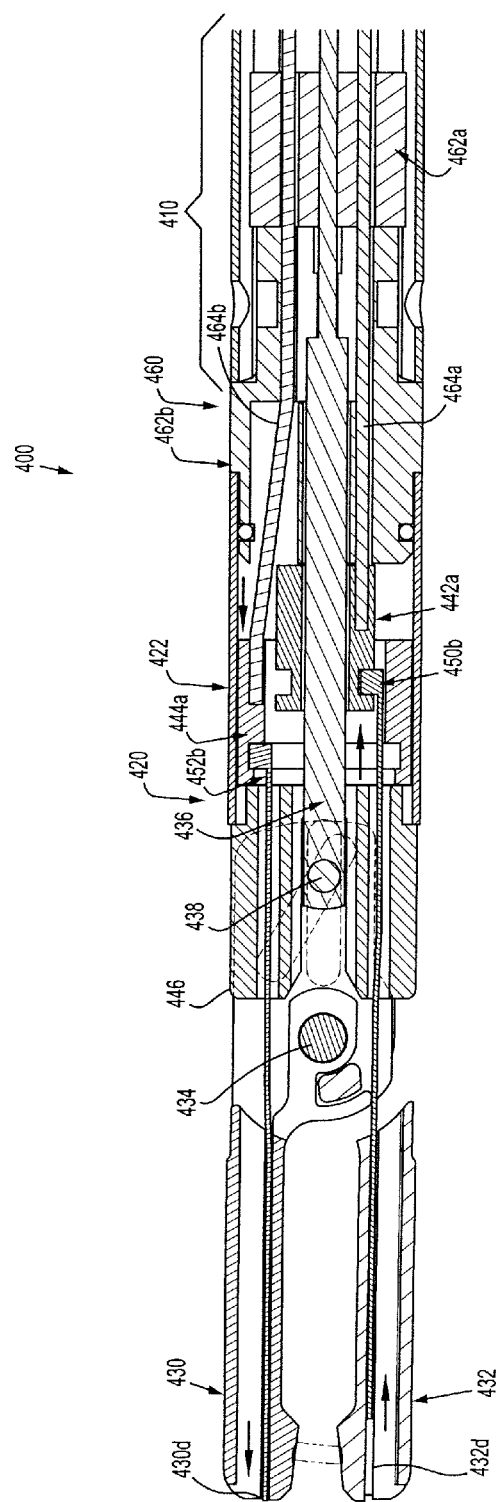
FIG. 49 is a longitudinal, cross-sectional view of the end effector of FIGS. 39 and 40, illustrating the end effector is a third condition.

A seen in FIGS. 47-49, when pusher-rod 464a is moved in a proximal direction to a proximal-most position, inner barrel 442a and blade 450b are moved in a proximal direction, and when pusher-rod 464b is moved in a distal direction to a distal-most position, outer barrel 444a and blade 452b are moved in a distal direction.

As seen in FIGS. 50 and 51, upon rotation of center rod 436 about a longitudinal axis thereof, camming pin 438 acts on arms 426 of support member 422 to cause support member 422 and tool assembly 420 to rotate relative to neck assembly 410. As tool assembly 420 is rotated, rings 450a, 452a of respective inner and outer drive assemblies 442, 444, are rotated relative to respective inner and outer barrels 442a, 444a, thereby allowing respective blades 450b, 452b to rotate with tool assembly 420.

Turning now to FIGS. 52-55, an end effector, according to another embodiment of the present disclosure, is generally designated as end effector 500. End effector 500 is substantially similar to end effector 400 and thus will only be described herein to the extent necessary to identify differences in construction and operation thereof. Throughout the following disclosure, like reference numeral will be used to identify like elements.

As seen in FIGS. 52-55, pusher-rods 464a, 464b have been replaced by arms 564a, 564b extending proximally from respective inner and outer barrels 542a, 544a. Tool assembly 520 of end effector 500 includes a camming hub 566 defining a lumen 566a therethrough configured and adapted to slidably receive a portion of center rod 536 therein. Camming hub 566 defines a substantially helical or spiral groove 566b in an outer surface thereof configured for slidable receipt of a nub projecting from arms 564a, 564b. Camming hub 566 is configured for rotatable disposition within lumen 524 of support member 522.

Figure 52:
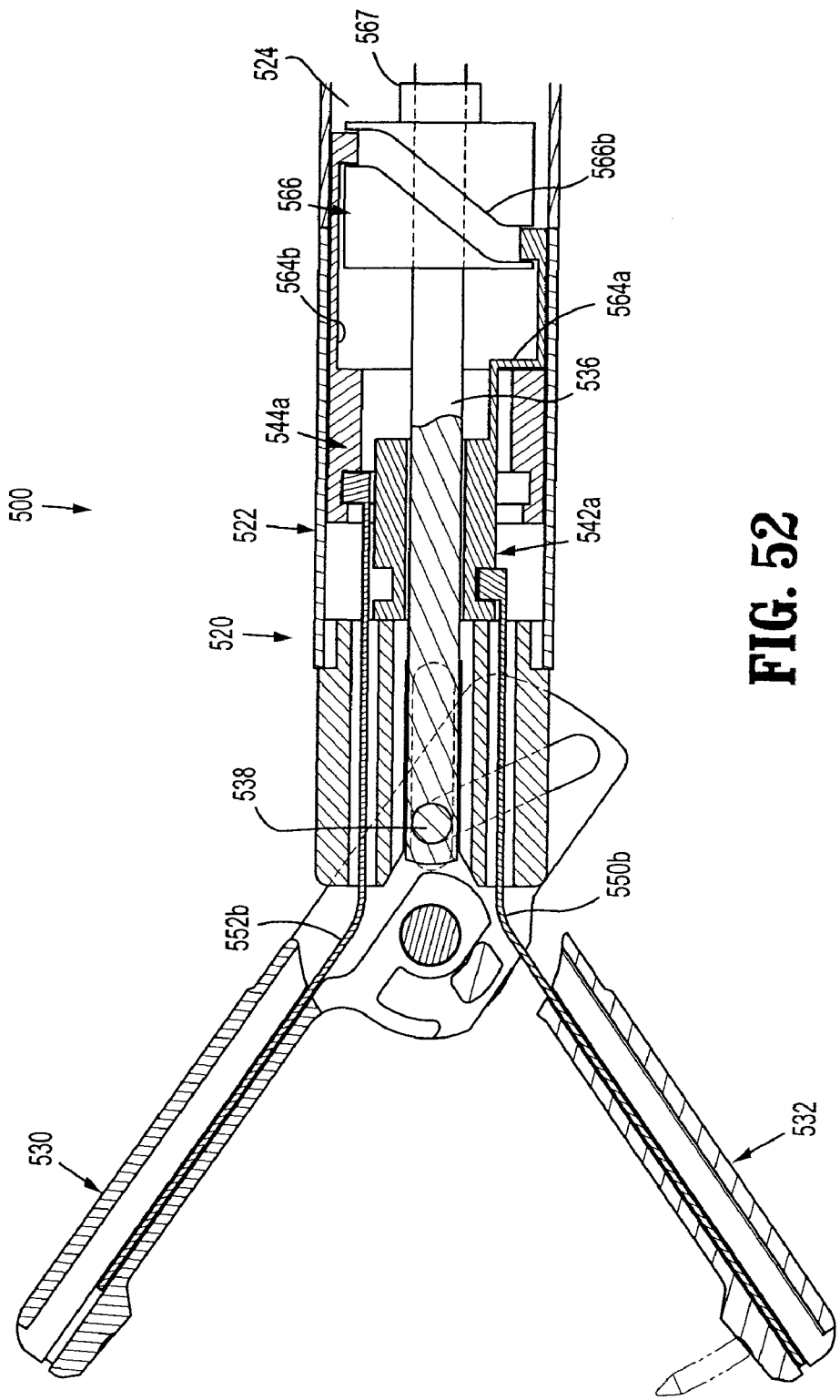
FIG. 52 is a longitudinal, cross-sectional view of an end effector according to a further embodiment of the present disclosure, shown in a first condition.
Figure 55:
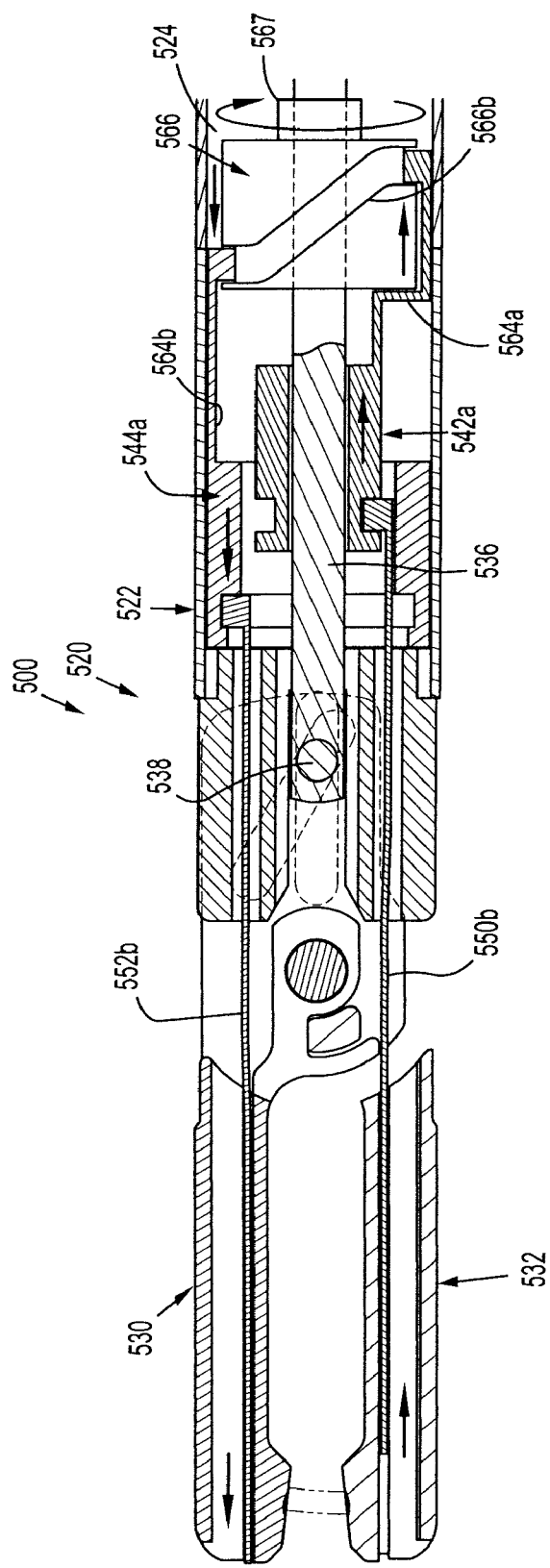
FIG. 55 is a longitudinal, cross-sectional view of the end effector of FIGS. 52 and 53, shown in a third condition.

With continued reference to FIGS. 52-55, a method of operating end effector 500 is shown and described. As seen in FIG. 52, when inner barrel 542a and blade 550b are at a distal-most position, outer barrel 544a and blade 552b are at a proximal-most position.

As seen in FIGS. 52 and 53, when center rod 536 is at a distal-most position, jaws 530, 532 are in an open condition, and when center rod 536 is retracted, relative to end effector 520, jaws 530, 532 are in a closed condition. Similar to end effector 200, in order to open or close jaws 530, 532, of end effector 500, central rod 536 is translated in an axial direction to move camming pin 538. Camming pin 538 rides through the camming slots of jaws 530, 532 thus causing jaws 530, 532 to pivot about pivot pin 534 and cause distal ends of jaws 530, 532 to open or close.

A seen in FIGS. 52-55, when camming hub 566 is rotated by a drive tube 567, nubs of arms 564a, 564b ride within groove 566b of camming hub 566 and are translated, in an axial direction, relative thereto. In particular, upon rotation of camming hub 566, as arm 564a is moved proximally, inner barrel 542a is moved proximally, and concomitantly therewith arm 564b is moved distally thereby moving outer barrel 544a distally, and vise-versa. As inner barrel 542a is moved in a proximal direction, blade 550b is also moved in a proximal direction, and concomitantly therewith since outer barrel 544a is moved in a distal direction, blade 552b is moved in a distal direction.

Turning now to FIGS. 56-59, an end effector, according to another embodiment of the present disclosure, is generally designated as end effector 600. End effector 600 is substantially similar to end effector 400 and thus will only be described herein to the extent necessary to identify differences in construction and operation thereof. Throughout the following disclosure, like reference numeral will be used to identify like elements.

As seen in FIGS. 56-59, pusher-rods 664a, 664b extend from respective distal and proximal barrels 642a, 644a. Distal and proximal barrels 642a, 644a are not configured for nesting within one another, in the manner of inner and outer barrels 442a, 444a.

Figure 56:
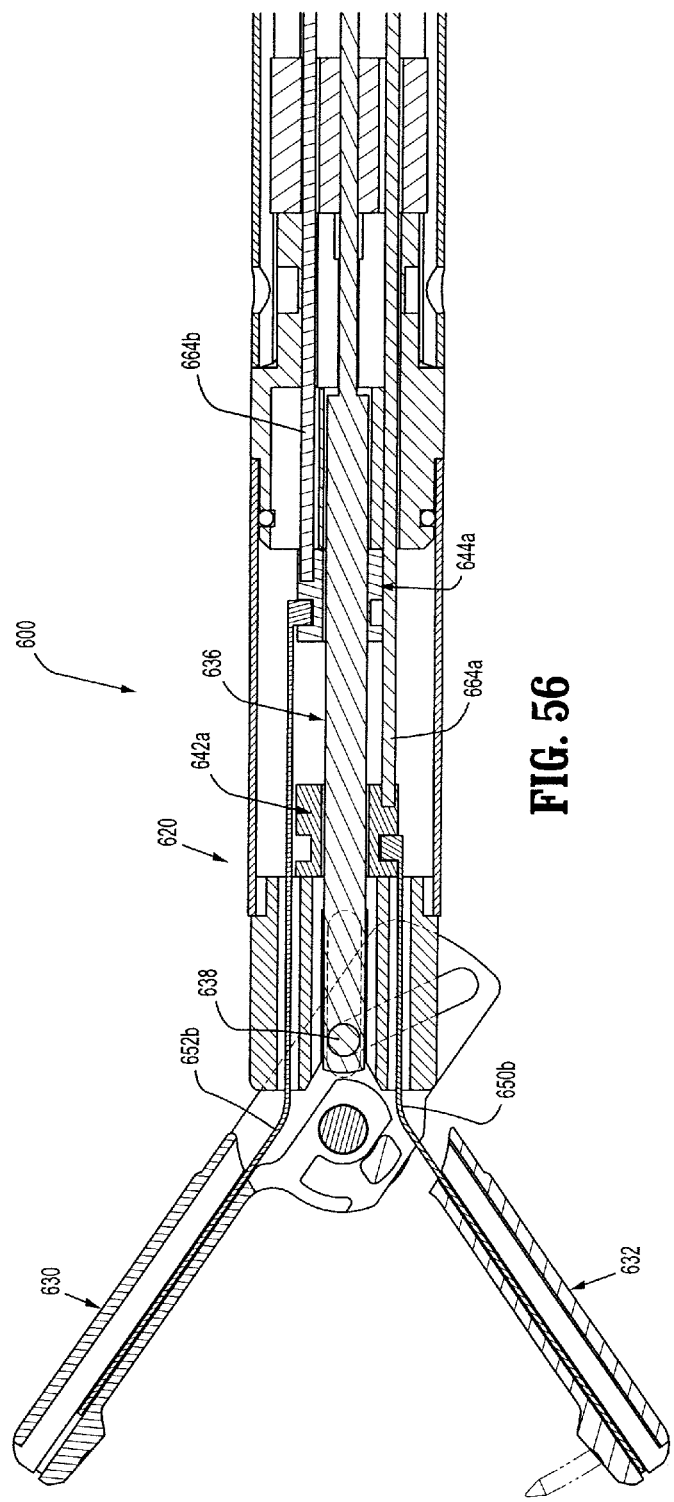
FIG. 56 is a longitudinal, cross-sectional view of an end effector according to yet another embodiment of the present disclosure, shown in a first condition.

With continued reference to FIGS. 56-59, a method of operating end effector 600 is shown and described. As seen in FIG. 56, when pusher-rod 664a is at a distal-most position, distal barrel 642a and blade 650b are at a distal-most position, meanwhile pusher-rod 664b may be desirably maintained at a proximal-most position so as to maintain proximal barrel 644a and blade 652b at a proximal-most position. It is contemplated that pusher-rods 664a, 664b may be maintained at any axial location relative to one another so as to maintain respective distal barrel 642a and blade 650b, and proximal barrel 644a and blade 652b at any axial location relative to one another.

As seen in FIGS. 56 and 57, when center rod 636 is at a distal-most position, jaws 630, 632 are in an open condition, and when center rod 636 is retracted, relative to end effector 600, jaws 630, 632 are in a closed condition. Similar to end effector 200, in order to open or close jaws 630, 632, of end effector 600, central rod 636 is translated in an axial direction to move camming pin 638. Camming pin 638 rides through the camming slots of jaws 630, 632 thus causing jaws 630, 632 to pivot about pivot pin 634 and cause distal ends of jaws 630, 632 to open or close.

Figure 59:
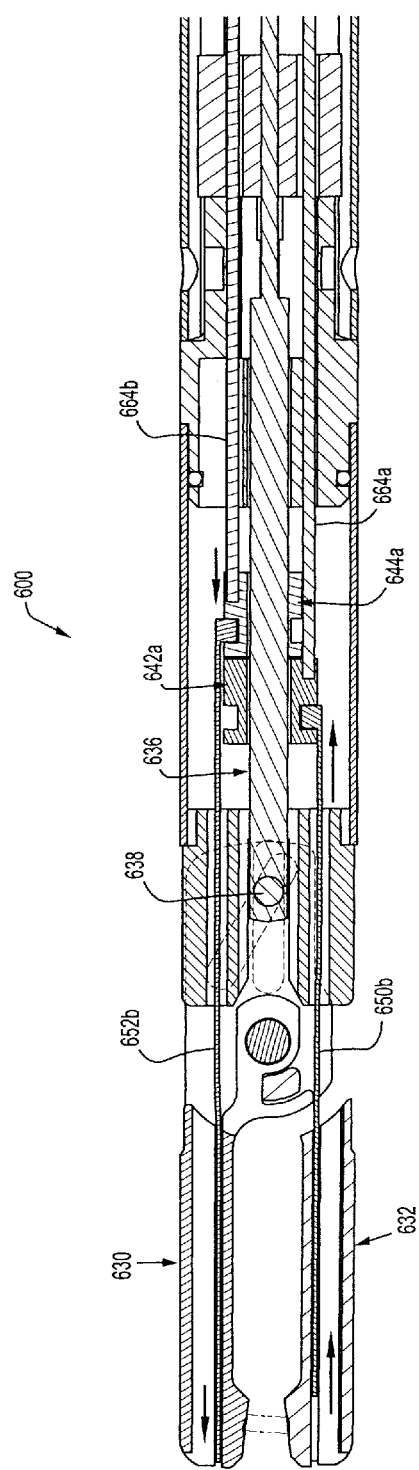
FIG. 59 is a longitudinal, cross-sectional view of the end effector of FIGS. 56 and 57, shown in a third condition.

A seen in FIGS. 56-59, when pusher-rod 664a is moved in a proximal direction to a proximal-most position, distal barrel 642a and blade 650b are moved in a proximal direction, and when pusher-rod 664b is moved in a distal direction to a distal-most position, proximal barrel 644a and blade 652b are moved in a distal direction. As seen in FIG. 59, either pusher-rod 664a, 664 may be moved until distal barrel 642a and proximal barrel 644a are in contact with one another.

Figure 60:
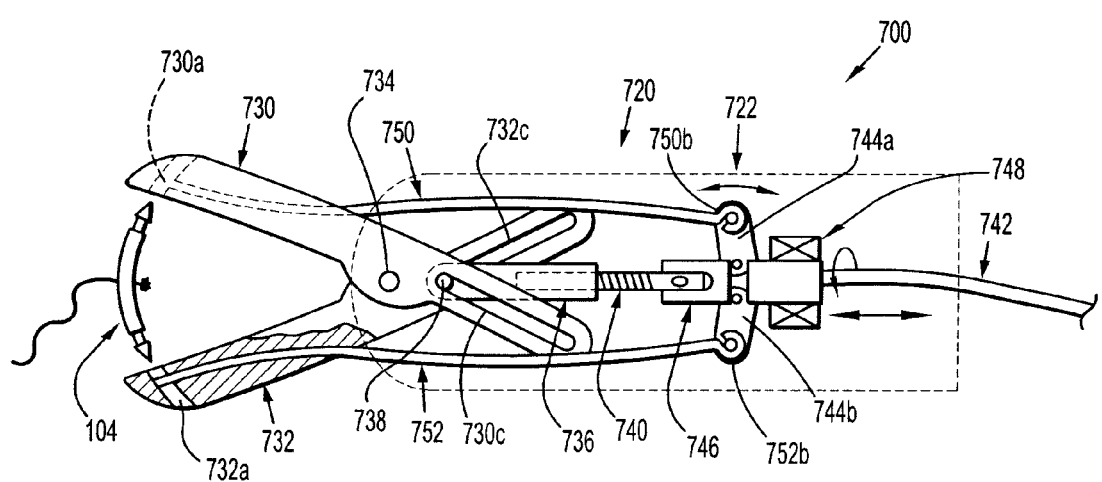
FIG. 60 is a schematic illustration of an end effector and drive assembly according to another embodiment of the present disclosure.

Turning now to FIG. 60, an end effector, according to another embodiment of the present disclosure, is generally shown as 700.

End effector 700 includes a neck assembly (not shown), and a tool assembly 720 supported on a distal end of the neck assembly. As seen in FIG. 60, tool assembly 720 of end effector 700 includes a jaw support member 722, and a pair of jaws 730, 732 mounted for pivotable movement on jaw support member 722.

Each jaw 730, 732 includes a needle receiving recess 730a, 732a, respectively, configured to surround and hold at least a portion of a surgical needle 104 disposed therein substantially perpendicular to tissue engaging surfaces thereof.

Jaws 730, 732 are pivotably mounted on support member 722 by means of a jaw pivot pin 734. To move jaws 730, 732 between an open position and a closed position there is provided an axially or longitudinally movable center rod 736 having a camming pin 738 mounted at a distal end thereof. Camming pin 738 rides in and engages angled camming slots 730c, 732c formed in respective jaws 730, 732 such that axial or longitudinal movement of center rod 736 causes jaws 730, 732 to be cammed between open and closed positions.

Tool assembly 720 includes a lead screw 740 having a distal end threadably connected to a proximal end of center rod 736. Lead screw 740 includes a proximal end fixedly connected to a distal end of an actuation cable 742 via a coupling 746. Actuation cable 742 rotatably and slidably extends through a bearing 748.

Tool assembly 720 further includes a bell crank 744 pivotally supported on support member 722. Bell crank 244 includes a pair of opposed arms or levers 744a, 744b.

In operation, rotation of actuation cable 742 imparts rotation to coupling 746 and lead screw 740 which, in turn, imparts axial reciprocal translation to center rod 736 and camming pin 738. Thus, rotation of actuation cable 742 results in the approximation (closing) or separation (opening) of jaws 730, 732 relative to one another.

Tool assembly 720 further includes a pair of needle engaging members or blades 750, 752 which are slidably supported within respective blade receiving channels of jaws 730, 732. The channels of jaws 730, 732 are dimensioned and configured so as to at least partially intersect needle recesses 730a, 732a. Thus, by advancing blade 750 or 752 within a respective channel, a distal end 750a, 752a of the advancing blade 750 or 752 engages or "locks in" a groove of needle disposed within the respective recess 730a, 732a. Each blade 750, 752 includes a proximal end 750b, 752b pivotably connected to a free end of a respective lever 744a, 744b of bell crank 744.

In operation, as actuation cable 742 axially reciprocated, levers 744a, 744b are actuated in opposite directions to move respective blades 750, 752 in a respective axial direction relative thereto. In particular, upon axial movement of actuation cable 742 in a first direction, lever 744a, and in turn blade 750, is caused to be moved in a first direction while lever 744b, and in turn blade 752, is caused to be moved in a second direction, and vise-versa.

Figure 61:
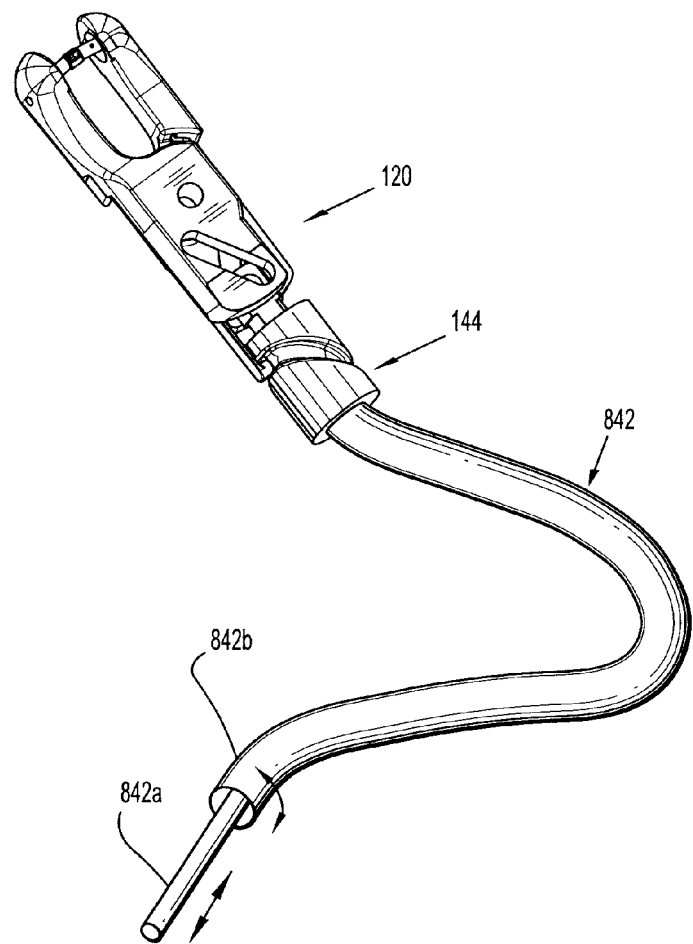
FIG. 61 is a schematic illustration of a drive assembly, for an end effector, according to another embodiment of the present disclosure.

Turning now to FIG. 61, a drive assembly or actuation cable assembly 842, for use with the end effectors of the present disclosure, is shown and will be described. Drive assembly 842 includes an inner cable 842a and an outer tube or sheath 842b rotatably and slidably extending over inner cable 842a. Inner cable 842a is fabricated from a suitable material capable or transmitting axial tensile and compressive forces, and torsional or rotational forces. Outer tube 842b is fabricated from a suitable material also capable or transmitting axial tensile and compressive forces, and torsional or rotational forces.

Figure 62:
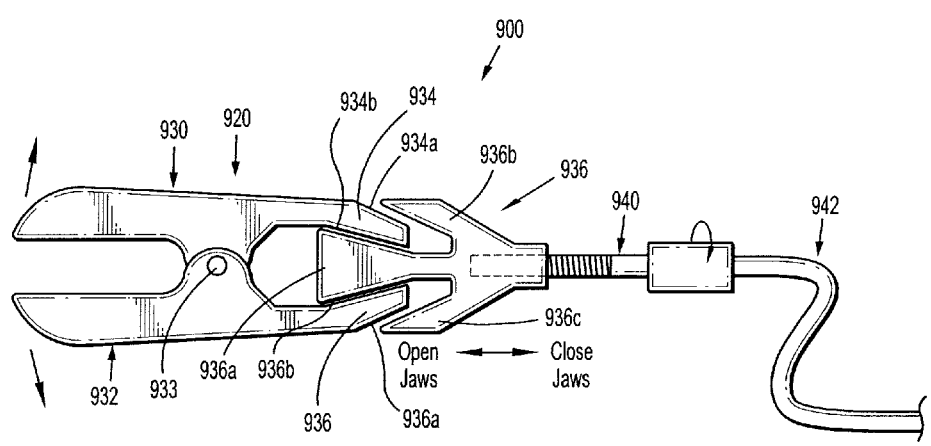
FIG. 62 is a schematic illustration of an end effector according to yet another embodiment of the present disclosure.

Turning now to FIG. 62, an end effector, according to another embodiment of the present disclosure, is generally shown as 900. End effector 900 includes a tool assembly 920 having a pair of jaws 930, 932 pivotably associated with one another. Jaws 930, 932 are pivotably associated with one another by means of a jaw pivot pin 933. Each jaw 930, 932 includes a respective proximal end or tail 934, 936 converging toward one another. Each tail 934, 936 includes a respective outer surface 934a, 936a, and a respective inner surface 934b, 936b.

Tool assembly 920 includes a lead screw 940, fixedly connected to actuating cable 942, and having a distal end threadably connected to a proximal end of a wedge member 936. Wedge member 936 includes a distally extending head portion 936a interposed between tails 934, 936 of jaws 930, 932, and arms 936b, 936c disposed outside of respective tails 934, 936. Head portion 936a may by triangular, conical or any other suitably shaped configuration selected for the intended purpose of separating tails 934, 936 from one another as wedge member 936 is moved in a first direction away from pivot pin 933. Arms 936b, 936c may extend distally or toward pivot pin 933, may comprise a portion of a flange or skirt extending toward pivot pin 933, or may comprise any other suitably shaped configuration selected for the intended purpose of approximating tails 934, 936 toward one another as wedge member 936 is moved in a second direction toward pivot pin 933.

In operation, to close jaws 930, 932 from an open condition, actuation cable 942 is rotated in a first direction to rotate lead screw 940 in a first direction and move wedge member 936 is a first direction axially rearward. In so doing, head portion 936a of wedge member 936 is moved in an axially rearward direction, away from pivot pin 933, to engage and separate tails 934, 936 of jaws 930, 932 from one another to thereby close jaws 930, 932.

Similarly, to open jaws 930, 932 from a closed condition, actuation cable 942 is rotated in a second direction to rotate lead screw 940 in a second direction and move wedge member 936 is a second direction axially forward. In so doing, arms 936b, 936c of wedge member 936 are moved in an axially forward direction, toward pivot pin 933, to engage and approximate tails 934, 936 of jaws 930, 932 towards one another to thereby open jaws 930, 932.

Figure 63:
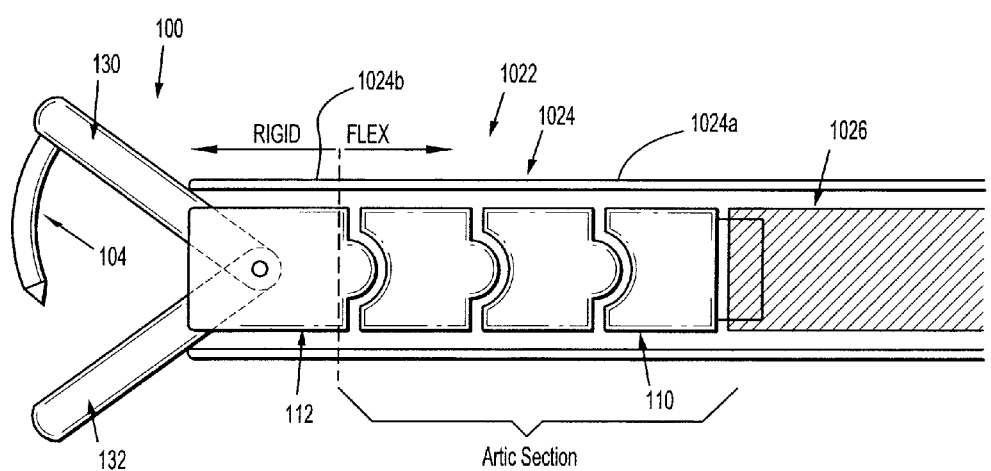
FIG. 63 is a schematic illustration of a closure member according to an embodiment of the present disclosure, for an end effector of the present disclosure.

Turning now to FIG. 63, a closure member in accordance with an embodiment of the present disclosure, for any of the end effectors disclosed herein, is generally shown as 1022. Closure member 1022 includes an outer tube 1024 having a proximal portion 1024a which is flexible or resilient and a distal portion 1024b which is rigid or has a fixed configuration. It is contemplated that proximal portion 1024a of outer tube 1024 is fabricated from a suitable material which is not axially compressible or extensible. Closure member 1022 includes an inner flexible tube 1026 rotatably and slidably disposed within outer tube 1024. Inner flexible tube 1026 includes a distal end configured to operatively engage and support joints 112 of neck assembly 110.

It is contemplated that jaws 130, 132 may be biased to an open condition by a suitable biasing member (not shown).

In operation, outer tube 1024 of closure member 1022 is reciprocably translated relative to inner tube 1026 and jaws 130, 132 to open and close jaws 130, 132 as needed and/or desired. With jaws 130, 132 in an open condition and distal portion 1024b of outer tube 1024 located proximal of jaws 130, 132, in order to close jaws 130, 132, outer tube 1024 is axially advanced relative to inner tube 1026 and jaws 130, 132 such that distal portion 1024b of outer tube 1024 engages a rear or back surface of jaws 130, 132 and cams or urges jaws 130, 132 relative to one another and biases the biasing member. With jaws 130, 132 in a closed condition, at least partially within outer tube 1024, in order to open jaws 130, 132, outer tube 1024 is axially retracted relative to inner tube 1026 and jaws 130, 132 such that distal portion 1024b of outer tube 1024 disengages a rear or back surface of jaws 130, 132 and jaws 130, 132 are separated relative to one another by the un-biasing of the biasing member.

Figure 64:
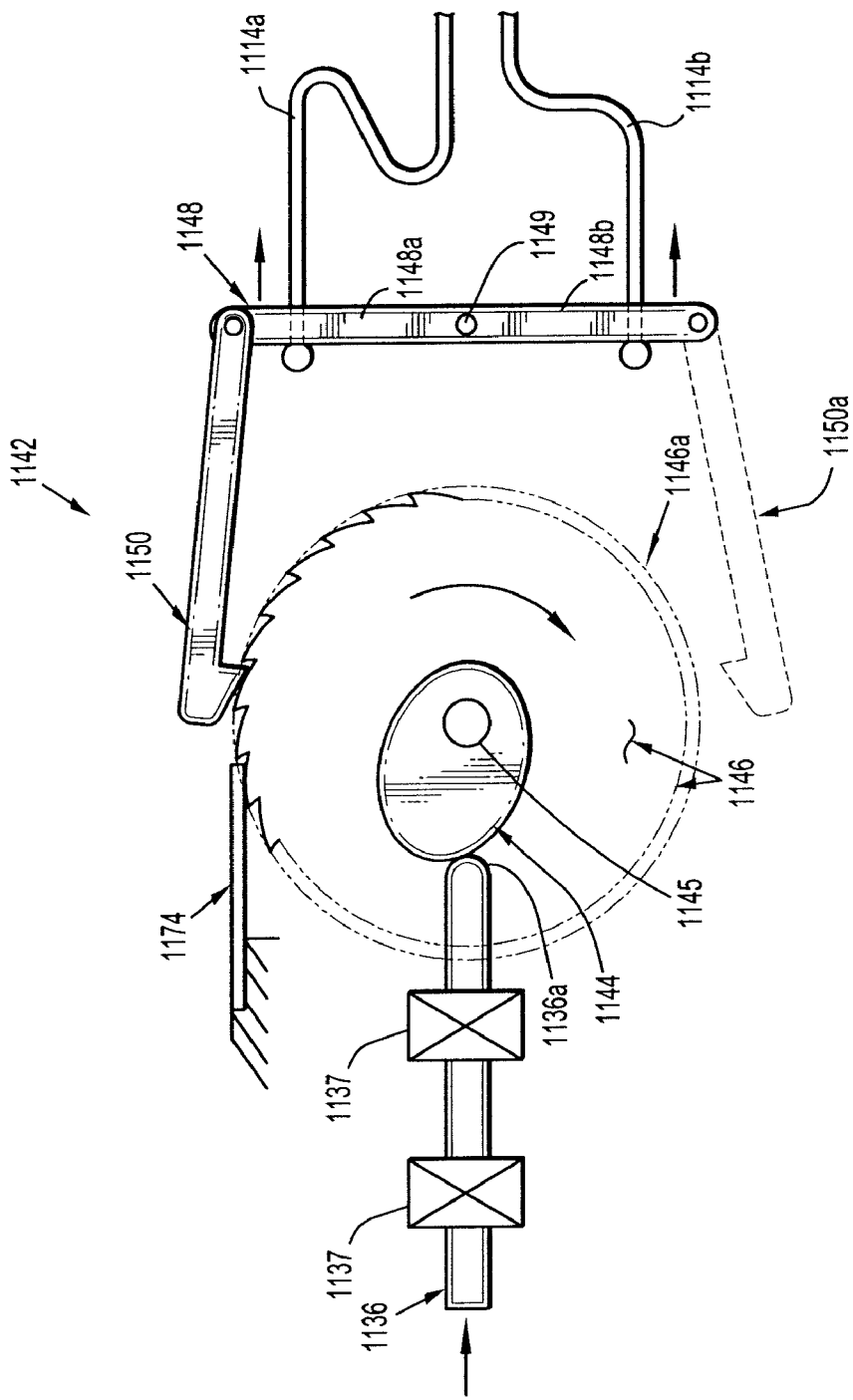
FIG. 64 is a schematic illustration of a drive assembly, for an end effector, according to yet another embodiment of the present disclosure.

Turning now to FIG. 64, a drive assembly 1142, for use with the end effectors of the present disclosure, is shown and will be described. As seen in FIG. 64, drive assembly 1142 includes a center rod or actuation rod 1136 slidably supported on at least one bushing 1137 and includes a proximal end 1136a. Drive assembly 1142 includes an eccentric cam 1144 rotatably supported on a pin 1145. A surface of cam 1144 is in slidable contact with proximal end 1136a of actuation rod 1136. It is contemplated that actuation rod 636 is biased into engagement or contact with the surface of cam 1144.

Drive assembly 1142 further includes a toothed wheel or gear 1146 supported on pin 1145 and keyed to cam 1144. Drive assembly 1142 may include a latch 647 operatively engaged with the teeth of gear 1146 to allow for gear 1146 to only rotate in a single direction.

Drive assembly 1142 further includes a bell crank 1148 pivotably supported on a pin 1149. Bell crank 1148 include a pair of arms 1148a, 1148b extending away from pin 1149. Drive assembly 1142 includes a pawl 1150 pivotably connected to arm 1148a of bell crank 1148 and biased against the teeth of gear 1146. Pawl 1150 is configured to impart rotation to gear 1146 in a single direction.

Drive assembly 1142 further includes a pair of reigns or actuation cables 1114a, 1114b. Actuation cables 1114a, 1114b may be connected to a respective arm 648a, 1148b of bell crank 1148.

In operation, as first actuation cable 1114a is pulled, arm 1148a of ball crank 1148 is moved to pull on pawl 1150 in a first direction. As pawl 1150 is moved in a first direction, gear 1146 is rotated in a first direction thus causing cam 1144 to rotate in a first direction. As cam 1144 is rotated, actuation rod 1136 rides along an outer surface thereof to move is an axially distal or proximal direction. Once the stroke or pull of first actuation cable 1114a is complete, second actuation cable 1114b is pulled to reset pawl 1150.

As second actuation cable 1114b is pulled, arm 1148b of ball crank 1148 is moved to move arm 1114a in a second direction to push pawl 1150 in a second direction. As pawl 1150 is moved in a second direction, pawl 1150 rides over the teeth of gear 1146 and latch 1124 prevents gear 1146 from rotating in a second direction and thus cam 1144 is prevented from rotating in a second direction.

The pulling of actuation cables 1114a, 1114b is continuously repeated to move actuation rod 1136 in a distal and a proximal direction to open and close jaws of an end effector, as described in embodiments disclosed herein.

If desired, a second gear 1146*a* and a second pawl 1150*a* may be provided to cause rotation of cam 1144 in a second direction as second actuation cable 1114*b* is pulled.

In an embodiment, it is contemplated that a first bevel gear may be keyed to gear 1146 such that rotation of gear 1146 may rotate the first bevel gear, and a second bevel gear may be operatively connected to the first bevel gear such that rotation of the first bevel gear may be used to impart an axial rotation to a drive rod via the second bevel gear.

Figure 65A:
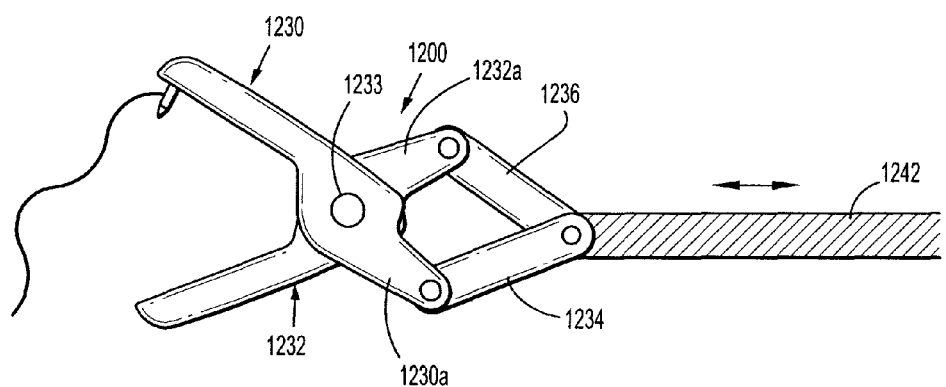
FIGS. 65A-65B are schematic illustrations of an end effector according to still another embodiment of the present disclosure.
Figure 65B:
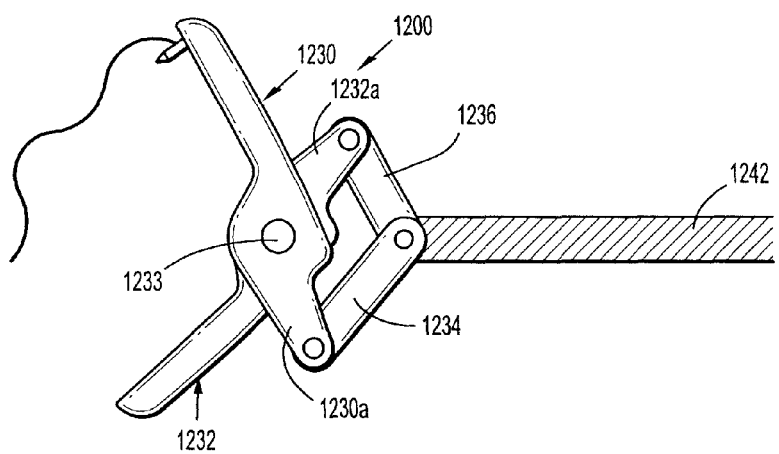

Turning now to FIG. 65, an end effector according to another embodiment of the present disclosure, is generally shown as 1200. End effector 1200 includes a pair of jaws 1230, 1232 pivotably joined to one another by a pivot pin 1234. Each jaw 1230, 1232 includes a tail portion 1230*a*, 1232*a* extending proximally of pivot pin 1233.

End effector 1200 further includes a pair of links 1234, 1236 pivotably connected to an end of a respective tail portion 1230*a*, 1232*a* of jaws 1230, 1232. A free end of each link 1234, 1236 is pivotably joined to one another and is operatively connected to an actuation cable 1242.

In this embodiment, as actuation cable 1242 is moved in a proximal direction relative to pivot pin 1233, jaws 1230, 1232 are caused to be approximated towards one another. Additionally, as actuation cable 1242 is moved in a distal direction relative to pivot pin 1233, jaws 1230, 1232 are caused to be separated from one another. Similar to a pantograph mechanism, links 1234, 1236 enable jaws 1230, 1232 to be opened to approximately 180° relative to one another in order to grasp flat gastric walls or the like.

Figure 66:
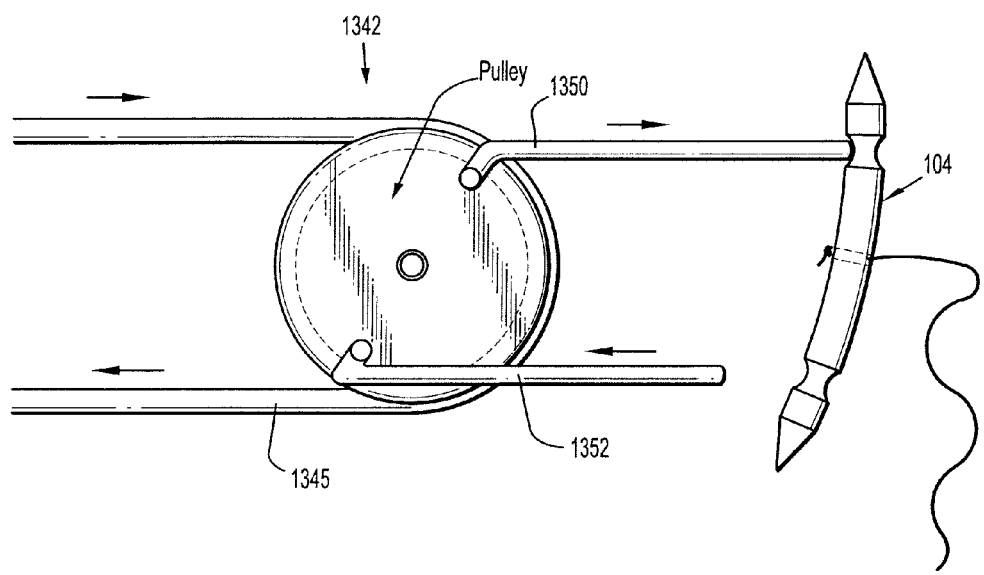
FIG. 66 is a schematic illustration of a drive assembly, for an end effector, according to still another embodiment of the present disclosure.

Turning now to FIG. 66, a drive assembly 1342 for any of the end effectors disclosed herein is shown and will be described. As seen in FIG. 66, drive assembly 1342 includes a pulley 1344 pivotably supporting blades 1350, 1352 at substantially diametrically opposed sides thereof. Drive assembly 1342 further includes a cable or belt 1345 extending around pulley 1344.

In use, as an end of cable 1345 is pulled in a first direction, blade 1350 is advanced, to selectively engage needle 104, and blade 1352 is retracted. Additionally, as an end of cable 1345 is pulled in a second direction, blade 1352 is advanced, to selectively engage needle 104, and blade 1350 is retracted.

Figure 67A:
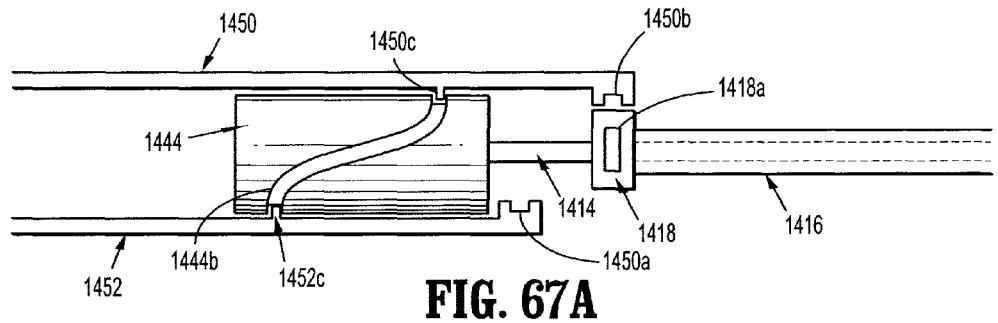
FIGS. 67A-67B are schematic illustrations of a drive assembly, for an end effector, according to another embodiment of the present disclosure.
Figure 67B:
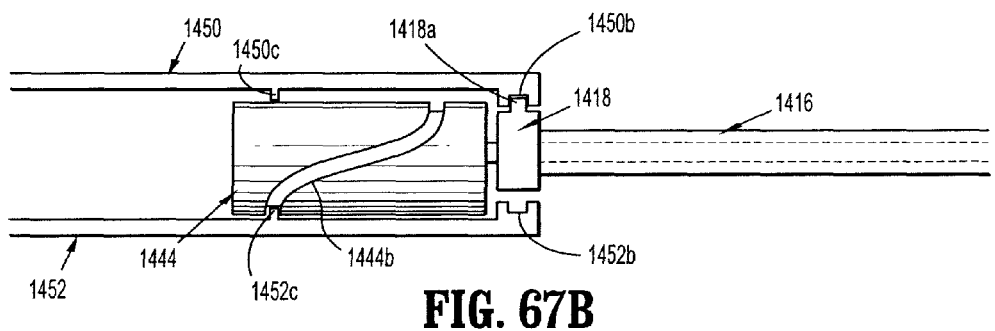

Turning now to FIGS. 67A and 67B, a drive assembly 1442 for any of the end effectors disclosed herein is shown and will be described. As seen in FIGS. 67A and 67B, drive assembly 1442 includes a camming hub 1444 supported on a drive cable 1414. Camming hub 1444 defines a spiral groove 1444*b* configured to slidably and selectively receive a follower 1450*c*, 1452*c* of a respective blade 1450, 1452.

Drive assembly 1442 further includes an actuation tube 1416 extending over actuation cable 1414 and including a cam 1418 supported on a distal end thereof. As actuation tube 1416 is rotated, a lobe 1418*a* of cam 1418 selectively engages and disengages a recess 1450*b*, 1452*b* formed in a proximal end of blades 1450, 1452.

In operation, actuation tube 1416 is rotated 90° to engage recess 1450*b* of blade 1450 with lobe 1418*a* of cam 1418. Lobe 1418*a* lifts blade 1450, pulling follower 1450*c* out of groove 1444*b* of camming hub 1444. Actuation tube 1416 is then moved forward, moving cam 1418 and blade 1450 forward to engage or release the surgical needle. The process is repeated as needed throughout the surgical procedure.

Figure 68A:
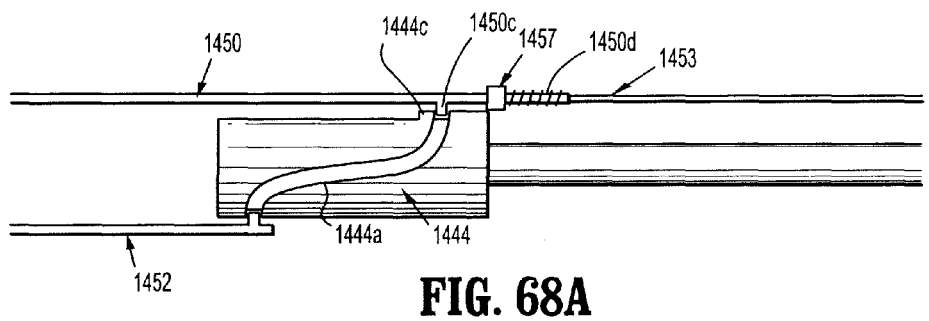
FIGS. 68A-68B are schematic illustrations of a drive assembly, for an end effector, according to another embodiment of the present disclosure.
Figure 68B:
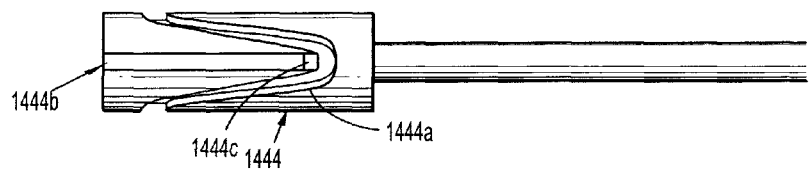
Figure 69:
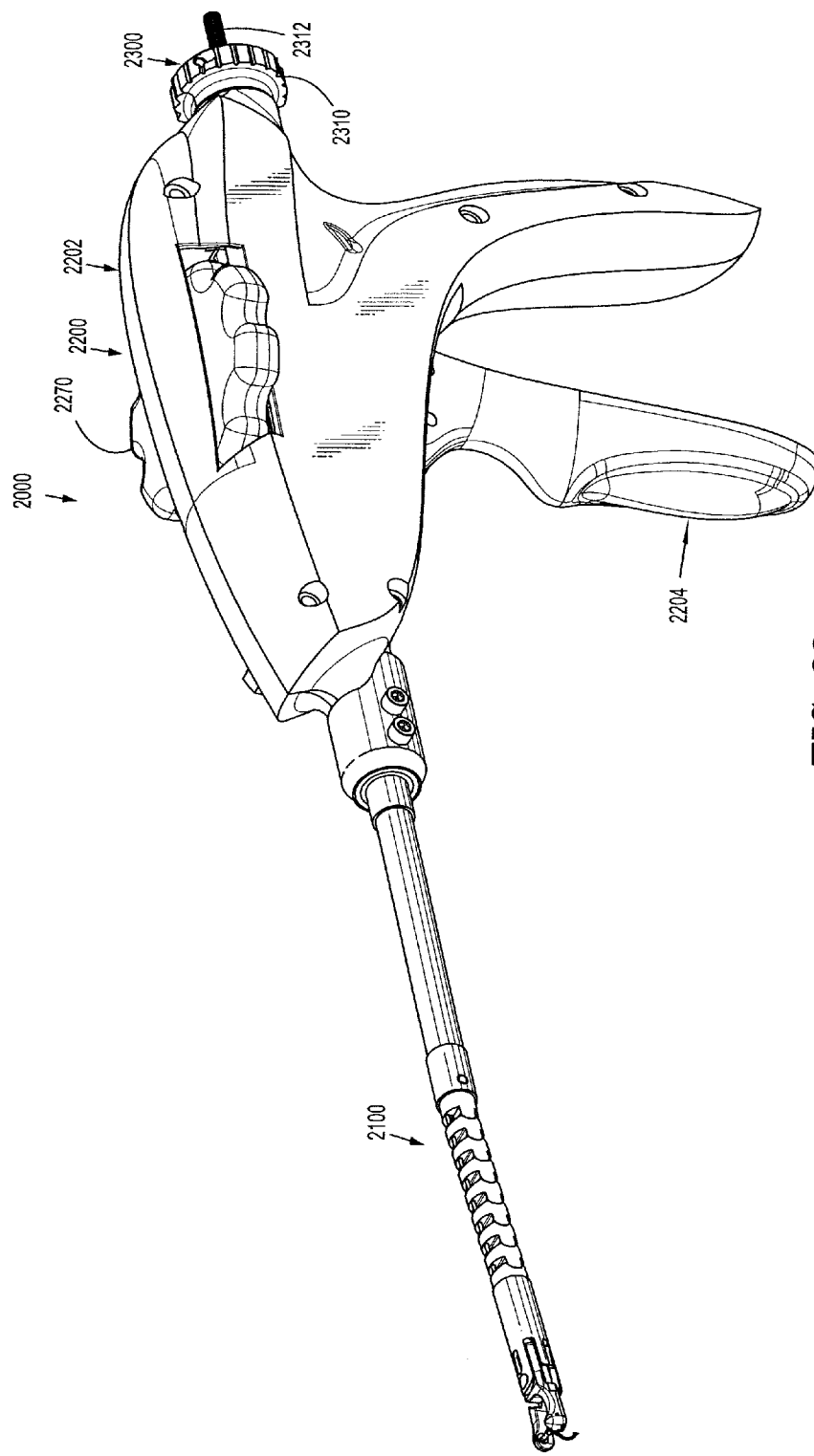
FIG. 69 is a perspective view of a flexible endoscopic stitching device according to another embodiment of the present disclosure.

In an alternate embodiment, as seen in FIGS. 68A and 68B, camming hub 1444 may be provided with a longitudinally extending slot or groove 1444*b* extending forward from a nadir of helical groove 1444*a*. A retention bump 1444*c* may be provided at or near a proximal end of longitudinal groove 1444*b*.

As seen in FIG. 68A, blade 1450 may include a threaded portion 1450*d* extending from a proximal end thereof through a threaded block or bushing 1451. An actuation or torque cable 1453 may be connected to threaded portion 1450*d* to push follower 1450*c* over bump 1444*c* as actuation cable 1453 is rotated to release the surgical needle.

Turning now to FIGS. 69-101, a flexible endoscopic stitching device, in accordance with an embodiment of the present disclosure, is generally designated as 2000. Endoscopic stitching device 2000 includes an end effector 2100 operatively supported on and extending from a handle assembly 2200.

In accordance with the present embodiment, end effector 2100 is substantially similar to end effector 100 and thus will only be discussed in detail hereinbelow to the extent necessary to identify differences in construction and operation. Reference may be made to end effector 100 for a detailed discussion of the construction and operation of end effector 2100.

As seen in FIGS. 72, 82-84, 90, 93, 94, 97 and 98, end effector 2100 includes a thrust bearing 2148 interposed between camming hub 2144 and distal-most knuckle 2112*a*. Thrust bearing 2148 includes a plurality of ball bearings 2148*a* rotatably supported in housing halves 2148*b*, 2148*c*.

In use, first housing half 2148*b* of thrust bearing 2148 is freely rotatable relative to second housing half 2148*c* of thrust bearing 2148, via ball bearings 2148*a*. In particular, thrust bearing 2148 enabled free or relatively free axial rotation of camming hub 2144 relative to distal-most knuckle 2112*a*.

Figure 79:
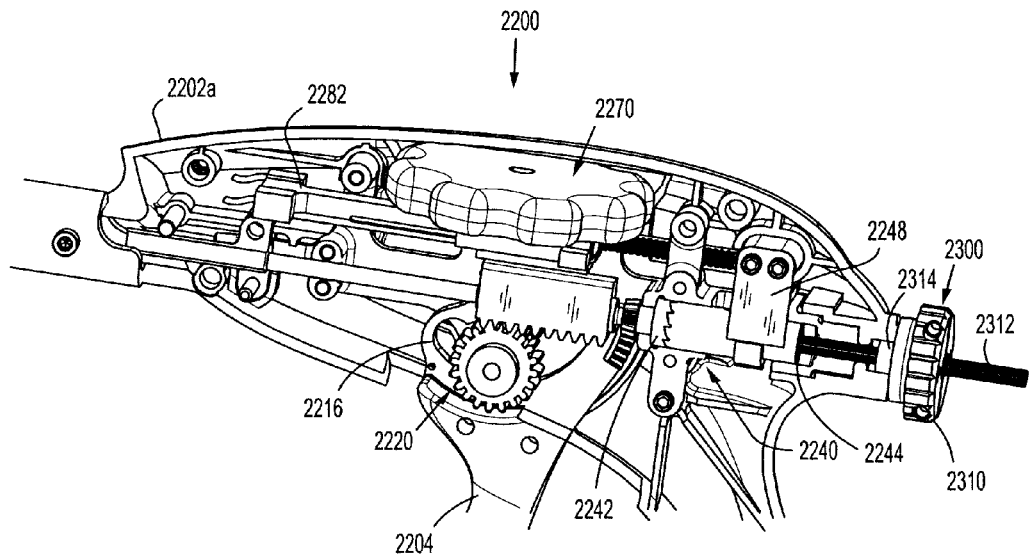
FIG. 79 is a left-side perspective view of the handle assembly of the endoscopic stitching device of FIG. 69, with a left housing and a left frame removed therefrom.
Figure 80:
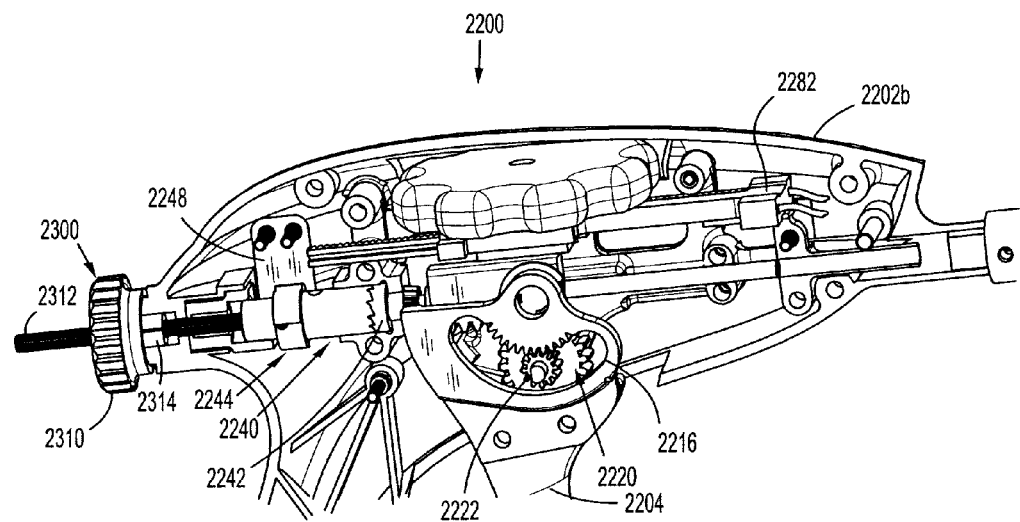
FIG. 80 is a right-side perspective view of the handle assembly of the endoscopic stitching device of FIG. 69, with a right housing and a right frame removed therefrom.

Handle assembly 2200 includes a housing 2202 having a right-half section 2202*a* and a left-half section 2202*b* joinable to one another by suitable fastening elements (not shown), such as screws. Handle assembly 2200 includes a trigger 2204 operatively supported in housing 2202 and extending therefrom. As will be described in greater detail below, trigger 2204 is movable between a first un-actuated position, as seen in FIGS. 69-71 and 68, and at least one second actuated position, as seen in FIGS. 79-81. In use, movement of trigger 2204 between the first and second positions results in actuation and/or operation of end effector 2100.

Trigger 2204 is operatively associated or otherwise connected to an actuation mechanism 2210 (see FIGS. 70-72 and 78-82) of handle assembly 2200. As will be described in greater detail below, in use, movement of trigger 2204 between the first and second positions results in two operations of end effector 2100.

As seen in FIGS. 70-72 and 78-82, actuation mechanism 2210 includes a trigger plate 2212 connected to and extending from trigger 2204. Trigger plate 2212 pivotally connects trigger 2204 to housing 2202. Trigger plate 2212 defines a first gear segment 2214 along a proximal or rear edge 2212*a* thereof. Trigger plate 2212 defines an arcuate slot 2216 therein having a second gear segment 2216*a* formed along an upper edge thereof. Slot 2216 has a radius of curvature having its center located on a pivot axis "Y" (see FIG. 73) of trigger 2204.

A gear set 2220 is operatively associated with slot 2216 of trigger plate. Gear set 2220 includes a first gear 2222 configured to mesh with and/or otherwise operatively engage second gear segment 2216*a* of slot 2216, and a second gear 2224 supported on a common rotational pin 2226 as first gear 2222. In this manner, as first gear 2222 is rotated due to a movement of trigger 2204, second gear 2224 is simultaneously and/or concomitantly rotated.

Second gear 2224 of gear set 2220 is configured to mesh with and/or otherwise operatively engage teeth 2228*a* of a rack 2228. Rack 2228 defines a lumen 2228*b* therethrough.

Lumen 2228b of rack 2228 is oriented in a direction tangential to pivot axis "Y". In one embodiment, lumen 2228b of rack 2228 is coaxially disposed on a longitudinal "X" axis of an actuation shaft of handle assembly 2200.

As seen in FIGS. 70-72 and 78-82, actuation mechanism 2210 includes a drive or actuation shaft 2230 extending through and operatively associated with rack 2228, and a follower block 2232 rotatably supported on actuation shaft 2230 at a fixed location distal of rack 2228. Actuation shaft 2230 is axially translatable and rotatable relative to rack 2228. Follower block 2232 is axially held in position relative to actuation shaft 2230 by a pair of ring clamps 2232a, 2232b secured to actuation shaft 2230 at a location distal and proximal of follower block 2232. Rack 2228 and follower block 2232 are connected to one another by a biasing member 2234, i.e., a tension spring, extending therebetween.

Figure 74:
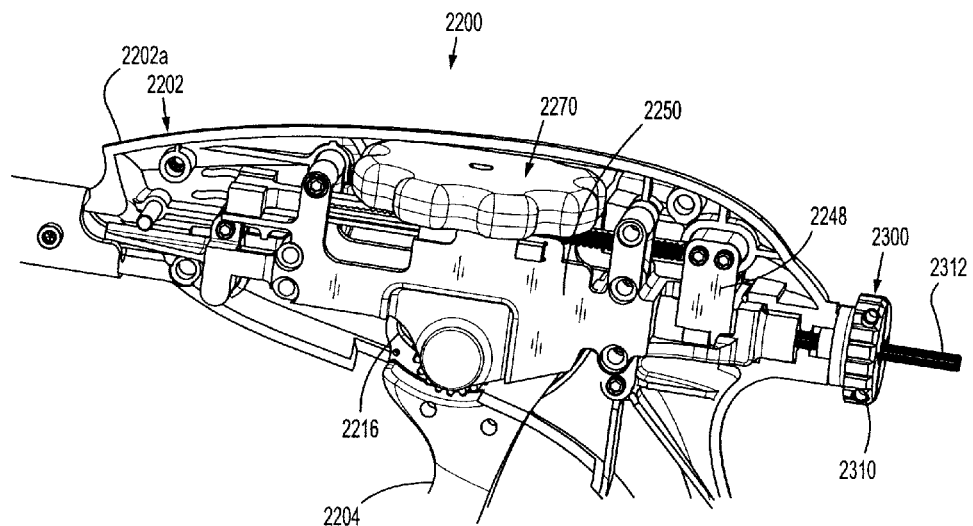
FIG. 74 is a left-side perspective view of the handle assembly of the endoscopic stitching device of FIG. 69, with a left housing removed therefrom.
Figure 77:
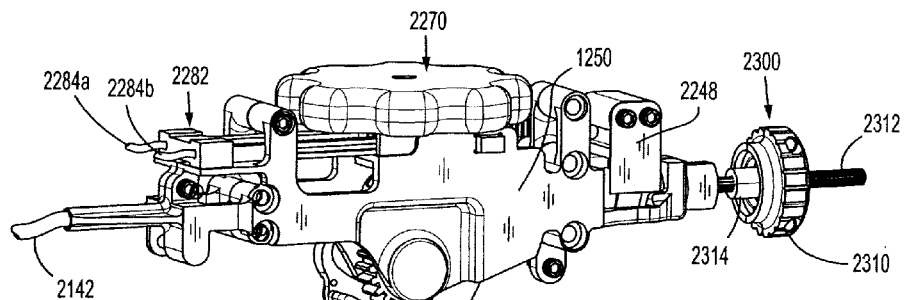
FIG. 77 is a left-side perspective view of the handle assembly of the endoscopic stitching device of FIG. 69, with a housing removed therefrom.
Figures 82, 83, 84:
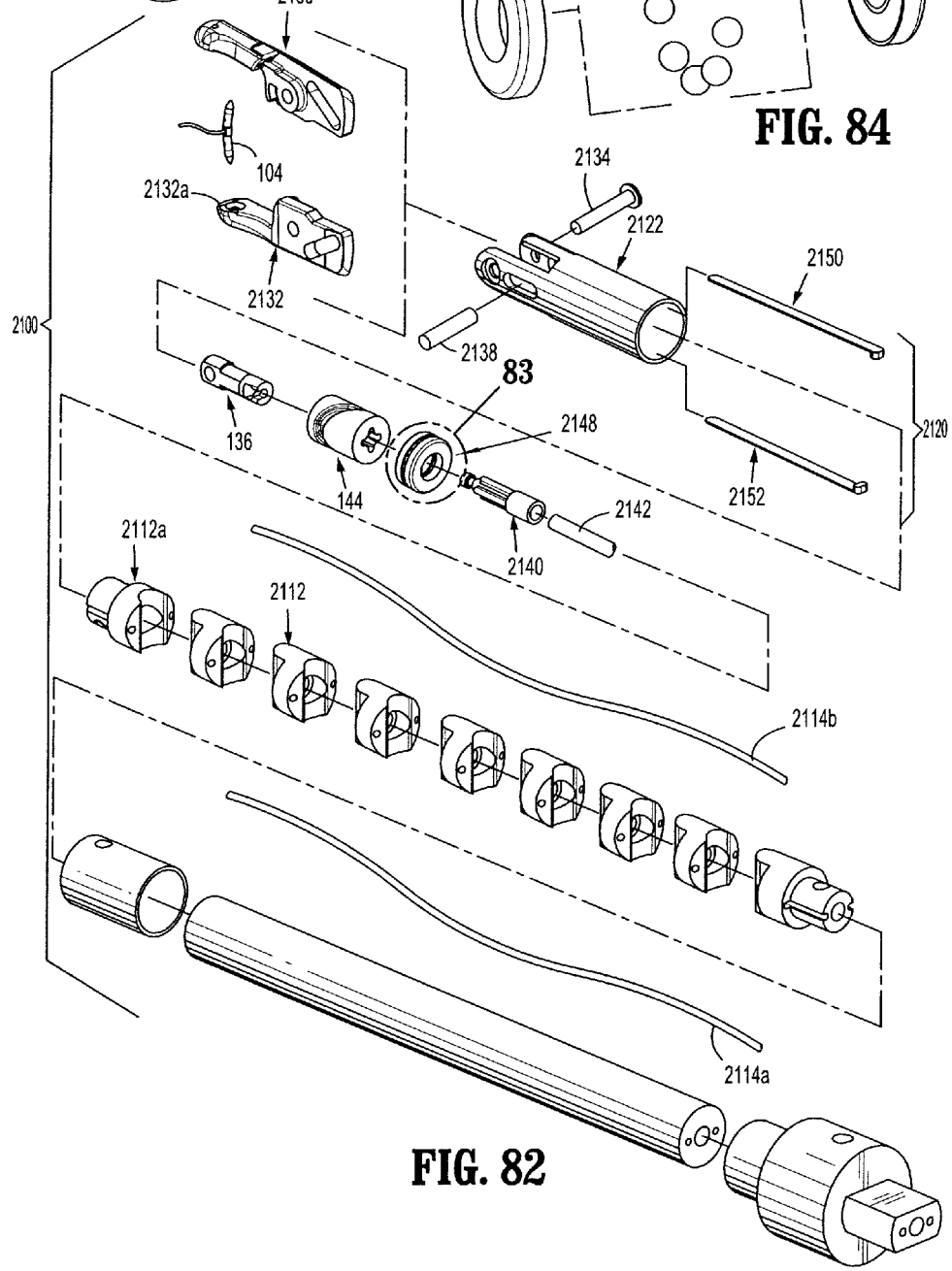
FIG. 82 is an exploded perspective view of the end effector of FIG. 70.
FIG. 83 is an enlarged perspective view of a thrust bearing of the end effector of FIGS. 70 and 82.
FIG. 84 is an exploded perspective view of the thrust bearing of FIG. 83.
Figure 85:
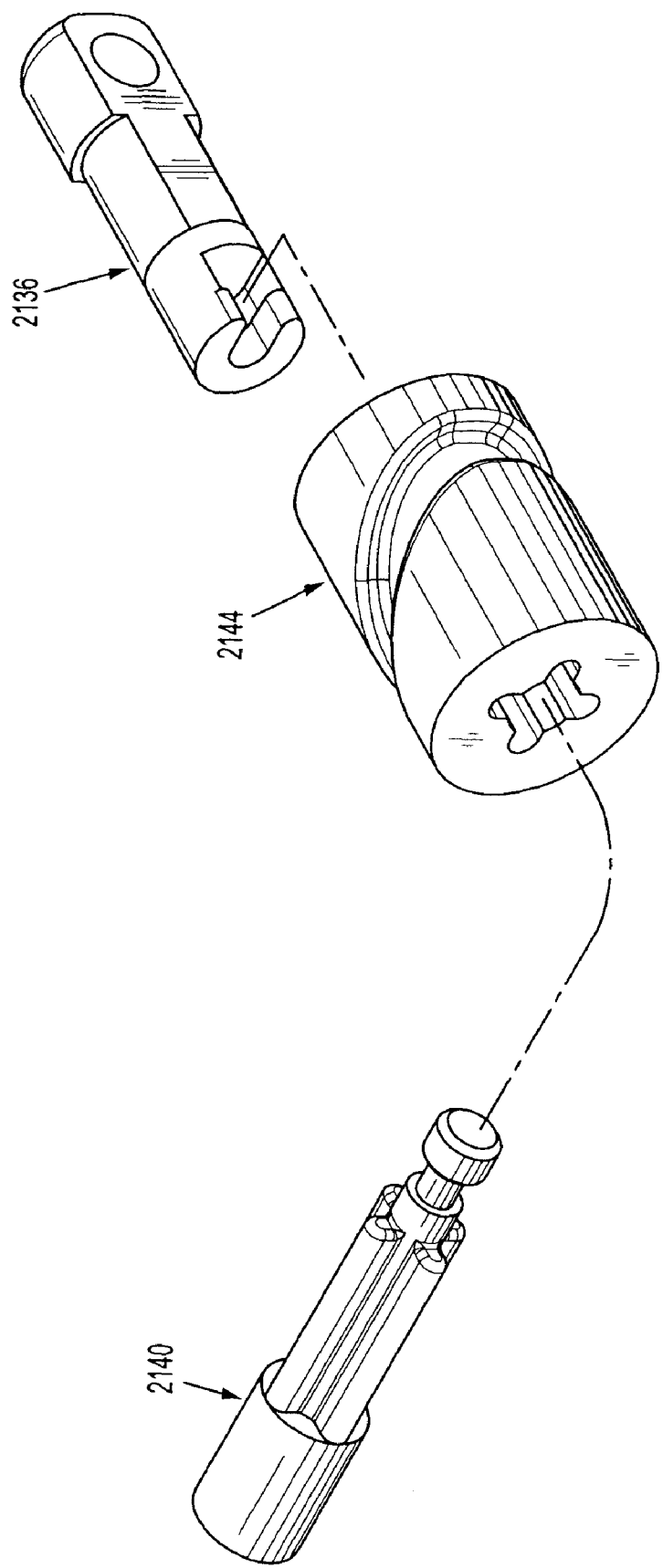
FIG. 85 is an exploded perspective view of a cam mechanism of the end effector of FIGS. 70 and 82.
Figure 88:
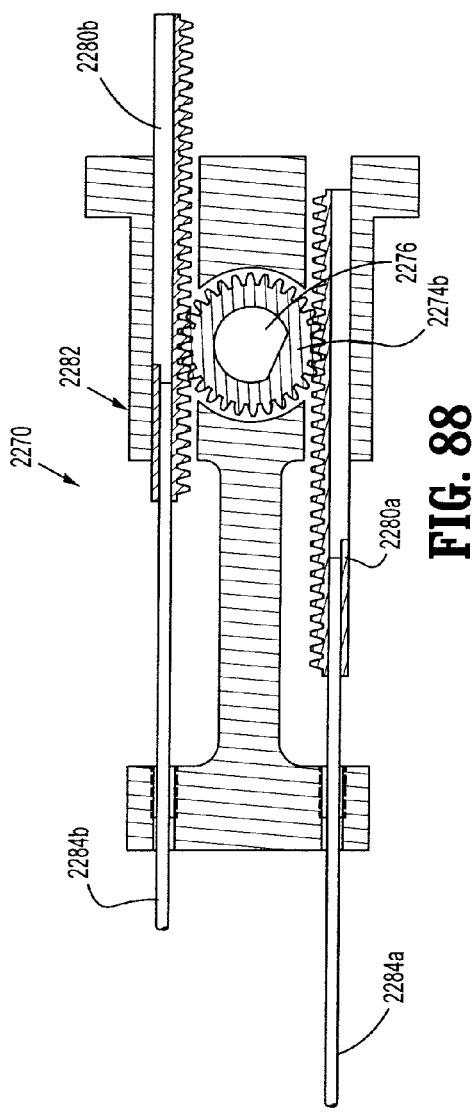
FIG. 88 is a cross-sectional view of the articulation control mechanism of FIG. 86 as taken through 88-88 of FIG. 86.
Figure 89:
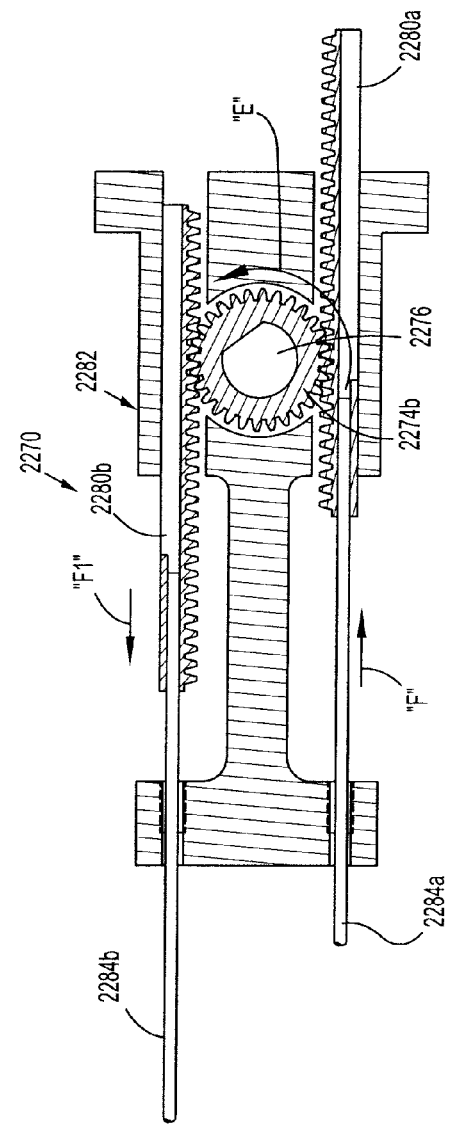
FIG. 89 is a further cross-sectional view of the articulating control mechanism of FIG. 86, as taken through 88-88 of FIG. 86, illustrating the operation thereof.
Figure 90:
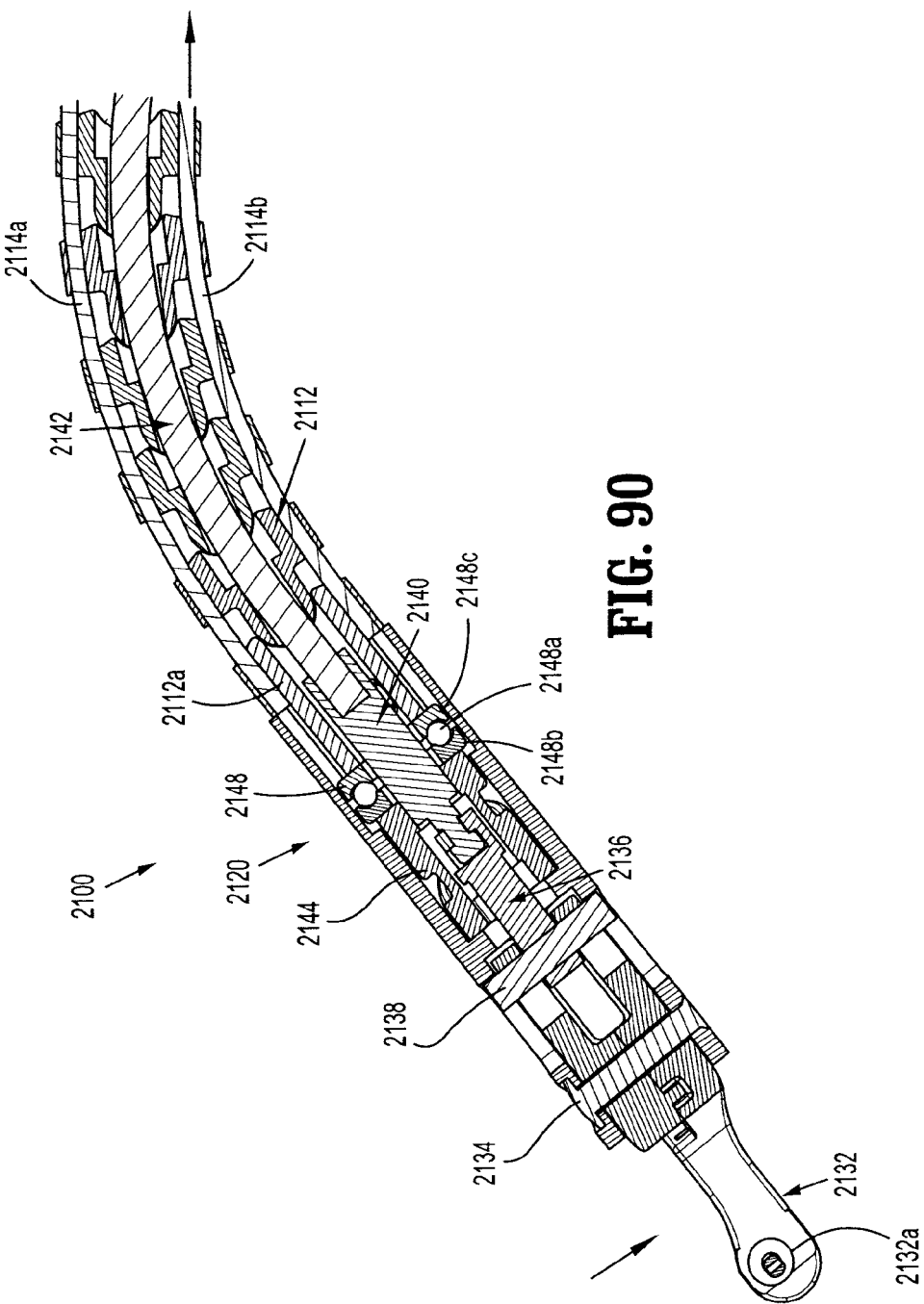
FIG. 90 is a longitudinal, cross-sectional view of the end effector of the endoscopic stitching device of FIG. 69, illustrating the distal end in an articulated condition.
Figure 91:
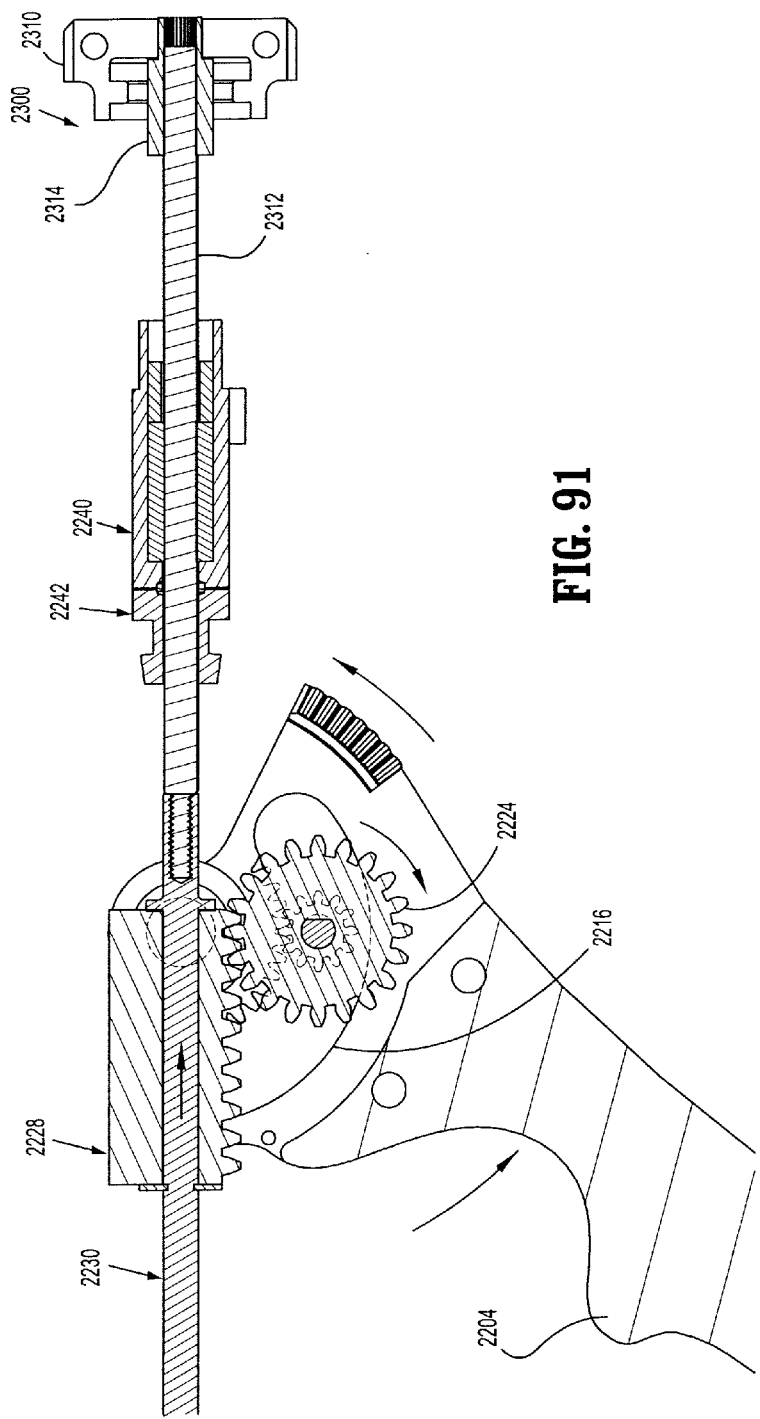
FIG. 91 is a side elevational view of a drive mechanism of the handle assembly of FIGS. 73-81, illustrating the drive mechanism and a trigger of the handle assembly being actuated from a first position.
Figure 95:
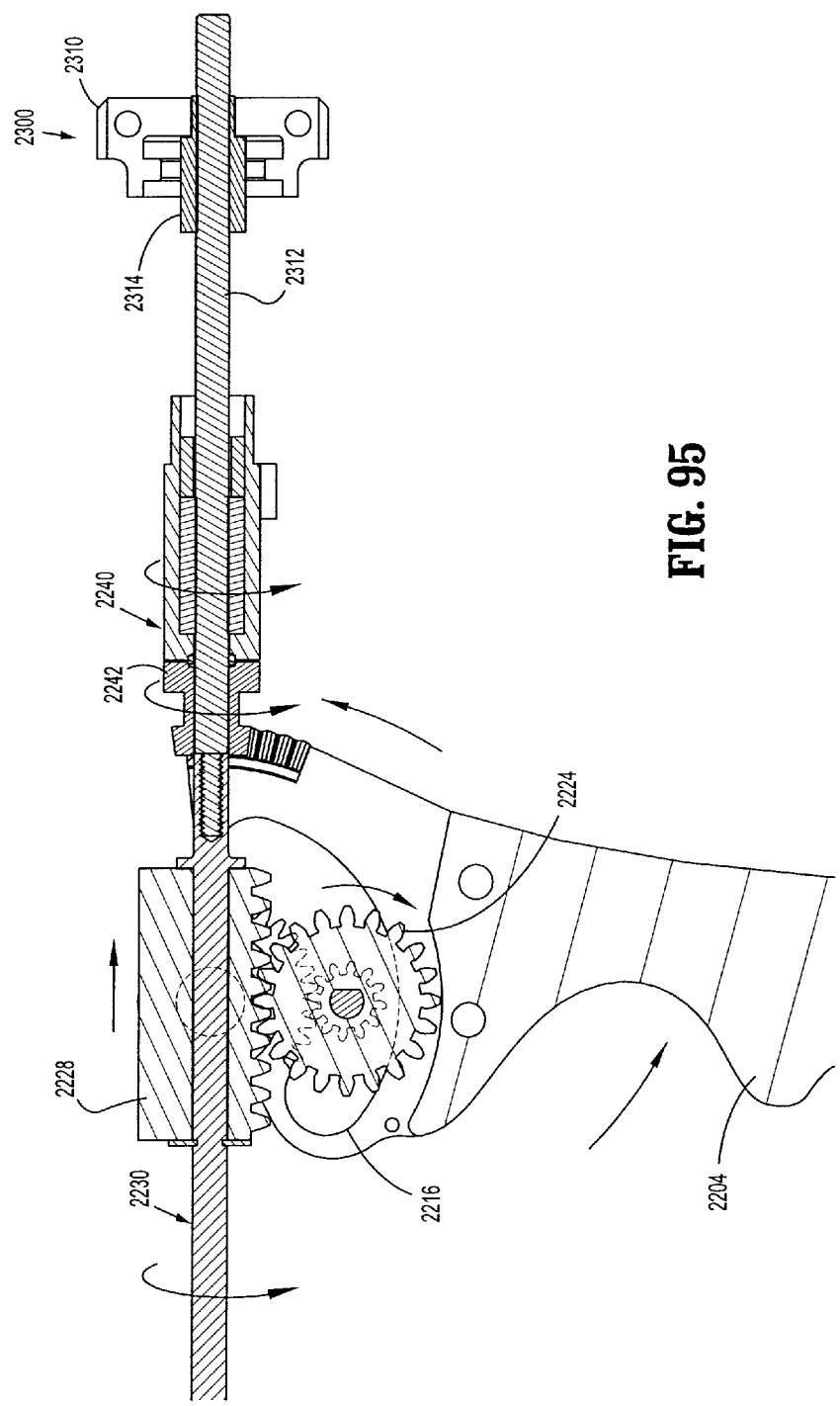
FIG. 95 is a side elevational view of the drive mechanism of FIGS. 73-81, illustrating the drive mechanism and the trigger of the handle assembly at a second position.
Figure 97:
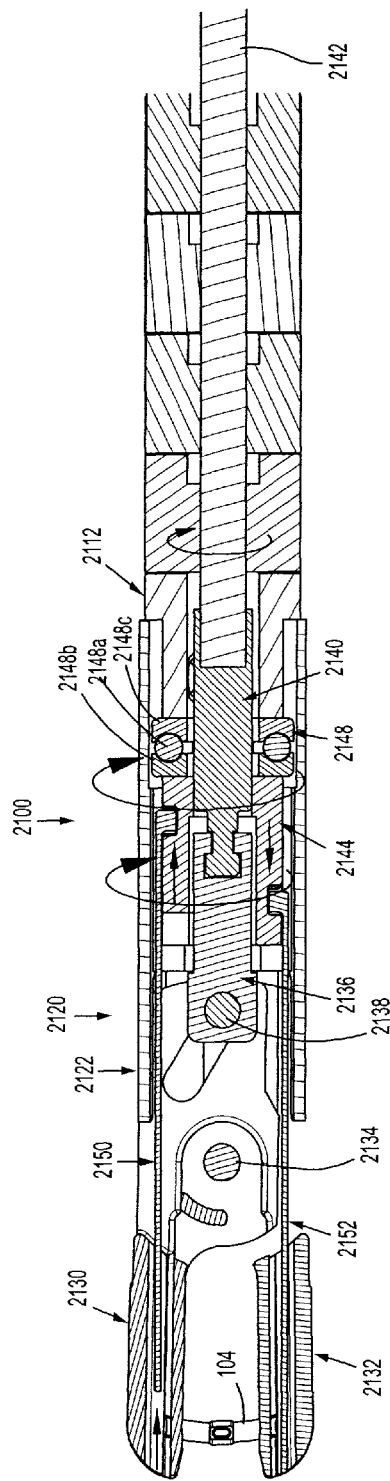
FIG. 97 is a longitudinal, cross-sectional view of the end effector of the endoscopic stitching device of FIG. 69, illustrating the blades thereof being advance and retracted.
Figure 98:
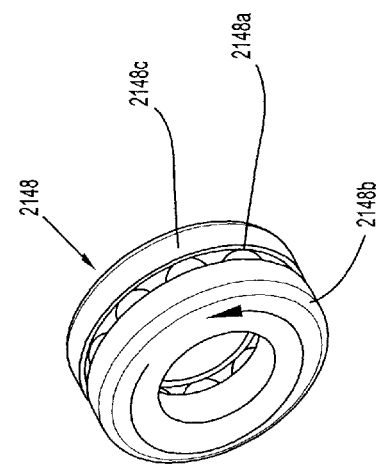
FIG. 98 is a perspective view of the thrust bearing of the end effector of the endoscopic stitching device of FIG. 69, illustrating the operation thereof.
Figure 99:
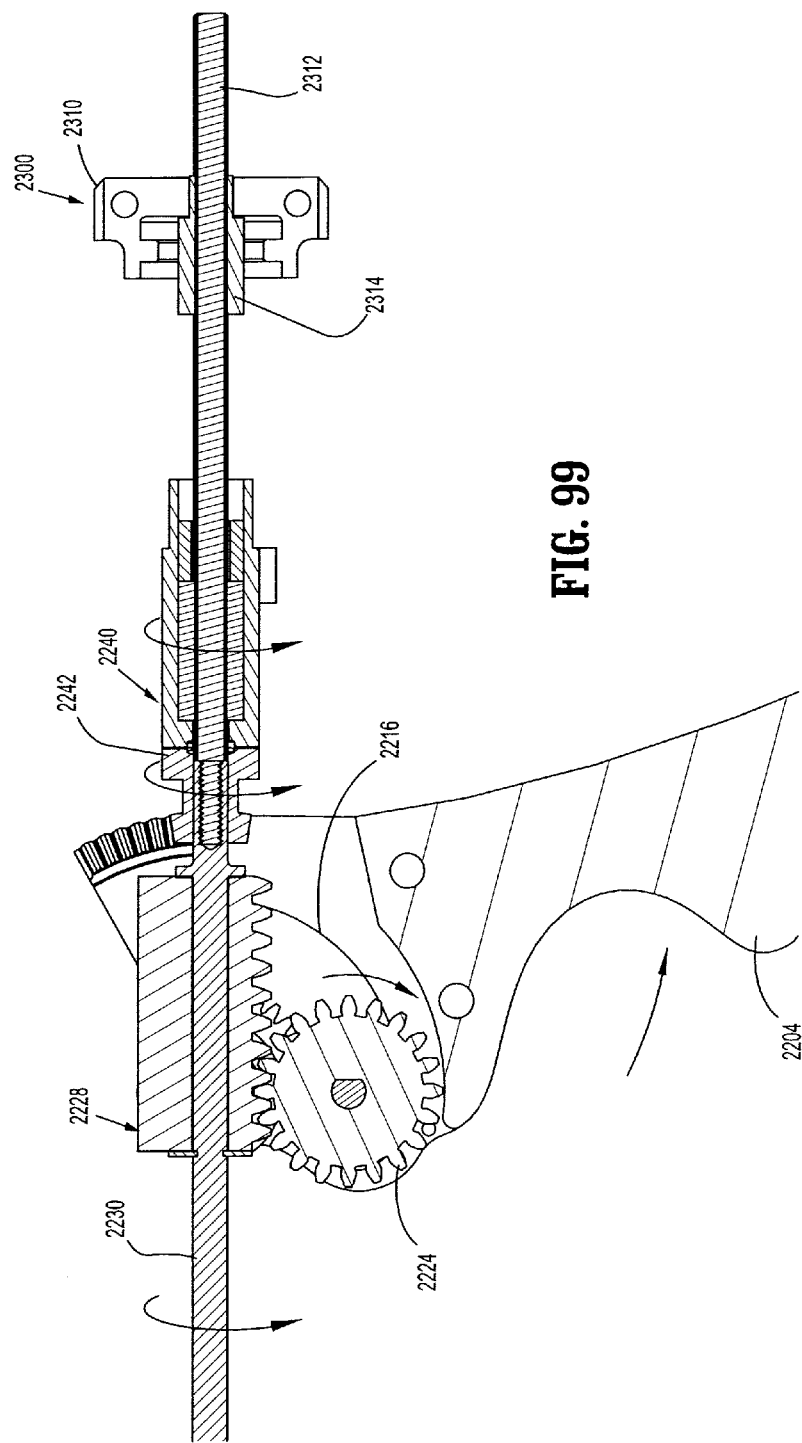
FIG. 99 is a side elevational view of the drive mechanism of FIGS. 73-81, illustrating the drive mechanism and trigger of the handle assembly in a third position.
Figure 100:
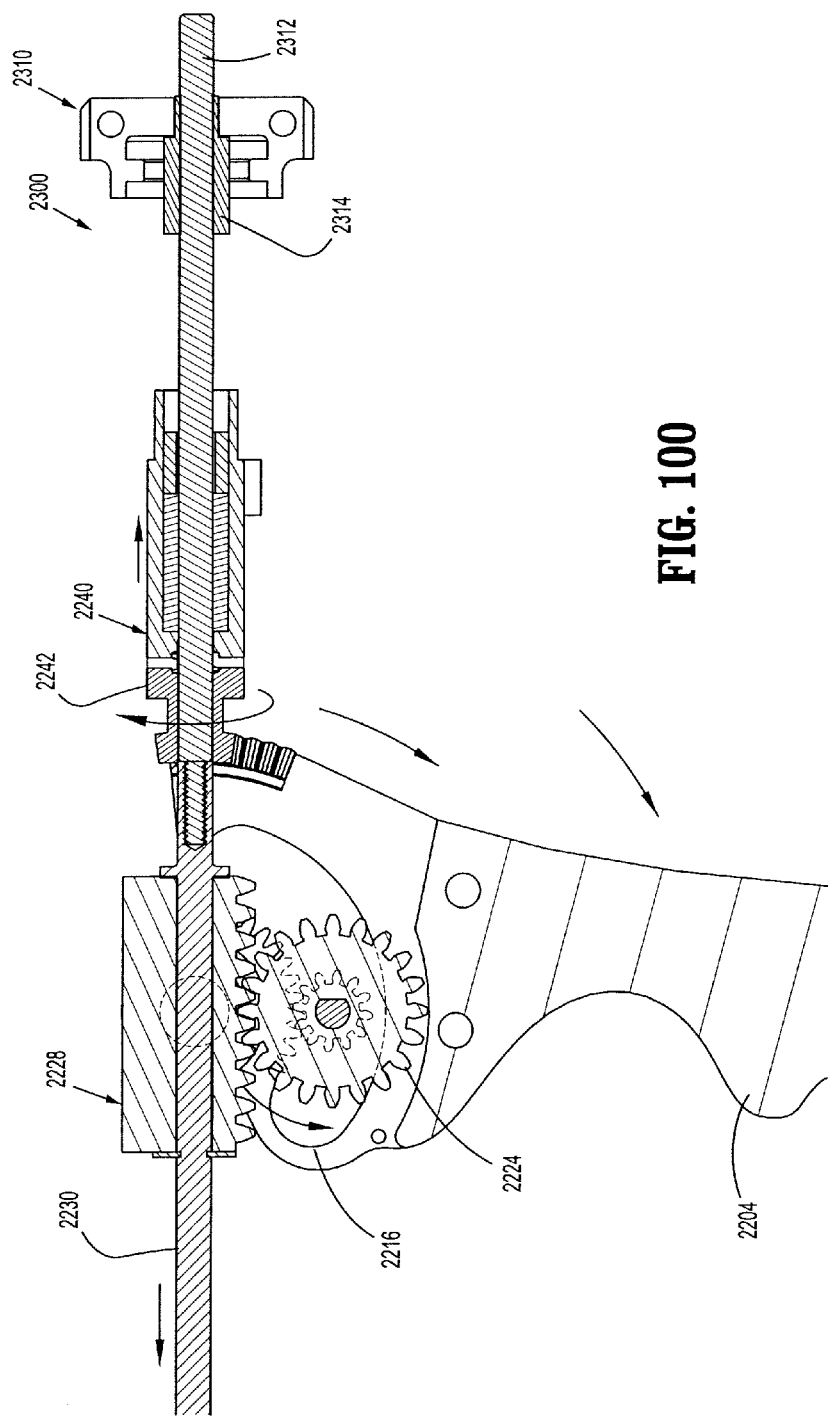
FIG. 100 is a side elevational view of the drive mechanism of FIGS. 73-81, illustrating the drive mechanism and the trigger of the handle assembly being opened.

Actuation mechanism 2210 includes a slip-clutch 2240 supported on a proximal end of actuation shaft 2230. As seen in FIG. 74, slip clutch 2240 includes a distal portion 2242 having a distal bevel gear 2242a configured to mesh with and/or otherwise operatively engage first gear segment 2214 of trigger plate 2212, and a set of proximally-facing gear teeth 2242b. Slip clutch 2240 further includes a proximal portion 2244 having a set of distally-facing gear teeth 2244a configured to mesh with and/or otherwise operatively engage the set of proximally-facing gear teeth 2242b of distal portion 2242, and a toothed wheel 2244b located proximal of the set of distally-facing gear teeth 2244a. Toothed wheel 2244b defines a pair of diametrically opposed teeth 2244c formed therein or thereon. As seen in FIGS. 77, 80 and 83, toothed wheel 2244b is keyed to actuation shaft 2230 so as to solely enable axial displacement of toothed wheel 2244b relative to actuation shaft 2244b.

In operation, as will be discussed in greater detail below, the set of distally-facing gear teeth 2244a cooperate with the set of proximally-facing gear teeth 2242b to impart rotation in a single direction.

Proximal portion 2244 of slip-clutch 2240 is biased against distal portion 2242 of slip-clutch 2240 by a biasing member 2246, such as, for example, a compression spring or the like, disposed between housing 2202 and proximal portion 2244 of slip-clutch 2240. A pawl 2248 is operatively associated with toothed wheel 2244b in such a manner so as to permit rotation of toothed wheel 2244b in a single direction.

Figure 70:
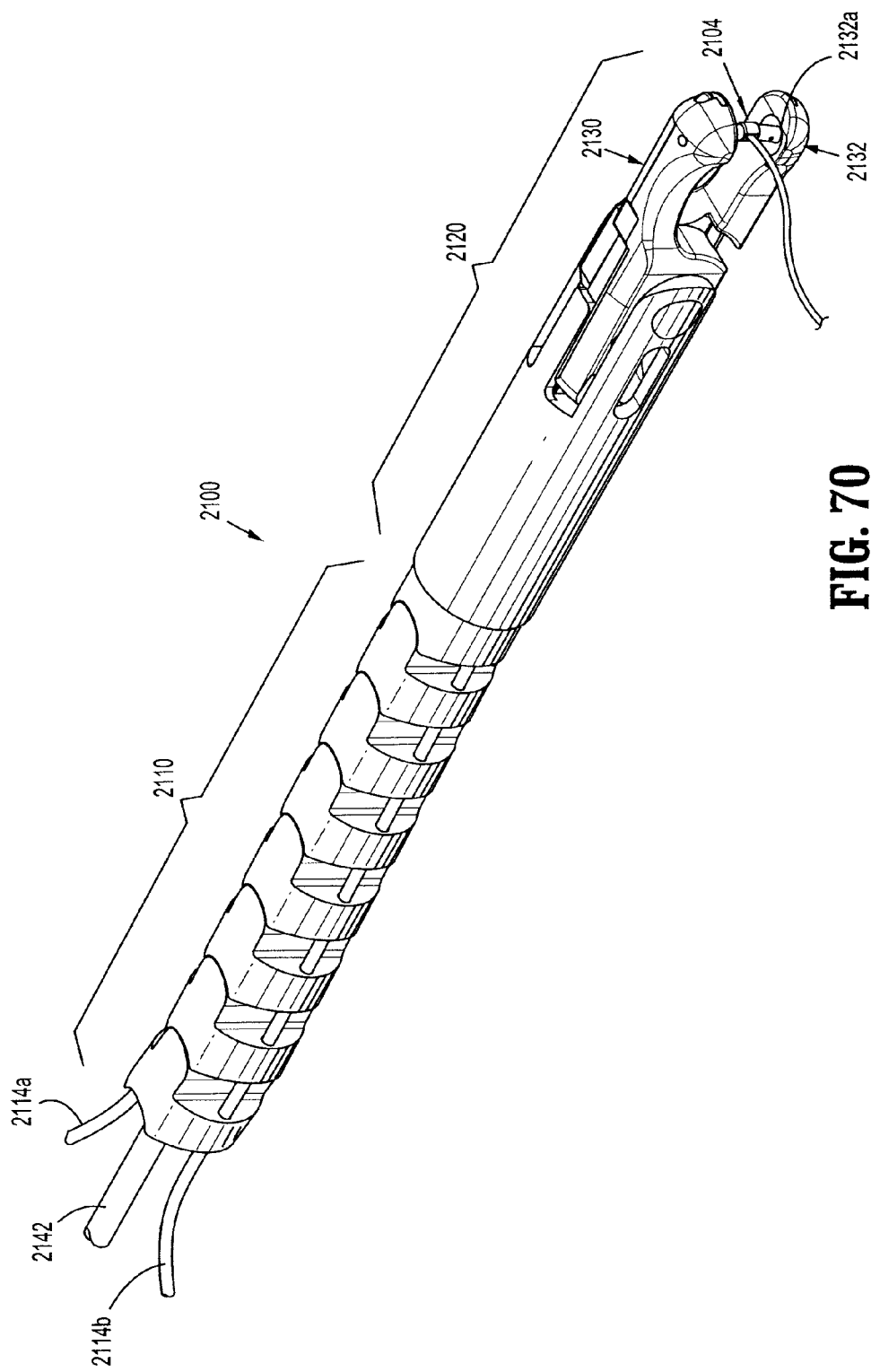
FIG. 70 is a perspective view of an end effector of the endoscopic stitching device of FIG. 69.

As seen in FIGS. 70-72, at least proximally-facing gear teeth 2242b of distal portion 2242 of slip-clutch 2240 is retained in a hub 2250 formed in housing 2202, and at least a boss 2244d, extending proximally from toothed wheel 2244b, is retained in a hub 2252 formed in housing 2202.

Figure 78:
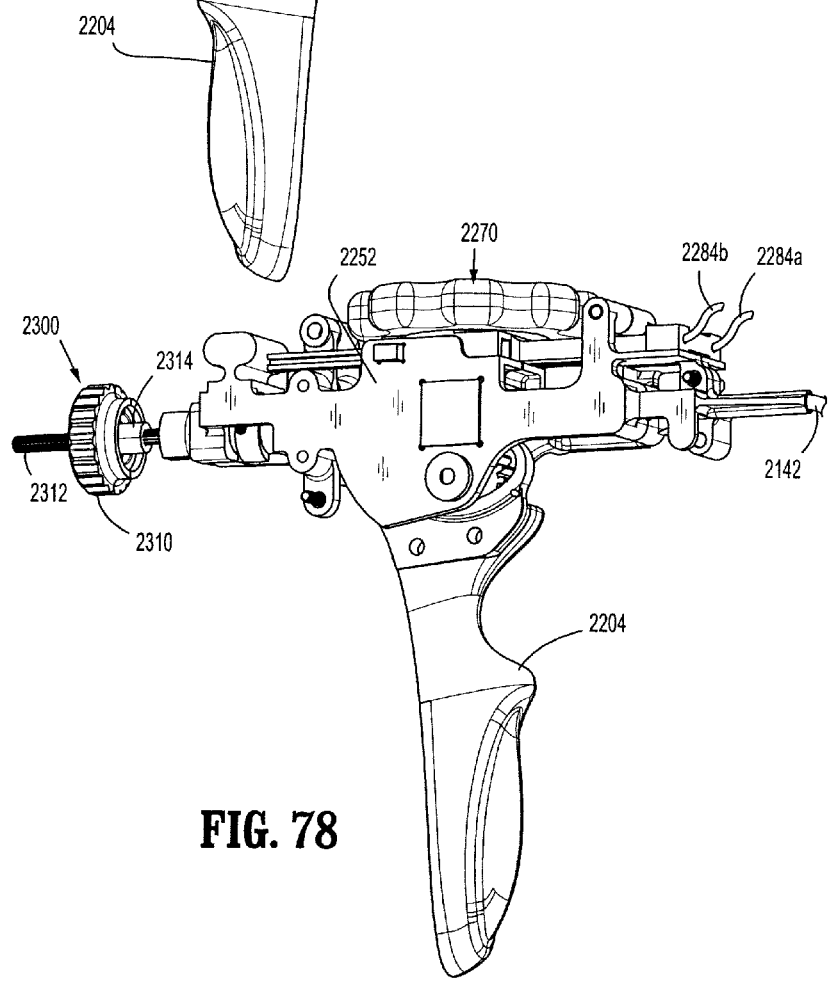
FIG. 78 is a right-side perspective view of the handle assembly of the endoscopic stitching device of FIG. 69, with a housing removed therefrom.

With continued reference to FIGS. 69-82, a method of using and/or operating handle assembly 2200 is shown and described. As seen in FIG. 78, when trigger 2204 is in a first or un-actuated position, rack 2228 is at a distal-most position relative to actuation shaft 2230 such that a proximal-most tooth 2228a thereof meshes with and/or otherwise operatively engages second gear 2224 of gear set 2220. Also, as seen in FIG. 78, when trigger 2204 is in a first or un-actuated position, first gear segment 2214 of trigger plate 2212 is spaced a distance from bevel gear 2242a of distal portion 2242 of slip clutch 2240.

As seen in FIGS. 78 and 79, as trigger 2204 is squeezed or moved to a second or at least partially actuated position, as indicated by arrow "A", second gear segment 2216a of slot 2216 causes first gear 2222 as well as second gear 2224 of gear set 2220 to rotate in the direction of arrow "B". As first and second gears 2222, 2224 of gear set 2220 are rotated in the "B" direction, second gear 2224 causes rack 2228 to move in the direction of arrow "C" (i.e., in a proximal direction). As rack 2228 is moved proximally, actuation shaft 2230 is also moved proximally, in the direction of arrow "C", due to the connection of follower block 2232 to rack 2230 via biasing member 2234. Proximal movement of actuation shaft 2230 may result in an operation or movement in end effector 2100 connected to a distal end of actuation shaft 2230 via an actuation cable 2231.

As seen in FIG. 79, as trigger 2204 is further squeezed or moved in the direction of arrow "A", first gear segment 2214 of trigger plate 2212 operatively engages bevel gear 2242a of distal portion 2242 of slip clutch 2240. As trigger 2204 is moved in the direction of arrow "A", first gear segment 2214 of trigger plate 2212 imparts rotation to bevel gear 2242a of distal portion 2242 of slip clutch 2240, in the direction of arrow "D". Rotation of bevel gear 2242a of distal portion 2242 of slip clutch 2240 in turn imparts rotation to proximal portion 2244 of slip clutch 2240, due to the meshing of respective gear teeth 2242b, 2244a, which in turn imparts rotation to actuation shaft 2230, due to the keying of toothed wheel 2244b of proximal portion 2244 to actuation shaft 2230.

As seen in FIGS. 77 and 80, as toothed wheel 2244b of proximal portion 2244 of slip clutch 2240 is rotated in the direction of arrow "D", pawl 2248 rides over and against an outer surface thereof.

As seen in FIG. 81, as trigger 2204 is further squeezed or moved in the direction of arrow "A", second gear 2224 of gear set 2220 is further rotated in the direction of arrow "B" causing rack 2228 to move further in the direction of arrow "C". However, since actuation shaft 2230 has bottomed out (i.e., movement in the direction of arrow "C" is stopped), rack 2228 is caused to move in the direction of arrow "C" along actuation shaft 2230, and since follower block 2232 is axially fixed along actuation shaft 2230, biasing member 2234 is caused to be elongated. Simultaneously or concomitantly therewith, first gear segment 2214 of trigger plate 2212 further rotates bevel gear 2242a of distal portion 2242 of slip clutch 2240 in the direction of arrow "D" further rotating actuation shaft 2230 in the direction of arrow "D", as described above. Rotation of actuation shaft 2230 in the direction of arrow "D" may result in another operation or movement in end effector 2100 connected to a distal end of actuation shaft 2230 via an actuation cable 2231.

Turning now to FIG. 82, as trigger 2204 is released or moved in the direction of arrow "A1", opposite to the direction of arrow "A", second gear 2224 of gear set 2220 is rotated in the direction of arrow "B1", opposite to arrow "B". Second gear 2224 is moved in the direction of arrow "B1" either by the movement of trigger 2204 in the direction of arrow "A1" or by the movement of rack 2228 in the direction of arrow "C1", opposite to the direction of arrow "C". Rack 2228 is moved in the direction of arrow "C1" due to the contraction of biasing member 2234 approximating rack 2228 toward follower block 2232. The spring bias of biasing member 2234, approximating rack 2228 toward follower block 2232, facilitates or aids in the return or movement of trigger 2204 in the direction of arrow "A1". As rack 2228 is moved in the direction of arrow "C1" actuation shaft 2230 is also moved in the direction of arrow "C1".

Simultaneously or concomitantly with the movement of trigger 2204 in the direction of arrow "A1", first gear segment 2214 of trigger plate 2212 imparts rotation to bevel gear 2242a of distal portion 2242 of slip clutch 2240 in the direction of arrow "D1", opposite to the direction of arrow "D". As bevel gear 2242a of distal portion 2242 of slip clutch 2240 is rotated in the direction of arrow "D1" gear teeth 2242b thereof slips-over and/or against teeth 2244a of proximal portion 2244 of slip clutch 2240, and since proximal portion 2244 of slip clutch 2240 is cammed in the direction of arrow "D", against the bias of spring 2246, no rotation is imparted to proximal portion 2244 of slip clutch 2240. In turn, since proximal portion 2244 of slip clutch 2240 does not rotate, no rotation is imparted to actuation shaft 2230.

As seen in FIG. 83, as toothed wheel 2244b of proximal portion 2244 of slip clutch 2240 is rotated in the direction of arrow "D1", pawl 2248 abuts against a tooth 2244c of toothed wheel 2244b, preventing rotation of toothed wheel 2244b in the direction of arrow "D1" and in turn preventing rotation of actuation shaft 2230 in the direction of arrow "D1".

Movement of actuation shaft 2230 in the direction of arrow "C1" may result in yet another operation or movement in end effector 2100 connected to a distal end of actuation shaft 2230 via an actuation cable 2231.

Turning now to FIGS. 69-73 and 75-76, handle assembly 2200 further includes an articulation mechanism 2270 supported on and/or in housing 2202. Articulation assembly 2270 may be operatively connected to end effect 2100 in order to impart articulation to end effector 2100 or any other suitable movement or operation to end effector 2100.

As seen in FIGS. 69-73 and 75-76, articulation mechanism 2270 includes a knob or dial 2272 rotatably supported on or in housing 2202, and a gear set 2274 keyed to and shaving a common rotational axis as dial 2272. Gear set 2274 includes a first gear 2274a and a second gear 2274b each supported on and keyed to a pin 2276 extending therethrough and through dial 2272.

Figure 73:
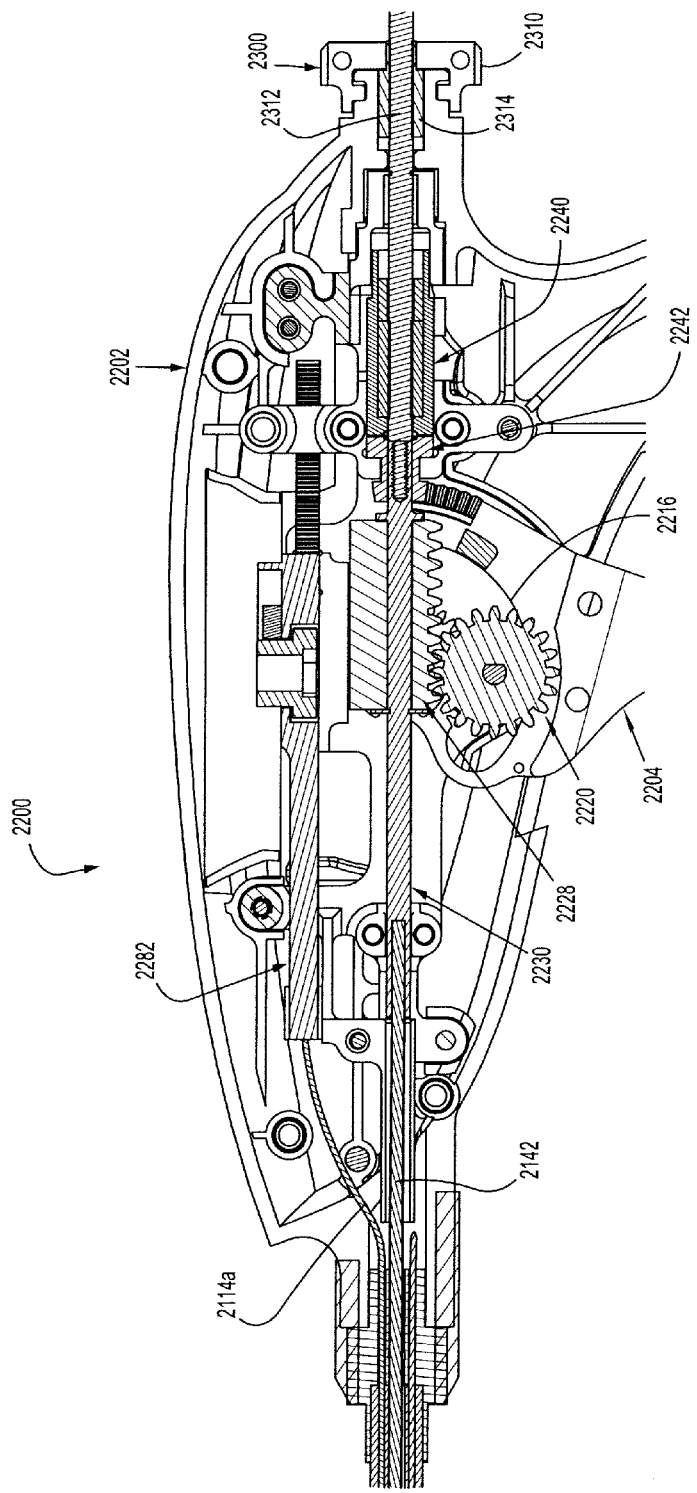
FIG. 73 is an enlarged view of the indicated area of detail of FIG. 71.

As seen in FIGS. 72 and 73, first gear 2274a of gear set 2274 operatively engages a locking/feedback member 2278 including a finger 2278a biased against the teeth of first gear 2274a. In operation, as first gear 2274a of gear set 2274 is rotated, due to a rotation of dial 2272, finger 2278a rides over the teach of first gear 2274a thereby providing the user with tactile and/or audible feedback. Additionally, when dial 2272 is not rotated, finger 2278a inter-engages with the teeth of first gear 2274a to thereby inhibit automatic rotation of dial 2272 and thus essentially lock or fix the position of dial 2272.

Articulation mechanism 2270 further includes a pair of opposed racks 2280a, 2280b operatively engaged with and on opposed sides of second gear 2274b of gear set 2274. Each rack 2280a, 2280b is slidably supported within a respective channel 2282a, 2282b of a support member 2282. Each rack 2280a, 2280b includes a respective articulation cable 2284a, 2284b secured thereto. In this manner, during operation, as each rack 2280a, 2280b is displaced so to is each respective articulation cable 2284a, 2284b.

Figure 75:
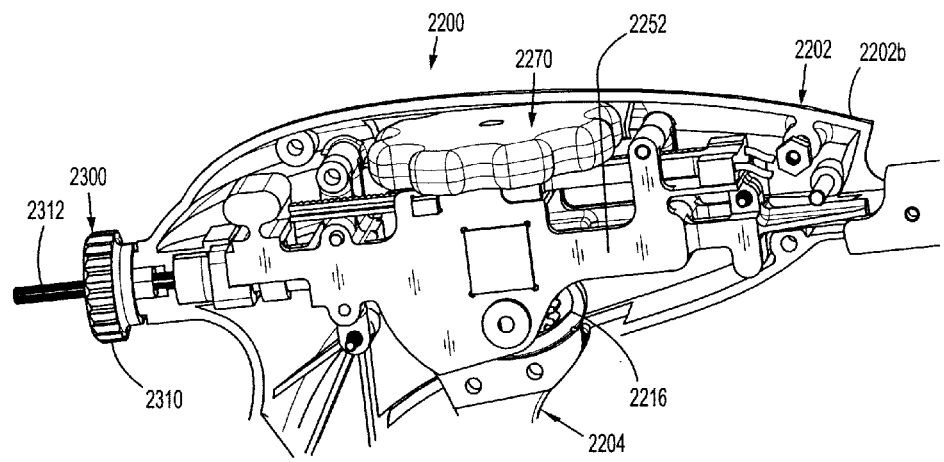
FIG. 75 is a right-side perspective view of the handle assembly of the endoscopic stitching device of FIG. 69, with a right housing removed therefrom.
Figure 76:
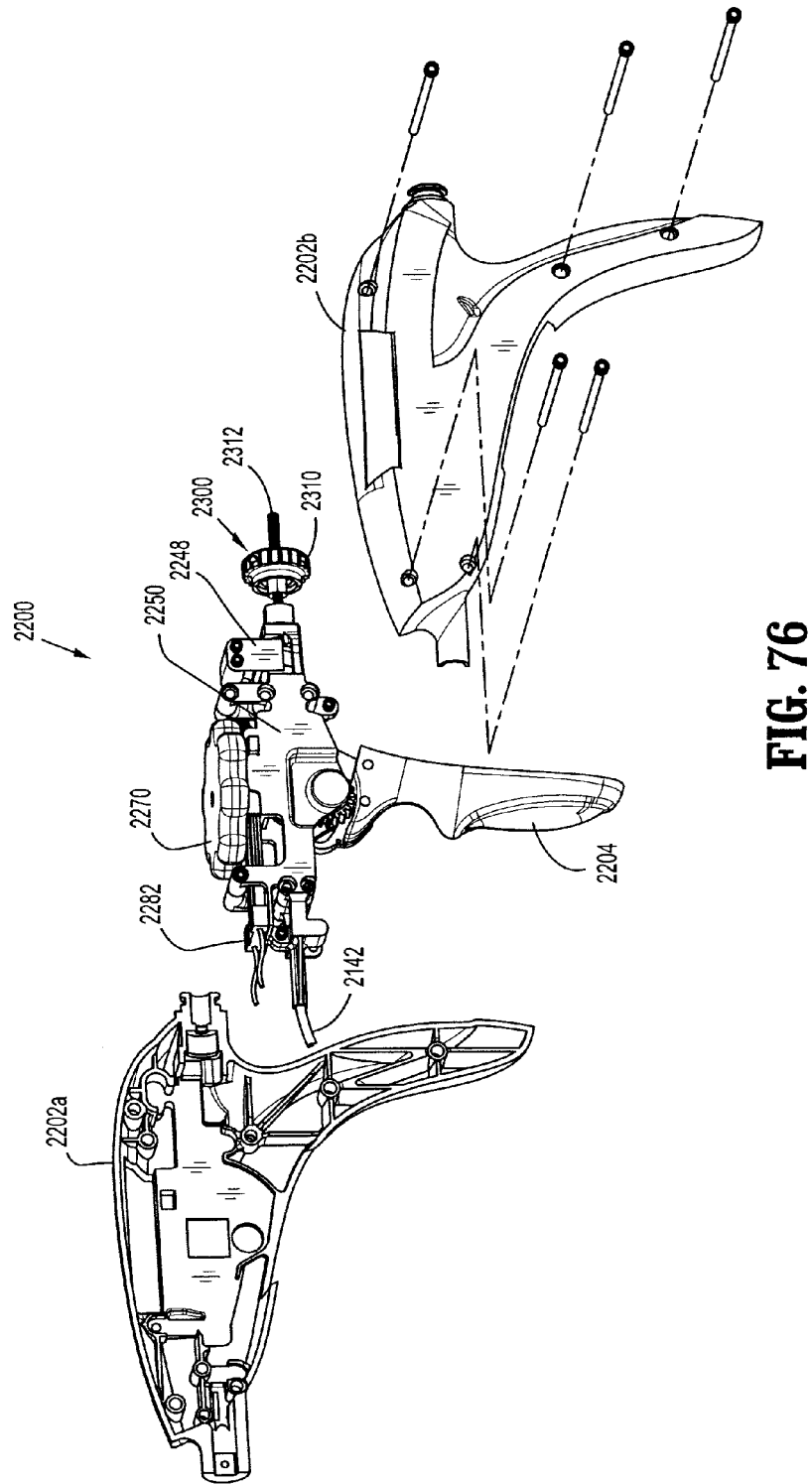
FIG. 76 is a partial exploded view of the handle assembly of FIGS. 74 and 75.

In operation, as best seen in FIGS. 75 and 76, as second gear 2274b is rotated in a direction of arrow "E", due to the rotation of dial 2272, first rack 2280a is moved in a proximal direction (i.e., in the direction of arrow "F"), thus displacing first articulation cable 2284a in the direction of arrow "F", and second rack 2280b is moved in a distal direction (i.e., in the direction of arrow "F1", opposite to arrow "F"), thus displacing second articulation cable 2284b in the direction of arrow "F1". It is understood that rotation of dial 2272 in an opposite direction and thus rotation of second gear 2274b in a direction opposite to arrow "E" will result in movement and/or displacement of racks 2280a, 2280b and cables 2284a, 2284b in opposite directions. Rotation of dial 2272 thus may impart an operation or movement in end effector 2100.

As seen in FIGS. 69, 71, 73-81, 91, 95, 99, and 100, handle assembly 2200 further includes a needle loading assembly 2300 including a knob 2310 supported on a rear end of housing 2202 and configured to enable loading of a surgical needle in jaws 2130, 2132. Knob 2310 is keyed to a spline shaft 2312 via a nut 2314. Nut 2314 has a shaped outer surface for receipt in a complementary shaped recess formed in knob 2310 such that rotation of knob 2310 results in rotation of nut 2314. Nut 2314 defines a shaped lumen 2314a (FIG. 81) for receipt of a complementary shaped outer surface of spline shaft 2312 such that rotation of knob 2310 also results in rotation of spline shaft 2312. Spline shaft 2312 is axially slidably disposed within lumen 2314a of nut 2314.

As seen in FIGS. 73, 81, 91, 95, 99 and 100, a distal end of spline shaft 2312 extends through slip-clutch 2240 and is fixedly secured to a proximal end of actuation shaft 2230 (a distal end of actuation shaft 2230 being connected to actuation cable 2142).

In use, in order to load a surgical needle into jaws 2130, 2132 of end effector 2100, knob 2310 is rotated, thereby rotating spline shaft 2312, actuation shaft 2230, actuation cable 2142 and camming hub 2144 (as described above). As knob 2310 is rotated, blades 2150, 2152 are moved axially until the distal ends of blades 2150, 2152 are out of registration with needle receiving recesses 2130a, 2132a (FIG. 93). With the distal ends of blades 2150, 2152 out of registration with receiving recesses 2130a, 2132a of jaws 2130, 2132, a surgical needle 104 is inserted into one of the receiving recesses 2130a, 2132a. Knob 2310 is then rotated until the distal end of one of blades 2150, 2152 engages surgical needle 104, as described above.

By way of example only, endoscopic stitching device 2000 may be configured such that knob 2310 is rotated until an audible or tactile feedback is sensed (e.g., when pawl 2248 snaps over tooth 2244c of toothed wheel 2244b). At this point, surgical needle 104 may be inserted or loaded in the recess 2130a, 2132a of jaws 2130, 2132 which is un-obstructed. With the surgical needle 104 in position, knob 2310 may be rotated to advance on of blades 2150, 2152 to engage surgical needle 104, in the manner described above, and to lock surgical needle 104 in position therein.

Figure 103:
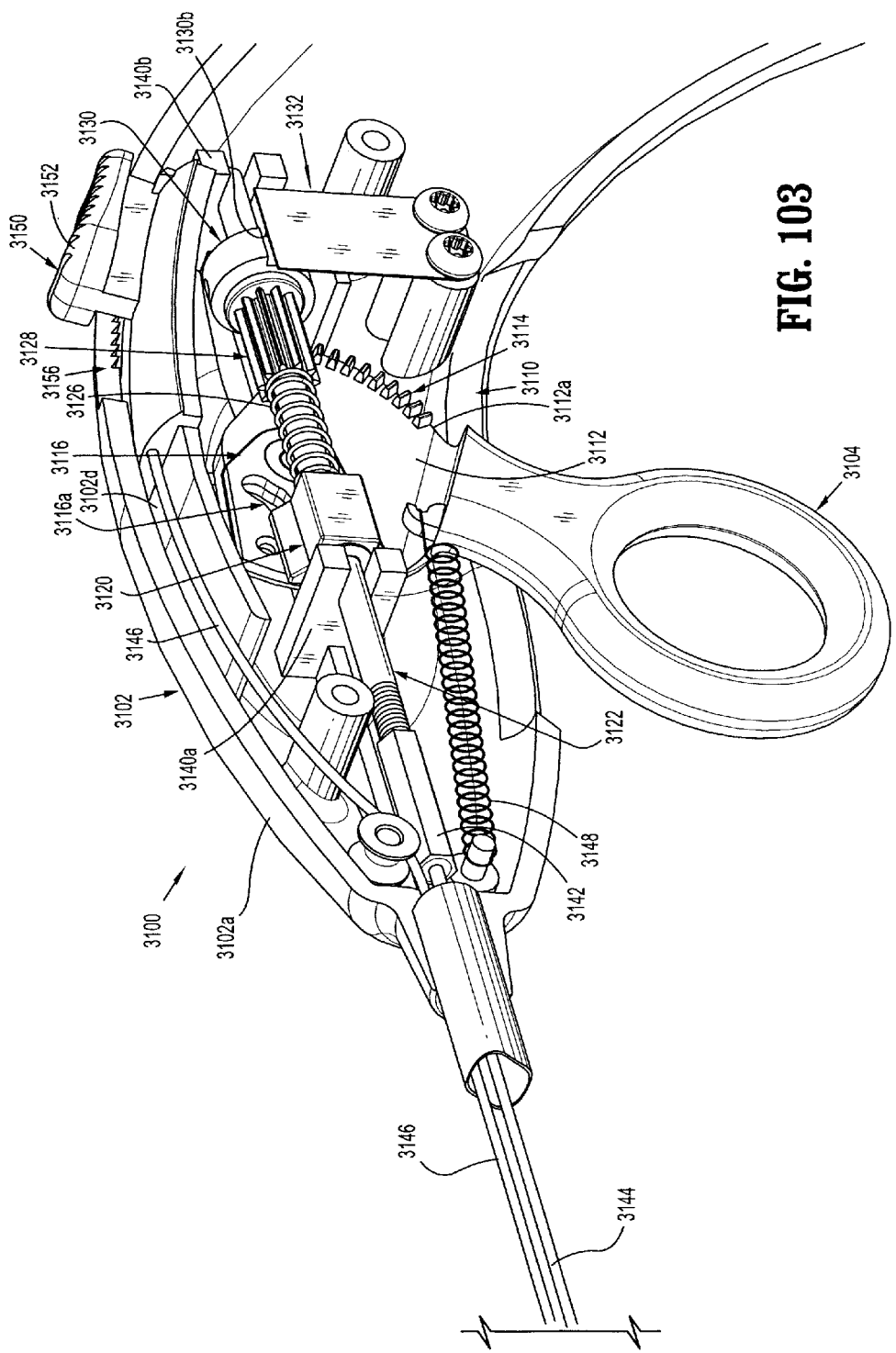
FIG. 103 is a perspective view of the handle assembly of FIG. 102, with a half-section of the housing removed therefrom.
Figure 104:
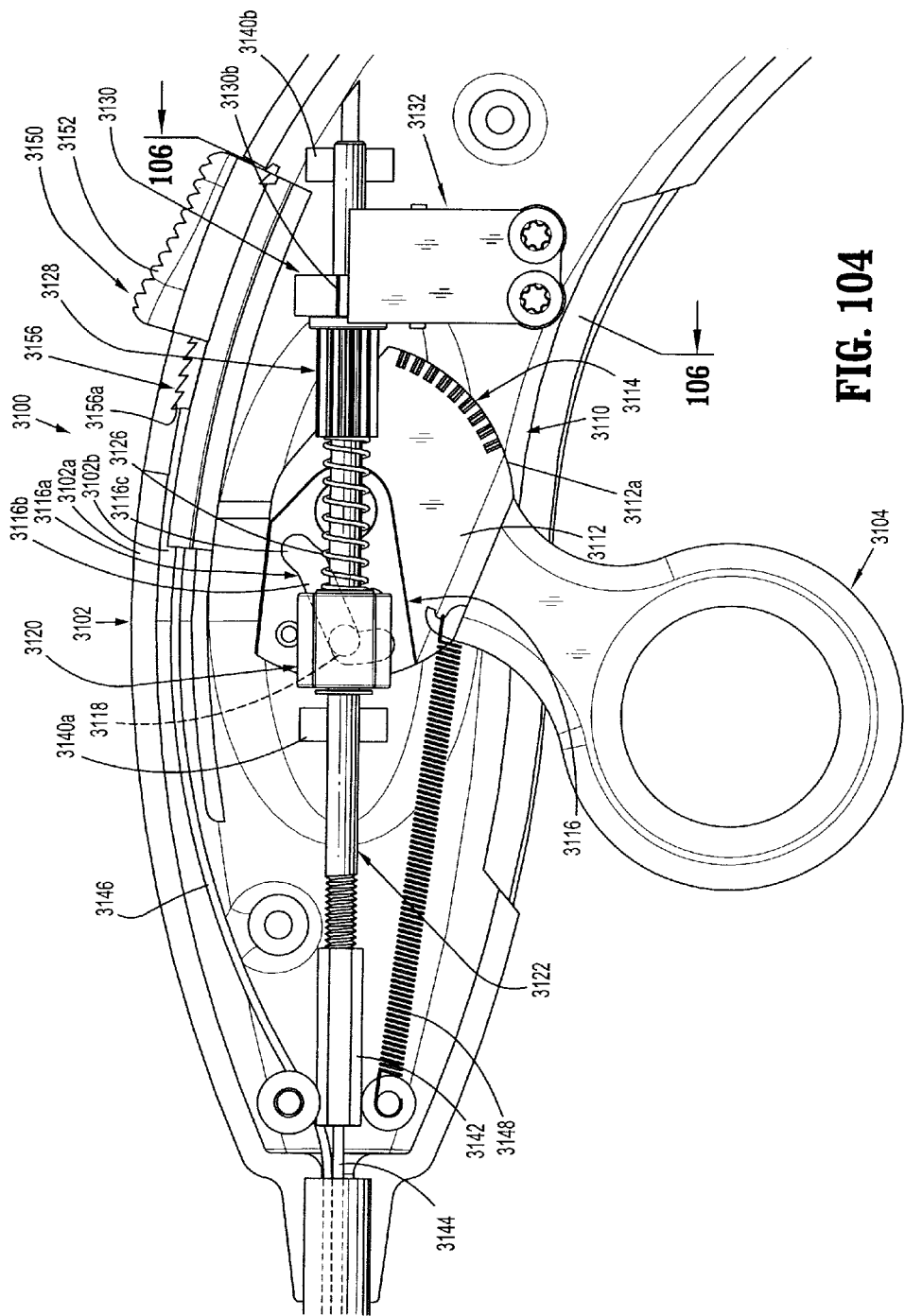
FIG. 104 is a side elevational view of the handle assembly of FIG. 103, illustrating a trigger of the handle assembly in a first position.
Figure 105:
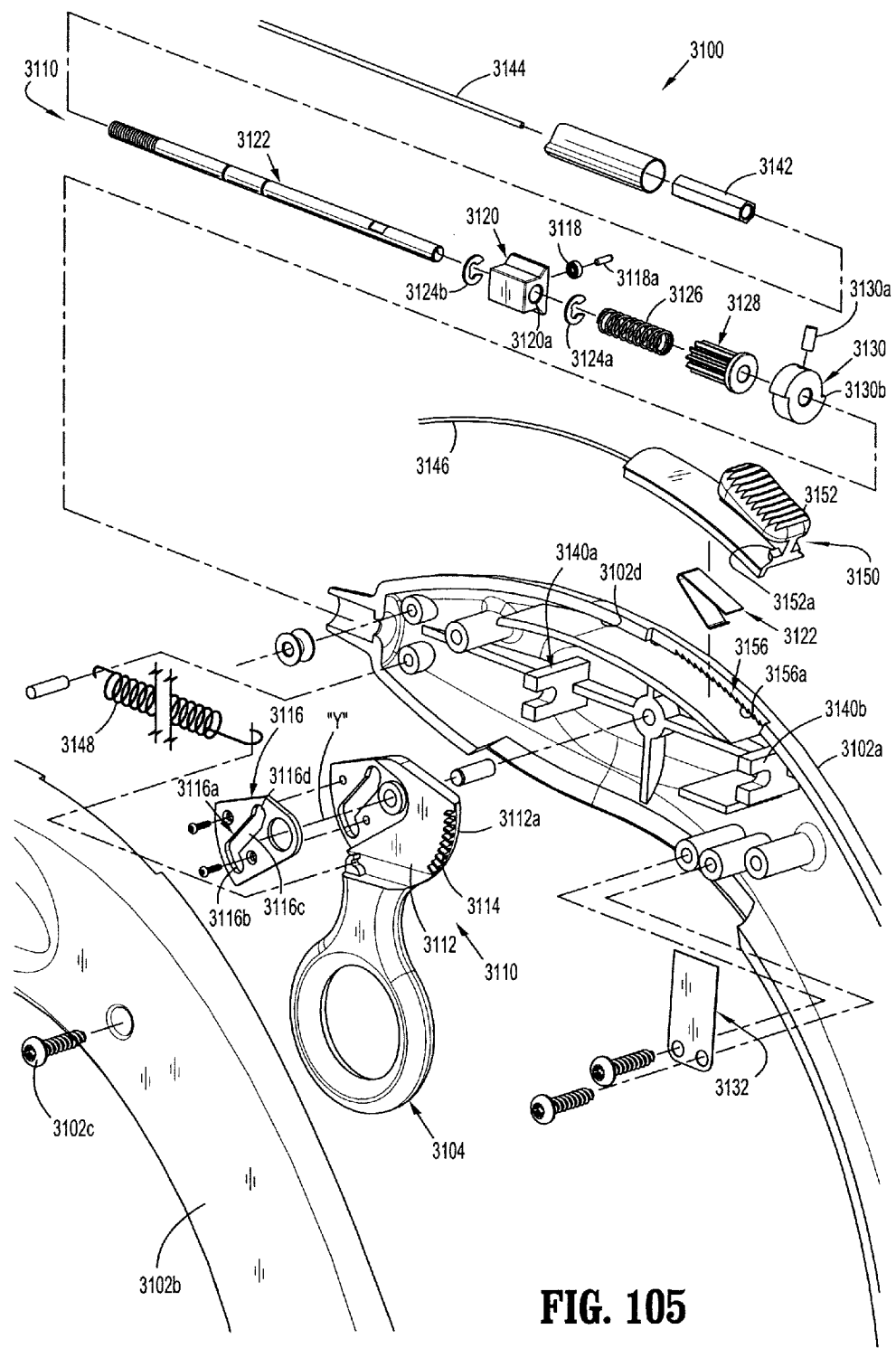
FIG. 105 is an exploded perspective view of the handle assembly of FIGS. 103 and 104.

Referring now to FIGS. 102-110, a handle assembly for operating, manipulating and/or controlling an endoscopic device, in accordance with another embodiment of the present disclosure, is generally designated as 3100. Handle assembly 3100 includes a housing 3102 having a right-half section 3102a and a left-half section 3102b joinable to one another by suitable fastening elements 3102c, such as screws 3102c, as shown in FIG. 105.

Figure 102:
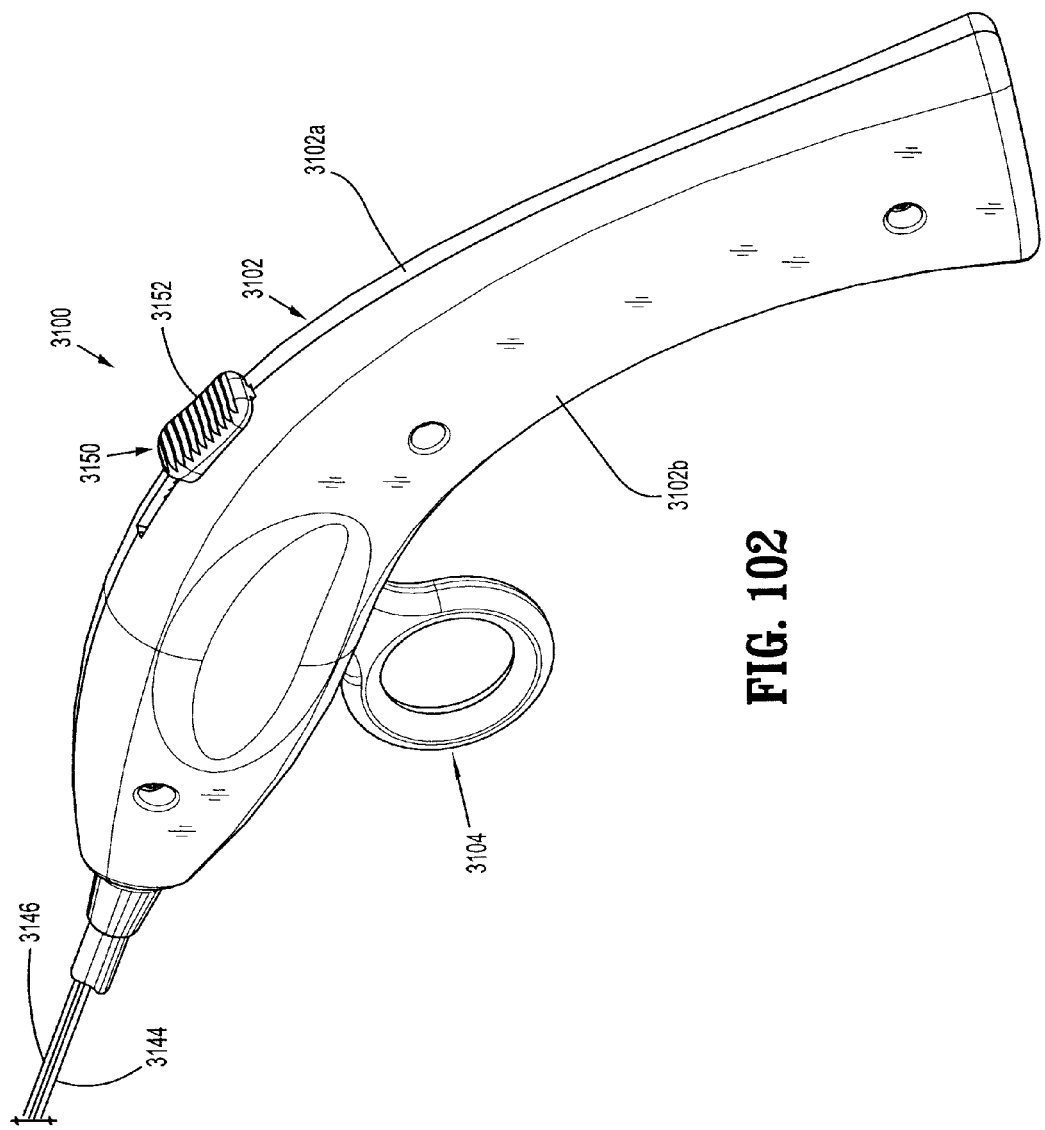
FIG. 102 is a perspective view of a handle assembly according to an embodiment of the present disclosure.
Figure 109:
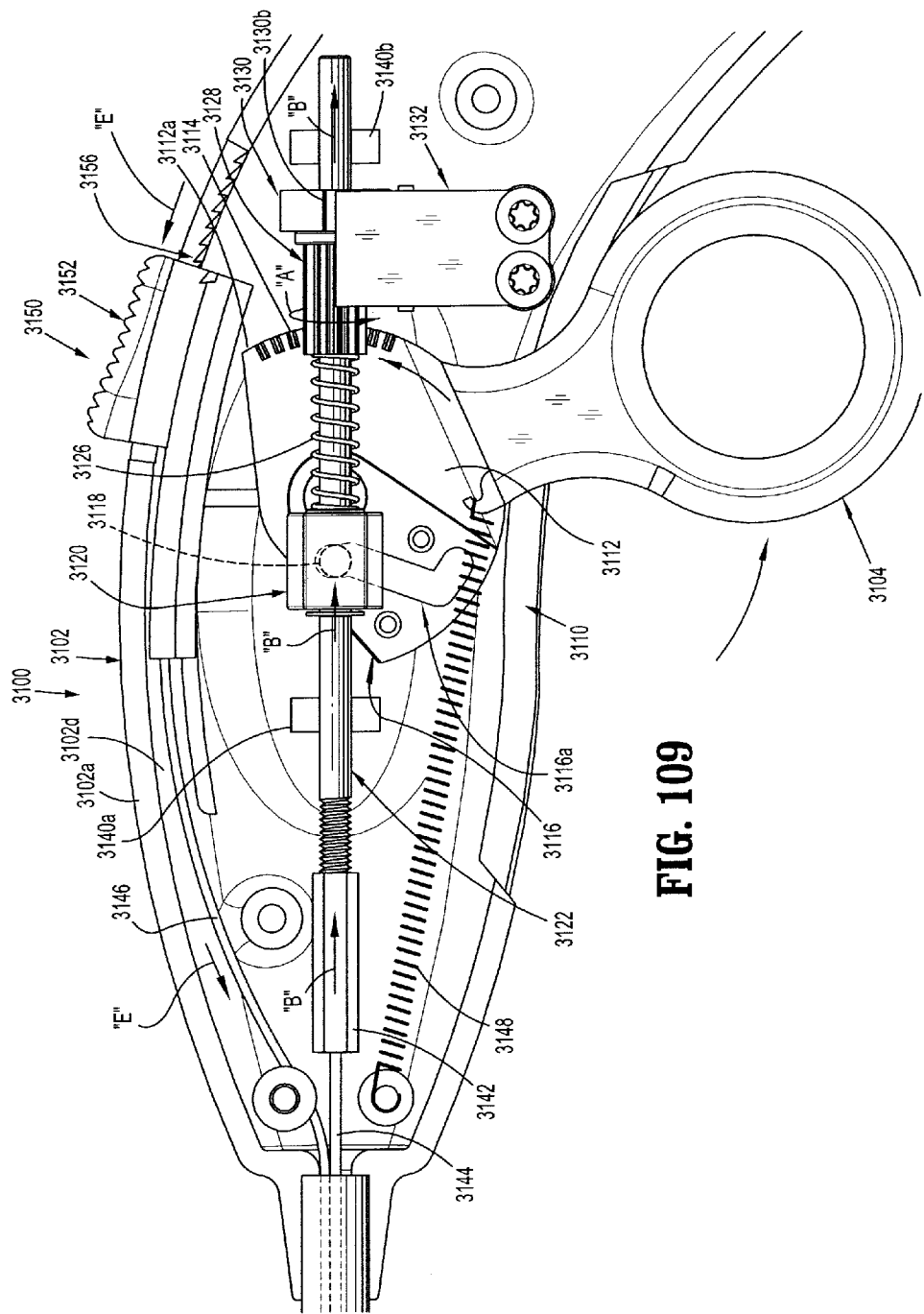
FIG. 109 is a side elevational view of the handle assembly of FIG. 103, illustrating a trigger of the handle assembly in a second position.

Handle assembly 3100 includes a trigger 3104 operatively supported in housing 3102 and extending therefrom. As will be described in greater detail below, trigger 3104 is movable between a first un-actuated position, as seen in FIGS. 102-104, and a second actuated position, as seen in FIG. 109. In use, movement of trigger 3104 between the first and second positions results in actuation and/or operation of an end effector (not shown).

Trigger 3104 is operatively associated or otherwise connected to an actuation mechanism 3110 (see FIG. 107) of handle assembly 3100. As will be described in greater detail below, in use, movement of trigger 3104 between the first and second positions results in two operations of an end effector.

As seen in FIGS. 103-105, 107, 109 and 110, actuation mechanism 3110 includes a trigger plate 3112 connected to and extending from trigger 3104. Trigger plate 3112 defines a gear segment 3114 along a proximal or rear edge 3112a thereof.

Actuation mechanism 3110 includes a cam plate 3116 fixedly supported or connected to trigger plate 3112. Cam plate 3116 is secured to trigger plate 3112 so as to rotate about a pivot axis "Y" (see FIG. 105) of trigger 3104 and trigger plate 3112. Cam plate 3116 defines a cam slot 3116a formed therein including a first, second and third section 3116b, 3116c, and 3116d (see FIG. 105), respectively. Cam slot 3116a has a substantially "S-shaped" configuration. As seen in FIGS. 105 and 107, a cam follower 3118 is slidably positioned in cam slot 3116a of cam plate 3116.

Actuation mechanism 3110 includes a cam follower block 3120 operatively associated with cam plate 3116. Follower block 3120 pivotably supports cam follower 3118 via a pivot pin 3118a or the like. In use, as will be described in greater detail below, as trigger 3140 moved between the first and second positions, cam plate 3116 is pivoted about pivot axis "Y" and follower block 3120 is displaced along cam slot 3116a of cam plate 3116. As best seen in FIGS. 105 and 107, follower block 3120 defines a lumen 3120a therethrough. Lumen 3120a of follower block 3120 is oriented in a direction orthogonal to pivot axis "Y". In one embodiment, lumen 3120a of follower block 3120 is coaxially disposed on a longitudinal "X" axis of a drive shaft of handle assembly 3100.

As seen in FIGS. 103-105, 107, 109 and 110, actuation mechanism 3110 includes a drive or actuation shaft 3122 extending through and operatively associated with follower block 3120. Actuation shaft 3122 is axially fixed relative to follower block 3120 by a pair of retaining rings 3124a, 3124b connected to actuation shaft 3122 at a respective location distal and proximal of follower block 3120. In this manner, actuation shaft 3122 is free to rotate about a longitudinal axis thereof, relative to follower block 3120, and moves distally and proximally with a corresponding distal or proximal movement of follower block 3120.

Actuation mechanism 3110 includes a coil or compression spring 3126 disposed on actuation shaft 3122 at a location proximal of follower block 3120. Actuation mechanism 3110 further includes a pinion gear 3128 rotatably supported on actuation shaft 3122 at a location proximal of spring 3126. Pinion gear 3128 is positioned on actuation shaft 3122 so as to operatively engage and/or mesh with gear segment 3114 of trigger plate 3112.

Actuation mechanism 3110 further includes a toothed wheel 3130 fixedly supported on or connected to actuation shaft 3122 via a screw or fastener 3130a. Toothed wheel 3130 defines a pair of diametrically opposed teeth 3130b formed therein or thereon. Toothed wheel 3130 is disposed at a location proximal of pinion gear 3128 and is in frictional engagement therewith. A pawl 3132 is operatively associated with toothed wheel 3130 in such a manner so as to permit rotation of toothed wheel 3130 in a single direction.

With continued reference to FIGS. 102-110, a method of using and/or operating handle assembly 3100 is shown and described. As seen in FIGS. 103 and 104, when trigger 3104 is in a first or un-actuated position, cam follower 3118 is positioned proximate a distal end of second section 3116c of cam slot 3116a of cam plate 3116.

As seen in FIG. 109, when trigger 3104 is squeezed to a second or fully actuated position, gear segment 3114 of trigger plate 3112 is pivoted about pivot axis "Y" and actuates (i.e., rotates) pinion gear 3128 in a first direction "A". Since pinion gear 3128 is rotatably supported on actuation shaft 3122, no rotation of actuation shaft 3122 is imparted thereto. Also, since pinion gear 3128 frictionally engages toothed gear 3130, rotation of pinion gear 3128 imparts rotation to toothed gear 3130. However, as seen in FIGS. 106 and 109, rotation of toothed gear 3130, in the direction of arrow "A", is prevented by the inter-engagement of pawl 3132 with a tooth 3130b of toothed gear 3130.

With continued reference to FIG. 109, simultaneously or concomitantly with the rotation of pinion gear 3128 in the direction of arrow "A", as trigger 3104 is squeezed to a second or fully actuated position, cam follower 3118 is caused to be displaced through cam slot 3116a of cam plate 3116. As cam follower 3118 is moved through cam slot 3116a, follower block 3120 is caused to be moved in a proximal direction, as indicated by arrow "B". Movement of follower block 3120 in the direction of arrow "B" results in the movement of actuation shaft 3122 in the direction of arrow "B". Movement of actuation shaft 3122 solely in an axial direction is accomplished through uprights or guides 3140a, 3140b, located near a distal end and a proximal end of actuation shaft 3122.

Movement of actuation shaft 3122 in the direction of arrow "B" results in movement of an adjustment screw 3142, operatively connected to a distal end of actuation shaft 3122, in the direction of arrow "B", which in turn results in movement of a first actuation cable 3144 in the direction of arrow "B". Movement of first actuation cable 3144, in the direction of arrow "B", may result in a first operation or movement of an end effector (not shown), such as, for example, an approximation or an opening or jaws of the end effector. In an alternative embodiment (not shown), a rigid or substantially rigid rod or shaft may be substituted for actuation cable 3144.

Figure 110:
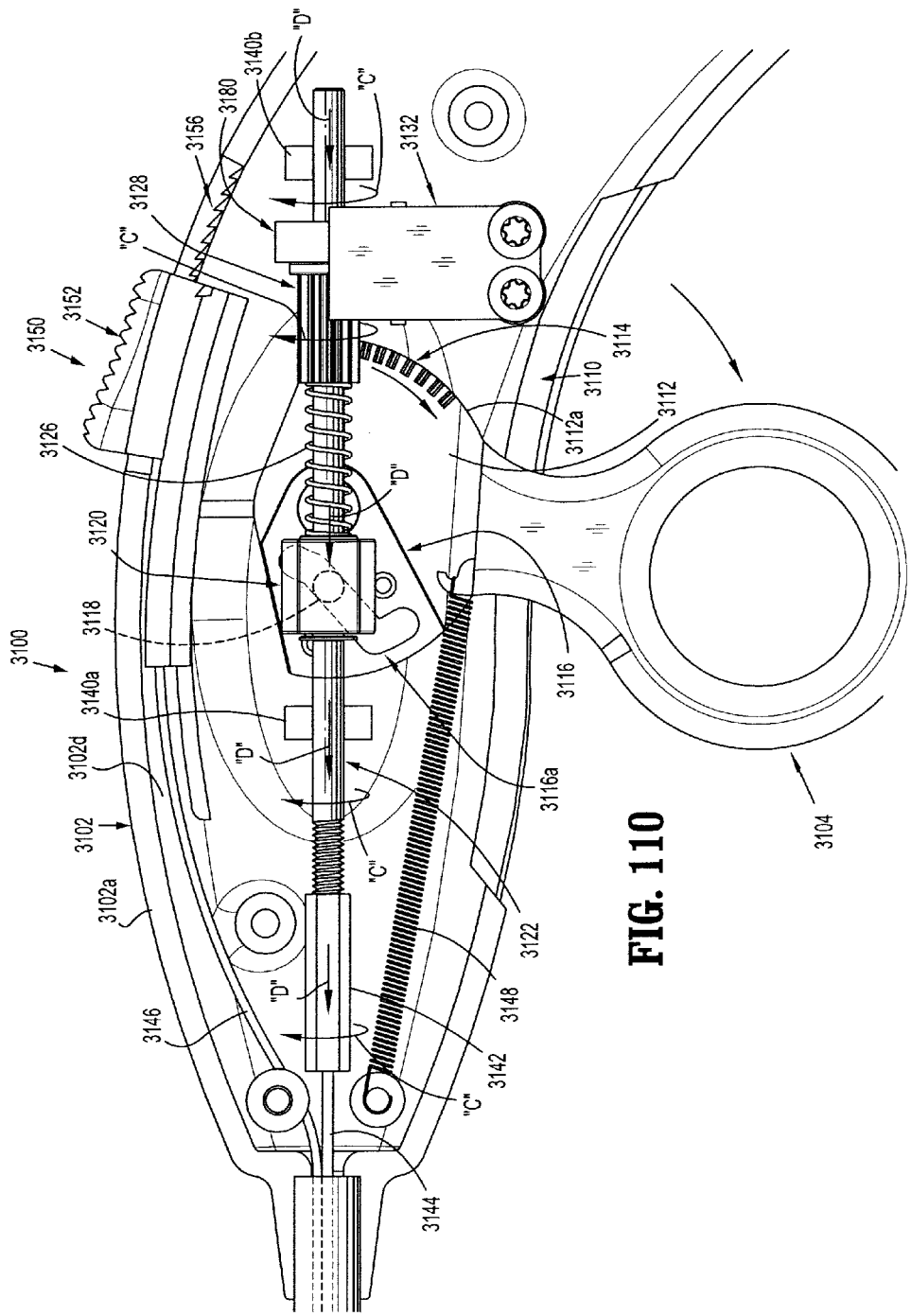
FIG. 110 is a side elevational view of the handle assembly of FIG. 103, illustrating a trigger of the handle assembly in a third position.
Figure 111:
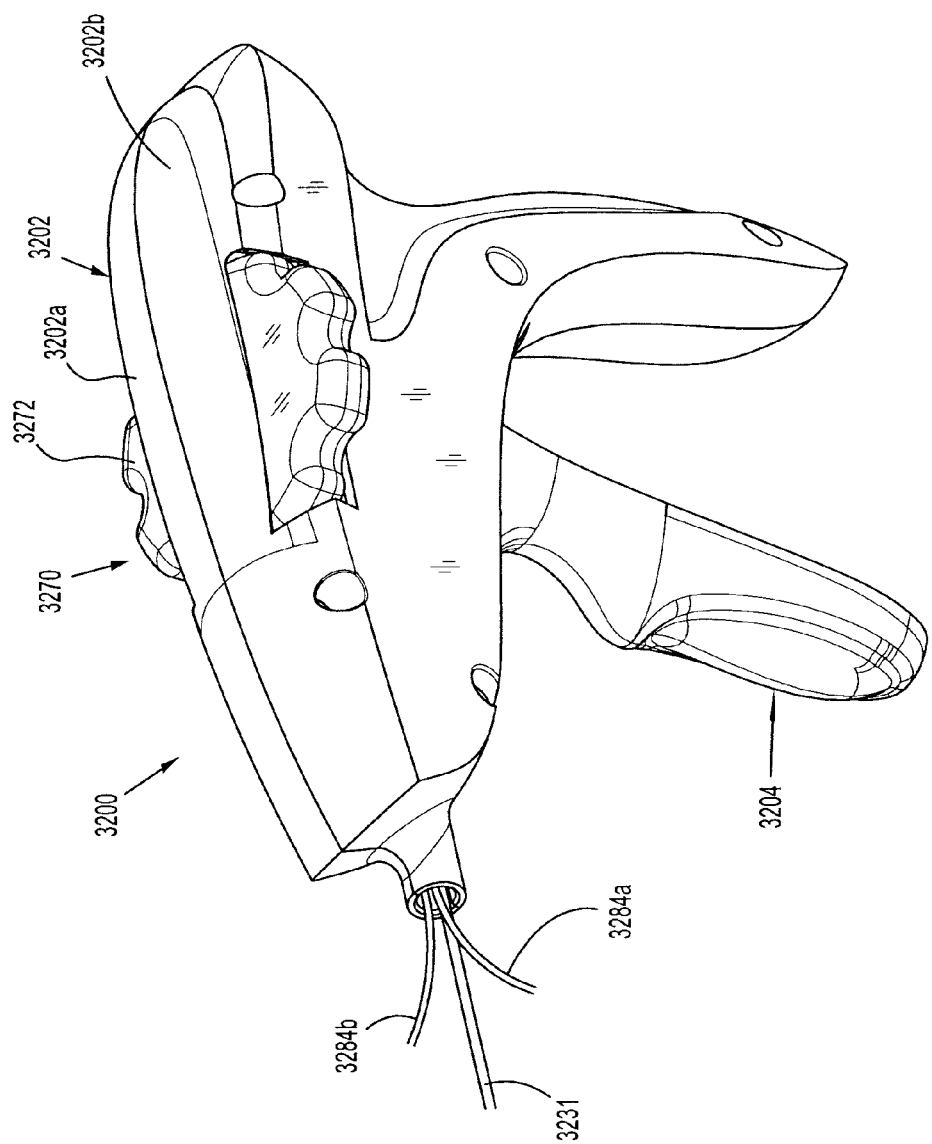
FIG. 111 is a perspective view of a handle assembly according to another embodiment of the present disclosure.

As seen in FIG. 110, upon release of trigger 3104 or upon the return of trigger 3104 to the first or un-actuated condition, gear segment 3114 of trigger plate 3112 is pivoted about pivot axis "Y" and actuates (i.e., rotates) pinion gear 3128 in a second direction "C", opposite to first direction "A". Since pinion gear 3128 fictionally engages toothed gear 3130, rotation of pinion gear 3128 in the direction of arrow "C" imparts rotation to toothed gear 3130. As seen in FIGS. 106 and 110, rotation of toothed gear 130, in the direction of arrow "C", is permitted since pawl 3132 does not engage tooth 3130b of toothed gear 3130 but simply slides thereover.

Since toothed gear 3130 is keyed to or otherwise fixedly connected to actuation shaft 3122, rotation of toothed gear 3130 in the direction of arrow "C" also results in rotation of actuation shaft 3122, and in turn first actuation cable 3144, in the direction of arrow "C". Rotation of first actuation cable 3144 in the direction of arrow "C" may result in a second operation or movement of an end effector (not shown).

With continued reference to FIG. 110, simultaneously or concomitantly with the rotation of pinion gear 3128 in the direction of arrow "C", as trigger 3104 is moved or returned to the first or un-actuated position, cam follower 3118 is caused to be displaced through cam slot 3116a of cam plate 3116. As cam follower 3118 is moved through cam slot 3116a, follower block 3120 is caused to be moved in a distal direction, as indicated by arrow "D". Movement of follower block 3120 in the direction of arrow "D" results in the movement of actuation shaft 3122 in the direction of arrow "D". Guides 3140a, 3140b once again solely permit movement of actuation shaft 3122 in an axial direction.

Movement of actuation shaft 3122 in the direction of arrow "D" results in movement of adjustment screw 3142, and in turn first actuation cable 3144 in the direction of arrow "D". Movement of first actuation cable 3144, in the direction of arrow "D", may result in a third operation or movement of an end effector (not shown), such as, for example, an approximation or an opening or jaws of the end effector.

Return or movement of trigger 3104 from the second position to the first position is facilitated by a tension spring 3148 or the like operatively connected to and extending between housing 3102 and trigger 3104.

With continued reference to FIGS. 102-110, handle assembly 3100 further includes another actuation mechanism or articulation controller 3150. Articulation controller 3150 includes a slider 3152 slidably supported in tracks 3102*d* formed in housing 3102. Slider 3152 is biased to a raised position by a biasing member 3154 (i.e., spring clip or the like). In the raised position, a tooth 3152*a* formed on slider 3152 engages with a tooth 3156*a* of a rack 3156 formed in housing 3102. A second actuation cable 3146 extends from slider 3152 and out through a distal end of housing 3102 to operative engage an end effector (not shown).

In operation, as seen in FIG. 109, as slider 3152 is actuated or moved in the direction of arrow "E" (i.e., from a proximal-most to a distal-most position), second actuation cable 3146 is also moved in the direction of arrow "E". Movement of second actuation cable in the direction of arrow "E" may result in an operation of an end effector (not shown), such as, for example, an articulation of an end effector in a direction or an approximation or an opening or jaws of the end effector.

In order to move slider 3152 in a direction opposite to arrow "E", slider 3152 is pressed toward housing 3102 to disengage tooth 3152*a* thereof from teeth 3156*a* of rack 3156. In this manner, slider 3152 is free to be moved from a distal-most position to a proximal-most position.

First and second actuation cables 3144 and 3146 may be sheathed in a flexible, non-radially expandable, sleeve 3147 or the like. Sleeve 3147 functions to ensure that first and second actuation cables 3144 and 3146 solely translate in an axial direction and do not deflect radially outward. Each actuation cable 3146, 3148 may be fabricated from a suitable material, i.e., stainless steel, capable of transmitting axial and torsional forces.

Turning now to FIGS. 111-125, a handle assembly for operating, manipulating and/or controlling an endoscopic device, in accordance with another embodiment of the present disclosure, is generally designated as 3200. Handle assembly 3200 includes a housing 3202 having a right-half section 3202*a* and a left-half section 3202*b* joinable to one another by suitable fastening elements (not shown), such as screws.

Figure 120:
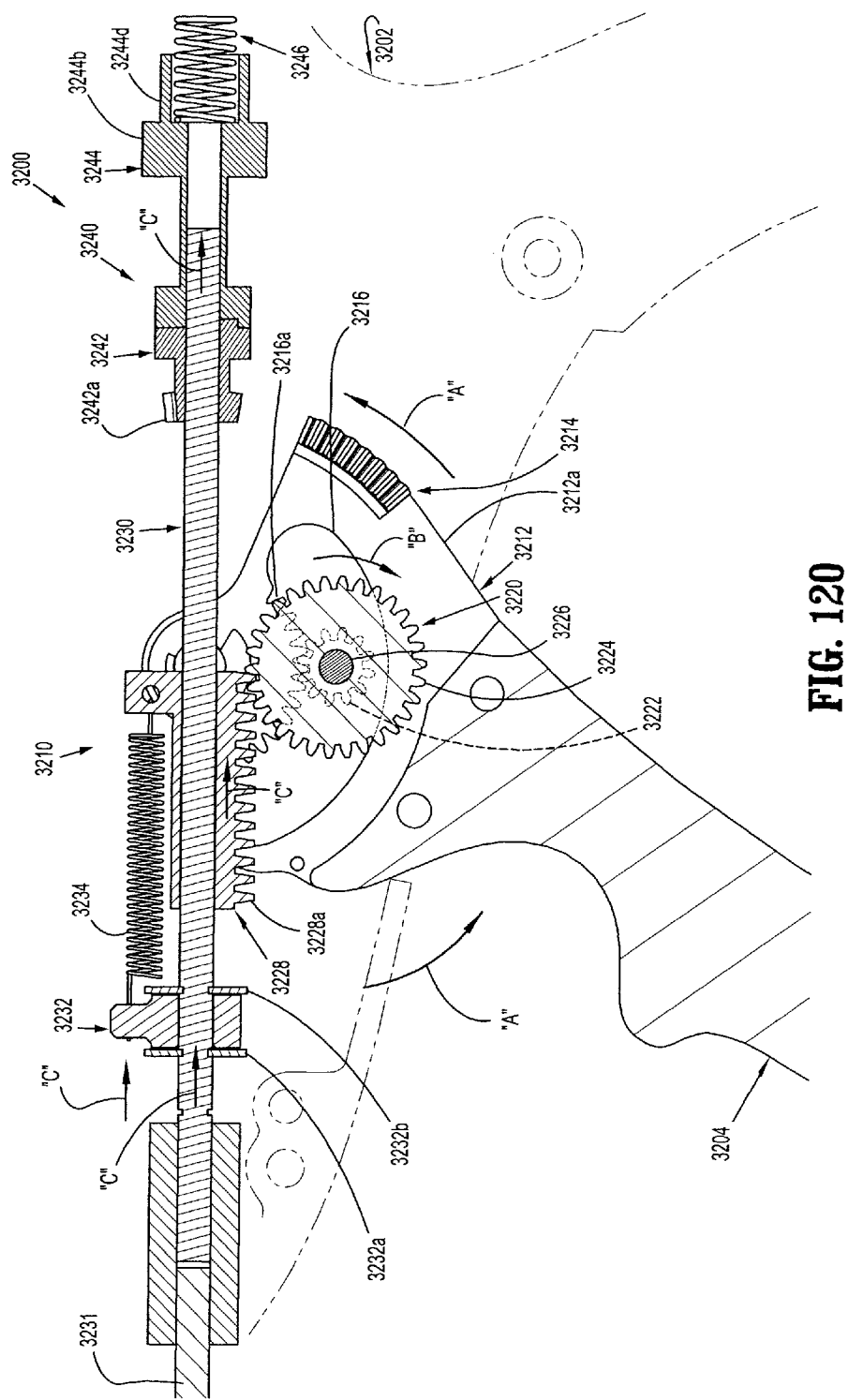
FIG. 120 is a side elevational view of a drive mechanism of the handle assembly of FIGS. 111-114, illustrating the drive mechanism and a trigger of the handle assembly at a first position.
Figure 121:
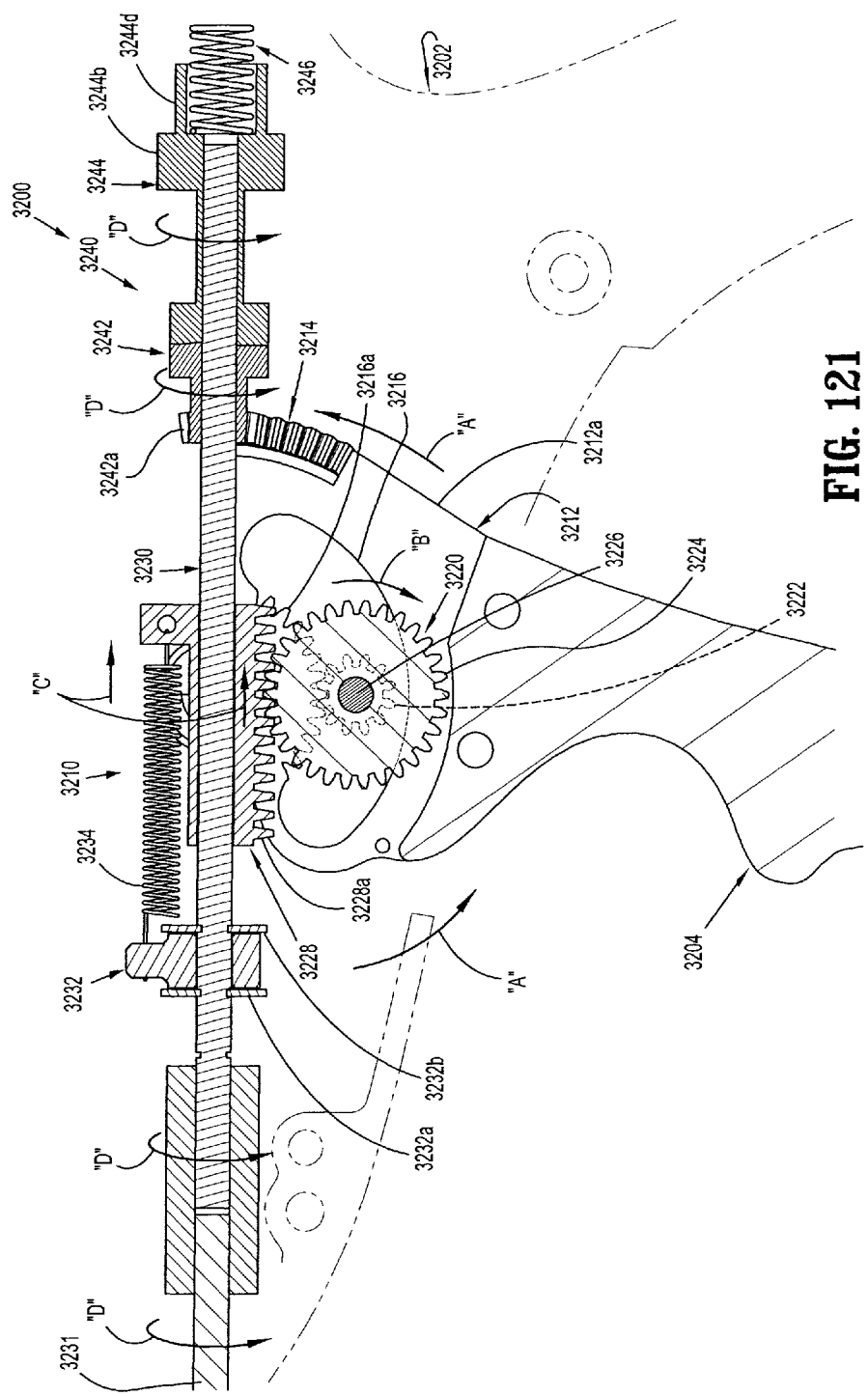
FIG. 121 is a side elevational view of the drive mechanism of FIG. 120, illustrating the drive mechanism and the trigger of the handle assembly at a second position.

Handle assembly 3200 includes a trigger 3204 operatively supported in housing 3202 and extending therefrom. As will be described in greater detail below, trigger 3204 is movable between a first un-actuated position, as seen in FIGS. 111-113 and 120, and at least one second actuated position, as seen in FIGS. 121-122. In use, movement of trigger 3204 between the first and second positions results in actuation and/or operation of an end effector (not shown).

Trigger 3204 is operatively associated or otherwise connected to an actuation mechanism 3210 (see FIGS. 112-114 and 120-124) of handle assembly 3200. As will be described in greater detail below, in use, movement of trigger 3204 between the first and second positions results in two operations of an end effector.

As seen in FIGS. 112-114 and 120-124, actuation mechanism 3210 includes a trigger plate 3212 connected to and extending from trigger 3204. Trigger plate 3212 pivotally connects trigger 3204 to housing 3202. Trigger plate 3212 defines a first gear segment 3214 along a proximal or rear edge 3212*a* thereof. Trigger plate 3212 defines an arcuate slot 3216 therein having a second gear segment 3216*a* formed along an upper edge thereof. Slot 3216 has a radius of curvature having its center located on a pivot axis "Y" (see FIG. 113) of trigger 3204.

A gear set 3220 is operatively associated with slot 3216 of trigger plate. Gear set 3220 includes a first gear 3222 configured to mesh with and/or otherwise operatively engage second gear segment 3216*a* of slot 3216, and a second gear 3224 supported on a common rotational pin 3226 as first gear 3222.

In this manner, as first gear 3222 is rotated due to a movement of trigger 3204, second gear 3224 is simultaneously and/or concomitantly rotated.

Second gear 3224 of gear set 3220 is configured to mesh with and/or otherwise operatively engage teeth 3228 of a rack 3228. Rack 3228 defines a lumen 3228*b* therethrough. Lumen 3228*b* of rack 3228 is oriented in a direction tangential to pivot axis "Y". In one embodiment, lumen 3228*b* of rack 3228 is coaxially disposed on a longitudinal "X" axis of an actuation shaft of handle assembly 3200.

As seen in FIGS. 112-114 and 120-124, actuation mechanism 3210 includes a drive or actuation shaft 3230 extending through and operatively associated with rack 3228, and a follower block 3232 rotatably supported on actuation shaft 3230 at a fixed location distal of rack 3228. Actuation shaft 3230 is axially translatable and rotatable relative to rack 3228. Follower block 3232 is axially held in position relative to actuation shaft 3230 by a pair of ring clamps 3232*a*, 3232*b* secured to actuation shaft 3230 at a location distal and proximal of follower block 3232. Rack 3228 and follower block 3232 are connected to one another by a biasing member 3234, i.e., a tension spring, extending therebetween.

Figures 115, 116:
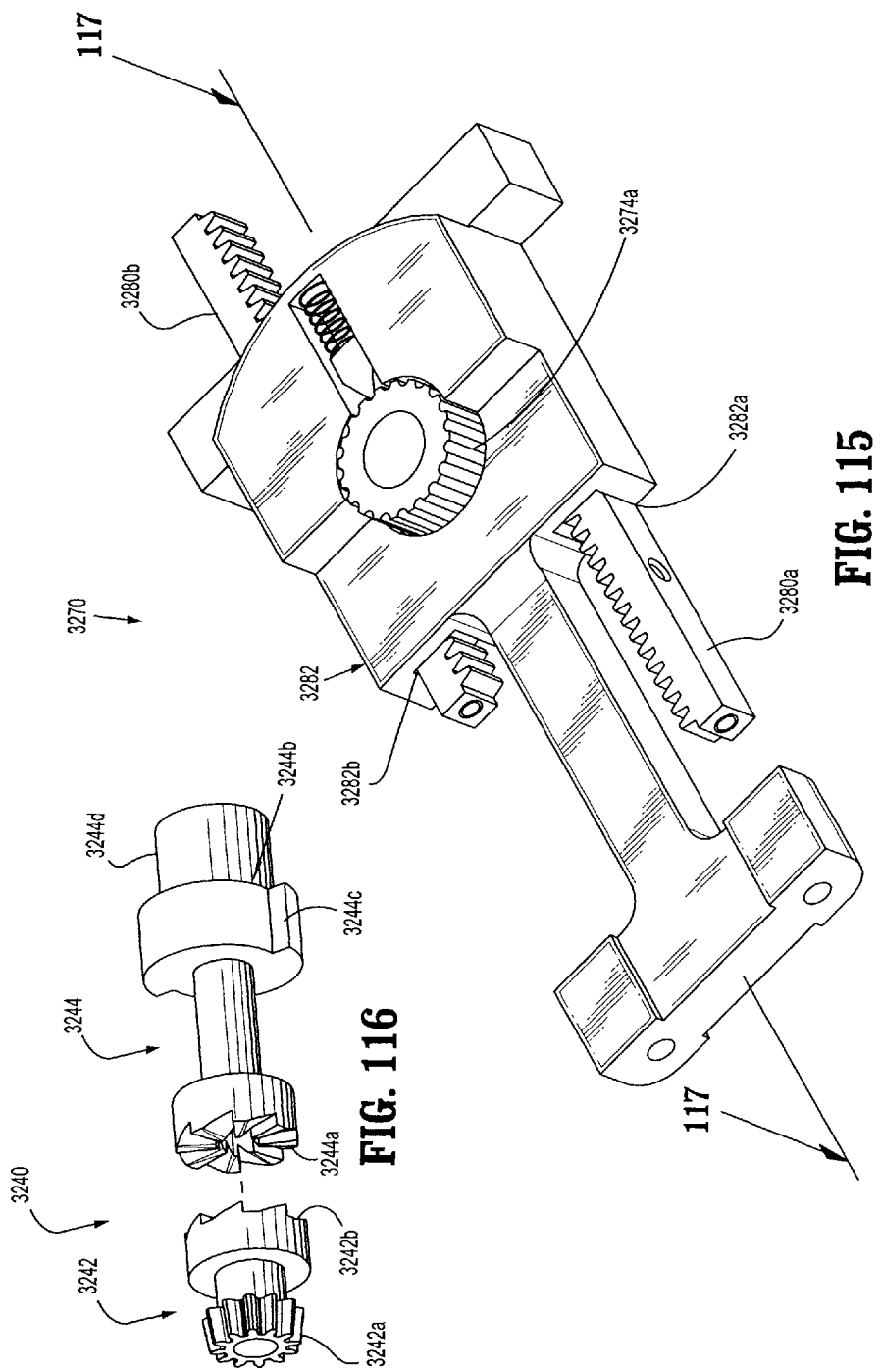
FIG. 115 is a perspective view of an articulation control mechanism of the handle assembly of FIGS. 111-114.
FIG. 116 is a perspective view of a slip-clutch of the handle assembly of FIGS. 111-114.
Figure 119:
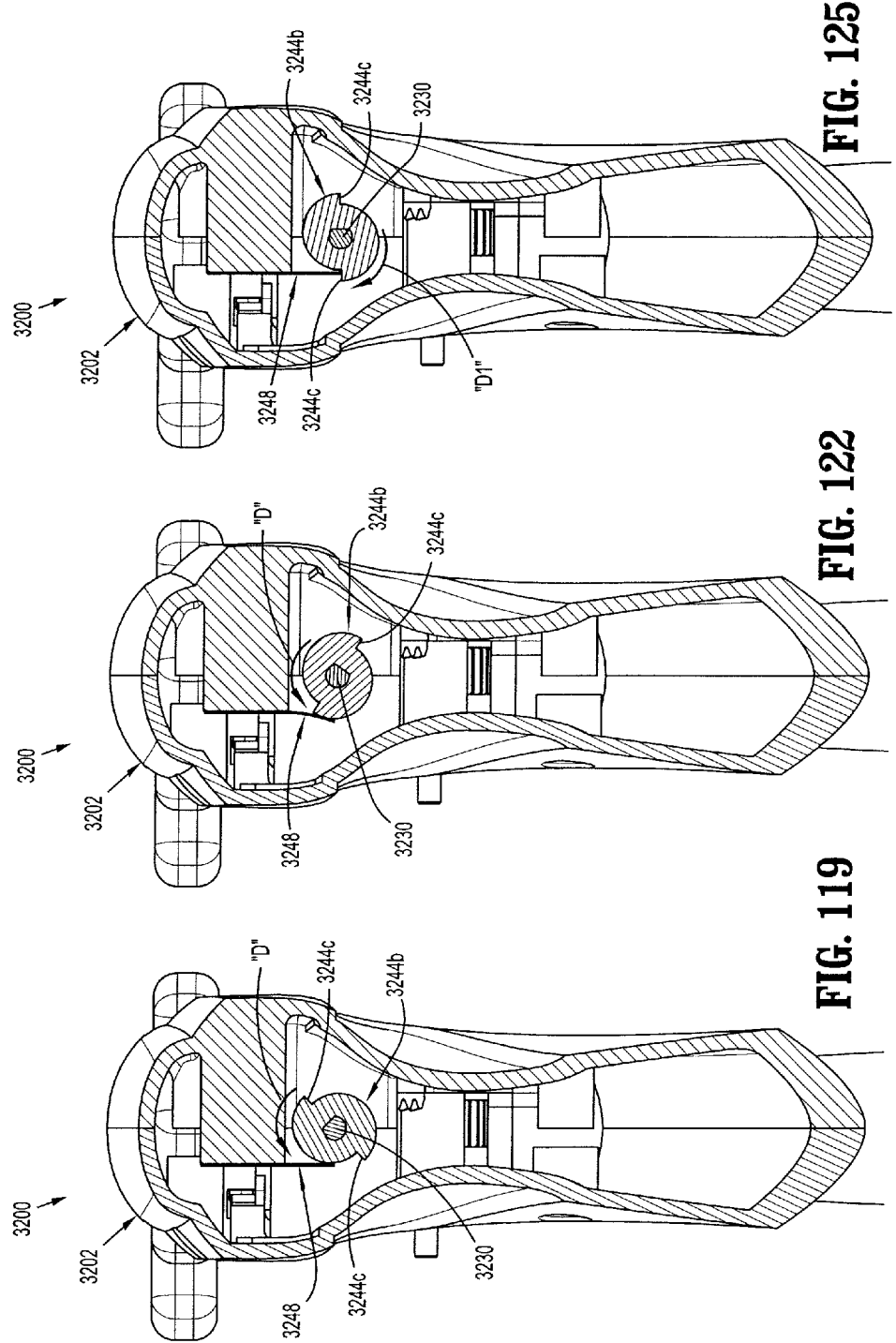
FIG. 119 is a cross-sectional view of the handle assembly of FIGS. 111-114, as taken through 119-119 of FIG. 112, illustrating a first position of a uni-directional pawl assembly.

Actuation mechanism 3210 includes a slip-clutch 3240 supported on a proximal end of actuation shaft 3230. As seen in FIG. 116, slip clutch 3240 includes a distal portion 3242 having a distal bevel gear 3242*a* configured to mesh with and/or otherwise operatively engage first gear segment 3214 of trigger plate 3212, and a set of proximally-facing gear teeth 3242*b*. Slip clutch 3240 further includes a proximal portion 3244 having a set of distally-facing gear teeth 3244*a* configured to mesh with and/or otherwise operatively engage the set of proximally-facing gear teeth 3242*b* of distal portion 3242, and a toothed wheel 3244*b* located proximal of the set of distally-facing gear teeth 3244*a*. Toothed wheel 3244*b* defines a pair of diametrically opposed teeth 3244*c* formed therein or thereon. As seen in FIGS. 119, 122 and 125, toothed wheel 3244*b* is keyed to actuation shaft 3230 so as to solely enable axial displacement of toothed wheel 3244*b* relative to actuation shaft 3244*b*.

In operation, as will be discussed in greater detail below, the set of distally-facing gear teeth 3244*a* cooperate with the set of proximally-facing gear teeth 3242*b* to impart rotation in a single direction.

Proximal portion 3244 of slip-clutch 3240 is biased against distal portion 3242 of slip-clutch 3240 by a biasing member 3246, such as, for example, a compression spring or the like, disposed between housing 3202 and proximal portion 3244 of slip-clutch 3240. A pawl 3248 is operatively associated with toothed wheel 3244*b* in such a manner so as to permit rotation of toothed wheel 3244*b* in a single direction.

Figure 112:
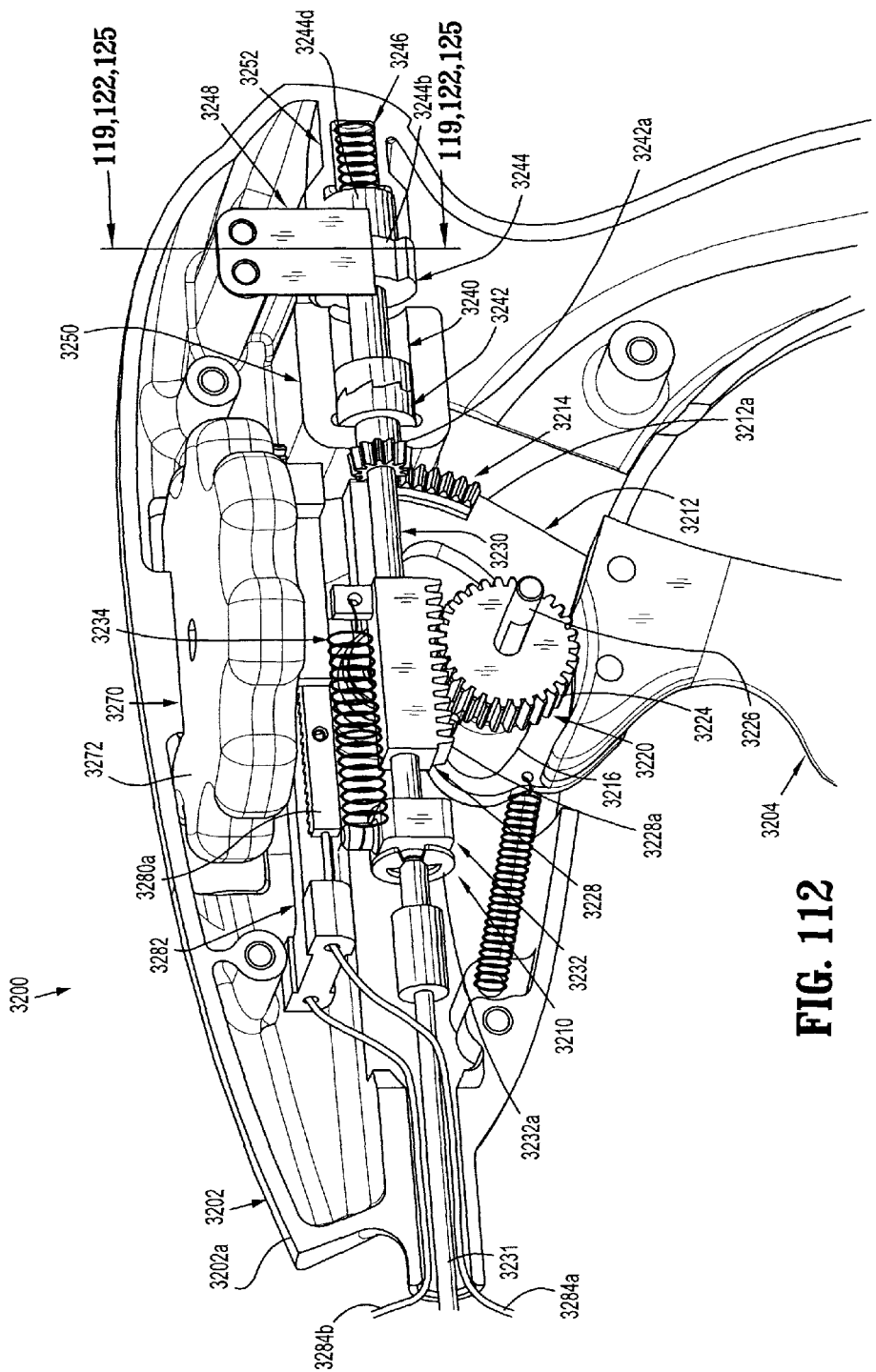
FIG. 112 is a left-side perspective view of the handle assembly of FIG. 111, with a left half-section of the housing removed therefrom.
Figure 113:
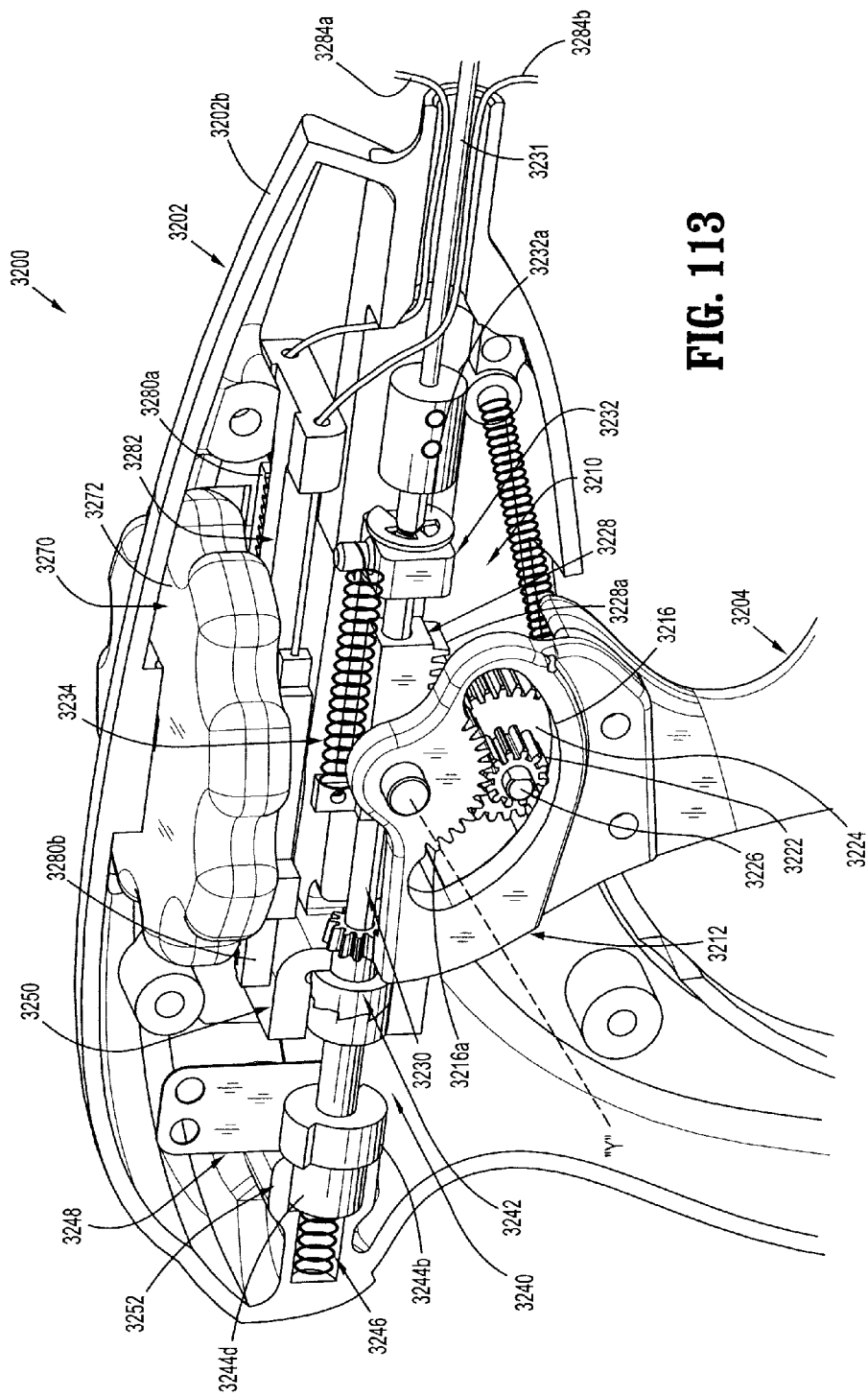
FIG. 113 is a right-side perspective view of the handle assembly of FIG. 111, with a right half-section of the housing removed therefrom.
Figure 114:
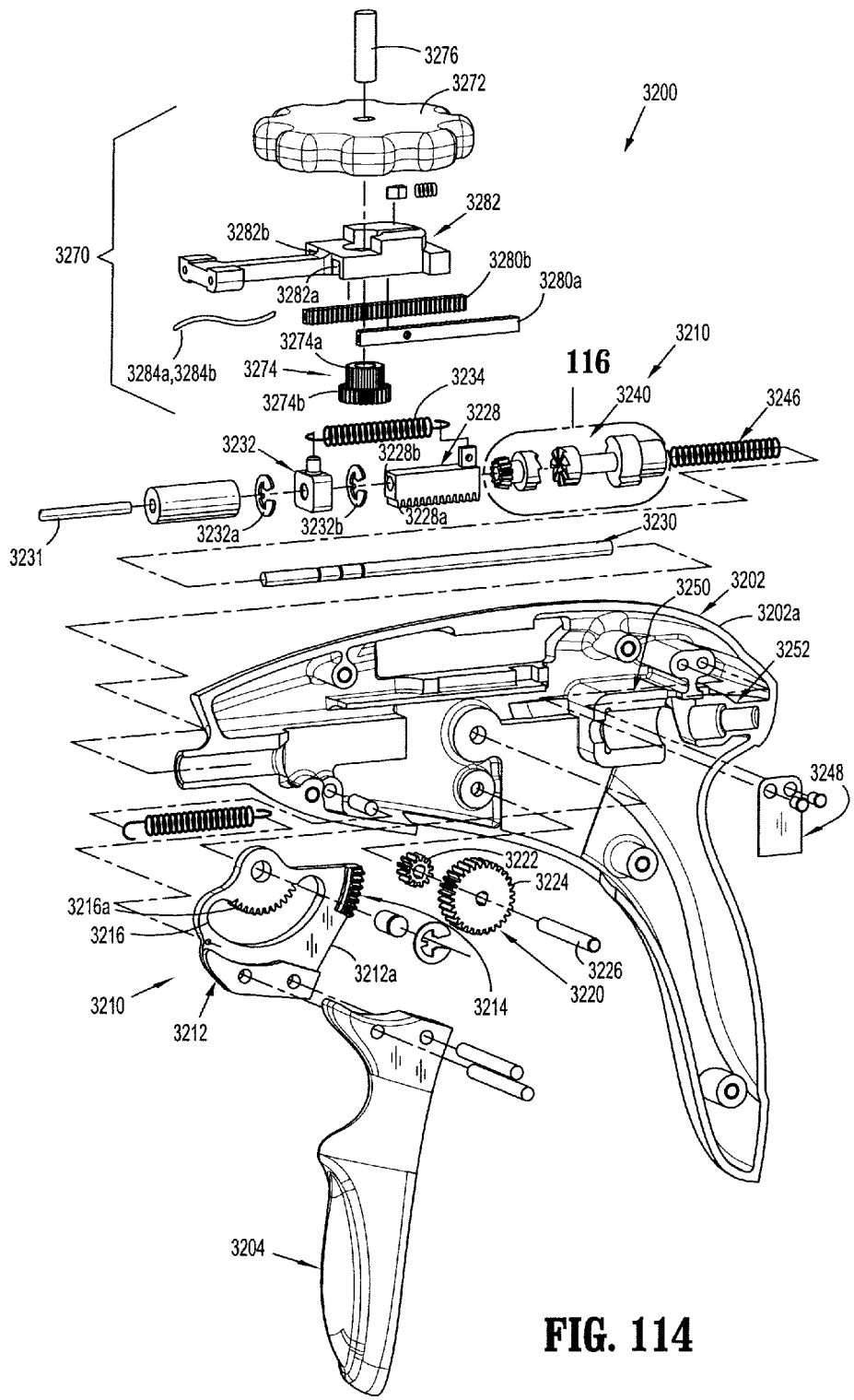
FIG. 114 is an exploded perspective view of the handle assembly of FIGS. 111-113.

As seen in FIGS. 112-114, at least proximally-facing gear teeth 3242*b* of distal portion 3242 of slip-clutch 3240 is retained in a hub 3250 formed in housing 3202, and at least a boss 3244*d*, extending proximally from toothed wheel 3244*b*, is retained in a hub 3252 formed in housing 3202.

With continued reference to FIGS. 111-125, a method of using and/or operating handle assembly 3200 is shown and described. As seen in FIG. 120, when trigger 3204 is in a first or un-actuated position, rack 3228 is at a distal-most position relative to actuation shaft 3230 such that a proximal-most tooth 3228*a* thereof meshes with and/or otherwise operatively engages second gear 3224 of gear set 3220. Also, as seen in FIG. 120, when trigger 3204 is in a first or un-actuated position, first gear segment 3214 of trigger plate 3212 is spaced a distance from bevel gear 3242*a* of distal portion 3242 of slip clutch 3240.

As seen in FIGS. 120 and 121, as trigger 3204 is squeezed or moved to a second or at least partially actuated position, as indicated by arrow "A", second gear segment 3216a of slot 3216 causes first gear 3222 as well as second gear 3224 of gear set 3220 to rotate in the direction of arrow "B". As first and second gears 3222, 3224 of gear set 3220 are rotated in the "B" direction, second gear 3224 causes rack 3228 to move in the direction of arrow "C" (i.e., in a proximal direction). As rack 3228 is moved proximally, actuation shaft 3230 is also moved proximally, in the direction of arrow "C", due to the connection of follower block 3232 to rack 3230 via biasing member 3234. Proximal movement of actuation shaft 3230 may result in an operation or movement in an end effector (not shown) connected to a distal end of actuation shaft 3230 via an actuation cable 3231.

As seen in FIG. 121, as trigger 3204 is further squeezed or moved in the direction of arrow "A", first gear segment 3214 of trigger plate 3212 operatively engages bevel gear 3242a of distal portion 3242 of slip clutch 3240. As trigger 3204 is moved in the direction of arrow "A", first gear segment 3214 of trigger plate 3212 imparts rotation to bevel gear 3242a of distal portion 3242 of slip clutch 3240, in the direction of arrow "D". Rotation of bevel gear 3242a of distal portion 3242 of slip clutch 3240 in turn imparts rotation to proximal portion 3244 of slip clutch 3240, due to the meshing of respective gear teeth 3242b, 3244a, which in turn imparts rotation to actuation shaft 3230, due to the keying of toothed wheel 3244b of proximal portion 3244 to actuation shaft 3230.

As seen in FIGS. 119 and 122, as toothed wheel 3244b of proximal portion 3244 of slip clutch 3240 is rotated in the direction of arrow "D", pawl 3248 rides over and against an outer surface thereof.

Figure 123:
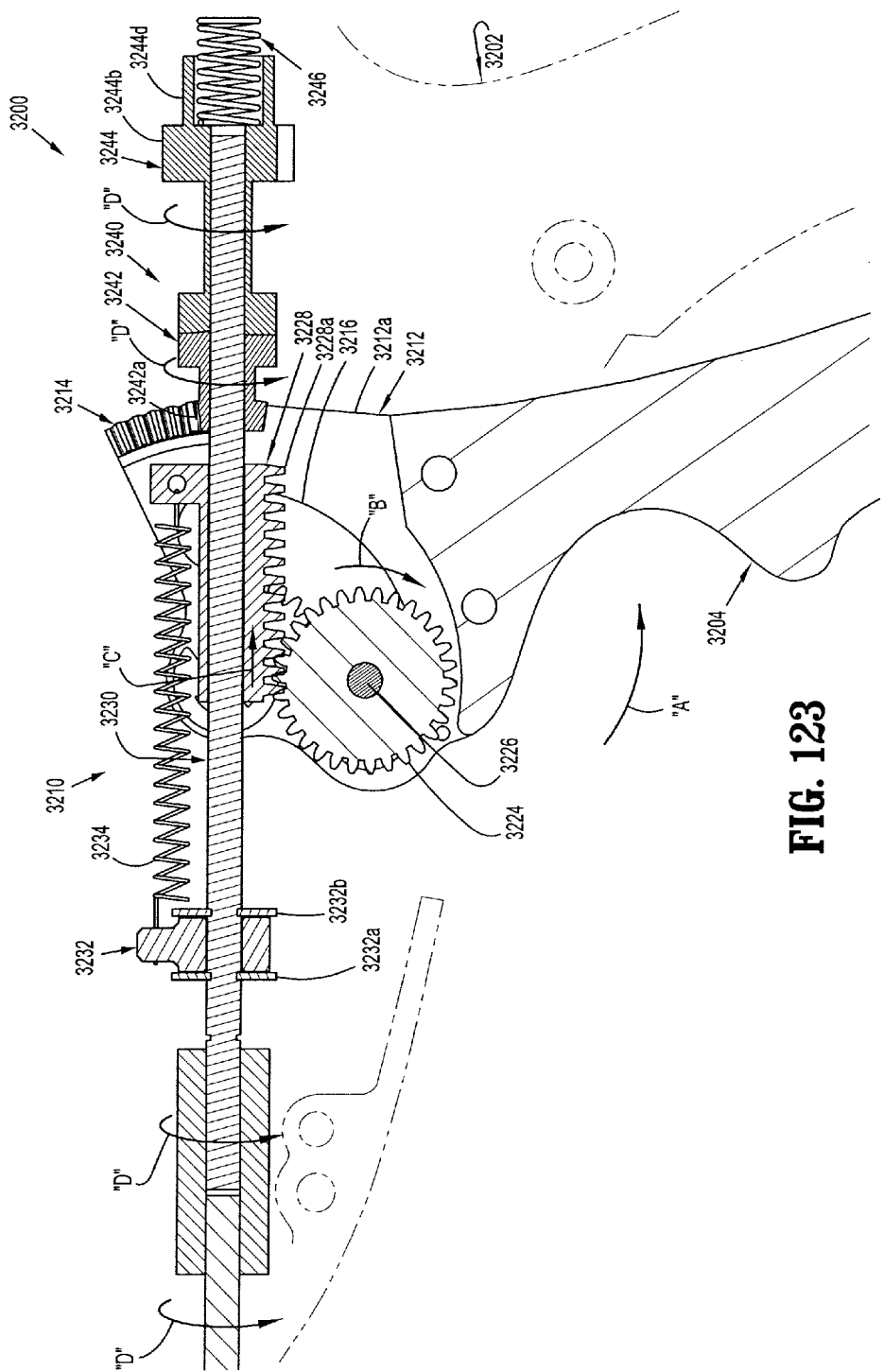
FIG. 123 is a side elevational view of the drive mechanism of FIG. 120, illustrating the drive mechanism and trigger of the handle assembly in a third position.

As seen in FIG. 123, as trigger 3204 is further squeezed or moved in the direction of arrow "A", second gear 3224 of gear set 3220 is further rotated in the direction of arrow "B" causing rack 3228 to move further in the direction of arrow "C". However, since actuation shaft 3230 has bottomed out (i.e., movement in the direction of arrow "C" is stopped), rack 3228 is caused to move in the direction of arrow "C" along actuation shaft 3230, and since follower block 3232 is axially fixed along actuation shaft 3230, biasing member 3234 is caused to be elongated. Simultaneously or concomitantly therewith, first gear segment 3214 of trigger plate 3212 further rotates bevel gear 3242a of distal portion 3242 of slip clutch 3240 in the direction of arrow "D" further rotating actuation shaft 3230 in the direction of arrow "D", as described above. Rotation of actuation shaft 3230 in the direction of arrow "D" may result in another operation or movement in an end effector (not shown) connected to a distal end of actuation shaft 3230 via an actuation cable 3231.

Figure 124:
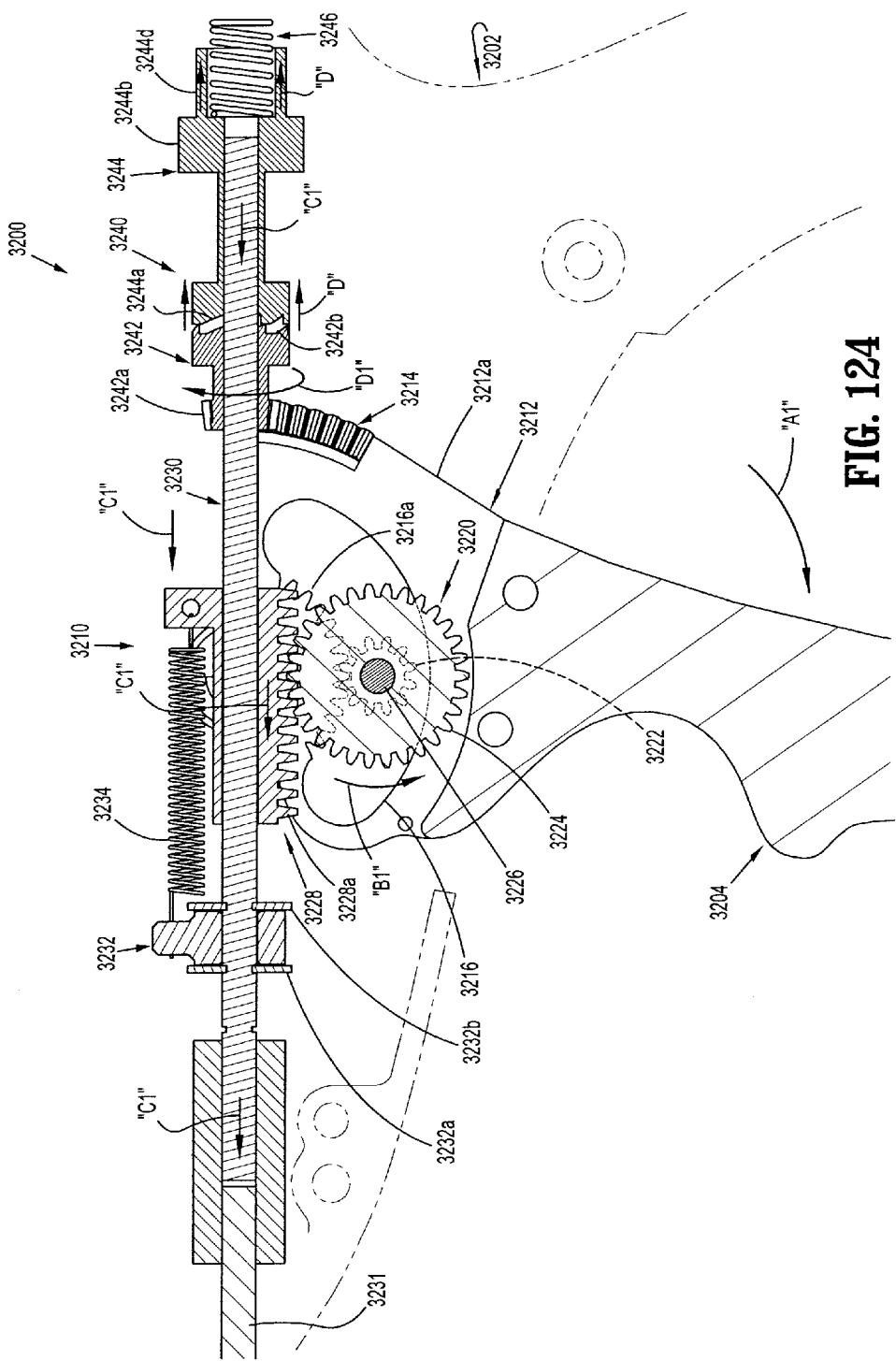
FIG. 124 is a side elevational view of the drive mechanism of FIG. 120, illustrating the drive mechanism and the trigger of the handle assembly in a fourth position.

Turning now to FIG. 124, as trigger 3204 is released or moved in the direction of arrow "A1", opposite to the direction of arrow "A", second gear 3224 of gear set 3220 is rotated in the direction of arrow "B1", opposite to arrow "B". Second gear 3224 is moved in the direction of arrow "B1" either by the movement of trigger 3204 in the direction of arrow "A1" or by the movement of rack 3228 in the direction of arrow "C1", opposite to the direction of arrow "C". Rack 3228 is moved in the direction of arrow "C1" due to the contraction of biasing member 3234 approximating rack 3228 toward follower block 3232. The spring bias of biasing member 3234, approximating rack 3228 toward follower block 3232, facilitates or aids in the return or movement of trigger 3204 in the direction of arrow "A1". As rack 5228 is moved in the direction of arrow "C1" actuation shaft 3230 is also moved in the direction of arrow "C1".

Simultaneously or concomitantly with the movement of trigger 3204 in the direction of arrow "A1", first gear segment 3214 of trigger plate 3212 imparts rotation to bevel gear 3242a of distal portion 3242 of slip clutch 3240 in the direction of arrow "D1", opposite to the direction of arrow "D". As bevel gear 3242a of distal portion 3242 of slip clutch 3240 is rotated in the direction of arrow "D1" gear teeth 3242b thereof slips-over and/or against teeth 3244a of proximal portion 3244 of slip clutch 3240, and since proximal portion 3244 of slip clutch 3240 is cammed in the direction of arrow "D", against the bias of spring 3246, no rotation is imparted to proximal portion 3244 of slip clutch 3240. In turn, since proximal portion 3244 of slip clutch 3240 does not rotate, no rotation is imparted to actuation shaft 3230.

As seen in FIG. 125, as toothed wheel 3244b of proximal portion 3244 of slip clutch 3240 is rotated in the direction of arrow "D1", pawl 3248 abuts against a tooth 3244c of toothed wheel 3244b, preventing rotation of toothed wheel 3244b in the direction of arrow "D1" and in turn preventing rotation of actuation shaft 3230 in the direction of arrow "D1".

Movement of actuation shaft 3230 in the direction of arrow "C1" may result in yet another operation or movement in an end effector (not shown) connected to a distal end of actuation shaft 3230 via an actuation cable 3231.

Turning now to FIGS. 111-115 and 117-118, handle assembly 3200 further includes an articulation mechanism 3270 supported on and/or in housing 3202. Articulation assembly 3270 may be operatively connected to an end effect (not shown) in order to impart articulation to the end effector or any other suitable movement or operation to the end effector.

As seen in FIGS. 111-115 and 117-118, articulation mechanism 3270 includes a knob or dial 3272 rotatably supported on or in housing 3202, and a gear set 3274 keyed to and shaving a common rotational axis as dial 3272. Gear set 3274 includes a first gear 3274a and a second gear 3274b each supported on and keyed to a pin 3276 extending therethrough and through dial 3272.

As seen in FIGS. 114 and 115, first gear 3274a of gear set 3274 operatively engages a locking/feedback member 3278 including a finger 3278a biased against the teeth of first gear 3274a. In operation, as first gear 3274a of gear set 3274 is rotated, due to a rotation of dial 3272, finger 3278a rides over the teach of first gear 3274a thereby providing the user with tactile and/or audible feedback. Additionally, when dial 3272 is not rotated, finger 3278a inter-engages with the teeth of first gear 3274a to thereby inhibit automatic rotation of dial 272 and thus essentially lock or fix the position of dial 3272.

Articulation mechanism 3270 further includes a pair of opposed racks 3280a, 3280b operatively engaged with and on opposed sides of second gear 3274b of gear set 3274. Each rack 3280a, 3280b is slidably supported within a respective channel 3282a, 3282b of a support member 3282. Each rack 3280a, 3280b includes a respective articulation cable 3284a, 3284b secured thereto. In this manner, during operation, as each rack 3280a, 3280b is displaced so to is each respective articulation cable 3284a, 3284b.

Figure 117:
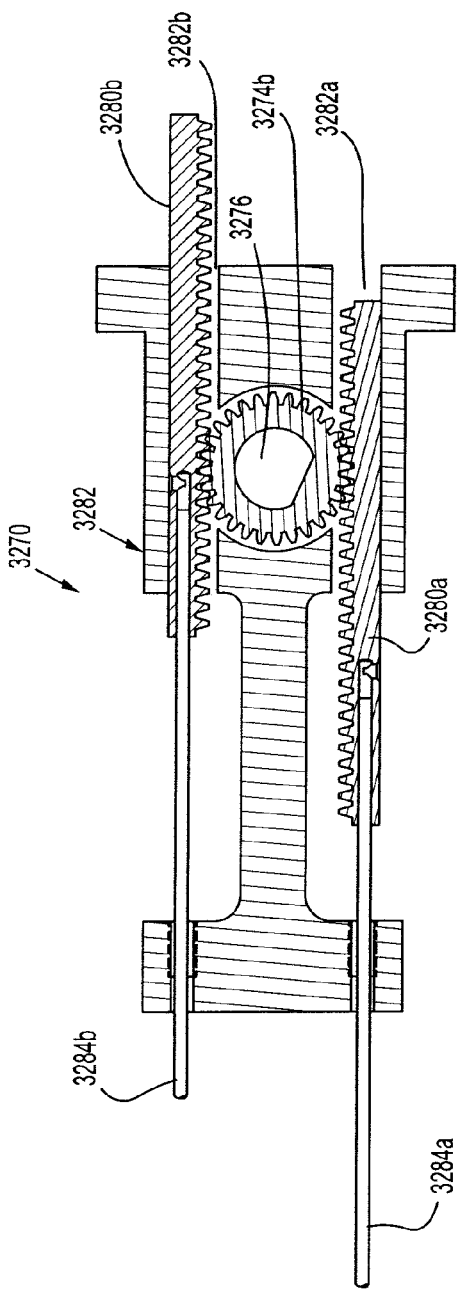
FIG. 117 is a cross-sectional view of the articulation control mechanism of FIG. 115 as taken through 117-117 of FIG. 115.
Figure 118:
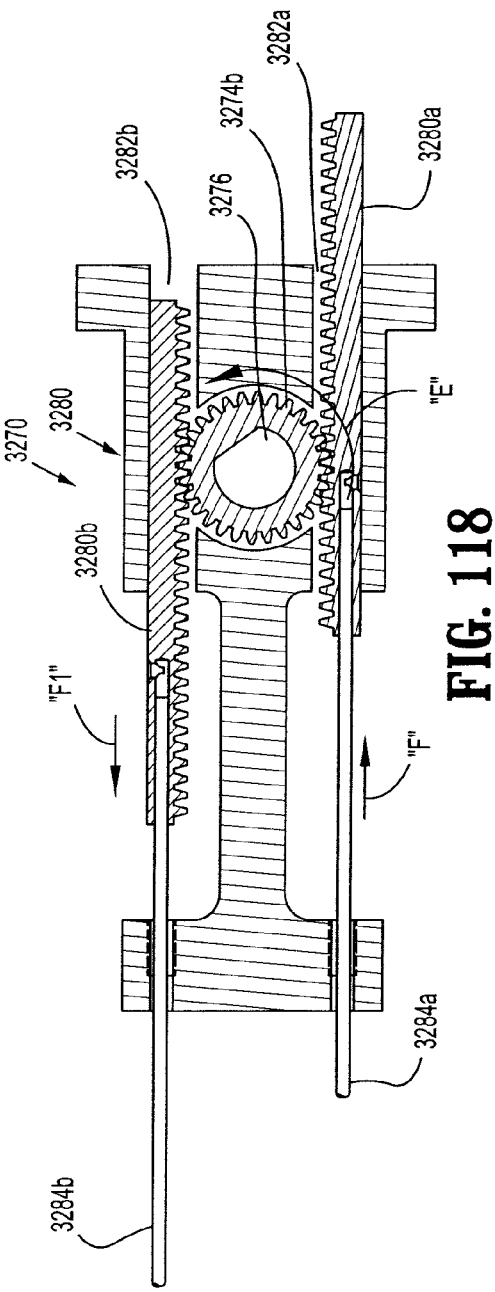
FIG. 118 is a cross-sectional view of the articulating control mechanism of FIG. 115, as taken through 117-117 of FIG. 115, illustrating the operation thereof.

In operation, as best seen in FIGS. 117 and 118, as second gear 3274b is rotated in a direction of arrow "E", due to the rotation of dial 3272, first rack 3280a is moved in a proximal direction (i.e., in the direction of arrow "F"), thus displacing first articulation cable 3284a in the direction of arrow "F", and second rack 3280b is moved in a distal direction (i.e., in the direction of arrow "F1", opposite to arrow "F"), thus displacing second articulation cable 3284b in the direction of arrow "F1". It is understood that rotation of dial 3272 in an opposite direction and thus rotation of second gear 3274b in a direction opposite to arrow "E" will result in movement and/or displacement of racks 3280a, 3280b and cables 3284a, 3284b in opposite directions. Rotation of dial 3272 thus may impart an operation or movement in an end effector (not shown).

Figure 126:
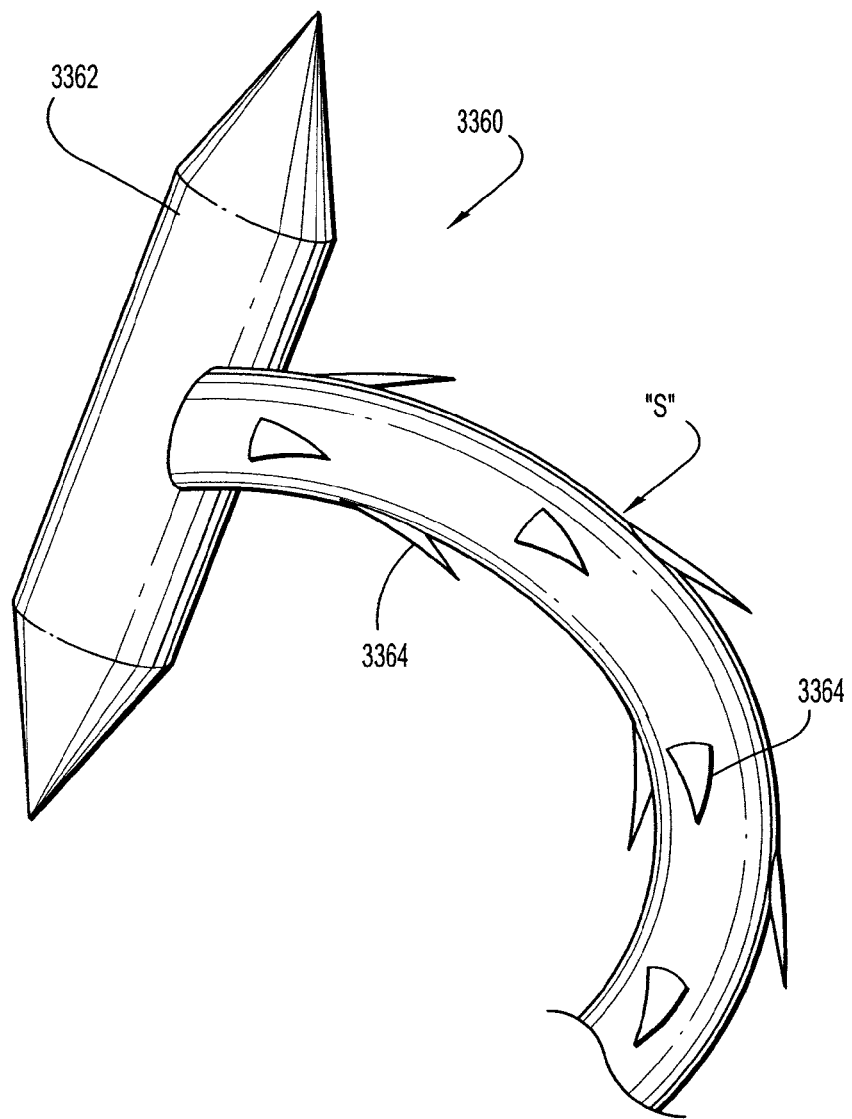
FIG. 126 is a schematic illustration of a suture for use in combination with the stitching devices of the present disclosure.
Figure 127:
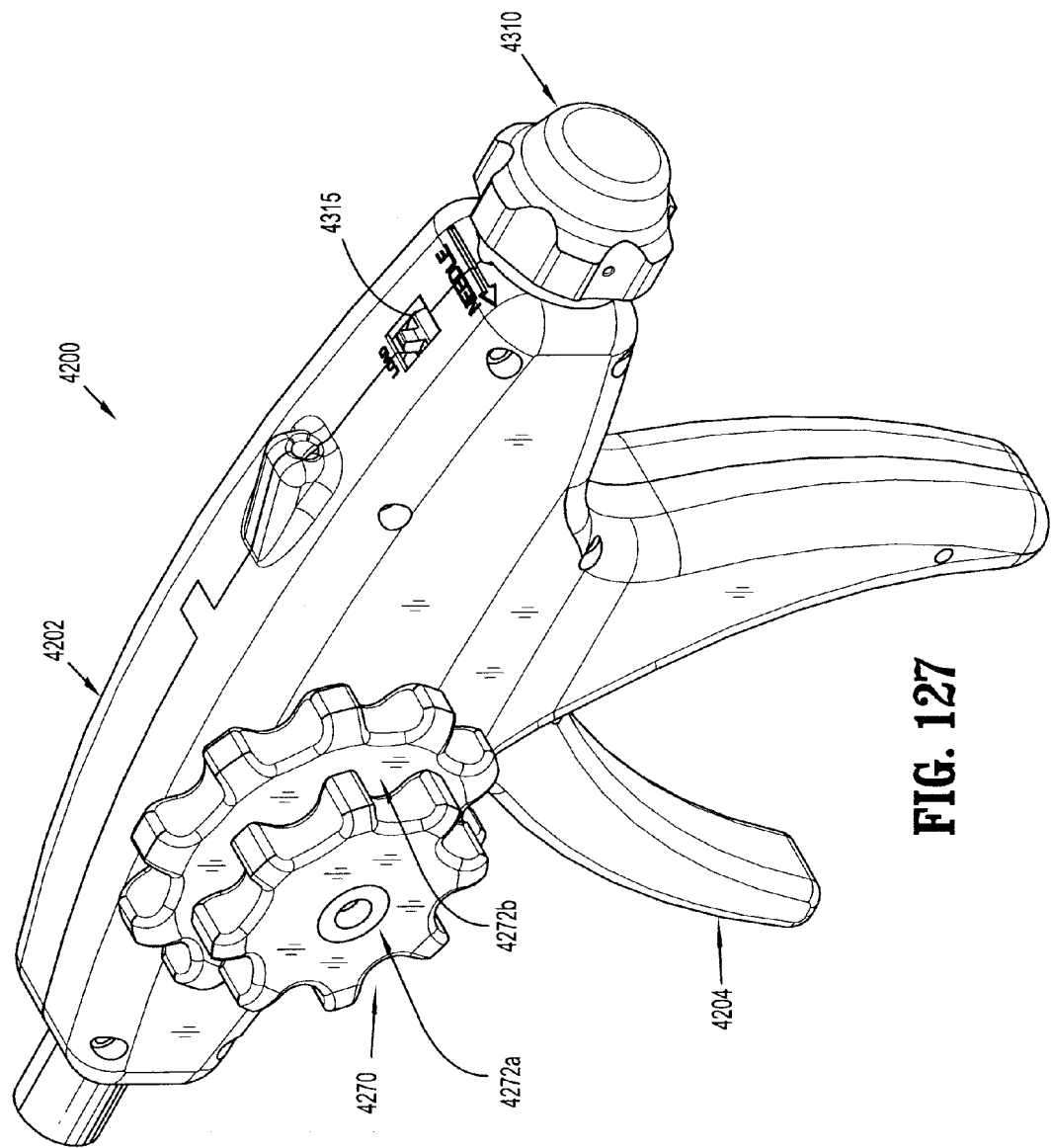
FIG. 127 is a perspective view of a handle assembly according to another embodiment of the present disclosure.
Figure 128:
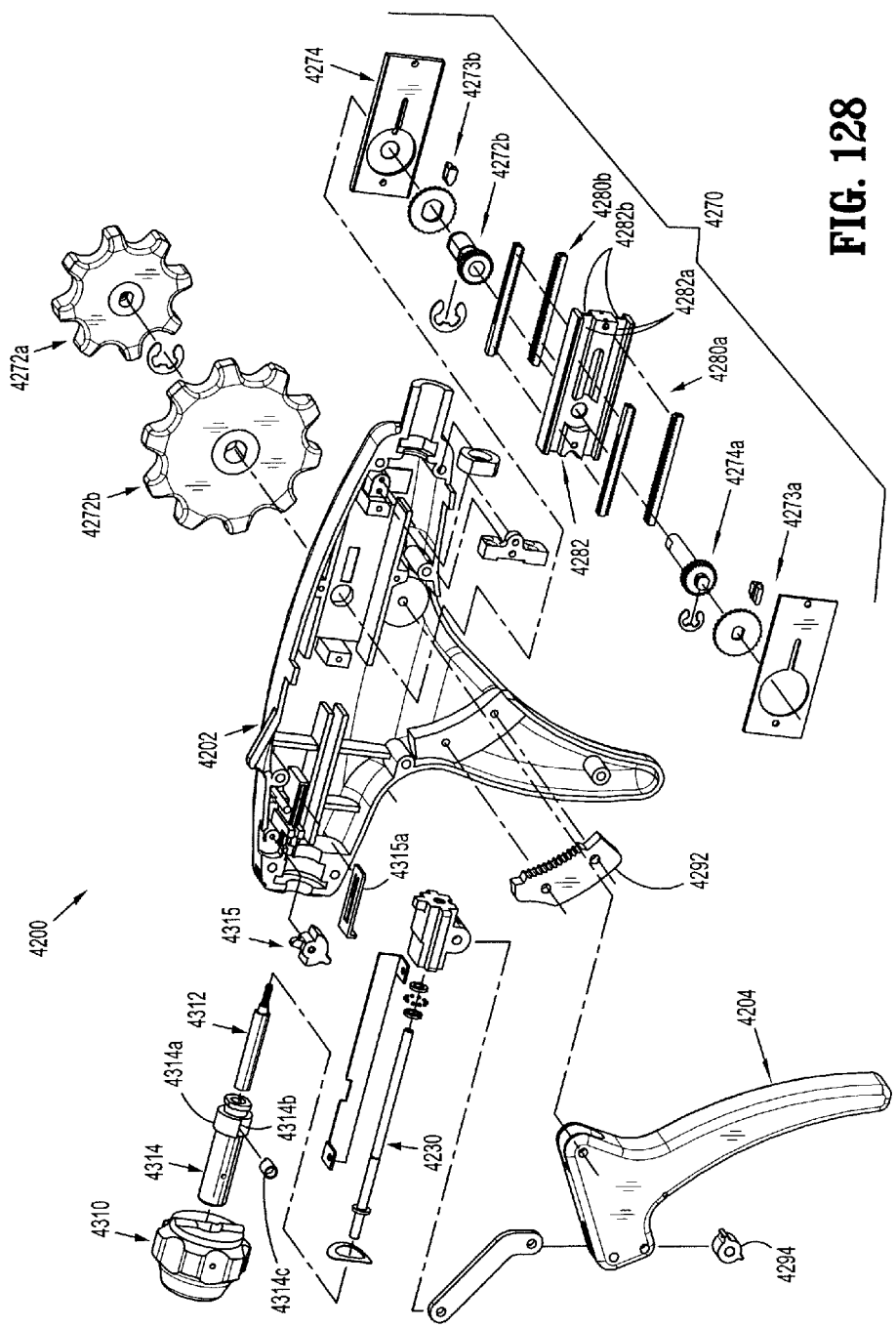
FIG. 128 is an exploded perspective view of the handle assembly of FIG. 127.
Figure 129:
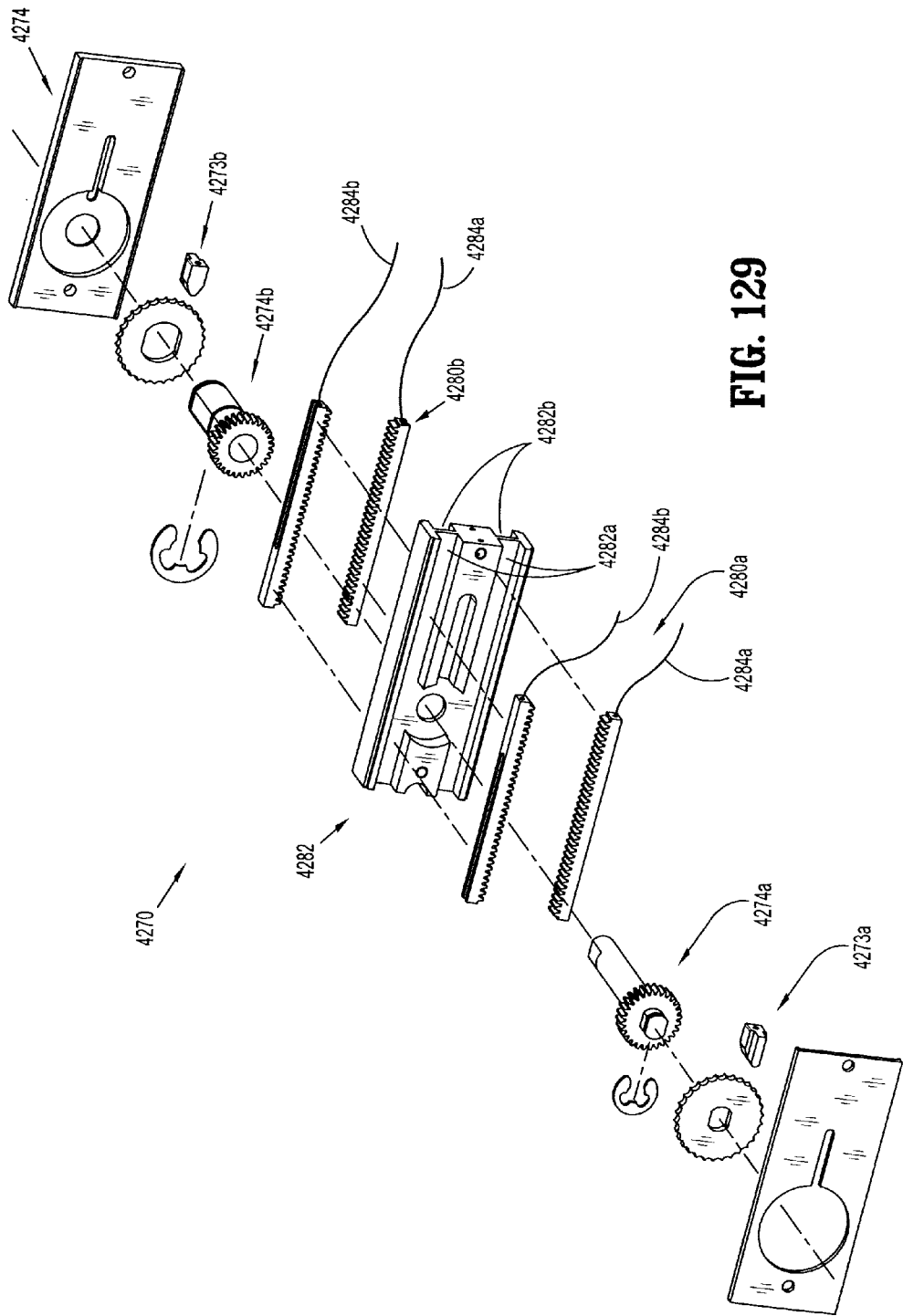
FIG. 129 is an exploded perspective view of an articulation assembly of the handle assembly of FIGS. 127 and 128.
Figure 130:
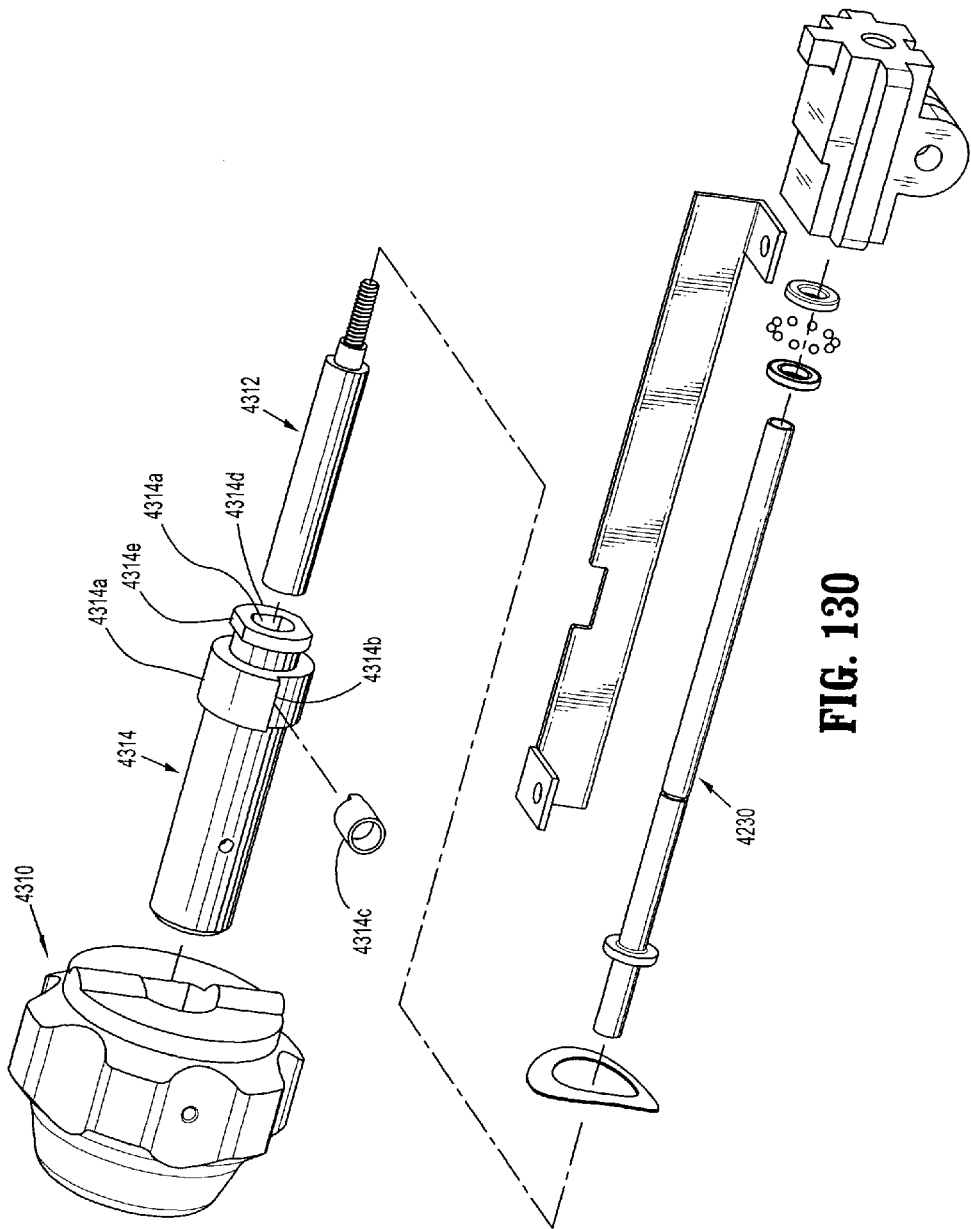
FIG. 130 is an exploded perspective view of a manual needle switching mechanism of the handle assembly of FIGS. 127-129.
Figure 131:
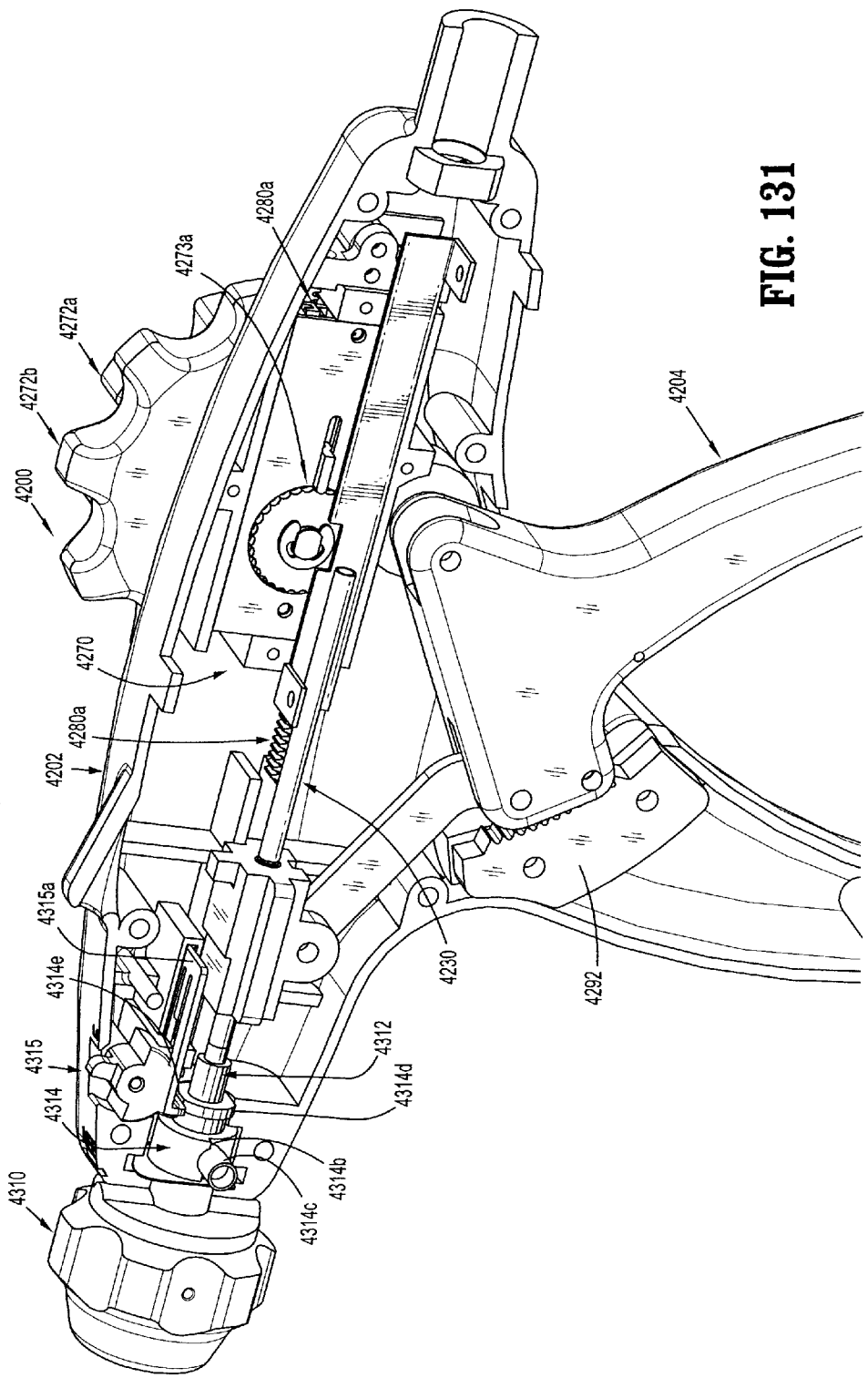
FIG. 131 is a perspective view of the handle assembly of FIGS. 127-130, illustrated with a housing half-section removed therefrom.
Figure 132:
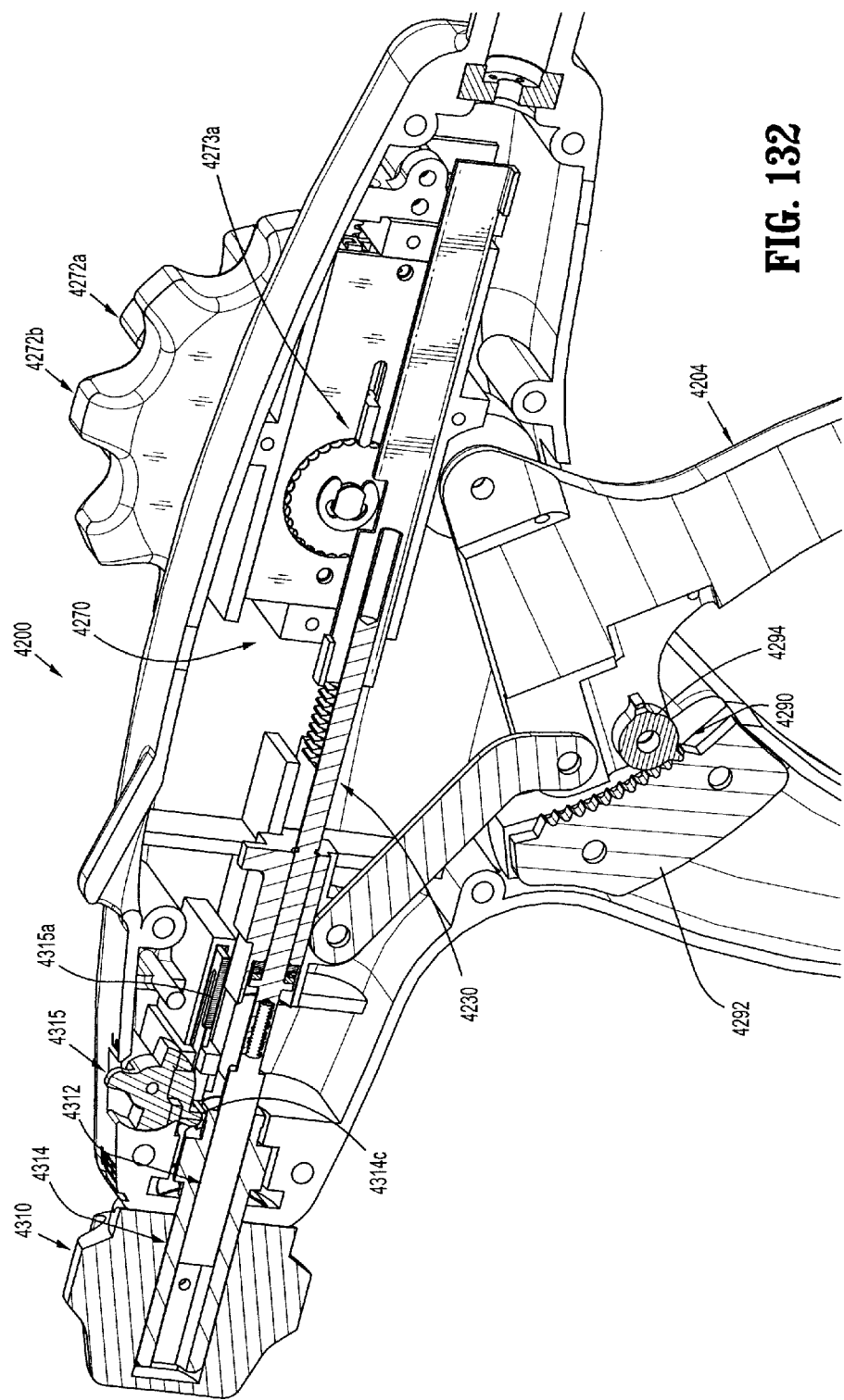
FIG. 132 is a longitudinal, cross-sectional view of the handle assembly of FIGS. 127-131.
Figure 133:
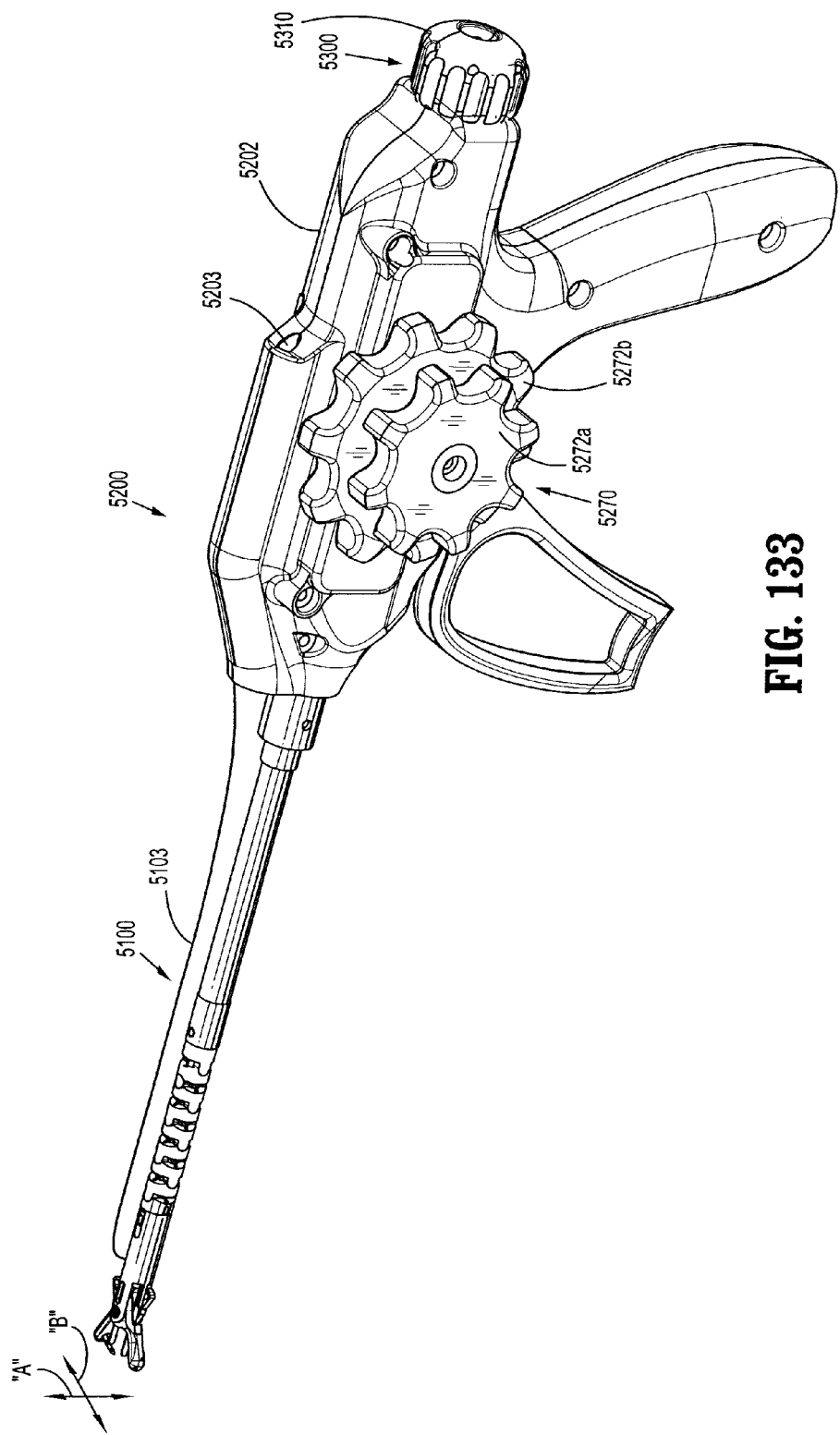
FIG. 133 is a perspective view of a handle assembly according to yet another embodiment of the present disclosure.
Figure 134:
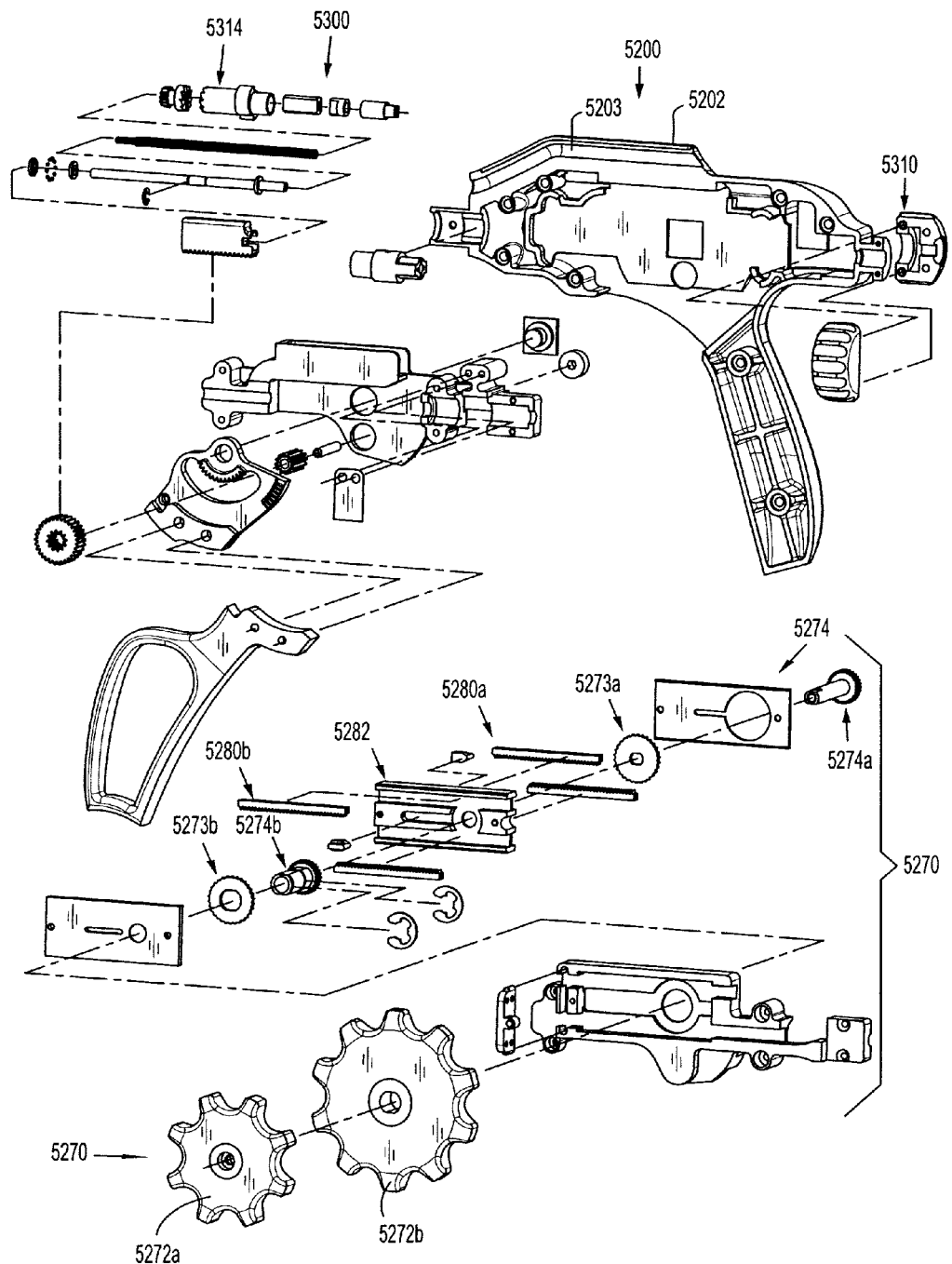
FIG. 134 is an exploded perspective view of the handle assembly of FIG. 133.
Figure 135:
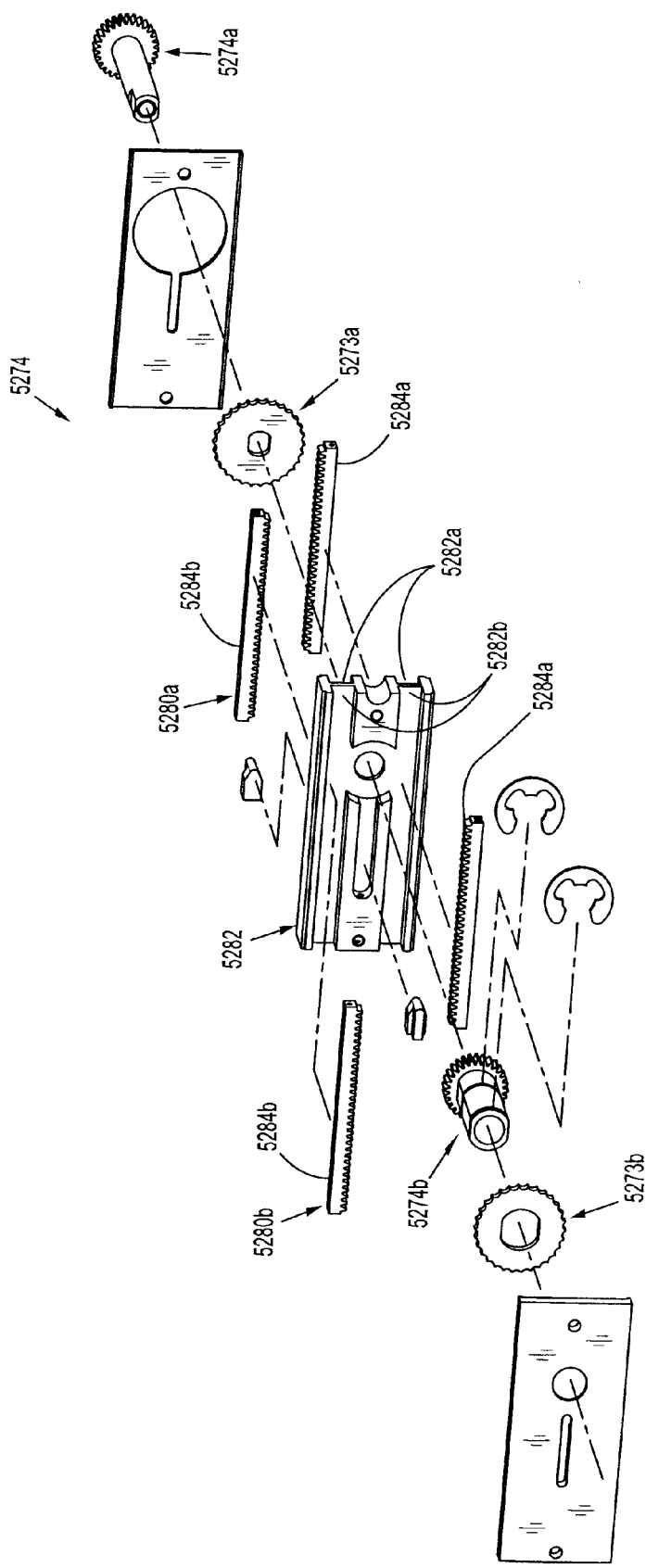
FIG. 135 is an exploded perspective view of an articulation assembly of the handle assembly of FIGS. 133 and 134.
Figure 136:
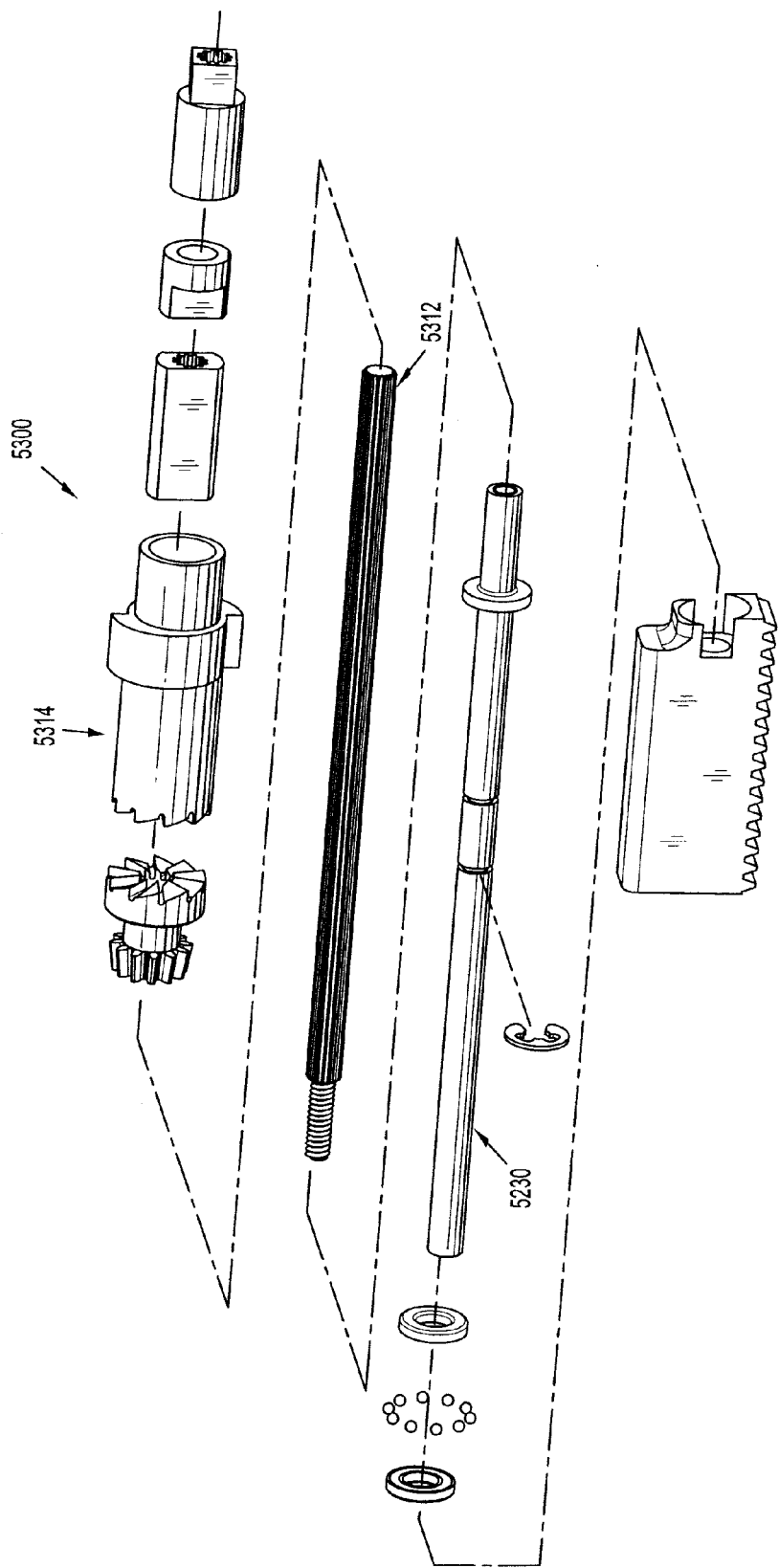
FIG. 136 is an exploded perspective view of a manual needle switching mechanism of the handle assembly of FIGS. 133-135.

Turning now to FIG. 126, an exemplary suture needle, for use with any of the endoscopic devices, instruments and assemblies disclosed herein, is generally shown as 3360. Suture needle 3360 includes a needle 3362 configured and adapted for the intended purpose of operation with any of the endoscopic devices, instruments and assemblies disclosed herein and for performing a surgical suturing procedure, including penetrating tissue and the like.

Suture needle 3360 includes a suture "S" secured thereto according to known techniques in the art. Suture "S" of suture needle 3360 may comprise a one-way or barbed suture "S". Suture "S" includes an elongated body having a plurality of barbs 3364 extending therefrom. Barbs 3364 are oriented such that barbs 3364 cause suture "S" to resist movement in an opposite direction relative to the direction in which barb 3364 faces.

Suitable sutures "S" for use in surgical needle 3360 include, and are not limited to, those sutures described and disclosed in U.S. Pat. No. 3,123,077; U.S. Pat. No. 5,931,855; and U.S. Patent Publication No. 2004/0060409, filed on Sep. 30, 2002, the entire content of each of which being incorporated herein by reference.

Turning now to FIGS. 127-132, a handle assembly according to a further embodiment of the present disclosure is generally designated as 4200. Handle assembly 4200 is substantially similar to handle assembly 2200 and thus will only be discussed in detail herein to the extent necessary to identify differences in operation and construction thereof.

As seen in FIGS. 127-129, 131 and 132, handle assembly 4200 includes an articulation assembly 4270 supported on and/or in housing 4202. Articulation assembly 4270 may be operatively connected to any of the end effectors disclosed hereinabove in order to impart multiple articulations to the end effector or any other suitable movement or operation to the end effector.

As seen in FIGS. 127-129, 131 and 132, articulation assembly 4270 includes a pair of knobs or dials 4272a, 4272b rotatably supported on or in housing 4202, and a set of gears 4274 keyed to and sharing a common rotational axis as dials 4272a, 4272b. The set of gears 4274 includes a first gear 4274a keyed to first dial 4272a and a second gear 4274b keyed to second dial 4272b.

As seen in FIGS. 128, 129, 131 and 132, a first ratchet mechanism 4273a is operatively associated with first gear 4274a and first dial 4272a, and a second ratchet mechanism 4273b is operatively associated with second gear 4274b and second dial 4272b. Each ratchet mechanism 4273a, 4273b is configured so as to maintain the position of respective first and second dials 4272a, 4272b relative to housing 4202.

In operation, as first gear 4274a is rotated, due to a rotation of first dial 4272a, first ratchet mechanism 4273a is actuated thereby providing the user with tactile and/or audible feedback as well as fixing the position of first dial 4272a relative to housing 4202. Additionally, when first dial 4272a is not rotated, as mentioned above, first ratchet mechanism 4273a inhibits automatic rotation of first dial 4272 and thus essentially locks or fixes the position of first dial 4272a. The operation of second gear 4272b is substantially similar to the operation of first gear 4272a and thus will not be discussed in further detail herein.

Articulation assembly 4270 further includes two pairs of opposed racks 4280a, 4280b each pair being operatively engaged with and disposed on opposed sides of respective first and second gears 4274a, 4274b. Each pair of racks 4280a, 4280b is slidably supported within respective channels 4282a, 4282b formed in a support member 4282. Each rack of the pair of racks 4280a, 480b includes an articulation cable 4284a, 4284b secured thereto. In this manner, during operation, as each rack of the pair of racks 4280a, 4280b is displaced so to is each respective articulation cable 4284a, 4284b.

In operation, as first gear 4274a is rotated in a first direction, due to the rotation of first dial 4272a, the first pair of racks 4280a are displaced in opposite directions to one another, thus displacing respective articulation cables 4284a, 4284b in opposite directions to one another. It is understood that rotation of first dial 4272a in an opposite direction and thus rotation of first gear 4274b in an opposite direction will result in movement and/or displacement of the respective pair of racks 4280a and cables 4284a, 4284b in opposite directions. Rotation of first dial 4272b thus may impart an operation, movement or first articulation in any of the articulatable end effectors disclosed herein.

Also, in operation, as second gear 4274b is rotated in a first direction, due to the rotation of second dial 4272b, the second pair of racks 4280b are displaced in opposite directions to one another, thus displacing respective articulation cables 4284a, 4284b in opposite directions to one another. It is understood that rotation of second dial 4272b in an opposite direction and thus rotation of second gear 4274b in an opposite direction will result in movement and/or displacement of the respective pair of racks 4280a and cables 4284a, 4284b in opposite directions. Rotation of second dial 4272b thus may impart an operation, movement or second articulation in any of the articulatable end effectors disclosed herein.

As seen in FIGS. 127, 128 and 130-132, handle assembly 4200 further includes a needle loading assembly 4300 including a knob 4310 supported on a rear end of housing 4202 and configured to enable loading of a surgical needle (not shown) in the jaws of an end effector disclosed herein. Knob 4310 is coupled to a keyed shaft 4312 via a keyed rotation hub 4314. Keyed rotation hub 4314 has a shaped outer surface for receipt in a complementary shaped recess formed in knob 4310 such that rotation of knob 4310 results in rotation of keyed rotation hub 4314. Keyed rotation hub 4314 defines a shaped lumen 4314a (FIG. 130) for receipt of a complementary shaped outer surface of keyed shaft 4312 such that rotation of knob 4310 also results in rotation of keyed shaft 4312.

Keyed rotation hub 4314 includes an annular flange 4314a defining a shoulder 4314b. In use, keyed rotation hub 4314 is permitted to rotate in a single direction due to the blocking of rotation in an opposite direction by the abutment of shoulder 4314b against a stop 4314c.

Keyed rotation hub 4314 further includes a distal annular rim 4314d defining a flat 4314e. Flat 4314e of keyed rotation hub 4314 is configured to selectively cooperate and engage with a release switch 4315 supported on or pivotally connected to housing 4202. In use, when switch 4315 is in registration with flat 4314e of keyed rotation hub 4314, keyed rotation hub 4314 is prevented from rotating and knob 4310 is prevented from rotating. When switch 4315 is out of registration with flat 4314e of keyed rotation hub 4314, keyed rotation hub 4314 is free to rotate and thus knob 4310 is free to rotate.

As seen in FIGS. 128 and 130-132, a distal end of keyed shaft 4312 is fixedly secured to a proximal end of an actuation shaft 4230 (a distal end of actuation shaft 4230 may be connected to an actuation cable extending in to the end effectors).

In use, in order to load a surgical needle into jaws of an end effector, release switch 4315 is moved in order to free rotation of knob 4310. Knob 4310 is then rotated, thereby rotating keyed shaft 4312, actuation shaft 4230, the actuation cable and the camming hub (as described above). As knob 4310 is rotated, the blades of the end effector are moved axially until the distal ends of the blades are out of registration with the needle receiving recesses (as described above). With the distal ends of the blades out of registration with the receiving recesses of the jaws, a surgical needle is inserted into one of the receiving recesses. Knob 4310 is then rotated until the distal end of one of the blades engages the surgical needle, as described above.

With the surgical needle loaded, release switch 4315 may be re-registered with flat 4314e of keyed rotation hub 4314, thereby preventing further rotation of knob 4310. It is contemplated that release switch 4315 may be biased to the registration position by a suitable biasing member 4315a.

Handle assembly 4200 may include a ratchet mechanism 4290 connected to trigger 4204. Ratchet mechanism 4290 include a ratchet rack 4292 supported in housing 4202, and a pawl 4294 supported on trigger 4204 and operatively engaged with ratchet rack 4292. Ratchet mechanism 4290 is configured such that trigger 4202 can not be opened without the completion of the stroke.

Turning now to FIGS. 133-142, a handle assembly according to a further embodiment of the present disclosure is generally designated as 5200. Handle assembly 5200 is substantially similar to handle assembly 2200 and thus will only be discussed in detail herein to the extent necessary to identify differences in operation and construction thereof.

As seen in FIGS. 133-135 and 137-140, handle assembly 5200 includes an articulation assembly 5270 supported on and/or in housing 5202. Articulation assembly 5270 may be operatively connected to any of the end effectors disclosed hereinabove in order to impart multiple articulations to the end effector or any other suitable movement or operation to the end effector.

As seen in FIGS. 133-135 and 137-140, articulation assembly 5270 includes a pair of knobs or dials 5272a, 5272b rotatably supported on or in housing 5202, and a set of gears 5274 keyed to and sharing a common rotational axis as dials 5272a, 5272b. The set of gears 5274 includes a first gear 5274a keyed to first dial 5272a and a second gear 5274b keyed to second dial 5272b.

As seen in FIGS. 133-135 and 137-140, a first ratchet mechanism 5273a is operatively associated with first gear 5274a and first dial 5272a, and a second ratchet mechanism 5273b is operatively associated with second gear 5274b and second dial 5272b. Each ratchet mechanism 5273a, 5273b is configured so as to maintain the position of respective first and second dials 5272a, 5272b relative to housing 5202.

In operation, as first gear 5274a is rotated, due to a rotation of first dial 5272a, first ratchet mechanism 5273a is actuated thereby providing the user with tactile and/or audible feedback as well as fixing the position of first dial 5272a relative to housing 5202. Additionally, when first dial 5272a is not rotated, as mentioned above, first ratchet mechanism 5273a inhibits automatic rotation of first dial 5272 and thus essentially locks or fixes the position of first dial 5272a. The operation of second gear 5272b is substantially similar to the operation of first gear 5272a and thus will not be discussed in further detail herein.

Articulation assembly 5270 further includes two pairs of opposed racks 5280a, 5280b each pair being operatively engaged with and disposed on opposed sides of respective first and second gears 5274a, 5274b. Each pair of racks 5280a, 5280b is slidably supported within respective channels 5282a, 5282b formed in a support member 5282. Each rack of the pair of racks 5280a, 580b includes an articulation cable 5284a, 5284b secured thereto. In this manner, during operation, as each rack of the pair of racks 5280a, 5280b is displaced so to is each respective articulation cable 5284a, 5284b.

In operation, as first gear 5274a is rotated in a first direction, due to the rotation of first dial 5272a, the first pair of racks 5280a are displaced in opposite directions to one another, thus displacing respective articulation cables 5284a, 5284b in opposite directions to one another. It is understood that rotation of first dial 5272a in an opposite direction and thus rotation of first gear 5274b in an opposite direction will result in movement and/or displacement of the respective pair of racks 5280a and cables 5284a, 5284b in opposite directions. Rotation of first dial 5272b thus may impart an operation, movement or first articulation in/of end effector 5100. For example, end effector 5100 may be articulated in the direction of arrows "A" (see FIG. 133).

Also, in operation, as second gear 5274b is rotated in a first direction, due to the rotation of second dial 5272b, the second pair of racks 5280b are displaced in opposite directions to one another, thus displacing respective articulation cables 5284a, 5284b in opposite directions to one another. It is understood that rotation of second dial 5272b in an opposite direction and thus rotation of second gear 5274b in an opposite direction will result in movement and/or displacement of the respective pair of racks 5280a and cables 5284a, 5284b in opposite directions. Rotation of second dial 5272b thus may impart an operation, movement or second articulation in/of end effector 5100. For example, end effector 5100 may be articulated in the direction of arrows "B" (see FIG. 133).

Handle assembly 5200 further includes a needle loading assembly 5300 including a knob 5310 supported on a rear end of housing 5202 and configured to enable loading of a surgical needle in jaws. Needle loading assembly 5300 is substantially similar to needle loading assembly 2300, shown and described above, and thus reference may be made to needle loading assembly 2300 for a detailed discussion of the construction and operation of needle loading assembly 5300.

In general, needle loading assembly 5330 includes a knob 5310 keyed to a spline shaft 5312 via a nut 5314. Nut 5314 has a shaped outer surface for receipt in a complementary shaped recess formed in knob 5310 such that rotation of knob 5310 results in rotation of nut 5314. Spline shaft 5312 is axially slidably disposed within lumen 5314a of nut 5314. A distal end of spline shaft 5312 extends through slip-clutch 5240 and is fixedly secured to a proximal end of actuation shaft 5230 (a distal end of actuation shaft 5230 being connected to actuation cable 5142).

In use, in order to load a surgical needle 104 into the jaws of end effector 5100, knob 5310 is rotated, thereby rotating spline shaft 5312, actuation shaft 5230, actuation cable 5142 and camming hub 2144 (as described above). As knob 5310 is rotated, blades 2150, 2152 are moved axially until the distal ends of blades 2150, 2152 are out of registration with needle receiving recesses 2130a, 2132a. With the distal ends of blades 2150, 2152 out of registration with receiving recesses 2130a, 2132a of jaws 2130, 2132, a surgical needle 104 is inserted into one of the receiving recesses 2130a, 2132a. Knob 5310 is then rotated until the distal end of one of blades 2150, 2152 engages surgical needle 104, as described above.

With continued reference to FIGS. 133, 134 and 137-142, housing 5202 of handle assembly 5200 may define a passage 5203 extending therethrough which has an open distal end and an open proximal end. Passage 5203 is configured and dimensioned to selectively receive and guide a surgical instrument therethrough. Suitable surgical instruments which may be introduced into and through passage 5203 include and are not limited to endoscopic graspers and/or forceps.

Figure 137:
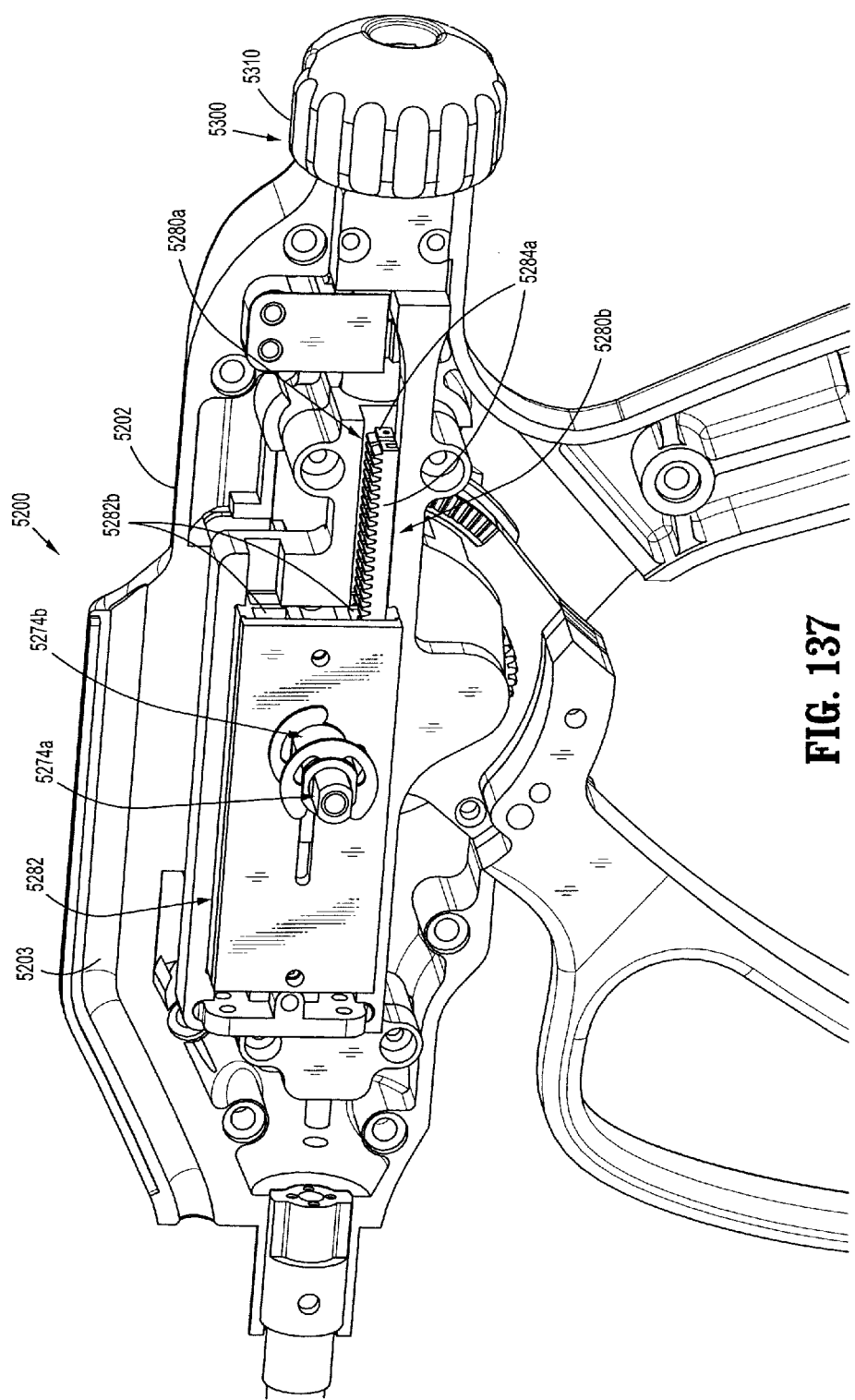
FIG. 137 is a perspective view of the handle assembly of FIGS. 133-136, illustrated with a housing half-section removed therefrom.
Figure 138:
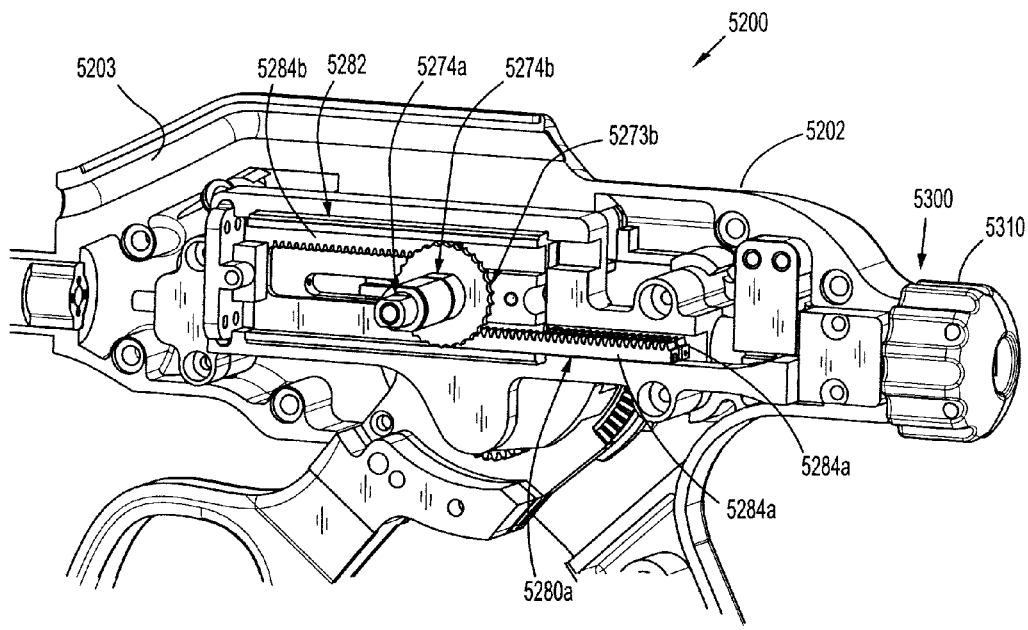
FIG. 138 is a perspective view of the handle assembly of FIGS. 133-137, illustrated with the housing half-section and a side plate of the articulation assembly removed therefrom.
Figure 139:
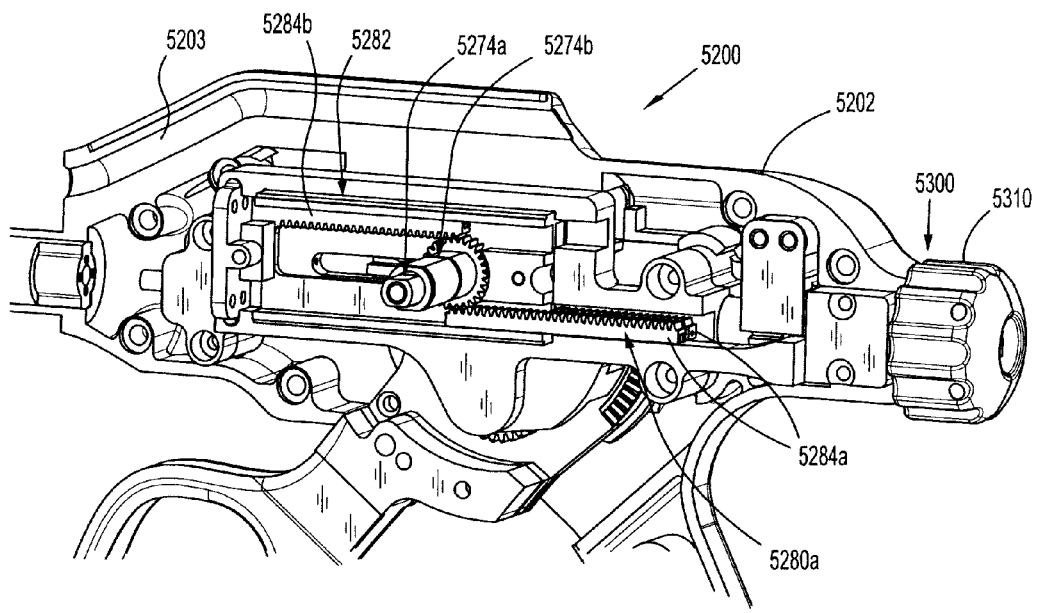
FIG. 139 is a perspective view of the handle assembly of FIGS. 133-138, illustrated with the housing half-section, the side plate and a ratchet wheel of the articulation assembly removed therefrom.
Figure 140:
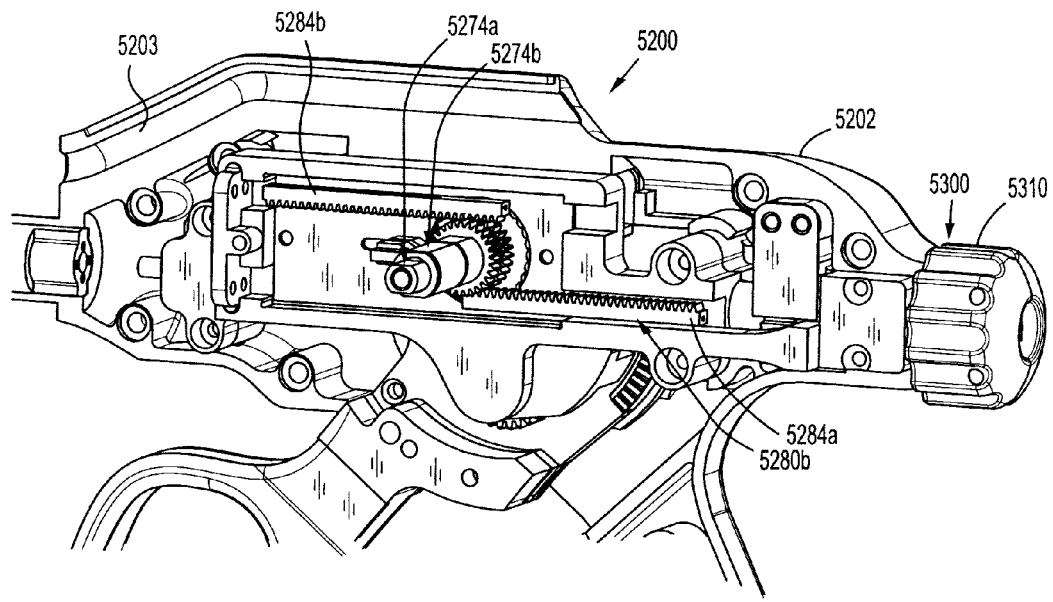
FIG. 140 is a perspective view of the handle assembly of FIGS. 133-139, illustrated with the housing half-section, the side plate, the ratchet wheel and a support member of the articulation assembly removed therefrom.
Figure 141:
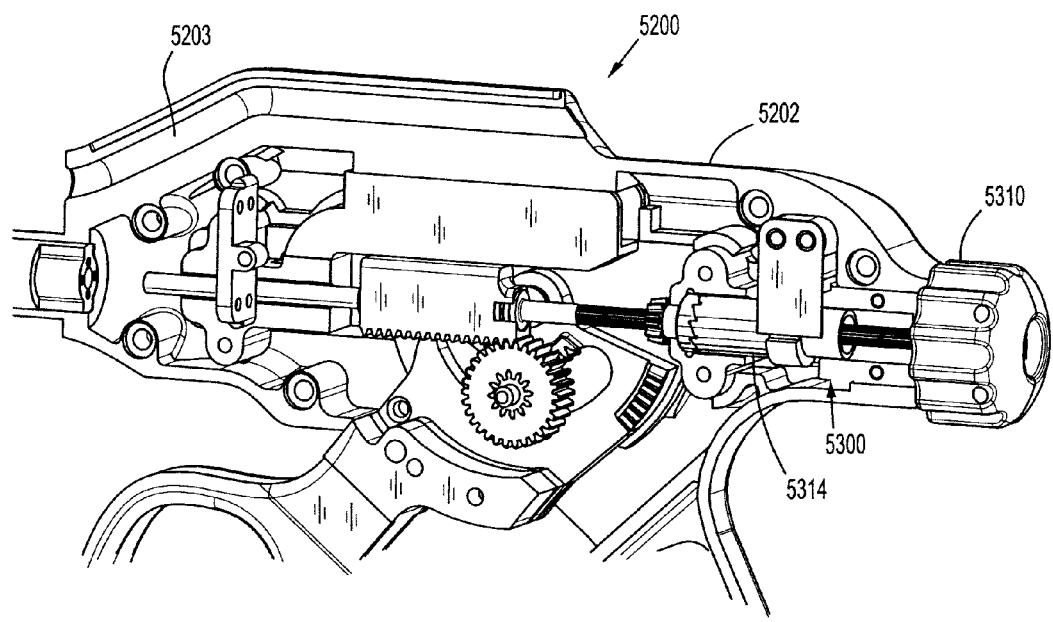
FIG. 141 is a perspective view of the handle assembly of FIGS. 133-140, illustrated with the housing half-section and the articulation assembly removed therefrom.
Figure 142:
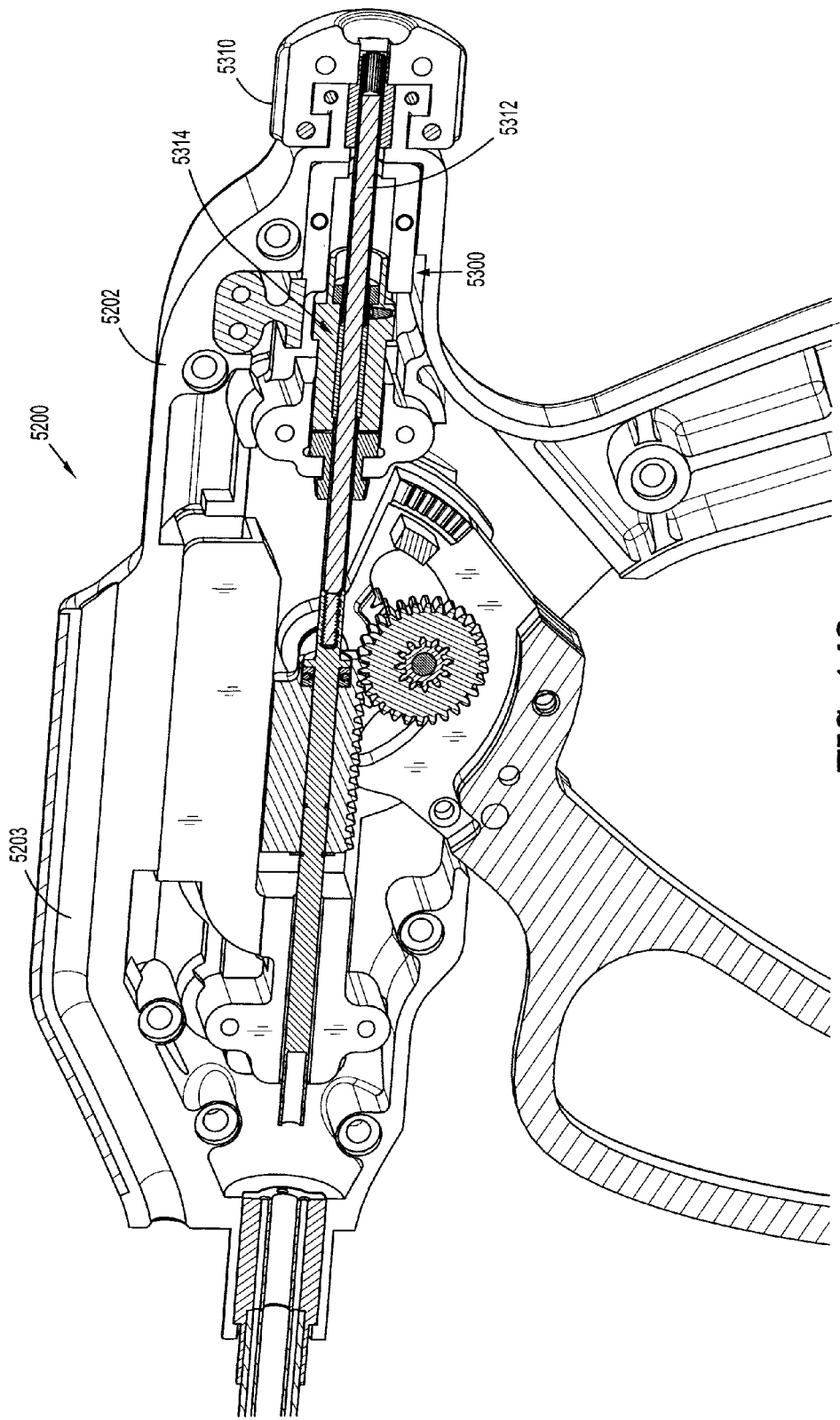
FIG. 142 is a longitudinal, cross-sectional view of the handle assembly of FIGS. 133-141.

As seen in FIG. 137, a channel 5103 may be connected to or otherwise secured to end effector 5100. Channel 5103 may extend from passage 5203 thereby defining a continuous passage from handle assembly 5200, along the neck portion and through to or proximate the tool assembly. In this manner, in use, the surgical instrument may be advanced through passage 5203 of handle assembly 5200 and through channel 5103 such that a distal end portion of the surgical instrument is in close proximity to the tool assembly in order to help or assist with the surgical procedure.

In this manner, end effector 5100 and the surgical instrument may be introduced into the target surgical site through the same or a common corporal opening.

Channel 5103 may be secured to an outer surface of the neck portion in such a manner so as to not interfere with the articulation of the neck portion and to not occlude the passage extending therethrough. Channel 5103 may be secured to the neck portion using adhesives, straps, shrink-wrapping or the like.

While the disclosure has been particularly shown and described with reference to particular embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A handle assembly for operating a surgical instrument, comprising:
    a housing;
    a trigger operatively supported on the housing; and
    at least one actuation cable operatively connected to the trigger and extending from the housing in such a manner that an actuation of the trigger imparts both axial translation and rotation to the actuation cable.

2. The handle assembly according to claim 1, further comprising at least one articulation cable operable from the housing.

3. The handle assembly according to claim 2, wherein each articulation cable includes a distal end operatively connectable with an end effector and a proximal end operatively connected to a control element supported on the housing.

4. The handle assembly according to claim 3, wherein the control element is selected from the group consisting of a slider, a dial, and a lever.

5. The handle assembly according to claim 3, wherein movement of the control element results in movement of the at least one articulation cable.

6. The handle assembly according to claim 3, wherein movement of the at least one articulation cable in a first direction causes an articulation of the end effector in a first direction and movement of the at least one articulation cable in a second direction results in an articulation of the end effector in a second direction.

7. The handle assembly according to claim 3, wherein the control element includes a trigger plate defining a gear segment operatively engaging at least one gear which is operatively connected to an actuation shaft, wherein movement of the control element results in at least rotation of the actuation shaft.

8. The handle assembly according to claim 7, wherein the control element is operatively connected to the actuation shaft in such a manner that movement of the control element results in axial translation of the actuation cable.

9. An endoscopic stitching device, comprising:
    a handle assembly, including:
        a housing;
        a trigger operatively supported on the housing; and
        an actuation cable operatively connected to the trigger and extending from the housing in such a manner that an actuation of the trigger imparts both axial translation and rotation to the actuation cable; and
    an end effector operatively connected to the handle assembly, the end effector including a tool assembly configured and adapted to perform at least a pair of operations, wherein the actuation cable is operatively connected to the tool assembly in such a manner that the actuation cable is capable of effecting a first operation of the pair of operations of the end effector upon the axial translation thereof; and wherein the actuation cable is operatively connected to the tool assembly in such a manner that the actuation cable is capable of effecting a second operation of the pair of operations of the end effector upon the rotation thereof.

10. The endoscopic stitching device according to claim 9, further comprising an articulatable neck assembly interconnecting the handle assembly and the end effector, wherein the neck assembly is configured and adapted for articulation in at least one direction transverse to a longitudinal axis thereof.

11. The endoscopic stitching device according to claim 10, further comprising at least one articulation cable slidably extending through the neck assembly and having a distal end fixedly connected to the tool assembly.

12. The endoscopic stitching device according to claim 11, wherein the articulation cable is disposed along an axis spaced a distance from a central axis of the neck assembly.

13. The endoscopic stitching device according to claim 11, wherein a proximal end of each articulation cable operatively connected to a control element supported on the housing.

14. The endoscopic stitching device according to claim 13, wherein the control element of the handle assembly is selected from the group consisting of a slider, a dial, and a lever.

15. The endoscopic stitching device according to claim 13, wherein movement of the control element of the handle assembly results in movement of the at least one articulation cable.

16. The endoscopic stitching device according to claim 13, wherein movement of the at least one articulation cable in a first direction causes an articulation of the end effector in a first direction and movement of the at least one articulation cable in a second direction results in articulation of the end effector in a second direction.

17. The endoscopic stitching device according to claim 13, wherein the control element of the handle assembly includes a trigger plate defining a gear segment operatively engaging at least one gear which is operatively connected to an actuation shaft, wherein movement of the control element results in at least rotation of the actuation shaft, and wherein the actuation cable is connected to the actuation shaft.

18. The endoscopic stitching device according to claim 17, wherein the control element of the handle assembly is operatively connected to the actuation shaft in such a manner that movement of the control element results in axial translation of the actuation cable.

19. The endoscopic stitching device according to claim 9, further comprising a suture needle operatively associated with the tool assembly, wherein the tool assembly includes a pair of juxtaposed jaws pivotally associated with one another, and wherein each jaw defines a needle receiving recess formed in a tissue contacting surface thereof.

20. The endoscopic stitching device according to claim 19, further comprising an axially translatable needle engaging blade slidably supported in each jaw.

21. The endoscopic stitching device according to claim 20, wherein each blade includes an advanced position wherein a distal end of the blade engages the suture needle when the suture needle is in the respective jaw to thereby secure the suture needle therewith, and wherein each blade includes a retracted position wherein a distal end of the blade is out of engagement with the suture needle.

22. The endoscopic stitching device according to claim 21, wherein the pair of blades are operatively joined to one another so as to translate in opposite directions relative to one another upon a rotation of the actuation cable.

23. The endoscopic stitching device according to claim 20, further comprising a camming hub keyed to the actuation cable so as to enable an axial translation of the actuation cable relative to the camming hub, wherein the camming hub rotates upon a rotation of the actuation cable.

24. The endoscopic stitching device according to claim 23, wherein the camming hub is operatively connected to a proximal end of each blade in such a manner that rotation of the camming hub results in axial translation of each of the pair of blades.

25. The endoscopic stitching device according to claim 19, wherein axial, reciprocal translation of the actuation cable results in opening and closing of the pair of jaws.

26. The endoscopic stitching device according to claim 25, wherein the actuation cable translatably extends between the handle assembly and the end effector.

27. The endoscopic stitching device according to claim 25, wherein when the actuation cable is in a first position the pair of jaws are spaced apart from one another, and when the actuation cable is in a second position the pair of jaws are in a close spaced relation to one another.

28. The endoscopic stitching device according to claim 19, wherein the suture needle includes a length of barbed suture extending therefrom.

\* \* \* \* \*